US008399639B2

(12) United States Patent
Ryan

(10) Patent No.: US 8,399,639 B2
(45) Date of Patent: Mar. 19, 2013

(54) ISOLATED GENOMIC POLYNUCLEOTIDE FRAGMENTS FROM THE P15 REGION OF CHROMOSOME 11 ENCODING HUMAN ACHAETE-SCUTE HOMOLOG 2 (HASH2)

(75) Inventor: James Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

(21) Appl. No.: 13/239,243

(22) Filed: Sep. 21, 2011

(65) Prior Publication Data

US 2012/0010268 A1 Jan. 12, 2012

Related U.S. Application Data

(62) Division of application No. 09/999,121, filed on Oct. 31, 2001, now Pat. No. 8,039,602.

(60) Provisional application No. 60/244,705, filed on Oct. 31, 2000.

(51) Int. Cl.
*C07H 21/02* (2006.01)
*C07H 21/04* (2006.01)
*C12Q 1/68* (2006.01)
*C12P 19/34* (2006.01)
*C12N 5/00* (2006.01)
*C12N 5/02* (2006.01)

(52) U.S. Cl. .................... 536/23.1; 536/24.3; 536/24.33; 536/24.5; 435/6; 435/91.1; 435/325; 435/375

(58) Field of Classification Search ................. 536/23.1, 536/24.3, 24.33, 24.1, 24.5; 514/44
See application file for complete search history.

(56) References Cited

U.S. PATENT DOCUMENTS

| | | | |
|---|---|---|---|
| 5,582,979 | A | 12/1996 | Weber |
| 5,591,623 | A | 1/1997 | Bennet |
| 6,150,092 | A | 11/2000 | Uchida |
| 6,184,212 | B1 | 2/2001 | Miraglia |
| 6,537,751 | B1 | 3/2003 | Cohen |
| 6,566,135 | B1 | 5/2003 | Watt |
| 6,812,339 | B1 | 11/2004 | Venter |
| 7,125,858 | B2 | 10/2006 | Fillion |
| 8,039,602 | B2 | 10/2011 | Ryan |

FOREIGN PATENT DOCUMENTS

| | | |
|---|---|---|
| WO | WO95/20678 | 8/1995 |
| WO | WO 9844152 A1 * | 10/1998 |
| WO | WO99/18198 | 4/1999 |
| WO | WO00/15795 | 3/2000 |
| WO | WO01/62778 | 8/2001 |

OTHER PUBLICATIONS

GenBank Accession No. AC002536, authored by Evans et al., submitted on Dec. 10, 1997.*
Wade-Martins (Nucleic Acids Research, 1999 vol. 27:1674-1682).*
Alders et al. "The human Achaete-Scute homologue 2 (ASCL2, HASH2) maps to chromosome 11p15.5, close to IGF2 and is expressed in extravillus trophoblasts." Human Molecular Genetics, 6: 859-867. 1997.
Altschul et al. Gapped BLAST and PSI-BLAST: a new generation of protein database search programs. Nucleic Acids Res. 25: 3389-3402. 1997.
Andria et al. "Genomic organization and chromosomal localization of the TAPA-1 gene." J. Immunol. 147: 1030-1036. 1991.
Bowie et al. "Deciphering the message in protein sequences: Tolerance to amino acid substitutions." Science 247: 1306-1310. 1990.
Burge et al. "Prediction of complete gene structures in human genomic DNA." J. Mol. Biol. 268: 78-94. 1997.
Examiner's Interview Summary dated Jul. 14, 2009 for U.S. Appl. No. 09/999,121.
International Search Report from counterpart international application PCT/US01/45381.
Itoh et al. "Proportions of cells with paternal 11p15 uniparental disomy correlates with organ enlargement in Wiedemann-Beckwith syndrome." J. Med. Gen. 92: 111-116. 2000.
Kenmochi et al. "A Map of 75 human ribosomal protein genes." Genome Research 8: 509-523. 1998.
Koi et al. "Tumor cell growth arrest caused by subchromosomal transferable DNA fragments from chromosome 11." Science, 260: 361-364. 1993.
Lee et al. "Two novel genes in the center of the 11p15 imprinted domain escape genomic imprinting". Hum. Mol. Gen. 8: 683-690. 1999.
Ngo et al. "Computational complexity, protein structure prediction, and the Levinthal Paradox." in The Protein Folding Problem and Tertiary Structure Prediction Merz, Jr., K. and LeGrand, S. eds. Birkhäuser. Boston. 1994.
Notice of Allowance/Allowability dated Jun. 3, 2011 for U.S. Appl. No. 09/999,121.
Office Action dated Aug. 24, 2004 for U.S. Appl. No. 09/999,121.
Office Action dated Sep. 8, 2005 for U.S. Appl. No. 09/999,121.
Office Action dated Jul. 27, 2006 for U.S. Appl. No. 09/999,121.
Office Action dated Oct. 6, 2008 for U.S. Appl. No. 09/999,121.
Office Action dated Jul. 7, 2009 for U.S. Appl. No. 09/999,121.
Office Action dated Jan. 5, 2010 for U.S. Appl. No. 09/999,121.
Office Action dated Nov. 8, 2010 for U.S. Appl. No. 09/999,121.
Oren et al. "TAPA-1, the target of an antiproliferative antibody, defines a new family of transmembrane proteins." Mol. Cell. Biol. 10: 4007-4015. 1990.
Pileri et al. "Binding of Hepatitis C Virus to CD81" Science 282: 938-941. 1998.
Reik et al. "Imprinting in clusters: lessons from Beckwith-Wiedemann syndrome." Trends in Genetics 13: 330-334. 1997.
Segade et al. "Differential Regulation of the Murine Ribosomal Protein L26 Gene in Macrophage Activation." Life Sciences 58: 277-285. 1996.
Sequence: EMBL Database 'Online' 1997 "Human chromosome II pac pdJI075f20" see nucleotides 17080-34380.
Sequence: GenBank Accession No. 003693 (version 003693.1) Human Chromosome 11 p15.5 PAC clone pDJ915f1 containing KvLQT1 gene, complete sequence, PRI Sep. 30, 1995.
Sequence: GenBank Accession No. AC026645 submitted by Waterston, R. H. et al. Mar. 22, 2000 bases 2312-4001.
Sequence: GenBank Accession No. BE295955 (version BE295955.1) 60117424SF1 NIH_MGC_17 *Homo sapiens* cDNA clone Image: 3529954 5-, mRNA sequence, Entry Created: Jul. 5, 2000 (Entry Updated: Jul. 20, 2000).
Sequence: GenBank Accession No. BE560890 (version BE560890.1) 601346329F1 NIH_MGC_5 *Homo sapiens* cDNA clone Image: 3679567 5-, mRNA sequence, Entry Created: Aug. 10, 2000 (Entry Updated: Aug. 15, 2000).
Sequence Alignments from Office Action dated Sep. 8, 2005 for U.S. Appl. No. 09/999,121.
Sequence Alignments from Office Action dated Jul. 27, 2007 for U.S. Appl. No. 09/999,121.
Sequence Alignments from Office Action dated Jul. 7, 2009 for U.S. Appl. No. 09/999,121.

(Continued)

*Primary Examiner* — Terra Cotta Gibbs
(74) *Attorney, Agent, or Firm* — Cheryl H Agris

(57) ABSTRACT

Provided herein are isolated genomic polynucleotide fragments from the p15 arm of chromosome 11 encoding HASH2 and methods of use.

22 Claims, No Drawings

OTHER PUBLICATIONS

Sequence Alignments from Office Action dated Jan. 5, 2010 for U.S. Appl. No. 09/999,121.

Siebert et al. "An improved PCR method for walking in uncloned genomic DNA. Nucleic Acids Res." 23: 1087-1088. 1995.

Virtaneva et al. "Chromosomal localization of three human genes coding for A15, L6, and S5.7 (TAPA1): all members of the transmembrane 4 superfamily of proteins." Immuogenetics 39: 329-334. 1994.

Westerman et al. "The human Achaete-Scute Homolog 2 gene contains two promoters, generating overlapping transcripts and encoding two proteins with different nuclear localization." Placenta 22: 511-518. 2001.

Witherden et al. "CD81 and CD28 costimulate T cells through distinct pathways." J Immunol. 165: 1902-1909. 2000.

Examiner's Interview Summary dated Oct. 6, 2005 for U.S. Appl. No. 09/999,121.

Examiner's Interview Summary dated Mar. 4, 2009 for U.S. Appl. No. 09/999,121.

Examiner's Interview Summary dated May 21, 2010 for U.S. Appl. No. 09/999,121.

Examiner's Interview Summary dated Mar. 31, 2011 for U.S. Appl. No. 09/999,121.

International Preliminary Examination Report from counterpart international application PCT/US01/45381.

Office Action dated May 14, 2012 for U.S. Appl. No. 13/235,404.

Office Action dated May 11, 2012 for U.S. Appl. No. 13/239,327.

Office Action dated May 11, 2012 for U.S. Appl. No. 13/244,463.

Office Action dated May 11, 2012 for U.S. Appl. No. 13/244,465.

Sequence Alignments from Office Action dated May 11, 2012 for U.S. Appl. No. 13/239,327.

Sequence Alignments from Office Action dated May 11, 2012 for U.S. Appl. No. 13/244,463.

Sequence Alignments from Office Action dated May 11, 2012 for U.S. Appl. No. 13/244,465.

* cited by examiner

SEQUENCE LISTING

```
<160> NUMBER OF SEQ ID NOS: 14

<210> SEQ ID NO 1
<211> LENGTH: 193
<212> TYPE: PRT
<213> ORGANISM: Homo sapiens

<400> SEQUENCE: 1

Met Asp Gly Gly Thr Leu Pro Arg Ser Ala Pro Pro Ala Pro Pro Val
1               5                   10                  15

Pro Val Gly Cys Ala Ala Arg Arg Arg Pro Ala Ser Pro Glu Leu Leu
                20                  25                  30

Arg Cys Ser Arg Arg Arg Pro Ala Thr Ala Glu Thr Gly Gly Gly
            35                  40                  45

Ala Ala Ala Val Ala Arg Arg Asn Glu Arg Glu Arg Asn Arg Val Lys
        50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
                100                 105                 110

Arg Asn Ala Leu Ala Gly Gly Leu Arg Pro Gln Ala Val Arg Pro Ser
            115                 120                 125

Ala Pro Arg Gly Pro Pro Gly Thr Thr Pro Val Ala Ala Ser Pro Ser
        130                 135                 140

Arg Ala Ser Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
                180                 185                 190

Tyr

<210> SEQ ID NO 2
<211> LENGTH: 132
<212> TYPE: PRT
<213> ORGANISM: Homo sapiens

<400> SEQUENCE: 2

Met Gly Arg Thr Trp Cys Gly Met Trp Arg Arg Arg Arg Pro Gly Arg
1               5                   10                  15

Arg Ser Ala Val Pro Arg Trp Pro His Leu Ser Ser Gln Ser Gly Val
```

```
                    20                  25                  30
Glu Pro Pro Asp Arg Trp Thr Gly Thr Pro Gly Trp Pro Ser Arg Asp
                35                  40                  45

Gln Glu Ala Pro Gly Ser Met Met Pro Pro Ala Ala Ala Gln Pro Ser
    50                  55                  60

Ala His Gly Ala Leu Val Pro Pro Ala Thr Ala His Glu Pro Val Asp
65                  70                  75                  80

His Pro Ala Leu His Trp Leu Ala Cys Cys Cys Leu Ser Leu Pro
                85                  90                  95

Gly Gln Leu Pro Leu Ala Ile Arg Leu Gly Trp Asp Leu Asp Leu Glu
                100                 105                 110

Ala Gly Pro Ser Ser Gly Lys Leu Cys Pro Arg Ala Arg Arg Trp Gln
            115                 120                 125

Pro Leu Pro Ser
        130

<210> SEQ ID NO 3
<211> LENGTH: 290
<212> TYPE: PRT
<213> ORGANISM: Homo sapiens

<400> SEQUENCE: 3

Met Val Thr Leu Thr Tyr Phe Gly Ala His Phe Ala Val Ile Arg Arg
1               5                   10                  15

Ala Ser Leu Glu Lys Asn Pro Tyr Gln Ala Val His Gln Trp Ala Phe
                20                  25                  30

Ser Ala Gly Leu Ser Leu Val Gly Leu Leu Thr Leu Gly Ala Val Leu
            35                  40                  45

Ser Ala Ala Ala Thr Val Arg Glu Ala Gln Gly Leu Met Ala Gly Gly
        50                  55                  60

Phe Leu Cys Phe Ser Leu Ala Phe Cys Ala Gln Val Gln Val Phe
65                  70                  75                  80

Trp Arg Leu His Ser Pro Thr Gln Val Glu Asp Ala Met Leu Asp Thr
                85                  90                  95

Tyr Asp Leu Val Tyr Glu Gln Ala Met Lys Gly Thr Ser His Val Arg
                100                 105                 110

Arg Gln Glu Leu Ala Ala Ile Gln Asp Val Phe Leu Cys Cys Gly Lys
            115                 120                 125

Lys Ser Pro Phe Ser Arg Leu Gly Ser Thr Glu Ala Asp Leu Cys Gln
    130                 135                 140

Gly Glu Glu Ala Ala Arg Glu Asp Cys Leu Gln Gly Ile Arg Ser Phe
145                 150                 155                 160

Leu Arg Thr His Gln Gln Val Ala Ser Ser Leu Thr Ser Ile Gly Leu
                165                 170                 175

Ala Leu Thr Val Ser Ala Leu Leu Phe Ser Ser Phe Leu Trp Phe Ala
            180                 185                 190

Ile Arg Cys Gly Cys Ser Leu Asp Arg Lys Gly Lys Tyr Thr Leu Thr
        195                 200                 205

Pro Arg Ala Cys Gly Arg Gln Pro Gln Glu Pro Ser Leu Leu Arg Cys
    210                 215                 220

Ser Gln Gly Gly Pro Thr His Cys Leu His Ser Glu Ala Val Ala Ile
225                 230                 235                 240

Gly Pro Arg Gly Cys Ser Gly Ser Leu Arg Trp Leu Gln Glu Ser Asp
                245                 250                 255

Ala Ala Pro Leu Pro Leu Ser Cys His Leu Ala Ala His Arg Ala Leu
```

```
                    260                 265                 270
Gln Gly Arg Ser Arg Gly Gly Leu Ser Gly Cys Pro Glu Arg Gly Leu
        275                 280                 285
Ser Asp
    290

<210> SEQ ID NO 4
<211> LENGTH: 145
<212> TYPE: PRT
<213> ORGANISM: Homo sapiens

<400> SEQUENCE: 4

Met Lys Phe Asn Pro Phe Val Thr Ser Asp Arg Ser Lys Asn Arg Lys
1               5                   10                  15

Arg His Phe Asn Ala Pro Ser His Val Arg Arg Lys Ile Met Ser Ser
            20                  25                  30

Pro Leu Ser Lys Glu Leu Arg Gln Lys Tyr Asn Val Arg Ser Met Pro
        35                  40                  45

Ile Arg Lys Asp Asp Glu Val Gln Val Val Arg Gly His Tyr Lys Gly
    50                  55                  60

Gln Gln Ile Gly Lys Val Val Gln Val Tyr Arg Lys Lys Tyr Val Ile
65                  70                  75                  80

Tyr Ile Glu Arg Val Gln Arg Glu Lys Ala Asn Gly Thr Thr Val His
                85                  90                  95

Val Gly Ile His Pro Ser Lys Val Val Ile Thr Arg Leu Lys Leu Asp
            100                 105                 110

Lys Asp Arg Lys Lys Ile Leu Glu Arg Lys Ala Lys Ser Arg Gln Val
        115                 120                 125

Gly Lys Glu Lys Gly Lys Tyr Lys Glu Glu Leu Ile Gly Lys Met Gln
    130                 135                 140

Glu
145

<210> SEQ ID NO 5
<211> LENGTH: 236
<212> TYPE: PRT
<213> ORGANISM: Homo sapiens

<400> SEQUENCE: 5

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Asp Ala Asn Asn Ala Lys
    130                 135                 140
```

-continued

```
Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
            165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235
```

<210> SEQ ID NO 6
<211> LENGTH: 329
<212> TYPE: PRT
<213> ORGANISM: Homo sapiens

<400> SEQUENCE: 6

```
Met Ala Glu Ala Gly Thr Gly Glu Pro Ser Pro Ser Val Glu Gly Glu
1               5                   10                  15

His Gly Thr Glu Tyr Asp Thr Leu Pro Ser Asp Thr Val Ser Leu Ser
            20                  25                  30

Asp Ser Asp Ser Asp Leu Ser Leu Pro Gly Gly Ala Glu Val Glu Ala
        35                  40                  45

Leu Ser Pro Met Gly Leu Pro Gly Glu Glu Asp Ser Gly Pro Asp Glu
    50                  55                  60

Pro Pro Ser Pro Pro Ser Gly Phe Leu Pro Ala Thr Val Gln Pro Phe
65                  70                  75                  80

His Leu Arg Gly Met Ser Ser Thr Phe Ser Gln Arg Ser Arg Asp Ile
                85                  90                  95

Phe Asp Cys Leu Glu Gly Ala Ala Arg Arg Gly Pro Ser Ser Val Ala
            100                 105                 110

His Thr Ser Met Ser Asp Asn Gly Gly Phe Lys Arg Pro Leu Ala Pro
        115                 120                 125

Ser Gly Arg Ser Pro Val Glu Gly Leu Gly Arg Ala His Arg Ser Pro
    130                 135                 140

Ala Ser Pro Arg Val Pro Pro Val Pro Asp Tyr Val Ala His Pro Glu
145                 150                 155                 160

Arg Trp Thr Lys Tyr Ser Leu Glu Asp Val Thr Glu Val Ser Glu Gln
                165                 170                 175

Ser Asn Gln Ala Thr Ala Leu Ala Phe Leu Gly Ser Gln Ser Leu Ala
            180                 185                 190

Ala Pro Thr Asp Cys Val Ser Ser Phe Asn Gln Asp Pro Ser Ser Cys
        195                 200                 205

Gly Glu Gly Arg Val Ile Phe Thr Lys Pro Val Arg Gly Val Glu Ala
    210                 215                 220

Arg His Glu Arg Lys Arg Val Leu Gly Lys Val Gly Glu Pro Gly Arg
225                 230                 235                 240

Gly Gly Leu Gly Asn Pro Ala Thr Asp Arg Gly Glu Gly Pro Val Glu
                245                 250                 255

Leu Ala His Leu Ala Gly Pro Gly Ser Pro Glu Ala Glu Glu Trp Gly
            260                 265                 270

Ser Pro His Gly Gly Leu Gln Glu Val Glu Ala Leu Ser Gly Ser Val
        275                 280                 285
```

His Ser Gly Ser Val Pro Gly Leu Pro Pro Val Glu Thr Val Gly Phe
    290                 295                 300

His Gly Ser Arg Lys Arg Ser Arg Asp His Phe Arg Asn Lys Ser Ser
305                 310                 315                 320

Ser Pro Glu Asp Pro Gly Ala Glu Val
            325

<210> SEQ ID NO 7
<211> LENGTH: 17290
<212> TYPE: DNA
<213> ORGANISM: Homo sapiens

<400> SEQUENCE: 7

```
gcccctgcct ggatcacaac aggcaggacg gctgagcagg cacacatctg tctctccctc    60
tgctgatctg tggccttgga caggggctac tctgggggag ctgacaggtg accccccag    120
gaggcccctc cctgcctctg gctgggaat ccacctctgt ggagccctg gaatggcct     180
gtttcaaata cgtaagtggg agcaaggtct catcctcagc gggggacatc gctgggggca   240
aggccagtgg gtgggtggga aggtttctgt ggcactgggg cctcctgttg attgattcac   300
ccaattaatc acagccagca gctggggagg gggtaggaag gcggtgaagg gaaaaggagc   360
ccacagccgg gaggccctgg gaggttggca gaggcctgca cctgcctgca gccagccctc   420
cggcccagcc ctcttccctc ctttcggagg ggccagagca tggggtgcta agggctcagt   480
cttttaacccc tccccagctc tcagggagcc cctcccatgc tccccaggcc tctgccccac   540
ttgcacctcc ccgggcccca gggcacagga cgctttcccc acccttggg aggctgaggg    600
tgtcaggagg cctgggctga gtgctggctt ccgtctcact ggcttgcaga caagaccctc   660
catttcggtg gaaaaacagc aagaacagca ccccctcca ggcagaccca agggaggcat    720
cggtgtgagg gcttcaagct ctgtactgtg ggtttaagcc ttgcacctct ggatacctgt   780
gggcctcggg cagatcactg agcctccctg catctggaag tcggggtgag acccctcaga   840
gggggctggg aggaggaagg gcccctcttg atgggcagcc cccacccctc cacctactgcc   900
ctgccctccc agccttcagg gtcctcccca gcttctgtgg gctcccaggt ggacctgggc   960
caccccctgag accccgaaga gctcaaggcc agctaatagc ccacaggctc aggacagcac   1020
tggacaggcc tctgggccca cctggcccca ctcccgattt tatgggaac aaagactgaa    1080
ggtgtggccc caaaggaacc acccctcccc cagtgccccg ctgctgggaa agggtcagc    1140
agagtttggg tctcccccca caagccctct gggctgtgcg tgctacagct gaggacatgg   1200
cgttgagggg caggccgcct ccaaccccgt ccaccttgcc ctgtctagct ctgtccaagg   1260
ctctctccgg ctggctaatc acctctgggc acagctgtgc tgctgaggtc tctgggatga   1320
ctgaaggtct ttgaaggcca cttgggaga agcgaaggtg catggacacc agggaccctg    1380
ctcacagcga gtgtccctgc ccatcccctt tctgcattga gtgggacaag cttgcttcca   1440
tttggggggat cgccatctga ctattccact tgtcttaggg tggggcagag attaggtgat   1500
gtggaggggc ttctctacat ggccccctg ccccagctct gagggggtagc accagagtgg    1560
gtttcaccag cgtagggcac gtaggccccg ccatgaacag ggccccaacc ttggtttaat   1620
gctttgctac tgccatctta agttctttt tttattttt atttttgctt attttttatt     1680
agagatgggg tctcccagtg ttgcccaggc tggtcttgaa ctcctggctc aagcaatcct   1740
ccggcctcag cctcccaaag cactgggatg acacgtgtga gccacttgc ctggccttttg    1800
gaatctgact acttttatct tctaacttgt tttgcaggtg caggccaacg gcatacagca   1860
```

```
gcactcacat aagcaaagga gagcgtgcac aaggcgccaa atgtatatcc accctcactc   1920 gtcccccac ttgagtagcg catccacgat gcccacagac accaggccac acagaaaagg    1980
tgccagggac ccacagcagt gcaaggcagc gtgtcacacc tacgcatgag caagccgggc   2040
gctgatggcc accgagcagc cacgttttcc attcaaatcc gcacttgcta aggatgcagc   2100
aggaagccag tggtgttcta caaacgtgc aggacccggg aacctgtcat gtcctttctt    2160
acttgtgcga cttctctgtg ttagccgagg tctcttgctg atggatctac ccacagtgcc   2220
ttttgtcttt gaacttgtcc cttccctcct tcctcgccca tcagcgagca ggaggtggag   2280
ggtgctggtg aacaagcct gcgtcaagga gtgaaatcag ctgatttcat ttttgtgcag    2340
tttccactgt tctagtagca aatgaaatag agacgcctgt gccaggacaa aacacacact   2400
gtgtcattcc agtgattccg catagaagtt aaatgctctt atgcttgcat tttaaactgg   2460
catcacataa tataaagatg gataactaca ttcacgctag tcacttaaat tcctaatctt   2520
tcttactcag aatggcatta aatagtgagt ataaaataag aagtataaaa tagtaagtca   2580
agaggttgac tatagaagaa agaaaaatgc tttatatttt agcaccttga acatgacatc   2640
acgatcacct tctccctgga atcagttcct aacttccagg tggggactag gcctggacca   2700
tgagctccta gcagagccct gctgccccca cagcagagcc caggacaggc tggcacctgg   2760
gccaggtgag gctctgtcca ggctcactga tctcaaatgc tgaactgcta aggatgtcat   2820
gtccccaaag gagccgccag gctcagcctc acttcctgga aggcgtgaac attgcaagaa   2880
tgtggaagtg aaagagtcca gggcttaaat ctcaattctc atcattttca agctgagtcc   2940
aagggagaga agacagtcat ggattcttag ttttctgttt tggttgagcc agcagggtcc   3000
cttcctcatc cctctttct gcttatcact agagacagaa actaaaacca tgactttagg    3060
ctgctgagag cctaaaacaa aacgacagca agagaaggtg ggttggacca gcttgcctgt   3120
gacttcaggc acttcatctt tactgggcac tgggtgaatg acagtgtggg gaggggtctt   3180
cataacacgg caatcagcag cccactgtgc caggagact cgcctgtggt cctggttatc    3240
aaccacagcc ctttccagtc tcaaaaatgt ccccgctggg acagcaagtt acatcgtcgc   3300
tacaagtcct gtcctgggg agatgcagtc cagcagcact acatcctctg agcagcaggt   3360
gccaagtggg atgaactgga taaggactgc attcggggaa acgcccgtgt gaaaggaaat   3420
acacaggaag gaggtggcaa cgggtgggaa gccactagac cacgacgcga ttctgcccca   3480
gtgaaggcga ggggatagcc tgggcctaga tcgctgtgag gtctatggaa gtttccacaa   3540
gcttgctggg tagttctcga ggcaaactcg gaaaggagt cccttgtctc cctggaacgg    3600
atctttcttg gcatctctgt cacactcatt aggtgggcct ggtgtcaacc ccatttgcag   3660 gccacccca acttgatcaa aggtccgctt ctggcacccc ataccctgtc ctacaggaaa    3720
tacagggaca ggctcccaat aacaacaccc agcacggtgc catcaacacc accacgcaca   3780
cgggggctca acggaacaga catctccgct tcttcaatga agacactgga gggaaattgc   3840
ttacaaggcg cttaagagac ctattaagca aacttgatgt gtggacctgc ggcggatccc   3900
gattctataa ggccaactgc acaaaaccac gagacccct gaggactgcg ccattggctg    3960
ggtccccgat gatatgaaag aacggtggtt catttgagcg ggtgatgttt ttgcggtttc   4020
ctttagaggc acacgtgaaa catgacgggg gaaaggattc aaagtctggg atttgcttca   4080
aagcaacgca gggatggcgt gggggatgga tgggcagga agggccttga aactggtgct    4140
ggaggcttcc cagggctgcc ctggagccca gtgcgtcctc caccggccag actgtacaac   4200
ggttggatcc tgtgtccact gctaggaccc aggctccacg agcacgggct tgtgtggcac   4260
```

```
acggatgcac cctaagtcct ggcacagaga ctgctcaaca aaggcctcgg tgcttttgtg      4320
tatgtttgaa attttccata ataaaatgaa aaatgggaaa atgggaaaac aaaaatggca      4380
gcactactta ccctctgcag agttttgtcc gcttcacgcc agtgggtggc agtcgtttcc      4440
tctgccctgg ccttccatcg tttccccct accctcttca cccacccaac agccccctgt       4500
ggtcctggca gctgtgggcc tttccttgag gtcaaggtgt ggagtcctgg ggagggctca      4560
gggaggccac cgacccgggt gtggattctg ggagaagcct gtgggatgtc cctccctggg      4620
tgaccacggc aatgtgcccc ctcctgtccc ttggccaagg ccagttccct gagccctgca      4680
gccccaagcc acagctggtc cactgacccc agttgagcct ggtcctcatc agaccagctg      4740 accccttttga cccccgctac agactcggct ttgaccttgg ctgctgagga gcccccacct     4800
ggactgaggc tgcagctggc gagagaggag ccctgagctc ctctgataag aagggacctg      4860
gccagcctga cgtttgagac ccaggcatcc cggtagcctg ggtgtcctgt tgccgtggtt      4920
attcaggagc cacccactct gggacaacac cagctgctcc cacctcgcag ggctcccacg      4980
gctctgtccc aaccactcct ttctgaagga aggggtgcct ctgcgcccta agaaaccgg       5040 gggagcccca caaccctcc cccaccagga cactaaaagg cagctttcgg tacagtgaga      5100
catcaaagcc tcctaggccc tgagtcaaag gtatagccgt gtaatatccc agtgccagct      5160
ctccggctgc ggggagcctg cgcaaagct tccaagcctt ccttgttcct ttcaagagcc       5220
gctcttagaa ttcaggtgag cggagacctg cagggcctcc ccagtgcggg caaaacccaa      5280
agctagcgag agggcagcct ccaggcacct ctcactaact cctcccagag gccgttgagg      5340
tgggtctggt caaacccatt tgcaagttaa cccacttgcc ctgggctgcc cagctgccac      5400
gttagtggag atctgagcgt ggtggcctgc gcaggagccc atgccctcag ccccacagcc      5460
ggtgctctct ggtcagacca cctcagccta gccccacacc cagcacttac cccagccctc      5520
gggatgggtc agcagcctcc agcctgcagc ttccaagcca gcgagtagcc ctgtctggac      5580
aacccaccag cccaccacct cctggaggat gcccccagcc tcacaaggtg tcccaatggc      5640
tccgctatca acggcctggc tgcactccag atctcaccca gacccaccct acggaggagg      5700
cagcagggtt tgaggagtag tgaccacgga agtctggccg tcacctggga agtgtaggtg      5760
ataggagcca ctggtaaaca gaactgattt atttataaag ttcacgctcc cttgaagagg      5820
tgtgccccac acaggcttct ccctagcaga gcagcagtgc ccacaaaccc accccagggt      5880
gggctgtcac gggggcctca cgccagggac cccgcccctc agggactgct cgtgtccaga      5940
tcttggccag catggaaaac tccagatagt ggggcaggg gtccaggtca tctttattac       6000
gccccaggtc aagggttctt tgtacaaaaa taggtctccg tttgccagca gtgtccctcc      6060
agcagctcaa gttaatgtgt agaaaatgga ttctctgtgc ccttagaaaa tcctctcccc      6120
tccggaaaaa tctccaagtg ttggtgcccc ccgccccact gcagtcgaga agctgtgggg     6180
aggggcggcg tcgaggaag ccgccagccc ttatggggcc agctccaagc ccgtttccac       6240
cgcggcattg gtcaggctgg gccggacgaa cgaggcggcg tcggcggtgc ggggggtggt      6300
gggtgggtcc ccggctcgct gggggcgag cgcgggccgg tccacctggc gggctccccg       6360
gcgatgagcg cgccggccgc tcgctcggct tccggggctg aggctgcggg gggaaggtgg      6420
ggaaccaaac gcgcgtcaac gcgggcgcgg gcccggggca gacccccgcc gggcggcc      6480 tgcccgcacc tcccccaagc gaactcggca gtttcgtttg ctcggttggt tttggagtct      6540
tgagtccgtg ggtgccgcga ctcggtctga gacacggcgg gggcggggcg ggcgctcgga      6600
gccgcggtga gtcagggctc cgcgcccgcc gactcatttc tgccgccccg gcccgggagc      6660
```

```
gcgatttgca atgcaaagtc accccgcctc cagcacccca atctgcccca ggatccgcca    6720
gcactagaga cctcaacggc ccgacggccg ctcccctccc ctcgtctacc cctccctcgt    6780
cggcggctga ccgcgaggg gaagttttgc aatcccggac aaacaaacgc cggtcttgca     6840
cgggcttgaa aaactttggg ggaaatgaag agtgagcgaa atcgaagcca tcgctcgggc    6900
ctggcgctcg gctccgcggg ctcctggggg cgcgacccgc cgggcctgcc cacccccgtcc   6960
ctccaccccg gcccccggcc ctccctcctc cctgcctccc ggctgttacc tcataggtcg    7020
agggcgctca gtagcccccct aaccagctgg agaagtcgag tagctcgcgc tccgcaggac   7080
tcagcgcgcc ttcgcagccg ctgtcgtccg acgagtaggc ggaacgcggg gagccgggct    7140
ccgagctgcc cccgcggccc ggggacgaag aagcgcggga gggcgaggcg gcgaccgggg   7200
tggtccctgg cggcccgcgg ggcgcagacg ccgcacggc ctgcggcctc agccctcccg     7260
ccagcgcgtt gcgcacggcg tcgtgctcgg ccagcaggcg ctgcagcgcg cggatgtact    7320
ccacggctga gcgcagcgtc tccaccttgc tcagcttctt gctggcgccg ccgtgcggca    7380
cgtgctgccg cagcgcctgg aagcccaagt tcaccagctt cacgcggttg cgctcgcgct    7440
cattgcgccg cgctacggcc gctgcgccgc ctccggtctc tgcggtggcc ggtcgccgcc    7500
gccggctgca gcgcaacagt tccggggacg cgggtctccg ccgggcagcg cagccgacag    7560
ggacgggggg cgcaggggc gcggacctgg gcagtgtgcc ccgtccatc gcgcctgcat      7620
ccacccgccc gctccaggtc ccggcgcgcc gcaggaaggt gcaggcagag gaaccggagg    7680
cgacggggaa aactgtggcg ccccaagggg gcttctggca cggcgccgcc aggcaactcc    7740
ccagggcacg cgtcctaggt cgtctggagc ccggggatag gaggcctagt ggtggcaggc    7800
cgtacgcgcc agggagcgtg ggacgctcgt gtcccgcgcg tgcggccgga ctctcccagg    7860
tctccgcagg cgcggcgcag gcggctggtt tttaaatgta tagataaccc tcctccgcgc    7920
cgccgccgtc gcctttctca cgccctcctt ccttcgcctc gccctcccgc cacgcttcgc    7980
cctcccccctc gcgcgatcac attctgtaag gcccaaagcg tgcgcatgtc ccctagccc    8040
atccccccgga cgcagtccac agatcccag tgcgcccaac tggcgaaatc tgcgagttcc    8100
cggtgcgccc cctgctcccg gcaggtgctt agtgcgcccc caaagcaagg tacgcaggtc    8160
ctgggttgag ccttcccgta ccccccaccct aaccccgcgc gcagcccgc cagtcccaag    8220
agccgccaga ccttcgcacg cgcagcgcgc gctgtgggag ggaaggcgcg gccctggcga    8280
caacacggct gttcgggagg cgcgcaagat ccccgggggc agcacgcgcc gcgcagccca    8340
cacccacgcc ccaccctcct ggggccgagg aggcggggc cagggtctca gccaatcgtg     8400
ggccacccgt ttggccaatc gcgcagggcg cggctccacg cccggcccca ttgaggaagc    8460
gcgtacgcgt ggcgcgtggc tcacgggag catcgctaac aaagctgggt tcctgctggg    8520
ccccgccctg ctcctcgccc ccgcgactgg gctgggcgcg ctgtcccta gcgcagctat    8580
gtcccgagcg cgccccacc tgtgcgttaa tctactggga atggggtgg actgcgcctt      8640
acctggggcg gggtggggct taaggagtgg tcgagactga ggcggggtgg gaggttcagg    8700
ttccggggc gccttcccca acccgcccg ctttccccgt ccctccacgc gcaccctgcc      8760
tgtggtttcc gtgcgccccc ggcctgaggg ctctgggcgg caccttaacc cggagggcct    8820
ggaggtctgc acccgaccgc cttgtgccag gacggtcagg tccacgccct ccccccaccgt   8880
ggctccctcc atctgcagta tcccccacct ccagcccgtc ctgccctcct gttctccgtc    8940
tcgcttcccg tcggtgcctc cgggatctca cagcccctcgc acctcttttg tgacccaggc   9000
tgtttttctg caccccccctc tccctgagg gcactgagat tgggcattg gcctgaaggt     9060
```

```
ctctgggagc agcacccttc caggggaggt gggacgtcga gaacttctcc ctaagagatg   9120
cggggaaatg gtggggcctg agagtgcaaa cactgcagaa atgcgaaaaa tgtagtgtta   9180
acggaagagt ttaggtcctg cctcactgtc cgggaaacgc gtgccctcgg gggagccttt   9240
gccaagccgg ttttttcccga aggtgaccag atgctcctgg gccactgcct ctgagacctc   9300
agggaacgga gattttgtg gacccagctg cctggagctg ctttcctgtt ccggccggag   9360
gaggtgaggc ccaagacccc tcctgggagc cggggggcag atagccagtg tttactgcca   9420 gcctcgggt gcccacctgc tcccattacc ctgcaggatg ctgctggctg cccacctgg   9480 gccccccagca cacctgtgtc tcgagtacgc ctggccctcc tgccttggga ggggccggaa   9540
gagtagcacc tgcctgggag ctggtggtct gcggtctcta tttggcagat gaggaagccg   9600
acttggagag aaccctggat gtgtccacag tcactcctcc gcccagtgga gcgatccagg   9660
cagaaatcgg ggccctgagt ctgaatccgg gttctgcaac cagggcagat gcgggcttgc   9720
ctctgctccc tgtccctggt ctgagagccc attcttccca gatggtcact tggcaaatca   9780
cagcctggca tggattgttc tgccctcctt ctgctgcctc cctccttccc cttgtcaagg   9840
ctgcaagacc aggatctagg aacgatcctg gagccctgca aactaggcct tggaaatccc   9900 tgctggatt ccacctcccg ggctgggagc ccctcggtca tctgttgctg tgtaaggagc   9960
caccaggatt ttagcggtct gaacaacgat gtattatttc tcaggattct gtgacttgat  10020
gggtgggccc tctgctgctc tgggtgtggc tgcatacacc ccgggggtca acagggacga  10080
gcggtacagc ggctgggttg ctctctaccc ggtcttcgtc caagcccctc cacagctggt  10140
aagatctccg gagcaggacc tgcaagccct cttcagatca cccagaact tcctgtctaa  10200 aaactgaagc ctctcactgc ccaggcatgg cttcttgcta ccctgccctc aggcacagtc  10260
ctgcacccac ctgcgtctgc tgtgccatgt ccaggccagt ccccccccac caccaacacc  10320
tctctctatc ttcatcctct tcccaatctg gtcctccac cgctgtggaa accccgtctg  10380
cccccaaagc ctagcttaaa aataattccc tagggacctg tgtctctccc tgcctcggcc  10440
cctccttcat tcctgggtgc ctccggctgt gcagcatttg acactgcagc accccccctta  10500 attcggaagc atgctgtctc ctggactggt gagtctccac actatctgag ccgtcttctc  10560
tggaactctt ggcctctcag tccgttctga aatacagcc ttggtaagca cggtgcccac  10620
atgaatgttt ccagcagcag gattcaaaat agccacatgt ccatcaacag atgagtggat  10680
aaacaaaaca tggtccagaa taatggaaga ttactcagcc ctaaaaagag acgaagctgg  10740
tgaacctcga gaacacgagg ccgcgtgaac gaagccagac accgaggacc acgtagcgtg  10800
agactctcag tctatgaaat gtgcggagtc gataaattca cagagacaga aaggagattc  10860
acggttgcca ggggctgggg agtgacaaca gagggatggg ggtgactgtg aaagggtacg  10920
tggtttcttt cccagaggat aagaacgttc taacatggcc tgtcctgttg gcttcacagc  10980
tctgtacaac acacaaaaaa accattgaaa tgtacacttt gtggaatgtg aactgtatct  11040
tgataaagca gttagaagac cttcgaacat aagcatgcgg cctcatgggg cctttgcctg  11100
ggcaccctgg cacctctccc aggctctacc tatctccgac ttcattcctg agctcttgaa  11160
caggggtaag gcaaactttt tctgcaaagg aacacgtggt aagtattttc ggccttgacg  11220
gtcacatgtc tctgccacga gtcgtctgcc ttggggcgca aatgcaggct tgggcaggga  11280
agaaataaca aaacttgctt cctggtcact gaaacatgaa gtccaggtca cactcactgt  11340
tacaaaatac tccgaatttt cagactgtgg ttcaatacac atgacataaa atggaccttc  11400
ttaaccattt gtaagtgcac ggttccgtgg aattcagtat attcatgtgg ctgtgcaatc  11460
```

```
atcaccacca tccatctcca aaagtttctc attttcccaa accgaaagtc tgtccccatt    11520
aaacagcagc ttcccatgac ccttccccca gcccctggca cccaccatcc actctgtgtc    11580
tgtagatttg actgctctgg agacctcctg taagtggaat cctacagcat ctgtcttttt    11640
gtggaccggc ttcttacact gatgctgatg ccctcgagct tcatccatgt cgtagcctgc    11700
ataaggattt cctctctttt tatgggtgaa taatattcca ctgtatgggt agaccacggt    11760
gttgatccgt tcctccgtca gtggatgctg ggtggtttc cacccttggg ctaccgtcag     11820
tgacgctact gtggacatgg gggtacaaat atctctttga gatcctgctt tcagttcttt    11880
tggggataga cggagaagcg gagttgccag gtcatacggc aaacctctgt ttaaccttttt   11940 gagggaccac catgttgttt tccgcagtgg ctgcccacag tacattcctg ctgcgcacga    12000
ggttctgatg tctccacatc cccgcccaca cttggtgctt tctgggtttg tttcgtttcg    12060
ttttgttttt gtttgttttt gagacggagt ctcgctctgt ctcccaggct ggagtgcagt    12120
ggcgcaatct tggctcactg cgacttctgc ctcccgagtt ccagccattc tctagtttca    12180
gcctcccgag tagctgagac tacagatacg tgccaccatg cccggccaaa ttttttatttt   12240 ttgtagagat agagtctgac tatgttgccc agcctggctg aggtgataat agttttttga    12300
tgatagctaa tgggtatgga ttttaatttt ttaaccactt aagaatttaa agaaaattcc    12360
tagcttttgg gcaatacaaa agcaggccag gggctggatc tggcccatgg gcctcggtct    12420
gctgacagct gctccagagg actggtatgt ccacgtgaca cctggcccga cccccatcct    12480
cctgcagctc ctcaaactca acttgttgca ggttgaactc ggcctccttt cctctaagga    12540
aagatcccct ccgcagcaga gaacaccagg tcggcagtgt gggcactgcc cttcctctcc    12600
cctgccctct gctgtacgtc agcccagccg cttctccagc caggtcccca tcttgccttg    12660
gacactgccc ctgcctctgc cctggtctcc tgggttctca gtttgctgct tctgtctgtg    12720
caccgcctgg aagtgggggg gccttaccca gcatccagcc cagctagatc atgtccgggc    12780
cctcggggtt caggcccagc accctcacgt gccatcactc actgcctcct ctccagctcg    12840
gacgttgtat ctcctggaag ccttccctga tcccagtggc ctcctgaagc ctcctcgccc    12900
ctgtgctcca caggagctg tgctgcccgg gcctgctctg tccaataggc taacctgacc     12960 tgctcccttcg acatctaagg tgctgctcat gtgtattcat gacctgggtg gatgttgggg   13020
agcccaggcc cagcaaagag gggcaggagc aggcagttcc ggggttggcg atggcccagg    13080
ggaagctttc ggcctggttg gtcagagctc ctggtgacca agggtgactt caaagtcaac    13140
gtgagcctca ctcacatgag atgagcctag agcgtccaag aacagctctg tagctggcca    13200
gccgggagct gcagccctcg gtcctgctgt cccccgggg agccggctcc tgctccaggg     13260
atgagcaagc tcaaattga ctttgaagtc tcccacaggc cgtttggaac tggggtgcag     13320
gagctggaag tgtggggcac cctggggagt cacgaagcct gactgattgt caggcagatg    13380
tgtggcggga gttggggaga tgcggtagga cacaggggg atctgggggg tgccagtgtg     13440
ggccgcgggc tgggaggtat catcagtaac ttcagatcgt ttcgtagcga cacttaaaaa    13500
atacctgaag agggacgggt ggaatgaact tcaacatcat acccaaaata ttagcatttc    13560
aacatgtaat cagtataaaa attacttgag agctgtttca cattttcttt tcataccaag    13620 gttttgaaa tccggcgtgc gtcttttac actcacagta cctctcactg tggaccggcc      13680
acgtctcaat gctcagtggc acccagggct ggtggctccc gtcttagaca acacacatct    13740
ggaccgggag agcctcaggt cccctgtgat accagttttc tagtctctgt atctgacagt    13800
gtgacatctt ggggacttgc tgactatgaa gggccacccc tcccaggata aactaattcc    13860
```

-continued

```
tagagacagt gaaggagacc cttttcatgg gcaaacccac caacgcagag cccaacccct   13920
tcctctatca gggtcttacc tttgagggca ctacacctgc ccttgttacc ccaagggaag   13980
gtcccagaca accagcagcc cctaggccct agagttctga acttatgtca gcctggccaa   14040
tcctaaaccc atatccctg ccttgccat tccttctaca gaaaccacaa gaaaggttct     14100
tgcccaggtc tccctgtggc tccccacct tctgaccgac cctgtgcctg tgcccgcccc    14160
gctgcctgtg gcatgccacc cgctttgaga actgtgagct aacaattatc tcttctatgg   14220
caattgactc tcgatctgtt ggcctcacca tacctgaata ataacggaac tacattttag   14280
aaagccagta gaaagccatt gcctcgcatg acagaccagg aagctgggc ccagagaaaa    14340
gccacgtgct caaggctggc cagtgagtga gaggcagaga ctcaggagtg gatcatgggc   14400
ttcccttggt tcagcctcct ttacatccgt ccccttaccc caccgtggag gcttggggct   14460
gagagggaga ttctgtggct gcactccaag gactggccag ttccaggcag gaggcggcac   14520
tcccagctgg ctgaaaaga agaggctgct tctctgtcaa gctcatgtca ttcccccatg    14580
aaactgaaag ctgcccgggt atgagaccat ggagaagaca ggtctcattc tctgggccac   14640
gtttcctaac cacagtacaa taaggctaga agaaaaccc caaagtccca gctctaacat    14700
ggcaaatgca tgaagaaaag aacagtcttc taaacaactc ttaggtttaa gaagaatgaa   14760
aacagtgatc atgggccttt cgaaaatcaa cagccaaaaa actttataac ctcaaacaaa   14820
ttcctccgaa acaagaaact ctgaacaaaa gtgaacaaag cattcaactc taggagatca   14880
ggaaaacaaa acccgaaata tgtgtgaaag aagtaataag ggctaattaa tgatgaggag   14940
gagagaaatt aacaaggcag aaaagtgaac tgttaactaa gttgatataa tgaaaaactg   15000
ctgttttta aaagaccaac aaaataggcg catttaaata agaaagaaga cacattttta    15060
aaataccaga aagggtgaaa ggtgacttaa gtacaaatat gtaaaagatt aaaaacagga   15120
tgttcattta tgaccacgat ggagtaacag ggactgaatt tactgctctc ctcccgcccc   15180
ctccaaaaca acaataacaa caaaaaggat caaattcagg aaacaacagt tttcaataca   15240
ctgcacatac gacaacaaag gacagtagtc ctcaagagat ggcaaacagg tgaacggggc   15300
cctacagctt cccagctgct ccctgagtt tcccaaccat ggcccagaag gaggtacctg    15360
ggcagagccc agtggagtac ttggaggagg agacagagct cagagccaag gaggcccagg   15420
cagctgggtt tcaggacag aggagtggat tggagagagc tgcatagagg gagagcccta    15480
gagagctgca gaaagttcct ccaaggactc agcagagaac tgatcaggga tgtgtgtgaa   15540
gagccagagc ctagggaaga aattgtccgg aaggatcaga gagaagtgcc cagttctcac   15600
tcaggactgg aggagggctg tcctaaccag cccacatggg aaactcatag ttcatgaggc   15660
cgtggacaga gtatacagca ggctcttgcc tcactggcgg ggatcatttg ccctagactg    15720
gacaccgttc caatcccacc tcaccccaaa aaatcaagtg tttctaagta actcaactat   15780
gccccaggca aaactaaaaa ataggaatac aaaaatatct ggcatctaaa aagataaaga   15840
ttacaatgta tgatatttaa taaaaaatgc caagcatgca taaagcagaa aaatatgcca   15900
tctaataagg atatagataa aaagtaaata aatatccaga gctgacaaag gcattaacaa   15960
ggaaagaaca tcaaaacagg tgttatgact gtatttccta tgttgaaagc caagtggaga   16020
catggaagag atgtatatat attacatatg tctcttctat gtctctagtt agggggattc   16080
tatggctgca ctccaaagac tggccaatca ctggccagag gcagcacccc cagcctgctg   16140
gaagaggaga ggctgcccct ctgtcaacct catgtcattc tcccatgcaa ccagaagctg   16200
tccggatatg agatcatgca gaaagtgacc atatactcag gacaggacag gttcatttgg   16260
```

-continued

```
gactatttat ttatttattt agagatgata gctacaatgt ctgagacaaa gaatacactg    16320
agctggaaaa acagtaagga tattatgaaa gaaaaggtta atgaacttga agacattgca    16380
atagataata ttcaaaatta agcatagaga gaaaacagaa ttgtttaaaa gtgaagagag    16440
cagcagtgag ctatggaaaa attcaagtgg tctaatatac atgtaatcaa agtccctgaa    16500
tgaaaggaca gaagagacag aaaaagtatt tggagaaaat aaatgacaga aaattttcca    16560
aagttgatga aaattataac acacagatct gcaaagctca acaaattctg ataaggagga    16620
acttgaagaa aatgacagca tcaagacaca tcttctttgt atatcttcat cttttctgag    16680
atagggtttc actcttgtcg cccaggctgg agtgcaatgg tgcgatctcg gctcaccgca    16740
acctctgcct cctaggttcc agcgattctc ctgccttagc ctcccgagta actgggatta    16800
caggcatgca tcaccatgcc cagctaattt tgtattttta gtagagatgg ggtttctcca    16860
tgttggtcag gctggtctca aattcccgac cttgggtgat cctcccacct tggcctccca    16920
aagtgctggg attacaggaa gacatatctt aatcaaattg cttgaaacca gtagtaaagc    16980
aaaataaaat aaaatgaaat aaaaccttaa aagcaaccag aggaaaaaag atacatttac    17040
atatgtacaa aagaatgact tatatacaga ggaatagaaa taaggatgaa acaatatttg    17100
tacacctgtg ctcatagcag cactatttac aatagccaaa aagtgaaagc aaccgactat    17160
ccattgatga tgaatgaata aacaaaatgt ggtccatcca tgcagtggaa tattatccag    17220
ccttaaaaag caagggaatt ctgatacatg tcacaacata gatgaacctg gaggacatta    17280
tgctgagtag                                                           17290
```

<210> SEQ ID NO 8
<211> LENGTH: 25970
<212> TYPE: DNA
<213> ORGANISM: Homo sapiens

<400> SEQUENCE: 8

```
aataagccag acacaaatat tgtatggttc cgcttacatg aggtagcatc attaaatcca      60
taaaggcaga cagtaaaatg gtggttgcca aggcctagga gttagtgatt aatgggatcg     120
agatacagtt tggaaagatg aaaaagttct ggagatggat ggtgataatg gctgcacaac     180
aatatgaatg tacttaatac cattgagtta tatacctaaa aatgattaag gtagtaaatt     240
tgtatgtcat gtatatttta ccacaattaa aaaattagac aaaatacaaa aataaaaaag     300
gatgatacaa atttctcact ggaaacaatg caaggagaag acaatggagc aacatcttta     360
aagaactaaa aaaatactgt caacctagaa ttctataccc agtgaaaata tctttcaaaa     420
gtacagatga aatcgtttgt tcagacattc aaaagctgaa agaattcatc accagcagac     480
ctgcactaca aaaatattaa aggaagtctt tcaggaagaa ggaaaattat atgagataga     540
attatagaat tagcaaacgg atgaagagca ccagaaatgg taactatatg gataaataca     600
tataaatttt tgttgctatt taaatatttt taaaaaatag gtgactactt aaacaaaaac     660
agtaactgat agggagttga taccatatgt aaaaatagat catatggcaa taccacaaag     720
gcaaggaggg gagaaatgga ggtatactat cataaaattc tcatactgta tgtgaagttg     780
tatcatttca ctttaaggtt gactgtgata agttgaagat gtaagctata taccctacag     840
gaagcactaa atttaaaaaa aagaattaca gtaaataaat taattaaaaa ttaatggaat     900
cattaacaaa ttattcaatt aattcttacc accaaaaaaa aaaaaaaaag aaacagaaaa     960
agagacgaaa tgggacaaag acagatgaaa cgaatagaaa tgcaggtttt atatactcag    1020
gcctaaccat aacaataaac acattaaatg tcaatggtct aaatacccag ttaaaacctc    1080
```

```
atagtcaggt tggataacaa agtaatacct aactgtctgc tgccttcaag aaacatgctt    1140
caaatataaa tatataaata tgtttaatgt aagatggtgc tatggtaagt ggcttttaag    1200
gaggcccgaa gcatcttagt attcacatcc atggctggga ctaggggag gcaagtaagc     1260 cacttgcctc ggtcatgaaa ttcaaagaag gaccacaaaa ttcagtaatc aagacaaata    1320
atatttcaat gcaatatttt taaaaataca aattaatgca aaaatatatg aagaccaaat    1380
tttcagaatt ttaaataaag acaggatgag taacagtacc atactatgct gagcctctgt    1440
tggagcctga agcaaaaggg aaaattcagc cttctgagaa gccctgattc ggaggcacca    1500
agataaactg tgcttagttt cctggcccac aggaatctgt gagataagta tctgttgttt    1560
taagctacta agttttgggg tatttgttag acagcagtag atagtatgaa gttcaggatt    1620
ctatgtcaaa accaatcaaa agaaagcaga agtggccatt taatagatt tcaggataaa     1680 gaatattacc aggcattaag aaggtcactt cagaacaatt aaggggccat tcatgagggc    1740 atgcaatcc caaatgttaa cgaataaagc aaaagcatca tgatagacct acaaggagaa     1800
atagattaac ccacaattac agtcagagtc ttcaacactc ctttctagat acttgataga    1860
ataaatagac agaacatcat aaaaaatata gaaaaggtaa acaacactat caacttgctt    1920
gacctaattg acattaatgg aaaatcccac ctgttaacag caaaatacac attcttttaa    1980
agtgcacgtg aagtatttac caaggtaaat tgtcttatgg gcaatagaac aagtcttgga    2040
aaatgtaaaa gaggattcaa gtcatacaaa gtatattctc tgaccataat gaagttaaat    2100
tctgctaata acagagatat atgaaaaatg cccaaatatt tggaaataaa taaaatagat    2160
ctaaataacc catggtttaa caaataaatc aaaagagaaa ttagaaacta ttttaaacca    2220
agtaaaaatg aaaacacagc atttcaaaat ttatgcaatg cagtacttgg aggggattt     2280 agacagctaa acacatatat tagaatagaa taaaagcctg aaatcaatga caccagctcc    2340
ttagaaacta ggaacacaaa cccaatgtaa gtgcaaggag tacaaaataa gaatcagagt    2400
agaatcagtg aaacagaaaa aaatagagct atcagtgaaa cacaaagctg gttcattgag    2460
aaggtcagta atatcaataa aagccagaat ggtcaggagg aaaaggaaaa agatgctatt    2520
tgccaatatc atgaatgagt gagaggtcat cattacagat cctacaggta ttaaaagtat    2580
aataaaagaa tattaggaac aactttatac caataaattc accgacttag atgaaataga    2640
caaaatcttt gtgagacaca aactaatagc acttacttaa gaagaattga ataaccagaa    2700
tagcaccata tttattcagt aaattaaatg tgtaggtaaa atccttcctt caaagaaaac    2760
cccaggccta tgtgatatca ctagtgaatt ctatcaaata tttaaggaag agataaaacc    2820
aattctacat aaaataaatcc agaagaattg aaaaagatgg aatacttta aattcattct     2880 ataagaacag cattaccctg ataccaaagc cagacaatca caacacaagg gaagaactac    2940
aggctgatat tcctcatgaa cgtagatgca agaattctaa aaaaaagttt agcaaattga    3000
acccaaccat atacaagtgg ggcctattca aggaatcaag gtgcgtttaa cattcaaaag    3060
atcaactcaa cgaattgacc atattaaatt taaaagaag gaccatataa taatgtcaat     3120
agcacagaaa aagcatttga caaaatccag tggccattca tgattttaa aatctcagcg     3180 aactaggaat agaaagaagg acaatttctc agcctgtaaa gggtatcaaa cttaatggta    3240
caagactggt tactttcctg ctaaaacaca tagacaagac aaaggtgtcc tcataatttc    3300
tatttagcaa tgtcctagag gttttagtca gtggaacaaa gcaagaaaaa ggaacaaaag    3360
ccttccagtt tggaaggagt aaaactatcc tcattcacag aaaatgatca gctgtgaaga    3420
aaatctgacc aaatctgcaa aaacactaca ttaattaaag tgagtttagc aaggttgcag    3480
```

```
gatacaagat caatctagat aatcaattgt atttccatat agtagcaaag aacaattgga    3540
aattgaagta aaaaatgcca tttgcaaaaa catcaaatat taaatactca gctataaata    3600
tggcaaaaga tttgcaaacc tgtacactga aaactgaaaa acattgatga gggacattaa    3660
agaagactta tctaagtgga gagatatgct gtgttaatgg attggaaaat tcagtattaa    3720
gatgtcaatt ttcctcacgt taatctatga attcaacaca attcaaataa aaaaaatatc    3780
agaaggcttc tttgtagaaa ctggcaaaat ggttttaaaa tctgtaaatt cttaatttcc    3840
catacgaatg tattttcgtt cttcaactga cattttatct gtaaaaatct gagaagtgtc    3900
aggttggcat ggagcatatc ataattttc acattaaaaa tattggaaat attttgttt     3960 aattgctttt tctttcacag aagggcagtt atgaatgaat gtatatctct atataataca    4020
tatacatata tataatacat atatagtata cataatatat atataaatatg tattgcatgc   4080 atatattcag agacagaatc tcactgtgtt gcccaggctg gagtgcagtg gtgcgatcat    4140
agctcactgc ggcctcaaac tcctgacttc aagatatttt cttgcctcgg cctcccaaag    4200
cactgtgatc acaggcatgt gagccactgc acccagccta aatggatgtt tgtaagtgtg    4260
gaatatgtgc atacaggagt ctgcctccaa actctctacc cctctgtctt tggtctaact    4320
ttcctcttat gccaatccca tgggattttc ctattaggct tcactgtatg tcttcatatc    4380
agacagagca aattcctctc tttttgttct tttcaatcaa agttgacatg taacaggcat    4440
atgccagaca tcactgtgga aacgctatac tcaactgagg actttggtag atttacggag    4500
agtacgcaga cagacatttc gtgtgggaat gccttaatat tacaaagctg tcaaaccccc    4560
ctacatgaac gtaaggatcc agtgcaatcc cagtccacat ctcagctggg gtgtggcaaa    4620
cgctccacga ccttactcca acactaagat cgaagtgtag aagtccgtga gtagctcagt    4680
cagctttgag tgtttgcaaa gtgagtgttt cagtggcaaa tattcctaat attctctgag    4740
gcttggtgtg cctaagggta ttttcatctc gctgctgcat ttaaacaata atcatacccg    4800
taaaatcctg tgttcaaagt taccttccac gcctttgaaa tattattctt ttgtcttctc    4860
acatccggta tcgctcttga gaagaatgat gcgattcttt cttgctcttt ttaggcaatt    4920
ctgccgattc tctatgggcc aattcaggac tttgatattt taaaacttca ccgtaacgca    4980
tctatgttct ttcttatctg tcctcgccgg cctgtcaaga gcccttgcgt gtgtttctgt    5040
aattctgggg tatttatttt cattatttct ttaaatacct cctctcttcc tctgctttct    5100
gagactcttc ctagccaatc cactactttc tccttttctc ctcaaacgtc tctgcttccc    5160
ttttaagttt ttttctcatt attgctcctg aaccttctag aacaattcca ccacacttga    5220
tattttatct cacttgtttc ctagcagcac ccatgctgtg atgtacccca ttcactgttg    5280
aactggcatc ttcctcacac tcagtatttt cccccagctc cttgtatatg cctcttcatc    5340
ccatttcaca ctgtgccagc accatccctt atgttttga gggtttttt ctttcaagtc     5400 tggagtgcag tggcacaatc ttggatcact cagcctcaat ctcctgggct caagcaatcc    5460
tcctgcctca gcctcccaag tagctgggac aacaggcacg aaccgccatg gttggttaat    5520
gtttgtatgt tttgtagaga tgggatcttg ctacgttacc caggctggtc ttgaactcct    5580
cagcccaagc gatgcgctca cctctgcttc ccaaaatgct gggattatgg catgaatcac    5640
tgcacccagc catgttttg agtttctacc aggattgctt tagcctcaca gttcatgttt     5700
ttcagcagtt cttgtctgta tgcaatgtga tgatcagatt gctgccttc cattctcgca     5760 ggtatgccca tgagttcagg ctccacctga agtgacggtg actgcgtcgg cagtgtgtt     5820 gggggaggaa ccagggcctg gccctggctg ggccatccca ggccgtggaa tgtagggacc    5880
```

```
agccccacag ggtcggtggg tctctccccg tgtgcggcga cgagagagtg taaaaataaa    5940
gacacaggac aaagagataa aagaaaagac agctgggccc gggggaccac taccaccaat    6000
gcgcggagac cagtagtggc cccgaatgtc tggctgtgct gatatttatt ggatacaaag    6060
caaaaggggc agggtaaaga gtgtgagtca tctccgatga tagataaggt cacgtgggtc    6120
acatgtccac tggacagggg gcccttccct gcctggcagc cgaggcagag agagagggga    6180
gacagagaga gaaacaactt acaccattat ttctgcatat cagagacttt tagtactttc    6240
actaatttgc tactgctatc tagaaggcag agccaggtgt acaggatgga acatgaagga    6300
ggactaggag cgtgaccgct gaagcacagc atcacaggga gacggttagg cctccggata    6360
actgcgggtg agcctgactc atgtcaggcc ctccacaaga ggtggaggag cagagtcttc    6420
tccaaactcc accagggcaa gggagactcc ctttcccggt ctgctaagta gcggatgttg    6480
ttccttgact cttttgcta ccgctagacc acggtccgcc tggcaacggg cgtcttccca    6540
gacgctggcg tcaccgctag accaaggagc ccttctggtg gccctgtctg ggcataacag    6600
aaggcttgca tgcttgtctt ctggtcactc ctcactatgt cccctcagct cctatctctg    6660
tatggcctgg ttttcctag gttatgatta tacagtgagg attattataa tattggaata    6720
aagagtaatt gctacaaact aatgattaat gatattcata tataatcatg tctatgctcg    6780
agatctagta taactcttgt tgttttatat attttattat actggaacag ctcgtgccct    6840
cggtctcttg cctcggcacc tggatggctt gccgcccacc gtggaagaag aggaaagcgt    6900
tcctcttccc ttcccttccc ctttccttta acacttaaaa catatttatc cctcccctcc    6960
catctcccct cccaactcat aaatatagta ggattccaac taataaacat agaaggcatt    7020
tggcaaccag cacagcaatt atttaggcac aaatcctcaa ctgatgctaa acgagtgag    7080
taaaagtcta agaagcaaca ggaagttaca cggcatcacg tttctcccca caaactggaa    7140
attacaaagc acagaacatc aacgtgacat tggagaaacc tgccagctac aattttaacc    7200
gtgttccaag ttaacactgc cgggtccttc ttcctctttg ggccgtgata gagcagttag    7260
gaccacacgt ggccttcact gcacacaacc agcaaccagg atgcagtcac acagtttgtg    7320
aggcaagttc tcaaacgctg gacagcgcgc cgtgggtggt ctgtgaagga cgtgaaacca    7380
gccgggggag cctggtgatc ttccagccga ccgagagtct ctgggctggg ccctgggtct    7440
cactgaggtg aggagacaga ggtcagagct cagcgaggat gaggcaacta gaattttcag    7500
ggtagatctt tgaagaggag gtggggaaa gagagaaaga cagaggagag agacagaggc    7560
agagatacgc agagagggag agagagagag cgggagaggg agagagggg aagagaggga    7620
ggaagagatg aagaagggg gagaaacagg gatacagaca gggagagaga taactaggca    7680
gagagagtta gaaaggggag aagagagaga tagaaaga cagagagaga gagagaaga    7740
gatacagaga gagagagaga gaaaaaaaaa aactccaggg atctgcagag accctcaggt    7800
ccttggctga atatggatcc acacatgcat gaagataaac cacctgaggc cagagaaaaa    7860
acccccgtag ctcaggtcac acggtctgga gacagtttgt gttcccacaa aactatataa    7920
tacacaggat gtcgggaagg gtcctcataa gagcctctct tgagtgctga ttctaaacca    7980
accctagact aaaggcagcc ctggattcac cctacaaagc atagaagcaa agctccaaag    8040
atccgatggg tatcaggaac tcatggatgc cagaacaaaa tccgacagca attaaaggaa    8100
tacaacaaaa tctagcaacg gactgtgcaa tatttgcaaa aaaaaaaaa aaggccaggc    8160
atgcagagga acagggaaac gtgacccaga accaggagaa aagccagtca gtggaggcag    8220
gtgcagaaag gccagaggtg ctactgtgac cagacaagga ttgaaacagc tgttttagag    8280
```

-continued

| | |
|---|---|
| gggccctacg tgtaagaagg tccagtaata gaaagagggt gataaagcaa tggtggtagg | 8340 |
| gtgctcacag ttggagaata ggcggaggta caggaatcct ttgtactatt aatgaagctt | 8400 |
| ttctgcacat tggaaatgat acaaaacaaa aagttaaaaa atgaaagaga ggtggggtga | 8460 |
| gcctagagca tggagcccca ggacccatag aatttgttg attcctctta gtgttcctgc | 8520 |
| tagccaggca ccttgtgtga aatttgccat taactctctg gaaaaaatcc gctttgggag | 8580 |
| gaggccactg cccgtgtggc cacctccagc cttgagacca gagcagaagg atacaggagc | 8640 |
| aactgcttgg agacggctgg cagatctgca cgtgtttcta tccatcccac ttcccctctg | 8700 |
| taaggttcta actctgccct gctgttctcc ctgctgtcca ggccattgct gctgatttct | 8760 |
| gcagtgacgg ggccagcaac aactgtctca aggcagcttg ggaaaagaca agcctgcctc | 8820 |
| caactgttgc tcttgtcact gcttctagct gtctcctccc caggttgcag ttcccaacac | 8880 |
| cacacacacg tgtgcacaca catgcatgca tgcacacaca tgcacatata gcacagcatt | 8940 |
| catgcataca catgtaccca cacacgcaca cacttgcaca cacatgcaca atgcatacac | 9000 |
| atgcacatac atgtgcacat gcacaccagc tcaccacagc ctgtagtctt ttttttttga | 9060 |
| gacggagtct cactctctcg cccaggctgg agtgcagtgg tgcaatcttg gctcactgca | 9120 |
| agctccgcct cccaggtttc caccattctc ctgcctcagc ctcccgagta gctgggacta | 9180 |
| caggcacgcg ccaccacgcc cggctaattt tttgtatttt tagtagagac ggggtttcac | 9240 |
| cgtgttaacc aggatggtct cgatctcctg acctaatgat ctgcccacct tggcctccca | 9300 |
| aagtgctggg actacaggcg tgagccaccg cgccctgccg cctctagtat tcttagagat | 9360 |
| gtgccacatt gttgatttt cctcaaggct gtttctccct ctagatgctg gagcttctcc | 9420 |
| agcattgatt ttggggacgg aagcctgggc gaggtacaca ttccggcagc cagtgccagc | 9480 |
| tcttagaagg tcacactgcc tattgtgtgg acagattaga tggggtgggg gtgggacttg | 9540 |
| tgagtccagc aaggggcta ttgtaggcag agctgcaaga ggcaccagca ggctgcatgg | 9600 |
| gctccaggag agaggtgcga cctgagagcc attctggaca ctgggctcag tgaaagaagc | 9660 |
| cggtcagaaa aggacaaatc ctgtgtgatt ccctgggtag aaggtcccta gggtggtcaa | 9720 |
| atccatagag acagaaagtg gatggtgggt gccaggcct aggagagggg atggggaacg | 9780 |
| agtgttaat ggggatagag tttcagttg gaagatgag aaagttctgg agatgaaggg | 9840 |
| tggtgacagc tgcacaacag cacgaatgtg tctaatgacg ctgaagtgta gtttaaaatg | 9900 |
| gttaagatgg tcagttttgt attatgtcga ttttaccaca ctgttttaa aaagaagcat | 9960 |
| cctggagaaa gcgtcagtac tgctcatggg ggtggggtga ggagtcagct ccagtggctg | 10020 |
| ctgggctctc gtccgagagg agaagggagg ctggccctcg ggggaagggc tgcagggatc | 10080 |
| cagggttcct gggtggatgt gcggagtctg gggtacctgg gaactatccc cacagaaatg | 10140 |
| ggaggccacc actgaaattc caatgagggg ctcgaagtta aaacttaaca catgaaagat | 10200 |
| aagtggggtg acagcgtgga gccccaggac ctgttgattc ctcttaccgt tgctgagggg | 10260 |
| ctaatggaag gggctgggct ggagggtccc ctgcagtcag tggcaactca gcccctgggc | 10320 |
| actgagggac catgcaagaa gcgggagaga gaacagaaaa ggcaggaaga gccctttcc | 10380 |
| tccactgagg gagtaggcag agtcagggag tggctgagaa agggcaacac agtcagcaac | 10440 |
| gggaaatgca aggaagacat gaggacccgg tcccccatg cctggagggc tggagtgagg | 10500 |
| acagaggggg cctgctggac ccaggagcgt ggagctcact ggtgactcct gagagtcagg | 10560 |
| ggactcccag gaatgcgtg gaatccagga tgccacttcc tcctgcctgg cagcagggca | 10620 |
| ggcagctggc tggggcccag actcccagga ggatgccact gctgcccaga cctactgcag | 10680 |

```
tgcacagcag agcggcaagg gccccctggtg cgttgagcaa acttccaggc ttaaaaagag   10740
cgtggctgcc tcatccctcc accacccaga gctggctcag gccacgtgtg acccacccta   10800
cccttaacaa ggcagctccg ggagtcctgg aagatgaaca tcccgctcag ctagggcgac   10860
actgtgccaa tccctcccat gggcttccac ctgtacctct tgttttctac acagctttat   10920
tgaaatataa ttcacatact ataaaattca ctgttttaac tgtaccattc aggggctttt   10980
agtatattca cagaagcatg cctccctcag caccccaaa aacaactccc cgctttagta    11040
tattcgcaga ggcgtgccac ccgcagcacc cccaaaaaca actccccact ttattcgcag   11100
aggcgtgcct cccgcagcac ccccaaaaac aactccccgc tttagtatat cgcagaggt    11160 gtgcctcccg cagcaccccc aaaaacaact cccgcttta gtatattcgc agaggtgtgc    11220
ctcccgcagc accccaaaa acaattcccc gctttattca cagaggcatg ccacccgcag    11280 caccccaaa aacaactccc cgctttagta tattcagagg cgtgccaccc gcagcacccc    11340
caaaaacaac tccctgcttc agtatattca cagaggcgtg cctcccgcag caccccaaa   11400 aacaactccc tgctttagta tattcagagg cgtgcctccc tcagcacccc caaaaacaac   11460
tccccgcttt agtatattca cagaggcgtg ccacccgcag caccccaaa aacaactccc    11520 cgcttcagta tattcacaga ggcgtgccac ccgcagcacc cccaaaaaca actccccgct   11580
ttattcacag aggcgtgcca cccgcagcac ccccaaaaac aactccccac tttattcgca   11640
gaggtgtgcc tcccgcagca ccccaaaaa caactcccg ctttagtata ttcacagagg     11700
cgtgccaccc gcagcacccc caaaaacaac tccccgcttt agtatattca gaggcgtgcc   11760
acccgcagca ccccaaaaa caactccccg ctttagtata ttcagaggcg tgccacccgc    11820 agcacccca aaaacaactc cccgctttag tatattcaca gaggcgtgcc acccgcagca    11880 ccccaaaaa caactccccg ctttagtata ttcagaggcg tgcctccctc agcaccccca    11940
aaaacaactc cccgcttcag tatattcaca gaggcgtgcc acccgcagca ccccaaaaa    12000 caactcccta cttcagtata ttcacagagg cgtgccaccc gcagcacccc caaaaacaac   12060
tccccgcttt agtatattca cagaggcgtg cctccctcag caccccaaa aacaactccc    12120 cgctttagta ttttcacaga ggcgtgccac ccgcagcacc cccaaaaaca actccccact   12180
cactagcagc cgctccctt gccccagcct ctgccaaaca ctgacccact tcccacctcc    12240
atggagttgc acgttctgga catttcatac aaatggggtc tctgattcc ccacccacaa    12300 tttttaatca tacttaactt ccaaataaag acaaagtcaa atccctcttc cacccaacaa   12360
gatgtggcca agcgtataca agagaacagc atgtccccct ctcccccaga gaagaggaga   12420
gcccctgatc ctgattcatc tctgggtgtt cttccccttaa aaaaaaaaa aaaaaaatca    12480 aaggggggaat aggattcagc tggaatggga ttcagctgat tctcattctc ctttgatat    12540 cctaattttt ttttttttt tttttttttt ttttgagac agactctgtc agccaggctg     12600
gagtgcagta gtgcaatctc ggctcactgc aacctccacc tcctgggttc aagcaattct   12660
cctgcctcag cctctcacat agctgggata acaggcacgg ccatcacgc ccggctaatt    12720 tttgtatttt tagtagagac ggggtttcac cacattggcc aggctggtct caaactcctg   12780
acctcaggtg attcgcctgc ctcagcctcc caaagtgcta gattacatg cctgagccac    12840 cgtgcccagc ctgatagcct aaaatttaaa cactgagatg tttgaaataa ttaaatatca   12900
actactatca aacgtacact tcatacacta gtaccgtatg aagtggtagg gaatggaaga   12960
ggagaagaaa cagtggctaa tgtggtccta cccaatacac tcggatcaaa ataagaaaca   13020
cgcacacctg tgataggctt cgtttctgca gcagccgagc agcgggaact agcgtttcag   13080
```

```
cctccgtctc ccgcatagcc ttcgcctccg caagcactca gctgatgtgg ctctttgcct   13140
ggtgggatgc cctaagcctt cattcctgga gagcctgggt cctgaatgac cctgcttgga   13200
tcaggggtga tggttttcca tgattttaat cacaggacat gggaacctta agaggcgctg   13260
caggggaccc tccgcattcc agacgtgctc ctcctcatcc tccttgtgca acccggccga   13320
ttccgcccga taaaatcagt cccgtggccc gggcagtaac tgcctttttt acctattgat   13380
tctctgcagt gaggatccca aaatggcctg gtgcaatctc accttccagt ctggtggagc   13440
cgttggtgtc tctgcgggaa actctcctcc ctcgagaact cagacttcta caccaagagg   13500
acctagagtt gtggggacag ggagcaaaca catcaccagc agaatgtcat gagggtgaag   13560
agaagccatt gccacttccc cttctggact cccagaaccg tgaggtctgg gcggcaggag   13620
aaaccgctcc atagactgac tctaattcag agcctggacc gcctcctgga ggacacggcc   13680
ctctctgcaa agcgtcccca ctcagcaggc gccgtgtgag tctcccgaag gccattccac   13740
ggtcctgttc gtgagctgct cggggagag gaggaccacg gaagacctcc aaggtcacaa   13800
gcattgggcc tttgccctac tccattaact gtggtgaatt ccttgagcag cagtgtgaga   13860
atgccgaatg aggcgctcca gagtccacag gtggtttcgg caaaagcacc gtgggcaagg   13920
agggccagtc cacctgcaga gcaagcctct atcctggtga aagcgcagcg gtgccagttc   13980
catgccggca gctgtctcat atcatccact ccacctggag gctggcagat cccctgcaac   14040 actgggcag gcgggcactt agtggatggg ccttggtgag tggagcccct gtgccgatcc   14100
catgtgtgac ctccatccct gctaccacag tctctatctt caccagcctg ctgacaatga   14160
cagggtggct ggggaaggag cctgactgat gcccaaagaa agggccatct tgtctacctg   14220
gtcactgagc ttctcctcgg ctgaggcggt tgcccttttgg caaatgtcac atgggctgcg   14280
aggatcttca cgctctgccc tttcagagac ctctaaccac acaacacttc cccacacctc   14340
ctgctaccgt tttcccaaat gtgttccttt caagtccctg accatccatc tggccaagcc   14400
aggagcaact gaccatgagt gggtggcacc tgtagctccg aactctcctt ccaggaaaaa   14460
tgaaaacacc taggggccct gcccagagta tggaccacgg gtgttggaac cactttttca   14520
tgtaacttgc ttgtgacttc agggcctgcc tgagcccgg gttgtatatt gctgcttcca   14580
cttgaagaca gaacacagct gtgcatgccc aactctgtgg ctcgctgggt ccagcaacat   14640
cccactcatg acgtacagtt cagatcacgt ggcgacttag tggcctgtcc agtctctatg   14700
gaggcctgga cgcaatccac agagttatcc agagaggatg gcagagcttg actccaaaat   14760
cctaagggcc ctgggctgtg attcacctgc aggagcctat catggccccc acgcagcatc   14820
cttacctgcc acagacacct caaatgccat gggatctgtt ggtcccgtgg ctcaagtggc   14880
tcagcagctt tcatgaccac atgcacttgc tgcagagcct tctcttgttc tgggactccc   14940
agaaagcaga cagcatttta ggtcattcct acatgggttt tcctacccat gtcttcctac   15000
ctacccgtgg gtcatatggc ccatgttgca aaacattttg gaaaaggcaa aactatgcag   15060
acaatgaaat gatcagtggt ttccaggagt cagtggggag ggagggaaga ataaatggag   15120
cacagacgga ttttagggca gtaaaataat tctgtgtgac actgtaatag tggagatatg   15180
ccattacaca tttgcccgaa ctcacagcat gtacaacaag aagagtgaac cctcatgtaa   15240
cctgatcaat gactaggtca atattggttc atcaattgca aagatgtatc acagtaattc   15300
aagatatgaa taataaggga aactgtgtgt agggagagat gctatatgag gactctcaaa   15360
tatgctcaat ttctctgtaa acatgaaact gctctgaaaa ataaaatcta tattaaaaat   15420
taaagctttc accagatcaa tggctgtaga ccaggtgtcc ggggatgctt tgatttgccc   15480
```

```
cagtgatcag tagtcatatc tggaacagca gttgcaattg gagtcctggt taagtttacc   15540
aggattcact gtccttcttt ctccgggacc ccctgtctt ccacacaagc caattagacg    15600
agtggaacga ggctgcagtg ggggtcacca ccctgcatct tccaagtcct cgatggcggc   15660
actgaccttt gcagtcctc cagggctgca ggttgctttt gactgacaat tttcctaggc    15720
agagttcacc ccaatggctt ccacctggcc tttcccagca tagtagcccc caccctcagg   15780
tcagggaaca aatgtggggg ctctgctggc tgccacatac gtctgtttac tcacccatct   15840
gaggctaggg aagtgacctc tgcacccacc gagggttgga cctgagctag aactccgtga   15900
gcccactgac ctccatacgc ccctcctctg actattagat ccgatgggtg tttgtgtccc   15960
caggagtggg tgtcaggtta gagttagagt ccagtaatcc cctgagtct gatgatcccc    16020 ctttccacta gccaccccag caaatggctg caggtccctg aggggagact ggggaaagaa   16080
gaataatgta aatttgtagg agtatggcaa ggtccttcct caggggcacc cagtcctcct   16140
tcactcaggc accaggcaag ggaggccacc cattgctcca gctcccgtgg caccgtgagc   16200
caccggccaa ggccacaggg ctccatgggc tggactgttc caatcactgc cggtgccagt   16260
tgccatctca gccacaggcc cggggcctcg tggccacccc cactgggctg tgccctgcct   16320
ccttaaagac tgtgagcgag ctcccaactg gacacccct gaccagctca ctcttatttt    16380
gtctgccctg gccctgatgc tggtgtttga gatatcagaa ctcacctcaa accaccctaa   16440
gcagagatca ctccggctga cgcaggggtg cggcccacat gtgagggacc ctcaggctgg   16500
gcagcattgg ctgagccccc accgcacctt ccctcccacc ctgggtcct cagcctccgc    16560 ccaaggcagg ggggacactg ctggcaactg gtcacccaga gagcatgggc tgcagggatg   16620
gccctgagta ggacacacag ctcccgagac ccctcactgg ggacacaggg gggccctgca   16680
gccagggtgt cagtgtgggg acagcccagc agaccccaag ccacccactg aggttgcttc   16740
tcaggggagc accactggtg ggctgtcagc tcctgcctgg gccccggcct cttgcccctg   16800
tcccacctcc cacctgcacg gcctccagca ttgcccaaat tcactgcctt cactcccaag   16860
tccacagagg tgtctcatcc aggcgggtga acactcgtgt gttgggaggc tggtgaagcc   16920
tggcattggg gggcaccacc catctccctt ctttgtctca ctgccttgaa acaccccaca   16980
tctatcacct ctgcccccga ggctcccag gttcacccca tgccagcctc agcccaacaa    17040
ggcctgtgct tctgaccagc accgctgggg ttctcagggc atctacccct tccgctgtag   17100
cccactgtct ctaaacatat ttcacacgtt gctgggggca gtgtgtgtga ctcactgctt   17160
cccagagcca gccagagct gtttagtaga catgaggtga gtgaatgaat gaatgaatga    17220
atgagtgctg ggagctgtct cagttagctc caatctgcca taaggaagca ctgcaggctg   17280
ggcatgtaaa cagcaggtgc ttatttcttg cagttctgga ggctggaagt ccaatatcaa   17340
ggtgctgctg attccagtct tggtgagggc tctcttcctg gcttacagat ggctgccttc   17400
tctctgtgtc ttcatacagc tgtccttcag tgcatgtaag agagagaga gagaagaggg    17460 agctcctaaa tgtctcttgg tataagggca ctaatcctat gggaccaggg accttcatgt   17520
cctcatctgt ccctaattac ctcccagaga tccacttcct aacactatct cattgcgggg   17580
cagggcttca acctatgaat tttgcaggaa cacgattctg tccatagcga acactgacac   17640
tgaacccgcc tcctaaagcc ttctctcacc atattcctca tgctgctcaa agatcctctg   17700
caaccttgtg ccctcccaa gggtccctgc acctgtccca gagagagggc agcctggcaa    17760
tgggcctggg ccctgacgct tgagcatcgg ggtctggcct gaaaggggat gggcgttcac   17820
ttctaggttc ctgagagagg caacactgca ccttaaagg tgtcaggagc tcactgcccc    17880
```

```
agctggtcat gaaacagtct cttcatcaag ggctaaataa agcacgctga ccaccaggaa   17940
tggggcagga agcttctgcc ctgcagcctg ccttgtctgc acagggagtg tggggaccat   18000 taggggagg gtccgatgtg cattttctg ccagcggac cttcccctgc ccccagtcct      18060
gcccaggccc gggggtcac tctgaaggca tctggctctt accccaggca tctcctgcct    18120
ctgccccact cctccacccc cacggggtgc cgagtctcag cccaggctgg ggtggcccag   18180
gcaggacagc aggcttggtg gtgcccggcc ccacatacta gtgggtggca cagcgtggat   18240
gtggatagag acgcctcccc tacagtctgt ccctggtatc tgtgacgcag gtgtggggtc   18300
cctttagact cccctgggag acagctgtgt ctatgaaggg gcagccatcc ctgggtcccc   18360
tctgccctca ctgagggcag agcctaggct ccttgggggg ggaagcaggg tgcccctcag   18420
tgcccactgg agttggccag cggaggcagc agcccacggc actgagaggg aaggcccggg   18480
cagccatgcc ccagaaactc ccttggttgg gagcagagca gtgcccagag cccagaaccc   18540
agtttgagta tggtcttggc tctcaaggga caggccaggg tgcctccagg ggaaggggc    18600 tgcccaggca gtaggggttc aaaggtcccc tggggcccac ccagctgacc caggcctagg   18660
gtaatccaga aggggagctg ccctcctcct ccctgggctc aggagaggct gcaaaggcag   18720
ctcctgggac gtggatttca gaatcagggc aaaggacaga catgagccag attcaggtgc   18780
ccgcgtggcc cccacaggtc tcttcaagct ccaggcccca ctcgctgtga cgcaggtggg   18840
aagctcttga gtgcctcccc ggtgggaggg gccgcgctca cagacagcac aggggccccc   18900
aggctccagc ctcagagccc ggctgctcac ctctgatgga cagaaagggg tccctgtctc   18960
aggaaggtag aggctgccac ctcctggccc gaggacacag ctttccagag gaggggcctg   19020
cttctaagtc caagtcccat cccagccgga tagccagggg caactgccca ggtaaactga   19080
gacagcagca gcaggcaagc cagtgcagag ctgggtgatc cacaggttca tgagcggtgg   19140
caggtggaac aagggcacca tgggcggagg gttgggcagc tgcaggtggc atcattgagc   19200
caggggcctc ctggtgggta aggacattgt agagtgagcg ggcgcacctg ggacccagga   19260
attcacagga aggagagagg aaaaaggaag tccctggcgg gtaaacacat atgcatgcac   19320
acacatccac gtctgcacac gcatccacgc ctgcacacgc atccatgcct gcacatgcat   19380
ccacgcccaa tctcttccct ggaaataaag ccaggggccc ttaggccagc ttgcagtggg   19440
gcccagccct taggacaggc tccttggtgg ggtaggggtg ggggcagctg tcctcctggg   19500
ccagctcctt ggggctgaac ccgctgctcg aggggtcttc caggctccca gcggccggca   19560
ccacctctag agcaggtggg cagggtgtgt tggggtgggc aggggtttgt gagggtgggc   19620
aggggtgtgt gggggtgggca ggggtgtgtg gggtgggcag ggcatgtgg ggtgggcagg   19680 ggtgtgtgag gttgggcagg ggcgtgtggg gtgggcaggg gtgtgtgagg gtgggcaggg   19740
gtgtgtgggg tgggcagggg tgtgtaaggt tgggtagggg tgtgtgggt gggcagggat    19800 gtgtggggtg ggcagcggtg tgcggggtgg gcaggggtgt gcggggtggg caggagggtg   19860
tggggtgggc agcagcctgc acagtggctt ccccctcaaca agccacttcc tcttgcagag   19920
ggaatgttgg ggtgggaggg tgtggctcag caaaggggcgt gggggttcca ccggctccct   19980
gcccccgctg gtgggcaca gtgaggggg ctgtggtcag acctggtctc tggagggcca    20040
gccgggggtt cccgtccacc tgtcaggggg ttcgacgcca ctttgagatg acaagtgagg   20100
ccacctgggc acagcgctgg tgtgagaagg aggccatcag acaggtcaa gaacccaggc    20160 ccgccctgct ccgaaattct tcagacctga tgaagaggtg tcccgaaagc gggtggtgct   20220
ccaggcccgc ctcaccagct ccagggaggt caaggttgga gagagacaat tctaggggcg   20280
```

```
aaccagacat agccaagagc agctcatctt ccctggagag gacgggctgc ccacttgcac    20340
agcccggggg cctcctgccc ctagacctgg taccttcact cttgttgcca cccctacatt    20400
catacctgcg ccccagtctg agccacacct aggcccccag ctgaagtgac actgtgggtg    20460
ccaggcatct gaggtctcca caagccccca cagactcagg gtgggaattc ctgggggcca    20520
gagctgcaga gggtgctgcc tgggggtgct gggctggacg ggggtcctgg ttgtccctcc    20580
tggttctcct ggttctccct ccgcagaggg agggaggcgg tggcctcagc agttcctcca    20640
gcagcgttcc tgagcgggcg gcagctgggc cctcttccca cagccacgct ggggttgcca    20700
tgcctgcagg tcttggggcc ccctcccect tgatgaggtc ctgaccaaat gcaggaggag    20760
caattccagc accgaggggc gagcagagcc gcctgttagc actcctggga gggcccggag    20820
tggtccctga atgatggatt cacctggaac attttcaccc tcttcaggcc caccctgccc    20880
cagaggccca cggaaaccct gcctgtactg gggccgcagc gctgccccca cccatacgta    20940
attacacggc tcggtgtaat tgcaaattcg aggtttacaa agcctccccc tggaggcccc    21000
acgtgagtgt gagcgaggcc ccagcccacc cctgtggccc caagaaggct ctgcgacaaa    21060
atatccatga gtgccgccca cgaaggcatt aaaaccaacg accttctcaa aacttaagct    21120
gtcacaggac atttcaaagg gtgtttccta agaacacctc aataatgatg ttccaaggag    21180
accccatcca aattcctcca aggattacgc ccccaaggcc cagtccacac ttgctcactc    21240
ccaggacggg gagctcacct cctcctcccc gggcgccgtc tcctccacat cccacaccag    21300
gtcctgccca tgactttccc cctctcagcg ccgtcctcag tggccacacc aagaacgagg    21360
ccatgtcttc ctgggaaggg cctcagatgt cagcaaatgc cctggtgtct tgggctgggc    21420
tgggggcacc agggtgaggt ggtgggggga gccaacctca ctgcccctcc ccttcctgcc    21480
tgcccttctt ccggggcacc cagcagctcg gtcctagggc gatgttgaca gacagacaga    21540
ggggcggatg cagcctacct cctgggcagt gagctgcggt ctgaggcccc tgcccagctg    21600
gaaaccacag ggaggggaag ggaggggagg agaggagagg agaggaaccg tcatgggggcc    21660 ttggagtcga gtcagggttg ccaaatgcca gatgctggtc acctgcttct ttatcttggt    21720
aacaggcagg tcgggcagga gtgggtggtg ggtgggggtg agcaggggtg aggggtggca    21780
gggcctcagc acaggggatta tccctcccct gacacacaca ccagccctac tgtccctgtc    21840
ctgcccttgc agacatgtgt cctgcccttg cagacagccg caggcaggca gggaccacca    21900
tgagcaaccc cgtctctcct cctgaggggc agcacagagc ctggaggagg cctgagtggg    21960
gctgaggcct ggggcgagct ggggtggagg ggcactggct gccgggctcc agggatcttc    22020
tccccttcct gccccggagg gtgctggcac aggggtgggg ctcactccca ctccgtagac    22080
acaatgatca gaggtcctgg gtgtctgggg aagctgggct gtgcgtgtat gcgtctacca    22140
tgtgggggtg cctgtgagtg tgctggggcg tctgcagtga aggcctcctg agaccactcc    22200
acggaaacac cgggaatccc tgcagctgag cctgtctctc acgggaccgg gaagctggag    22260
agagccccaa ccctgcccgc tggggccgag ctccctgctc ctgcagcagt cccatgcccc    22320
acactctgag tctgccctat ccacagctgc tgggcctctc tgtggccacc atggtgactc    22380
ttacctactt cggggcccac tttgctgtca tccgccgagc gtccctggag aagaacccgt    22440
accaggctgt gcaccaatgg ggtaagtgag gtccaggcct ggctgcatcg ggaggggcct    22500
cgggtgcaag ggtggctggc acgagcccag ctggacgcct cacagccaga atggtgccag    22560 gcccctaggca ggagccagag gtggtcaggg gcagggaggg gctgccctgg agtcctagct    22620
cccctgggca gggcctcggg tctgggtgac agccagtgtt cctgcctggt tctcgtgccc    22680
```

```
cacaggagcg tgggcacagt gtgggtatat gtcgggcagg gtcaggaagt ggctctgtgc  22740
ggtcaggacc tggctctgtg cagtcagggc tcagtcccag gcaggcctgg gactggcctg  22800
gggctgggca cagcaggtcc atgagggctc cacatggctg atgttccact caggacctgg  22860
gatgtgggtg gggaggggt gggggctgct ctagccagac gcctccctgc agggactcag  22920
cagcgactta tccaacatcc agagagcggg agcgagggcc agagcctgct ggggccactc  22980
aggggtaagg ctgaggaagg cccctttaat gagggatgt cagagccaga tctgcagggg  23040
actctcaggc aggagctcag ggggcccagg aaggctgcag cccggtgggc agatgtaggg  23100
aaactgaggc ccaggaggtc agggatactg ccttagaacc caatgctttt ccccaagtcc  23160
taggaccagg gcctccctgg aggaggacgc ctggggccca ggtccaggtc cggactgata  23220
agattacagc tccagtccgg ccacttgtca ctaggacatg gcaggaggat gcctgggcc  23280 caggtccagg tccagactga taagattaca gctccagtcc ggccacttgt cactagggca  23340
tggcagggag catgtggctt ccaagatagc cccacaggca tggagggcag ggaggaaaag  23400
agggaaggag gggcagtccc ccaggctgaa cgagtcccac ctccctcctc cttccctcag  23460
ggccgtctga tggagagaca ggcccattca gagcccccca ggagtccctc acggcccctg  23520
actcccaagt tagatttcac acccaggctg tgtgcactca ggacctgtcc tgggcacccc  23580
taaccctcct cctctctcct cccaaccagc cttctctgcg gggttgagcc tggtgggcct  23640
cctgactctg ggagccgtgc tgagcgctgc agccaccgtg agggaggccc agggcctcat  23700
ggcaggggtg agttcattgt gttcccagat gcccaggccc ccagaaaaga attagaaagg  23760
agtgaagagc tggcagggct gtgtgccacc cccacacctg agtgaccagg cagaaccaga  23820
ggccccaggg atgctggcca gccgagaccc ccacgtcaac cccacacctg agtatctagg  23880
cagaaacaga ggccccaggg atgctagcca gccgagaccc cctacctggg tagccaaggc  23940
ccctccacca ggcctacct cacccctgtca tctacacgcc caacaagggt tcctatagga  24000
gctctgaaag agagagacgg ccctcctgac cctgggagct gtttccaaag tccctgggag  24060
ggtctggttc tattgcccag caagctctgg gagggcactg ggagcatccc atttcctgtt  24120
cggaggaggc cgggccaggc tcaggaaacg ccccttgagc tctccagcct gggctctccg  24180
gagctgcaca ctctccttcc cagctgccgg aggtgtctcc ccagccccga ggtcccatag  24240 gccccctccac cccaccccat agcagtggcc tcttgtcacc ctcattccta ctcctcccca  24300
tgggcttctg tcttggtccc tgccactcga tggtcatcgc agaccccacc tggcggcagc  24360
ctccccacgc ctgtcctgcc cctgctaggc ccacagccct cttctctcac cccagctggg  24420
gcagctcctc cctggcgccc cgggctccca cctgtccctc tagcctcccg tctcccctt  24480 ccagccatga ggagcttgtg ctgggggctt tgcttccctg tttagcctgt gaagctggac  24540
cactctgggg gtccctgagg gcagagcctc ctgggtcccc agggctggca ggttttcag  24600 ctcagccttc aagttcagca aatgcttgtt taatgaccct ggtttataaa tgtctccaag  24660
aataggaata gagtcacctc ctggagctgc tgccgggcca accagccctg ggtgggccca  24720
tggtgggcag aggaggaccc agcagctcca gcactagcca ggattcctgc tccgggcac  24780 acgagcatgg gcagggacaa ccccggcctg tgctatctgg cttcagggcc aggtgggagg  24840
ccccagtggg gagatgacaa ggcaggtagt ctgcccccc cccagagggt gtgtggcct  24900 gcaaagggac acctggatgg aagaaaaggt tggcaacagg gccaggccaa ggggtccagg  24960
tcagagctgg aggcccagaa agaaccagcg ctggggctgc agtaccgtcc accagggggt  25020
gccatggtgc tgggcttgag gccacatatg cagaagccag ccgctgggcc acggggctcc  25080
```

-continued

```
tgtcccagtc accagccttt cccacccac cttgcccccg tgcacaaacc agtctagcac      25140
cctcatctgt ggccaaggcg gtcagggagc acctgggctc aggttctgtg tccccagcca     25200
gccccaaggc cagggtgact tgacatgtgg gtcaggcctg tagagcagcc ttggaggccc     25260
ccaactggat gcctgcactg ggctggggtc ctgaggacac tccagtccca gctgggtggg    25320
ctccagcaca gctcccaagc cccaatgcac ttagacccag cctggatggt gagctcagca     25380
tggccacagc agggagctgg gagacccag tcaagagacc tgctccattg agctgcatgc      25440
atgtgtgtgc atgagggtga gcctatgtgt atgcgtgtgc aaatatacat gtgtgtgtgc     25500
atgtgcatga gtgtgtgtgt gcatgtgtgt gtgcgtgtgc aggtgcctct gtgtgtgtgt     25560
gtgtgtgtgt gtgtaagtat ctgtcaccgg tcttcacctg ccctgttgc catacgggtg      25620
tggtgtctgc gtgttgcatc tggcacatct gtatgtgtgt ctgcacgcat gagcacaagt     25680
gaagggcta gggaagggga gcagggagtg gaaagatttt ttccaatggg ctgggcgcct      25740
ggatgctccc cacaaagccc cttcctgcct gcccccaccc ctccggcctc tcccctagct     25800
ggcctctcgc acaggaaatg aaagagcttg ctgggctgag agagcagagc tggcagcgcc     25860
gcccaaggaa gcacattcaa ttcgcttatg tatctattta tttatttcca tttagaatga     25920
ggagaaagaa aatggccagg gcagacctga ccacccagca gcctctgatg                25970
```

```
<210> SEQ ID NO 9
<211> LENGTH: 30196
<212> TYPE: DNA
<213> ORGANISM: Homo sapiens

<400> SEQUENCE: 9
tggtgagggc tctcttcctg gcttacagat ggctgccttc tctctgtgtc ttcatacagc       60
tgtccttcag tgcatgtaag gagagagaga gagaagaggg agctcctaaa tgtctcttgg      120
tataagggca ctaatcctat ggaccaggga accttcatgt cctcatctgt ccctaattac      180
ctcccagaga tccacttcct aacactatct cattgcgggg cagggcttca acctatgaat      240
tttgcaggaa cacgattctg tccatagcga acactgacac tgaacccgcc tcctaaagcc      300
ttctctcacc atattcctca tgctgctcaa agatcctctg caaccttgtg cccctcccaa      360
gggtccctgc acctgtccca gagagagggc agcctggcaa tgggcctggg ccctgacgct      420
tgagcatcgg ggtctggcct gaaagggat gggcgttcac ttctaggttc ctgagagagg       480
caacactgca cctttaaagg tgtcaggagc tcactgcccc agctggtcat gaaacagtct      540
cttcatcaag ggctaaataa agcacgctga ccaccaggaa tggggcagga agcttctgcc      600
ctgcagcctg ccttgtctgc acagggagtg tggggaccat taggggagg gtccgatgtg       660
cattttctg ccagcgggac cttccctgc cccagtcct gcccaggccc gggggtcac          720
tctgaaggca tctggctctt accccaggca tctcctgcct ctgccccact cctccacccc      780
cacgggtgc cgagtctcag cccaggctgg ggtggcccag gcaggacagc aggcttggtg       840
gtgcccggcc ccacatacta gtgggtggca cagcgtggat gtggatagag acgcctcccc     900
tacagtctgt ccctggtatc tgtgacgcag gtgtggggtc cctttagact cccctgggag      960
acagctgtgt ctatgaaggg gcagccatcc ctgggtcccc tctgccctca ctgagggcag     1020
agcctaggct ccttgggggg ggaagcaggg tgccctcag tgcccactgg agttggccag      1080
cggaggcagc agcccacggc actgagaggg aaggcccggg cagccatgcc ccagaaactc     1140
ccttggttgg gagcagagca gtgcccgag cccagaaccc agtttgagta tggtcttggc      1200
tctcaaggga caggccaggg tgcctccagg ggaagggggc tgcccaggca gtaggggttc     1260
```

```
aaaggtcccc tggggcccac ccagctgacc caggcctagg gtaatccaga aggggagctg    1320
ccctcctcct ccctgggctc aggagaggct gcaaaggcag ctcctgggac gtggatttca    1380
gaatcagggc aaaggacaga catgagccag attcaggtgc ccgcgtggcc cccacaggtc    1440
tcttcaagct ccaggcccca ctcgctgtga cgcaggtggg aagctcttga gtgcctcccc    1500
ggtgggaggg gccgcgctca cagacagcac aggggccccc aggctccagc ctcagagccc    1560
ggctgctcac ctctgatgga cagaaaaggg tccctgtctc aggaaggtag aggctgccac    1620
ctcctggccc gaggacacag cttttccagag gaggggcctg cttctaagtc caagtcccat    1680
cccagccgga tagccagggg caactgccca ggtaaactga gacagcagca gcaggcaagc    1740
cagtgcagag ctgggtgatc cacaggttca tgagcggtgg caggtggaac aagggcacca    1800
tgggcggagg gttgggcagc tgcaggtggc atcattgagc caggggcctc ctggtgggta    1860
aggacattgt agagtgagcg ggcgcacctg gacccagga attcacagga aggagagagg    1920
aaaaaggaag tccctggcgg gtaaacacat atgcatgcac acacatccac gtctgcacac    1980
gcatccacgc ctgcacacgc atccatgcct gcacatgcat ccacgcccaa tctcttccct    2040
ggaaataaag ccaggggccc ttaggccagc ttgcagtggg gcccagccct taggacaggc    2100
tccttggtgg ggtaggggtg ggggcagctg tcctcctggg ccagctcctt ggggctgaac    2160
ccgctgctcg aggggtcttc caggctccca gcggccggca ccacctctag agcaggtggg    2220
caggggtgtg tggggtgggc aggggtttgt gagggtgggc aggggtgtgt ggggtgggca    2280
ggggtgtgtg ggtgggcag gggcatgtgg ggtgggcagg ggtgtgtgag gttgggcagg    2340
ggcgtgtggg gtgggcaggg gtgtgtgagg gtgggcaggg gtgtgtgggg tgggcagggg    2400
tgtgtaaggt tgggtagggg tgtgtggggt gggcagggat gtgtgggtg ggcagcggtg    2460 tgcggggtgg gcagggggtgt gcgggtggg caggaggggtg tggggtgggc agcagcctgc    2520
acagtggctt cccctcaaca agccacttcc tcttgcagag ggaatgttgg ggtgggaggg    2580
tgtggctcag caaagggcgt gggggttcca ccggctccct gccccgctg gtggggcaca    2640 gtgagggggg ctgtggtcag acctggtctc tggagggcca gccggggtt cccgtccacc    2700 tgtcagggg ttcgacgcca ctttgagatg acaagtgagg ccacctgggc acagcgctgg    2760
tgtgagaagg aggccatcag gacaggtcaa gaacccaggc ccgccctgct ccgaaattct    2820
tcagacctga tgaagaggtg tcccagaagc gggtggtgct ccaggcccgc ctcaccagct    2880
ccagggaggt caaggttgga gagagacaat tctaggggcg aaccagacat agccaagagc    2940
agctcatctt ccctggagag gacgggctgc ccacttgcac agcccggggg cctcctgccc    3000
ctagacctgg taccttcact cttgttgcca cccctacatt catacctgcg ccccagtctg    3060
agccacacct aggcccccag ctgaagtgac actgtgggtg ccaggcatct gaggtctcca    3120
caagccccca cagactcagg gtgggaattc ctgggggcca gagctgcaga gggtgctgcc    3180
tgggggtgct gggctggacg ggggtcctgg ttgtccctcc tggttctcct ggttctccct    3240
ccgcagaggg agggaggcgg tggcctcagc agttcctcca gcagcgttcc tgagcgggcg    3300
gcagctgggc cctcttccca cagccacgct ggggttgcca tgcctgcagg tcttggggcc    3360 ccctcccct tgatgaggtc ctgaccaaat gcaggaggag caattccagc accgaggggc    3420
gagcagagcc gcctgttagc actcctggga gggcccggag tggtccctga atgatggatt    3480
cacctggaac attttcaccc tcttcaggcc caccctgccc cagaggccca cggaaaccct    3540
gcctgtactg gggccgcagc gctgccccca cccatacgta attacacggc tcggtgtaat    3600
tgcaaattcg aggtttacaa agcctccccc tggaggccca acgtgagtgt gagcgaggcc    3660
```

```
ccagcccacc cctgtggccc caagaaggct ctgcgacaaa atatccatga gtgccgccca    3720
cgaaggcatt aaaaccaacg accttctcaa aacttaagct gtcacaggac atttcaaagg    3780
gtgtttccta agaacacctc aataatgatg ttccaaggag accccatcca aattcctcca    3840
aggattacgc ccccaaggcc cagtccacac ttgctcactc ccaggacggg gagctcacct    3900
cctcctcccc gggcgccgtc tcctccacat cccacaccag gtcctgccca tgactttccc    3960
cctctcagcg ccgtcctcag tggccacacc aagaacgagg ccatgtcttc ctgggaaggg    4020
cctcagatgt cagcaaatgc cctggtgtct tgggctgggc tggggcacc agggtgaggt    4080
ggtgggggga gccaacctca ctgcccctcc ccttcctgcc tgcccttctt ccggggcacc    4140
cagcagctcg gtcctagggc gatgttgaca gacagacaga ggggcggatg cagcctacct    4200
cctgggcagt gagctgcggt ctgaggcccc tgcccagctg gaaaccacag ggaggggaag    4260
ggaggggagg agaggagagg agaggaaccg tcatggggcc ttggagtcga gtcagggttg    4320
ccaaatgcca gatgctggtc acctgcttct ttatcttggt aacaggcagg tcgggcagga    4380
gtgggtggtg ggtgggggtg agcaggggtg aggggtggca gggcctcagc acagggatta    4440
tccctcccct gacacacaca ccagcccgac tgtccctgtc ctgccctgc agacatgtgt    4500
cctgcccttg cagacagccg caggcaggca gggaccacca tgagcaaccc cgtctctcct    4560
cctgaggggc agcacagagc ctggaggagg cctgagtggg gctgaggcct ggggcgagct    4620
ggggtggagg ggcactggct gccgggctcc agggatcttc tcccttcct gccccggagg    4680
gtgctggcac aggggtgggg ctcactccca ctccgtagac acaatgatca gaggtcctgg    4740
gtgtctgggg aagctgggct gtgcgtgtat gcgtctacca tgtggggtg cctgtgagtg    4800
tgctggggcg tctgcagtga aggcctcctg agaccactcc acggaaacac cgggaatccc    4860
tgcagctgag cctgtctctc acgggaccgg gaagctggag agagcccaa ccctgcccgc    4920
tggggccgag ctccctgctc ctgcagcagt cccatgcccc acactctgag tctgccctat    4980
ccacagctgc tgggcctctc tgtggccacc atggtgactc ttacctactt cggggcccac    5040
tttgctgtca tccgccgagc gtccctggag aagaacccgt accaggctgt gcaccaatgg    5100
ggtaagtgag gtccaggcct ggctgcatcg ggagggggcct cgggtgcaag ggtggctggc    5160
acgagcccag ctggacgcct cacagccaga atggtgccag gcctaggca ggagccagag    5220
gtggtcaggg gcagggaggg gctgccctgg agtcctagct cccctgggca gggcctcggg    5280
tctgggtgac agccagtgtt cctgcctggt tctcgtgccc cacaggagcg tgggcacagt    5340
gtgggtatat gtcgggcagg gtcaggaagt ggctctgtgc ggtcaggacc tggctctgtg    5400
cagtcagggc tcagtcccag gcaggcctgg gactggcctg gggctgggca cagcaggtcc    5460
atgagggctc cacatggctg atgttccact caggacctgg gatgtgggtg gggaggggt    5520
gggggctgct ctagccagac gcctccctgc agggactcag cagcgactta ccaacatcc    5580
agagagcggg agcgagggcc agagcctgct ggggccactc aggggtaagg ctgaggaagg    5640
cccctttaat gagggggatgt cagagccaga tctgcagggg actctcaggc aggagctcag    5700
ggggcccagg aaggctgcag cccggtgggc agatgtaggg aaactgaggc ccaggaggtc    5760
agggatactg ccttagaacc caatgctttt ccccaagtcc taggaccagg gcctccctgg    5820
aggaggacgc ctgggcccca ggtccaggtc cggactgata agattacagc tccagtccgg    5880
ccacttgtca ctaggacatg gcaggaggat gcctggggcc caggtccagg tccagactga    5940
taagattaca gctccagtcc ggccacttgt cactagggca tggcagggag catgtggctt    6000
ccaagatagc cccacaggca tggagggcag ggaggaaaag agggaaggag gggcagtccc    6060
```

```
ccaggctgaa cgagtcccac ctccctcctc cttccctcag ggccgtctga tggagagaca    6120
ggcccattca gagcccccca ggagtccctc acggcccctg actcccaagt tagatttcac    6180
acccaggctg tgtgcactca ggacctgtcc tgggcacccc taaccctcct cctctctcct    6240
cccaaccagc cttctctgcg gggttgagcc tggtgggcct cctgactctg ggagccgtgc    6300
tgagcgctgc agccaccgtg agggaggccc agggcctcat ggcaggggtg agttcattgt    6360
gttcccagat gcccaggccc ccagaaaaga attagaaagg agtgaagagc tggcagggct    6420
gtgtgccacc cccacacctg agtgaccagg cagaaccaga ggcccaggg  atgctggcca    6480
gccgagaccc ccacgtcaac cccacacctg agtatctagg cagaaacaga ggccccaggg    6540
atgctagcca gccgagaccc cctacctggg tagccaaggc ccctccacca ggccctacct    6600
caccctgtca tctacacgcc caacaagggt tcctatagga gctctgaaag agagagacgg    6660
ccctcctgac cctgggagct gtttccaaag tccctgggag ggtctggttc tattgcccag    6720
caagctctgg gagggcactg ggagcatccc atttcctgtt cggaggaggc cgggccaggc    6780
tcaggaaacg cccccttgagc tctccagcct gggctctccg gagctgcaca ctctccttcc    6840
cagctgccgg aggtgtctcc ccagcccga ggtcccatag gcccctccac cccacccccat    6900
agcagtggcc tcttgtcacc ctcattccta ctcctcccca tgggcttctg tcttggtccc    6960
tgccactcga tggtcatcgc agaccccacc tggcggcagc ctccccacgc ctgtcctgcc    7020
cctgctaggc ccacagccct cttctctcac cccagctggg gcagctcctc cctggcgccc    7080
cgggctccca cctgtccctc tagcctcccg tctcccctt  ccagccatga ggagcttgtg    7140
ctgggggctt tgcttccctg tttagcctgt gaagctggac cactctgggg gtccctgagg    7200
gcagagcctc ctgggtcccc agggctggca gggttttcag ctcagccttc aagttcagca    7260
aatgcttgtt taatgaccct ggtttataaa tgtctccaag aataggaata gagtcacctc    7320
ctggagctgc tgccgggcca accagccctg ggtgggccca tggtgggcag aggaggaccc    7380
agcagctcca gcactagcca ggattcctgc tccggggcac acgagcatgg gcaggggacaa   7440
ccccggcctg tgctatctgg cttcagggcc aggtgggagg cccagtggg  gagatgacaa    7500
ggcaggtagt ctgcccccccc cccagaggg  tgtgtggcct gcaaagggac acctggatgg    7560
aagaaaaggt tggcaacagg gccaggccaa ggggtccagg tcagagctgg aggcccagaa    7620
agaaccagcg ctggggctgc agtaccgtcc accagggggt gccatggtgc tgggcttgag    7680
gccacatatg cagaagccag ccgctgggcc acggggctcc tgtcccagtc accagccttt    7740
cccacccac  cttgccccccg tgcacaaacc agtctagcac cctcatctgt ggccaaggcg    7800
gtcagggagc acctgggctc aggttctgtg tccccagcca gccccaaggc cagggtgact    7860
tgacatgtgg gtcaggcctg tagagcagcc ttggaggccc caactggat  gcctgcactg    7920
ggctggggtc ctgaggacac tccagtccca gctgggtggg ctccagcaca gctcccaagc    7980
cccaatgcac ttagacccag cctggatggt gagctcagca tggccacagc agggagctgg    8040
gagacccag  tcaagagacc tgctccattg agctgcatgc atgtgtgtgc atgagggtga    8100
gcctatgtgt atgcgtgtgc aaatatacat gtgtgtgtgc atgtgcatga gtgtgtgtgt    8160
gcatgtgtgt gtgcgtgtgc aggtgcctct gtgtgtgtgt gtgtgtgtgt gtgtaagtat    8220
ctgtcaccgg tcttcacctg cccctgttgc catacgggtg tggtgtctgc gtgttgcatc    8280
tggcacatct gtatgtgtgt ctgcacgcat gagcacaagt gaaggggcta gggaaggga     8340
gcagggagtg gaaagatttt ttccaatggg ctgggcgcct ggatgctccc cacaaagccc    8400
cttcctgcct gcccccaccc ctccggcctc tcccctagct ggcctctcgc acaggaaatg    8460
```

```
aaagagcttg ctgggctgag agagcagagc tggcagcgcc gcccaaggaa gcacattcaa    8520
ttcgcttatg tatctattta tttatttcca tttagaatga ggagaaagaa aatggccagg    8580
gcagacctga ccacccagca gcctctgatg gtgaaggccc tggggaggtc tgggtgggcc    8640
catccaccac ccaagatcct ctctgcgcgg gaggttggtg gtgggggag agagagaaag     8700 agagaaagag agaaagagag agagaggccg tgatgctct ttctcctgag gaatgaaatg     8760
gtttctggaa aatgctggtc tcctgagctg gctcagggcc tcaagcctgg gaggcagcat    8820
tgagtgatag cttccagatg gggatggtgg ccctcagcca gcaaggagga ggaggaggag    8880
gacgaagaag gaggagggca gaggagaagg agggagaaag agggagaggg aagaggagga    8940
aaaggaggga aaagggggga gaagggagag ggagaggggg agggagaggg aggggaggg    9000 gggagaagaa ggagggaggg ggagaaggga agaggaggga gaaggaggga ggacaaggga    9060
ggaggagatg gaggaggggg aaggaggaga aggaggaggg agaaggagga ggaaagagaa    9120
aagaggaaag aaggtgagga gaagaaagaa ggggagggtg gaaggaggag gaggaagagg    9180
aggaaggagg aggagagaga agagaggagg aggaggcagc tcccaggcca tccccatca    9240 ggccttgcag cctccagggc aggcaggagg gccatgagga gccgccagcg ccctgtccct    9300
gcagggctgg aggccccatg ctcacgcctg tgcttggggg ccagcagggc tccccagctc    9360
tttccacgcc cctctggccc agcttcccct ggcatgccag cgttgtcgct gcccacctgc    9420
cagcatgtgt gggtctccgt ctatcccacg ggcacccatg ctcctggcat caccctgaat    9480
ggggccccag ggtttgaagg gcccagaccc aacctgctcc agcctgtgga ccacccaggc    9540
gggcacagtg ctgcctgagg gggctggcgt ttcaccgggg cctcaggact cctgggggag    9600
ctgcccggtc ggtggctaga ctcaccgtca ggtactccag gtcctcaggg caccagcatg    9660
aaggcaaagg cggctgccca gaccctgagt gggaggacat ccccagggtt cttagcctgg    9720
gtgacctctg ccaccatcca taaaactgta tcggggcat ctgtatgctc tcagaggagg     9780
ggtctctcgt gttccttagc ttccgcaagg gggctctcaa aagcctggaa gccttgaccg    9840
agagaacaac gggcaagtgc cgggggcggg tgcgcagacg tttccaccag agaacgcccc    9900
actccacgac taggggcacg ggcatcagtg agagagaggg gacagtggtt ggccgggcca    9960
tggagaccca ggcagagtat ggagagaaag tgaggtgagg gaggtgggct caactgcaaa    10020
gagagaggcc acagcatcct gagcaggcac cacacctgtc ccaagcctca ccagcactgg    10080
gctagctggt gccttgtttc agaaaagaag gcaaaacaga agatcctaca gccccggccc    10140
tggagaggct caggctcagg ggagactctg cccggccctg tccaggtcca tgcccctcag    10200
gaagcagccc cagtgggcag aggtctccat cttctcaggg gtgccctgcc cctgctgggc    10260
aggggtgcag tgttgccatc aacaggcccc tgggggccaa aatgggagaa caagggatga    10320
attcccaaaa agcgcagggg aaggggatgg gaaggtgcta tggaacccac gcacccagcg    10380
cccacgctct ccccaggcca agtctccctc tcaggcagtg gggagcggga ctcagaccca    10440
cacctcgacc aagcatcctg ctgggggcgc agcctgaggg cactgccctg cccaggcctg    10500 ccaggccccaa ccaggccccg cagtgactgc ccccaccccc gcagtgacca ccccccaca    10560 gtgaccggcc ccccgcagtg accagccccc cgcaatgacc agcccccaac agtgaccagc    10620
cccccatagt gaccggcccc ccacagtgac cagcccccg caatgaccag ccccaacag    10680 tgaccagccc ccatagtgac cggcccccc gcagtgacca gcccccgca atgaccagcc     10740 cccaacagtg accagccccc catagtgacc ggccccccac agtgactggc cgcccacag    10800 tgaccggccc ccccagcag cgaccagccc ccgcagtga ccagccctca acagtgacca     10860
```

```
gccccgctct gcccccaggg cttcctgtgc ttctccctgg cgttctgcgc acaggtgcag   10920
gtggtgttct ggagactcca cagccccacc caggtgagca ccagctgccc ctaccctgca   10980
gtggagggtc ccccagtaag ccagtgggca cctggggact ggggagcagt cctgggagga   11040
gcagccccag cttccaggct tgtgctgacc gggtggggtg ggggagaccg cagcctgggt   11100
tccctctgcc tgaggcttca gggaggccaa gcgctggagg tgggtgaggg ccagcagctc   11160
cctggtgggg agggacctat gctgtacccc tgccttcgcc ccagtctcat tttcttaaag   11220
cccctcagcc caccccctcc tgagctgatg cccctcgggt ttgagggagg gaatgaggag   11280
gaagaagaag gaaagccact ggcttggcct taggggttga ctagaaggag cagagtgttc   11340
cagaaaatga gacctgaggg ccagcgctcc tgatggcctg gtggggcaga cggtaccagt   11400
ggggaaggga cctggagacc cgcggactgg ggtgtcgcag cctccacccc ctccacggaa   11460
cagcacccat ccttccgtcc tggatgctga cctgcctgga ggagggtccg gcctagctga   11520
ccgtgggcag gggccaaggg cgtccccgtg gaaaggccag cagcttggag aggaaggagg   11580
cctccctggc ccagcagaga atgagagctc ggtagcagag ccagccccac cttcccctgg   11640
agagccagac ctggtgagag cccccagggc agccggcgg caccagggac agccacgggc   11700
agggtcatgg agtggggcag gagagcctgg caggtcacaa gaggtgattt cttggagccc   11760
tagctggagt cctagtggcc tcgtgtattc aagtgcctgg ttgcccaggg ccctcaaaca   11820
caggcttggc catgagagat accgaggctg gtagcaggca ggtcctctgg ctgagctctg   11880 caggggggcct gctgtgcagt ttcttgagct gtgctggcag cctgagtgtg gtggtccca    11940 ccgtggtttg caaatggggg gactcaggcc ctctgggggt ggggggagct caaggttacc   12000
ctggcagtgc cggggctgga tggggctcc aggcttacga caaaggctct tggccccaaa    12060
gtgcccaccc acccctggca tcatttggga ggaaccgcct gaaccaggtg ggagaaacac   12120
cattttatca ggcccagaag gatcccagag gggctgagcc cccagaagag ggctgtggct   12180
ttgaggactg gcacaggagt cttaccaggg tggtgagctg ggccaggtcc gtgtttcggc   12240
ctcacgtttc ctgtccactg aggggtggtc tggctcattt gaggtctggg tcacagtgtg   12300
ggtggccgag gtcaagacag ctgccagggt tccccgggct cgtctgggc agctgcggcc    12360 catgccccat gcttctgtgt gtttatggct ctgatcgtgg agccacaatt ctggagggga   12420
gggggccata caggggccac aggacagaac gcagctgggg cctgctctcc aggaagggaa   12480
gggggtgcaa gaagatagat gccccagccg ggctcaccta tggcctgtcc cagccccagg   12540
cagcatcccc cacacacatg gtccttgtct ggcccgtgcg cccagctgcc cttcaggggt   12600
cagttctcag ggccttgcct gaccccaggc aggggactgg ggcttcctcc tgggcctctg   12660
gtccccatct gcccctccca gtgggtcttg acttctggca tcatctgtgt caggcctggt   12720
ggccatggag gtggcctggg tgaaggagct ctgaatatga agtcagtgtc cttgggccgc   12780
ccttgggcaa gccactttaa cttcctgggc ctcagtttcc ttttctgtga agggagcacc   12840
aagatccagg ggctgcatgg gtgggaatgg ccaggtgtgt gcaaagactc ttcctcctca   12900
cctgcgtgcc tcctgccgtg ccccgttgcc caggctggtc ctccaggacg tgggacttgc   12960
tcgaagctgt cctgggtgtg gatggagtgg ctttggtgcc agggcccggg ccctgagcag   13020 gagggcggc tgcacatccc gtctcctgcc ctccaccctc agggcccacc agagccgaat    13080
gggcttcaac cttgggctcc ctgtccaaca aagtcctgct ggcagcctag acagtggcaa   13140
aggccaaagg ccccaagctg ttggcaccgg aaacgtcgag gtgagagccg ggggcccaga   13200
gcccagcccg gcccattcac ccattccccc tgtccctccc cacagggcca ctgaggtgtc   13260
```

```
ctgaacacag ggtcaggtg actcatgtgg tgccctgcg gatgggaagg cagaggacag     13320
aggagggaag ggaccagcca catgcccttg gtggtgccct gtggccacag acccgggccc   13380
agagctgaaa gtggggtgcc cctccacctc cccaactctt gccccaggga gtcctggctg   13440
ccacttccct gggatgctca tgcgggcagg aggcgtggac cgggcttcag ggatgaatgt   13500
ggagcttgag ggctattaat tacgttctcc tcgagggctg agagccactt tgccttaacc   13560
ctcccctgt gccctgacga gtctgcttcg ggaataattc atgctcaaat taagtacagc    13620
agtgtggggt gcagcctcgt cctcacagtc tgccccaccc tggagccact accctccctg   13680
gatcctccag ccgccgagtg ggctcaggcc agagccagct ctgtacctgt ggggctggtc   13740
cacaggcctc ctgcagctcc tggtccccac ctgccgttca ggacctgtct gtaccttcct   13800
gagcactttc agcagacaca ggatggggtc gccaagccca gcagacacc agggaagatc     13860
tggtcatggg gaaaagcccc cgggcaccgg aagacggagc ttagtgcgtt gatacctgtc   13920
aggcagcacc ttcccccagg tgtcctgaga acacaggcc ccaggctcct tcagagcccc     13980
cagagcctgg aatggagaca gacggtgaag catcacctag gagcccaggc cccgtggaga   14040
gcagccggcc cggcctccag ggccctccag ggccagacaa ccggctttgg ggtaggaggc   14100
ctacctcgct gagctctgct tccccagtcg tggggagagc tgcttggcag agccaggcag   14160
ggcaggaaga gccaggcagg gcaggcaggg caggcagggc aggcagagcc aggcagggca   14220
ggcagagcag gccccctcagc cactagcagg agttgtcact ctcgcccatg ctgtggtaat   14280
aatgacacct tgctcacagc ctcagaggca ccttttgtcct ccttgggcca tggcaggcgc   14340
ctgacaatgg gaacagtcat tggagttggg agggaagcag gaggggaggt ccgagccaac   14400
ccccgggccc actccgctgg gcctccagtc ctcaccagga cctccaccca cgaggacaca   14460
atggccaggc cagactccac ccccatttca cactcacaga cgctgaggct gaacaaggcc   14520
cccgccctgg ccgacagtgg tgtgccagc ttggtgcctg cccgcccctg ggcactgcgg    14580
ggaggacaag gctggctgag tcggggatga ctcacggaga gtggtctgac ttttattagc   14640
atcaatggga gggatgcatt agggtcagga gccaagtttg gcctggaaag tccatctgac   14700
tcctgttggg gcctccaggc ttgggcaggg ctgaccgaga gcctccactg cccactgccc   14760
gcccagttgg ccgctgtcag ggcctgccac ggggctggg ccccagtgca atgaggaccg    14820
ccgtaagcca cccttccttt ctggagggca ggtgtgagtg gctagagcgg gcctgggct    14880
tccatcctcc cccagccctt tggggcagct gctgagcacc cccttcatgt gtcttgactg   14940
tcagcatggc atttggggga gaactgaggg cctctgaggc aggaaggaga catcagaggg   15000
cagggacctc aaagagggcc tcgccctgtg ccaggagacc agcgactcct ggagcagtca   15060
cagaagcctt cctgtaggag gcgagattcc agtttgtctt tgaaggagta acttggcagg   15120
ggagagcatc ttgcttagga gggtggagac atgaggtcca ggtgttggtg aggtgtggag   15180
cgcaggcagc acatccagcc aggccccgtc accttccacc ttcttcaccc cctgccccac   15240
agtggcctcg tccacccaga tctggcctca ggtgcccaag gcttctctgg tcaaaagcct   15300
tacccggagc ccagctgccc gggcttccag aaggcagccg ggtgattctt gggaaagatc   15360
tagaatcccc aagctttctg ggagctgagg tcctggcaca gggtctctca gccttttcc    15420
accaggccca gccccatccc ccatttccgg gtcaacagta gcgtgctgga aacttctgtg   15480
ggccaacctt gtaagaccac agcggaggcg gacgcagagc ttggcctctg ctttatcctg   15540
cgggaccctc tggggcagg agggccactc tgacggccat tgtgtgaagg ccccatcgtt    15600
gatgttggga agcactgtga ctggctgccc agggacccag gttccgcttt ggggagatcc   15660
```

-continued

```
acctgctaca aggagggcag tgctgggacg tcactcagca ctaagggccc actagcgttt    15720
gggatgtcgt ggggaggggg ctgtgtcccc ggatctccca ccagggccag gacctccctg    15780
tggtctctcg gtgcaggtgg aggacgccat gctggacacc tacgacctgg tatatgagca    15840
ggcgatgaaa ggtacgtccc acgtccggcg gcaggagctg gcggccatcc aggacgtggt    15900
gagcgtgggg acggctgggt ggcagggcgg tcagcttctg cttggactgc agttcagaga    15960
acaggcgcag ggtggccagt gagaggtctg gccaggcacc gaggggttc caggacacag     16020
gccagagttg cccctcaggg ctggggggcaa aaagctccca ccctctgtct gcccaggaca   16080
aggccgccta ccagattctc gagcccagt gcaaaacgag agggcagggc cctgtattca     16140
gaaacactga aggatttcaa gagcattaaa gcaaatacgg ggccgaacat agtggctcac    16200
acctgtaatc ccagcacttt gggaggaggt tgaggcaggt gaattgcttg agcccaggag    16260
ttcgagacca gcctgagcaa catagggaga ccttgtctct actttaaaaa aaaaaaaaa    16320
agaaaagaaa aaataaaagc acatacacg cacaggccct gtgaacaggg cggggaagct     16380
gcctggctcc agcaggtgtt ctgtcaccag caggcaggca gcgcagcttg agagagctcc    16440
ccttaccagg gcccggctgt gcaatggctg gagcccagc agaagcagct gcaataccag     16500
tagccccagc cctggcctgc agggaacccc acctggatac ttgtggtgcc tcagtttccc    16560
catatgtgct gcccgcctcc tggggtctcg ggagcacatc accactccct cccttctgtt    16620
cctgtagttt ctgtgctgtg ggaagaagtc tcctttcagc cgtctgggga gcacagaggc    16680
tgacctgtgt cagggagagg aggcggcgag agaggtgagg gggggacctg gatgctggcc    16740
aggcaagacc ctcgggggct ggacaccctg gggcccaacc ccaagaccca gggccatcct    16800
cccaccccac cccttggcct ccccagaccc ttgggaactg ccgctgaagg gctcagggaa    16860
ggttctgatg tgatcggagg ctagttaggg ttcatggtac gccaagccca ttgggtggcc    16920
aggctgggct caagacataa acacaggccc ctttgcccag ctggacgcag gccccatgcg    16980
ccattcactc cttcaagcca gttccagcct ggggacttcc caaggccagc taagtccaca    17040
gaagcctctt ggagtgcacc catgagggct ctgtgccaag ggctgcaggg ctggtgtggt    17100
gggctctgtc taggggaag ggtgcaggcg tcctggggg catcagaagg agttgaaggg      17160
cactcagagg agaagaagta ggccagggtg tggccagggc ttcagcaaca acagagcggg    17220
gcccgaggcc aggaagcctt tcctccccag ggccctggga gagactgggc cctcctctct    17280
ttctcctggt gcccggcagc cctcccccag cccaccctgc cccctccctg ctcccctccc    17340
cgctcccctc ccctactgtc ctggaaacaa acccacccta tctcacagtg ggaggcacct    17400
ggcgaccctc caagaaacag aggggaggag agcaaatggc tggaggcctg gtgaggggtg    17460
gagccacagc caaggctctg agggcagaag ggctggcgct gaggatggtg ctggggaggg    17520
accagcggca ttgggggcag ggctaacagt caggacccct gtgccaccca aggagagact    17580
gaaaaggccc ccgactgaaa agcaggagcg agggcctgcc tcgagcaccc ttgggatggc    17640
agggccatgg gcccgactgc aaagcctcct ggggagccgg aagagccagc acaggcggca    17700
ggcacggagc cacccagatg ggctggcatg gcgggaggg aggcagacct gcctgcgggg     17760
gacaggaggg tgagccctga gaccctgcgg aggcctccac aggccgcccc agttgccatc    17820
atctccaggt tcagagaca ggcctgccac ctccctttc tgaaaagatg cctctggtg       17880
ccatgccctg gggtggcact ggaagcctgg gatggaacca ggaagctggg actgtgcggg    17940
gaccccctc acacccctcc accagctggc ttcctgccct ccctgttagc catcaccctc     18000
tggtcaccaa ggtgctgtgc ccggccctgg gctggatgct gggaacccag agtgaattcg    18060
```

-continued

| | | | | | |
|---|---|---|---|---|---|
| aagtggcccg | gcccagggga | gccaacgtgt | ggcccaacat | ggacgctcag | gacagctggg | 18120
| agacggcacc | ggccgggccc | agggcagtgc | cagagtgccc | acagaggcca | gccctgtccc | 18180
| actgggcttc | acctgctcgt | gctgcctttc | cctagagccc | tggggcttc | ctaggaatgt | 18240
| gccgcacccg | ccgccctgct | gccctggcat | tggcctaggt | gggcgctgca | gctccatggc | 18300
| cccacagagg | ccgcttgtcc | aggcaggag | ggccgctcag | ggcgggtacc | atgcctgctg | 18360
| ccctctcaca | ggactgcctt | cagggcatcc | ggagcttcct | gaggacacac | cagcaggtcg | 18420
| cctccagcct | gaccagcatc | ggcctggccc | tcacggtacc | ctctcgcctc | cctcactgcc | 18480
| ccttcccacc | tcctgcccct | cagcctgccc | agccccgac | tcagatggaa | gggtgacccg | 18540
| ggacaggatc | tctggtcttg | agcctcactg | gctgccaacc | tcagggagct | gctctggtgt | 18600
| gacagggcct | gcctcctaca | gctgggccgc | ccccttacac | tgcagagtcc | tgatgcttcc | 18660
| tggggagggg | cgcccgcacc | ctggggcagt | ggggcagccg | cgggtgtctc | cctcccaggt | 18720
| gtccgccttg | ctcttcagct | ccttcctgtg | gtttgccatc | cgctgtggct | gcagcttgga | 18780
| ccgcaagggc | aaatacaccc | tgaccccacg | gtagggcccc | ctgcctgccc | ccacaccctc | 18840
| tggaagggtc | ctccagctct | gctcgagagg | catctgctct | gccagctgct | aggagggagc | 18900
| cccgggacca | agccccaggc | tgacactgta | gaggaaacgc | tttgggggtg | gctgagcacc | 18960
| agggtggggt | gggagacctg | gagagtttcc | agacccaatg | caccgcaccc | catgcccac | 19020
| atggggaccc | ccctttgctt | accccaggc | cttaccaaga | cctggagatg | gatgcttctg | 19080
| ggcctccagg | ttatagcccc | aggccaggat | ctctgtgctt | gaataccca | gagctcctca | 19140
| tgcttagggg | gcagggaggg | tccaacccac | agccaggcag | ctcttcctgc | ccccacggag | 19200
| cctggcccgt | ctctgcctgc | catgcccatt | aacccaccca | cttgctcttc | ctggccatcc | 19260
| aagccctcat | ccctgggtcc | tctgcattct | acaatagcct | cacagtcccg | tctagaacat | 19320
| tctgcaacag | cctcacagtc | ccctagaac | attccacagc | agctccataa | tccctccag | 19380
| aacattctgc | aacagcccca | tgatccctc | tagaacattc | cacaatagcc | tcacaggtcc | 19440
| cctgtagaac | attccaccac | agccccatga | tcccttgct | cctcagagca | tgtggccgcc | 19500
| agccccagga | gcccagcctc | ttgagatgct | cccagggtgg | acccacacat | tgtctccact | 19560
| ccgaagcagt | tgctattggt | ccaagaggat | gctcgggtag | tcttcggtgg | ctgcaggaga | 19620
| gcgatgctgc | gcctctgccc | ctctcctgcc | acctggctgc | ccacagaggt | gaagacgccc | 19680
| ctgctgtcag | ccctcatggg | atccctgagg | ggagggtccg | agctgtgagg | agggaaggga | 19740
| gtgaaggccc | agccagagag | ccaggctcca | ttgggaacag | atgcaagggt | aagggtagc | 19800
| tcaccaaatc | cctccatggg | aacgggctgg | gagcaagcac | aaaggaaacc | acactggagg | 19860
| cagcagccca | gggcagactg | caagacactg | gtgggccacg | gcctggaggg | ctccacccag | 19920
| acacaagctg | cactggtttt | ctatgctgcg | taagaagcag | catggatgta | aggactgcaa | 19980
| gcagtgccca | tttatgatct | cgcagctctc | cagggcagaa | gtcgcggtgg | gctcagtggg | 20040
| tgccctgagc | ggggtctctc | agactgacgt | caggccttgg | tgggctgcac | tctcacctgg | 20100
| aggctccggg | gaagcatctg | cctccaggac | cattcaggct | gttgacaagt | caactcctca | 20160
| tggctgtagg | actgaggatc | ccaagtcctt | gtccctggtc | ctgtggtccc | tccaccttca | 20220
| aaccagcaat | ggtgcattga | gcaaattgtg | gtcaaatata | catcacatca | aatttaccat | 20280
| cttaaccatt | gttaagtgta | tggtttgtgg | cattaaatac | attcacattg | ttgtgcaacc | 20340
| atcaccacca | tctatctcca | gaactttcca | tcttctcaag | ctgaacctct | gtccccagta | 20400
| aacaccaact | cccattctct | gccccggtcc | ctggcaccca | ccatccactt | ttcgtctcta | 20460

```
tggattcagc tgctccagga acctcatatg tgtggggtca cacaggattc atccttttgt   20520
gtctggttta tgtcacttac tgttatgtcc ataaggtcca tccgtgttgt agcctgtgtc   20580
agaattcttg aaagagaaat cttatcagct ttcccatcat ctcacagcca catggtccgt   20640
gattaaggca ggacatttag tgggaagcgt ggagcatttt agatattctg cctgccacac   20700
ccactcttac tggacgttca gaccacgttg atgacgaatt agctctaatg gtccctaaat   20760
gtttgcacaa tttgctcaaa attctaagtc ctgggtggaa cgccaagttg gcccagccta   20820
ggccaaggtc ctaatgaagc cgacaaaaga gaaggaatgt caaggcccct ctaacttcca   20880
tagagggtgt gtggccccat ctcccaccaa caatcctgta atcccaacac tttgggaggc   20940
cgaggcagga gactgcttga agccaggagt ttgagaccag cctgggcaac atggcaagat   21000
cttgtttcta caacaacaac aaaaagaaaa cattagccag gcatggtggc acacacctgt   21060
ggtcccagcc actcaggggg ctgaggtggg aggatctctt gagcccagga tgtcgaggct   21120
gcagtgagcc atgatcacgg taccgcactc cagcctgggt gacagagtga cccctgtct   21180 caaaatataa acaaataggc gggggcagt ggctcacgcc tgtaatccta gcactctggg   21240
aggccgaggc aggcagatct cttgaggtca ggagttcaaa gccagcctgg ccaacatagt   21300
gaaaccccat ctctactaaa aatacaaaaa aaattagcca ggtgtggtgg cgggcgtctg   21360
taatcccagc tactgagcag gctgaggcgg gagaatcgct tgaacttagg aggcagaggt   21420
tgcagtgagc cgagatcgca ccattgcacc ccagcctggg tgacaagagc aaaactccat   21480
ctcaaataaa taaataaata ataaaataa ataaagtaca aaaaaattag ctgggcatgg   21540
tggtgggtgc ctgtaattcc agctactcag gaggctgagg cagaagaatc acttgaagtc   21600
aggaggtgga gggtgcagtg agccaagatt gcgccactgc actccggcct gggtgacaga   21660
gcaagacacc atctcaaaaa aaaaaaaaaa tttaatatat atatatatat gtgtgtgtgt   21720
gtgtgtgtgt gtgtgtgtgt gtgtatacat atatacacat atatgactaa ctaaataaat   21780
aaatgctaat aaataaaata aataaattaa aataaatctc caaactagaa gagtaaggac   21840
taacagggcc aagagtgtaaa cttttgtgaa tgttccaacc ataagtgctg ccctcactct   21900
cacccgtagg cccccggcct gtggattctg gtttagggga acggcaccat tcaccagggt   21960
ccagggtcat atgctgtagg actctctgca gtcttgtggt ggcatcttcc agctgagctc   22020
ctaaataatc ctgagtggtc ctgagaagcc agatcaccat cccacagggg tgggtcctgt   22080
ggagggacag ggtacatgga accctagtga atcccatggg gtctccccac tgccctgtcc   22140
tttggctgta aggcgatgc cttggctgga aacagcagta cgtgcaggag caggcagtag   22200
gctgggaagg aaagtgccgg tgccggagga agcagtgcta gtggagggga gtgggtccag   22260
atcaagaagg gttaagtgca gtcatctttc ccatcatctc atagttgcac ggtccaggga   22320
tgaagacagg acagttagca aggagagggg aaccggatca tttaagacca cagctggaag   22380
atgtccctga atgtttgcac aatttgttga aggttctaag tcccgggtcg aacaccaagt   22440
tggcccagcc taggctgagg ccctaatgta gcttggctaa caagagagaa ggaatgttgg   22500
ggcccttcta acctccatag gggggtgtgg ccccccatga agtggaaata gtgccagtgg   22560
gggagcatca aggagcaggg ccatatccta taggacttca ctgcagtctt gcggtggcat   22620
ctcccagctg tgctcctaaa tgattctgtc ccctccgcac taaatgtcct cccttcgtcc   22680
ctgggaaaag ctagacccctc tccatgaagg aaggcgtcca aagccagtca gcccttggcc   22740
aggtgaccaa tcggtctccc atgagatgtg gtgcgcttct gcggggcggg acggcacact   22800
gctgaccttg atcgggcatc ggctgcagtg caggggtgtc tggaagagct tggtaagctg   22860
```

```
agtccctgtg gctgggccac ggcggctccc ctcccctcca tgtctgcctc agggcagcaa    22920
cagctccctt ggggcagagg ctgcctgtct gccacgggtt ccaagaacct tattagagta    22980
cagtacccca tgcgcttgac agtatgccca gcctgtccag ctacaggact cagcagacaa    23040
acaacaccca ggtcagacta cacctgatgc ccatagacag ggctcagtct ccacccaggc    23100
ccaggggaaa ccgagcgctg tatatccaag cgagaagagg tcctggacac agagggcaaa    23160
ctctgctctc ctcgacgggc actgtggcct ccaccatggc ttggctcagg ctccgagggc    23220
gccttggtca gccaagaccc caagaggacc cttaggtccc tgggtcacaa ctgagtggct    23280
cagtccacac aggaacaaga ccacatgggc atcgtcactg gctgtgcctc ctgcagaaag    23340
caggccaccc ctggcgtgcc tggacacagg ggaagcacac acccaaatgc aggctgtgtt    23400
tcctccaaag agtgctgcgc acggatgact cagggtgcag gactggtcct tcaccaccac    23460
ggagtaggca tgcccggctt cgttggaccc cagagagagc ttcaggagaa agcaggagtc    23520
tctgttttta cagggtttcc ttctcaccct gccactcatg ttttttgtta aagcaaccta    23580
caacttcctc acctccaggt catatcagcc caatgtcctg tgggctgggg agacggtcaa    23640
ggtccacatg ggctaaattg tggctgagag ctaggttatt catgtaatcc caaggcaggt    23700
ccacgctgct gtccctccca ggtgagagca aaccacctt atggttttct atatgttggg    23760
atagactgaa aaacaacaac aaaacaggtg tttgctggcg aaatagctgc ttgccagtac    23820
aaatgcctgt gctgatttgt tccaattaag aagaaaactg gtgcttgctt cagccacaca    23880
tacactaaaa ttggaaccat acagagaaga ttagcatggt cctccctgcg caaggatggc    23940
acgcaaattc ttgatgcatt ccatattttt ggaacatacc tcaaaataat aagagccata    24000
tatgacaaac ccacaaccaa tatcgtactg aatgggcaaa agctggaagc gttcccttg     24060 aaaaccagcg caagacaagg atgtcctctc tcaccactcc tatttaacat agtagtggga    24120
agttctggcc agggcaatca gacaaggaa agaaataaaa agtattcaaa taggaagaga    24180
ggaagtcaaa ctatctttat ttgcagataa catgatccta tatctagaaa accccatcat    24240
ctcagcccaa aagcttctta agctgataag caacatcagc aaagtctcag gatacaaaat    24300
caatgtgcaa aaatcgctag cattcctgta caccaacaac aggcaagcca aatgaactct    24360
cattcacaat tgccagaaaa agaataaaat acttaggaat acagctaaga agggatgtga    24420
aggacctcct caaggagaac tacaaatcac tgctcaaaga aatcagagat aacacaaaca    24480
aatggagaaa cattccatgc tcatggatag gaagaatcaa tatcatgaaa atggcctcac    24540
cgcccaaagc aatttatgga ttcaatgcta ttcccattaa actaccattg acattcttca    24600
cagaattaaa aaaactattt taaaattcat atggaatcaa aaaagagcct gaatagccaa    24660
ggcaatccta agcaaaaaga acaatgctaa aggcatcatg ctacccaact tcaaactata    24720
ctacaggaat acaataacca aaacagcatg gcactggtac aagaacagat acgtagactg    24780
atggaacaga ataagaaca cagaaataaa actgcacacc tgcaaccatc tgatctttga    24840
caaacctgac aaaaataagc aatggggaaa ggattcccta tttaataaat ggagctgtga    24900
gaactggcta gccatatgca gaaaattgaa actggacccc ttccttacac catatataaa    24960
aatcaactca aggtggatta aaaacgtaaa tgtaaaaccc aaaactttaa aaaccctaga    25020
caaaaaccta ggcaatacca ttcaagacac aggcatgggc aaagatttca taacaaagac    25080
accaaaagca attgcaacat aagcaaaaat tgacaaatgg gatctaatta aactaaagag    25140
cttctgcaca gcaaaagaaa ctataaacag agtaaacaca cagcctaagg aatgggagaa    25200 aattttttgca acctatgcat ctgacaaagg tctaatatcc agtgtctata aggaacataa    25260
```

```
acaaatgtac aagaaaacaa acaaacaaac aaacaaaccc attaaaaaag tgggcaaagg    25320
acttgagcaa atacttctca caagatgaca tacacgcggc caacatttga aaaaaagctc    25380
aacatcactg accattagca aaatgcaaat gaaaaccaca atgaaatact atcccacacc    25440
agtcagaatg gccattatta aaaagtcaaa aaataacaga tgctggtgag gttgtggaga    25500
aaaaggaatg cttttacact actggcagga gtgtaaatta gttcaaccat tgtggaagac    25560
agtgtgataa ttcctcaaaa acctagaggc agaaatatca ttctacccag caatcccatt    25620
gctaggtata tacccaaagg aatataaatt gttctgccat aaagacacat gcacgtgtat    25680
gttcacttca gcacaattca caatagccaa gacatggaat caagccaact gctcatcaat    25740
gatagactgg ataaagaaaa tgtggtacat atacaccatg tagtactatg cagccataaa    25800
aagaaacgag ttcatgtcct ttgcaggggac atggatggag ctggaggcca ttatcttcag    25860
caaactgaca caggaacaga aaaccaaata ccgcacgttc tcacttataa gtgggagcta    25920
gatgatgaga acacaaggac acatgggggg aaacaacaca cagtgggacc tgttgttggg    25980
ttggggggtgg gaggagggag agcatcagga agaatagcta atggatgctg ggctgaatac    26040
ctgggcgatg gaatgatctg tgcagcaaac cgccatggca catgtttacc tatgtaacaa    26100
acctgcacat cctgcacatg tacccctgaa cttgaaagct ggaattttt tttttttttt    26160
ttttactttt taagctcttt tgttaaaaac taagacacaa acacacatag cctcggcctg    26220
cacagggtca gaatcatcag tttcactgtc tttcactgtc acatcttgac cagttttgtg    26280
accggaaggt cttatgggca gtgacatgca tgcaactgtc atcttacgtt atagcaatgc    26340
cttcttctgg atacctcctg aagaaactgc ctgaggttgt tttacattta acttgttta    26400
tataagta gaaggagtac actctaaata aaaagtatag taaatacata aacgagtaac    26460
gtagttgttt gttatcattg tcaagtactg tgtgctgtgc ataaatatat gtgccagatt    26520
tttatatgac tggtagcacg gcaggtttac ttacaccagc attgcacaaa acacaggagt    26580
aattgatacg gtttggctgt tccccaccg acatctcatc ttgaatcgta attcccataa    26640
tccccatgtg ttctgaaagg gacccggtgg gaggtaattg aatcatggag gtggttaccc    26700
ccatgctgtt ctcgtgatag tgagtgagtt ctcacaagat ctgatggttt tataaggagt    26760
ttttccccct ttcatttggc acttctcctt gctgctgcca tgcgaagaaa gacctgtttg    26820
ctcccccttc caccatgatt gtaagtttcc tgaggcctcc ccagccatgc ttaactgtga    26880
gtcaattaaa cctctttcct ttataaatta cccaagttcg ggtatgtctt tattagcaat    26940
gtgaggatgg actaatacaa aatgcattgt gctacaacat cattaggtga taggaatttt    27000
tcagctccac tataatctta tgggaccact atcacacatg tacccgttct tgaccaaagc    27060
atcctcatgc tgtgcacaac tgtactcagc caccggctga gtccccacat tggtttcctg    27120
acgtgtgggg tgagggccac tattgtgggc caactggaag ccattagagg tgcctctacc    27180
tagaaaaata gtcaaaagcg atacaataat agtcagtcaa aagctgcatt tccagaggaa    27240
tttcagaggt tagtgccacc atcaaatacc tgaaagatgc aggggcagtg atccccacca    27300
cagccccatt ccactcacct atttggccag tatggaagac aggcgggtcc tggagaatga    27360
caagggattg tcctaagctt gactccaact gcagctgctg ggccagattt ggttccattg    27420
cttgagcaaa ttagctcatc tcttgctacc tggtgtgcag ttattgatct ggcgaatgtg    27480
tccttctcca cccctgtcca caaggcccag cagaagccag gccagcaatg caccctcact    27540
gtcccacctc agggggcctct cgcctctcca gcctgtgtca gaggtaatcc tcagggtct    27600
ggatcaccct tcccttcccc ggcatgtcac actggcccat tacactgatg acattatgct    27660
```

```
aactggacat aaggcacaag aagcagcaat tattctatac ttgttggtgt cagagggtgg   27720
gaaataaatc caactaaaat tcagaacctt ctacctcggt gaaatttta ggagtctagt    27780 gctgtggggc ctgctctaag gtgatacata gattgttgca actgaaccct cccacgatca   27840
aaagagaacg acaccaggtg agcccgtttg atgtgaggaa gacaggttct tcctcattta   27900
ggtgtctgac tctggcccat ttactgagtg atttgaaaag ctgctagttt tgaatgtggc   27960
ccagcagcag gtccaggctc tgtgcaagct gttctgccac ctgggccaat gacccagcag   28020
atccagtctg aggtgtcagt ggcagacagg gacactgtgt agagcctttg ccaagcccca   28080
gtaggtgact catagctcag gcccttacag ttttggagca aggccctgtc atcatccaca   28140
gataaccact ccgttttgag aaacaggttt tggactgtgt attagtctgt tcacactgc    28200 tataaagata ttacctgaga ctgggtaatt tataaagaaa aggggttag ttgactcact    28260 gttctgcatg gctggggagg cctcaggaaa cttacaatca tggcggaagg gaaagcagac   28320
acattttaca tggcggccag tgggagaaga atgagcaaga caggaactac caaaacttat   28380
aaaaccatca gatctcgtga gaactcactc attgtcatga ggacagcatg gaggaaacag   28440
cccccacgat ccagtcacct ccggccaggt ctctccctta acacctgggg attacaattc   28500
aagatgagat ttgggtgggg acacaaagcc taatcatatc agcctgtgtc taggtcttca   28560
tagaaactaa acacttgacc aagggccacc aagttaccac atggcctgag ctgcccatca   28620
tgatctgggg attatctgac ccatgttgct ataaagttgg gcgtgcacag cagcgctcca   28680
tttgaatgaa agtgatgtat tgtgatcagg ctcaagcagg tcctgaaggc aaaagtaggt   28740
tacgtgaaga agtggcccaa atgcctgtgg cccccactcc tgctccaggt gccttctctc   28800
tccccacctg catctgttgc tgcacaggga ggtccctctc atcaattgac atgggaagag   28860
aagactcagg ccatacttac aggtggtctg ctcgatatgc aggtgctatc agaaaatgga   28920
cagctgcagc cctacagccc ctgcggcaga ggcaaaggat ggaaaattcc attccaaaca   28980
cgagaaatgg gaaggaaagg actaactgag catgaccaaa tccaaaaccc aacaggacaa   29040
aattaaatct taaagctgaa gaataatttt ctttgactct ttgtcctacc ttctggacac   29100
actgggacaa ggctcctggt ggccccactc ctacggcttt gtgtgcctgt ggctttccca   29160
ggctggtggt gcatgctggt ggctctacag gtcccgagtg tcctctgctc ccttgggcac   29220
cactacacat tgtcctgtgg ggactctcca tggcccaaac ctgtagcagt tctcggcctg   29280
ggccccaggg tctccatgac acccagtgga atccaggagc aggaactttt cctccacagc   29340
acgtgcactc cgtgcatctg cagagctggc accgtgctga caccatcgag gtttaccgcc   29400
tgcgccttct gggctggcag cccaaggaac acctgtaccc acgtgagcct ccatggggt    29460 gggccaggag tgatgcacca gcttgcaggg aggaacagag attgaggcaa gtctgggcag   29520
cacgccccga ggtctcatgg aggccctggg cccttctttt gaagccattc tgccctcaag   29580
accccggcac cctgagcctg tgatgggcat gacagtctgg aaggtctcgg aaatgccttg   29640
ggggtcattc tcccattgtc ttgatgagca gcttctgacc tccttctacc cgtactaatc   29700
tccttatcca aatttgcttg actacaccct tgctattctc tcctgaacat gctttcttat   29760
tctttttttt tttttatta tactttaagt tttagggtac atgtgcacaa tgcgcaggtt   29820
tgttacatat gtatacatgt gccatgctgg tgtgctgcac ccattaactc gtcatttagc   29880
attaggtata tctcctaatg ctatccctcc ccgctccccc caccccaaaa cgggcccccag  29940 agggtgatgt tcccccttgac gtgggcaggc taagagtttt ccaagtcttt aagttttgtt  30000
tcctttctat tatcaattct ttaactcatt tctcttttct cgccttttgc tataagcggt   30060
```

| | |
|---|---:|
| caacagaagt catgcagtac ccggagtgct ttgcttagag atttcttcca acaaatattc | 30120 |
| tagttcatcg cttttaaatt ctgcctccca caaagcccca gggcatggac acaattcagc | 30180 |
| caagttcttt gccact | 30196 |

<210> SEQ ID NO 10
<211> LENGTH: 21630
<212> TYPE: DNA
<213> ORGANISM: Homo sapiens

<400> SEQUENCE: 10

| | |
|---|---:|
| tgttgttggg ttgggggtgg gaggagggag agcatcagga agaatagcta atggatgctg | 60 |
| ggctgaatac ctgggcgatg gaatgatctg tgcagcaaac cgccatggca catgtttacc | 120 |
| tatgtaacaa acctgcacat cctgcacatg taccoctgaa cttgaaagct ggaattttt | 180 |
| tttttttttt ttttacttt taagctcttt tgttaaaaac taagacacaa acacacatag | 240 |
| cctcggcctg cacagggtca gaatcatcag tttcactgtc tttcactgtc acatcttgac | 300 |
| cagttttgtg accggaaggt cttatgggca gtgacatgca tgcaactgtc atcttacgtt | 360 |
| atagcaatgc cttcttctgg atacctcctg aagaaactgc ctgaggttgt tttacattta | 420 |
| acttgtttta tatataagta gaaggagtac actctaaata aaaagtatag taaatacata | 480 |
| aacgagtaac gtagttgttt gttatcattg tcaagtactg tgtgctgtgc ataaatatat | 540 |
| gtgccagatt tttatatgac tggtagcacg gcaggtttac ttacaccagc attgcacaaa | 600 |
| acacaggagt aattgatacg gtttggctgt tccccaccg acatctcatc ttgaatcgta | 660 |
| attcccataa tccccatgtg ttctgaaagg gacccggtgg gaggtaattg aatcatggag | 720 |
| gtggttaccc ccatgctgtt ctcgtgatag tgagtgagtt ctcacaagat ctgatggttt | 780 |
| tataaggagt ttttccccct ttcatttggc acttctcctt gctgctgcca tgcgaagaaa | 840 |
| gacctgtttg ctccccttc caccatgatt gtaagtttcc tgaggcctcc ccagccatgc | 900 |
| ttaactgtga gtcaattaaa cctctttcct ttataaatta cccaagttcg ggtatgtctt | 960 |
| tattagcaat gtgaggatgg actaatacaa aatgcattgt gctacaacat cattaggtga | 1020 |
| taggaatttt tcagctccac tataatctta tgggaccact atcacacatg tacccgttct | 1080 |
| tgaccaaagc atcctcatgc tgtgcacaac tgtactcagc caccggctga gtccccacat | 1140 |
| tggtttcctg acgtgtgggg tgagggccac tattgtgggc caactggaag ccattagagg | 1200 |
| tgcctctacc tagaaaaata gtcaaaagcg atacaataat agtcagtcaa aagctgcatt | 1260 |
| tccagaggaa tttcagaggt tagtgccacc atcaaatacc tgaaagatgc aggggcagtg | 1320 |
| atccccacca cagcccccatt ccactcacct attttggccag tatggaagac aggcgggtcc | 1380 |
| tggagaatga caagggattg tcctaagctt gactccaact gcagctgctg ggccagattt | 1440 |
| ggttccattg cttgagcaaa ttagctcatc tcttgctacc tggtgtgcag ttattgatct | 1500 |
| ggcgaatgtg tccttctcca cccctgtcca caaggcccag cagaagccag ccagcaatg | 1560 |
| caccctcact gtcccacctc aggggcctct cgcctctcca gcctgtgtca gaggtaatcc | 1620 |
| tcagggtct ggatcaccct tcccttcccc ggcatgtcac actggcccat tacactgatg | 1680 |
| acattatgct aactggacat aaggcacaag aagcagcaat tattctatac ttgttggtgt | 1740 |
| cagagggtgg gaaataaatc caactaaaat tcagaacctt ctaccicggt gaattttta | 1800 |
| ggagtctagt gctgtgggc ctgctctaag gtgatacata gattgttgca actgaaccct | 1860 |
| cccacgatca aaagagaacg acaccaggtg agccgtttg atgtgaggaa gacaggttct | 1920 |
| tcctcattta ggtgtctgac tctggcccat ttactgagtg atttgaaaag ctgctagttt | 1980 |

```
tgaatgtggc ccagcagcag gtccaggctc tgtgcaagct gttctgccac ctgggccaat    2040
gacccagcag atccagtctg aggtgtcagt ggcagacagg gacactgtgt agagcctttg    2100
ccaagcccca gtaggtgact catagctcag gcccttacag ttttggagca aggccctgtc    2160
atcatccaca gataaccact ccgttttgag aaacaggttt tggactgtgt attagtctgt    2220
ttcacactgc tataaagata ttacctgaga ctgggtaatt tataaagaaa agggggttag    2280
ttgactcact gttctgcatg gctggggagg cctcaggaaa cttacaatca tggcggaagg    2340
gaaagcagac acattttaca tggcggccag tgggagaaga atgagcaaga caggaactac    2400
caaaacttat aaaaccatca gatctcgtga gaactcactc attgtcatga ggacagcatg    2460
gaggaaacag ccccacgat ccagtcacct ccggccaggt ctctccctta cacctgggg     2520 attacaattc aagatgagat tgggtgggg acacaaagcc taatcatatc agcctgtgtc    2580
taggtcttca tagaaactaa acacttgacc aagggccacc aagttaccac atggcctgag    2640
ctgcccatca tgatctgggg attatctgac ccatgttgct ataaagttgg gcgtgcacag    2700
cagcgctcca tttgaatgaa agtgatgtat tgtgatcagg ctcaagcagg tcctgaaggc    2760
aaaagtaggt tacgtgaaga agtggcccaa atgcctgtgg cccccactcc tgctccaggt    2820
gccttctctc tccccacctg catctgttgc tgcacaggga ggtccctctc atcaattgac    2880
atgggaagag aagactcagg ccatacttac aggtggtctg ctcgatatgc aggtgctatc    2940
agaaaatgga cagctgcagc cctacagccc ctgcggcaga ggcaaaggat ggaaaattcc    3000
attccaaaca cgagaaatgg gaaggaaagg actaactgag catgaccaaa tccaaaaccc    3060
aacaggacaa aattaaatct taaagctgaa gaataatttt ctttgactct ttgtcctacc    3120
ttctggacac actgggacaa ggctcctggt ggccccactc ctacggcttt gtgtgcctgt    3180
ggctttccca ggctggtggt gcatgctggt ggctctacag gtcccgagtg tcctctgctc    3240
ccttgggcac cactacacat tgtcctgtgg ggactctcca tggcccaaac ctgtagcagt    3300
tctcggcctg ggcccaggg tctccatgac acccagtgga atccaggagc aggaactttt    3360
cctccacagc acgtgcactc cgtgcatctg cagagctggc accgtgctga caccatcgag    3420
gtttaccgcc tgcgccttct gggctggcag cccaaggaac acctgtaccc acgtgagcct    3480 ccatggggt gggccaggag tgatgcacca gcttgcaggg aggaacagag attgaggcaa    3540
gtctgggcag cacgccccga ggtctcatgg aggccctggg cccttctttt gaagccattc    3600
tgccctcaag accccggcac cctgagcctg tgatgggcat gacagtctgg aaggtctcgg    3660
aaatgccttg ggggtcattc tcccattgtc ttgatgagca gcttctgacc tccttctacc    3720
cgtactaatc tccttatcca aatttgcttg actacaccct tgctattctc tcctgaacat    3780
gctttcttat tctttttttt ttttttatta tactttaagt tttagggtac atgtgcacaa    3840
tgcgcaggtt tgttacatat gtatacatgt gccatgctgg tgtgctgcac ccattaactc    3900
gtcatttagc attaggtata tcctcctaatg ctatccctcc ccgctccccc caccccaaaa    3960 cgggcccag agggtgatgt tcccccttgac gtgggcaggc taagagtttt ccaagtctttt    4020 aagttttgtt tccttttctat tatcaattct ttaactcatt tctcttttct cgccttttgc    4080
tataagcggt caacagaagt catgcagtac ccggagtgct ttgcttagag atttcttcca    4140
acaaatattc tagttcatcg cttttaaatt ctgcctccca caaagcccca gggcatggac    4200
acaattcagc caagttcttt gccactttgt aagagggaca gccctccccc agtttctaat    4260
aagatagttc tcatgtctgt ctaagacctc acgagaatgg ctttgactgt gtggatctcc    4320
accagcattc tgatcacgac cactgagatc attgctacca gcccagaggc tctctctaca    4380
```

```
gccctgccct cctcggcctg cactggagtc accttagcac caactccgtt cgcaggagtg   4440
tgtgcttttc cagcgtgcac ttcaaaacgt ttccagcctc tcccgtgacc cggttccggc   4500
tctgctgcca cattttcagg tgtttgttac agcaacagcc ccgcttcctg gtagcaatgt   4560
ctgtcttagc ctgtttgtgc tgctgtaaca aagcaccata gaataggtca tttatacgtc   4620
atagaaattg attgctcaca gttccagagg ctgggaatcc tgcactgcag gtgatgtctc   4680
gagaggacct tcttgccgcg tcctcacatg gcagaaaggg aaagggcaca caggcaccga   4740
gctcattcct cgccctttc taaagcactg atcccaccca ggagggcgga gccccacgg    4800 cctcatcgcc ttccaaaggc cccacctctc actaccgttg cgttgggac ttttcaacat    4860 gaattttgga gggacacaaa tattcagacc acagtaagcc atgactaatg cacacagaaa   4920
actgaagttt caggatgtat ttgctctcat tcctctccat caactcaatg gcagctgtca   4980
gaaggctctc agacttgaat gggccttaat cccatctttg tcttctgttg atcggtccaa   5040
gtcaggcatt ttattgggcc tttgtctccc aaagcttgtt aaaatcctaa ctcttggagc   5100
agttggtttt tctgcccttg cggtgctctg aatttctgga tccatctctc tgttcacttt   5160
catctctgct tgtaagctgg gccttctttc tcaagctggt ctccgtctcg tgttgcggga   5220
cctaacacaa aactcgcaat gtggtgtttt cccacttcgc cccttatgct cctggctgag   5280
ccttcttgta ttcagcctgc caggtcacca ggagtgattt tagcaagttt gctgctccag   5340
ctccaccaag tccccatcac tcgggccccc ggtgcctgct ctcttggcag cagctgggtt   5400
tgggggttcc gactgctacc acaatacagc ctggcctgtc ctgactaata cagaagcagg   5460
ctctgtgaag gagggtgctg ccataagaag aaacgcaaat taacacgtat ctacacagtc   5520
tccgtggtgc acaacagtca gctttctcctg cttatgtgtc tgggctctgc ttgactgatc   5580
ttggctgggt gcattcccaa gacagcaagt cgtggctggc ctcgggcaca ggaaagggcg   5640
agagactggg gtcacagata caatctagca taggggaca gataactcaa tgtttaaatt     5700
catagggtgc tggaccaaga gagggcatat ccaaacctga tgtgctcatc catcggagat   5760
gctgggtctg gagaaggtgt agtgactggg tggactttgg caggtcaaca gaggggtgga   5820
tggcggaaca gacgatacca tgtgttcacc acactgtttc ttcctcctag gcaaatggaa   5880
agactgcatt tcccagtcac ctctatggtt agtgtggttg catgagggtc atgtgaccga   5940
gttctgacct gtgggatatg ggaggaagca acgtaagcta cttcccaatc gcccttccct   6000
ttccaaggtg accttacagg acacacgttc ccaaagtcag ctcaaagatg aagagtcact   6060
tgaccaccat atgcaagtga aaaataaccc cgagacctca gggggtattt gttaactgca   6120
acgtagccta ctttcaaagc atggttcctg gaccagctgc atcacccggg aatgcggtag   6180
aaatgcagat tctcaggccc tgcccaggcc tcccaaatta aggatgctgg ggtggagcct   6240
agcaatctgc gtctaaaaag ctctccaggg caatctgaag gctgttcctg gccaggaaca   6300
gtggctcatg tctgtaatcc cagcactttg ggattacttg agaggacctt cttgccgtgt   6360
cctcacatgg cagaaaatga agggcacac aggggatcg aggcgggtgg atcacttgaa    6420
gtcaggagtt ggagacaagc ctggccaaca tgatgaaacc ccatctctat aaaaatatca   6480
aaaattagcc aggtgtggtg gtgcatgcct atagtcctag ctactcagga ggccgaggca   6540
ggagaattgc ttgaacccag gaggtggagg ttgcagtgag ccgagatcgt accactacgc   6600
tcccgcctgg gcgacagagc cagattccat ctcaaaataa ataaataaat aaaggctgtt   6660
ccaactatat aggagttcag gatactggca agggtgtgat taaagtgaag gaccaggtgt   6720
tcccagctgt gcaggcaaag aagtgcagtg aggaaagcat gcagtacggc tgcgtagagc   6780
```

```
actcccagca aagcaggtgg gcaaagcaaa cacacagggc ctggaggtgt ggaaggggtg    6840
caaggtttgg actttaaatc tcagagagga agcaacccaa aattaaagag accccaggga    6900
tggtgatggg cacagtgggg cagatgaagt tcactggaca ggggaggtca ggggcctagg    6960
ggccgtggtg tggggttgct tgtcccagct gggatggaca caggaattgg gctggagaag    7020
atgtacatga ggtggtcttg tctaaaccct gcacatccag ctccaagcat gcaggtaaat    7080
tcccccggaa ccaactccca tgccaacgtc agactcgaac aagtccaagg atgctgagta    7140
acagtcaggg ttctccagag aaaccgagtc agtaagatgt gtacatacac acagagagag    7200
attattgtaa ggacttggct cacacaatta cagaggctga gcagtcccaa gatccgtagt    7260
tgggaacctt ggagacccag gaggactgat ggtgtaagct cccgtctgaa aggcagcagg    7320
ctcaagaccc aaggagagcc aatgtttcag tttgagtttg aagacaggaa aaaccaatg    7380 tcccagctca cccaggtaag aggacttccc tcttatttgt cacgcgcctc tgtgtgaaga    7440
gaccaccaaa taggttttgt gtgagcaatg aagcttttta atcacctggg tgcaggcaga    7500
ctgggtccaa aaaggagtc agcaaaggga gatagggtg gggcagtttt ataggatttg    7560
ggtaggtagt ggaaaattac agttaaaggg ggttttcctt ttgtgggcag gggcggggg    7620 gttacaaagt gctcggtggg gaccttctga tactcattga ccaggagaag gaatttcaca    7680
aggtcaattg attagttagg gtggggcagg aacaaatcac catggtggaa tgtcatcagt    7740
taaggcagca actgtctact ttcacttctt ttgtggttct tcagttgctt caggccatct    7800
ggatgtatac atgcaggctt gggctcagaa ccctgacacc actcagccat tttgttctat    7860
gcaggccttc agtgggtggg atgaggccct ctagaaaata aaaggtttcg ctctccctct    7920
ccctctcctt ctccctctcc gtctccctct ccctctcccc acggtctccc tctcatgcgg    7980
agccgaagct ggactgtact gctgccatct cggctcactg caacctccct gcctgattct    8040
cctgcctcag cctgccgagt gcctgcgatt gcaggcacgc gccaccacgc ctgactggtt    8100
ttggtggaga cgggattttg ctgtgatggc cgggccggtc tccagcccct aaccgcgagt    8160
gatccgccag ccttggcctc ccgaggtgcc gggattgcag acggactctc gttcactcag    8220
tgctcaatgg tgcccaggct ggagtgcagt ggtgtgatct cggctcacta caacctacac    8280
ctcccagccg cctgccttgg cctcccaaag tgctgagatt gcagcctctg cccggccgcc    8340
accccgtctg ggaagtgagg agtgtctctg cctggccgcc catcgtctgg gatgtgagga    8400 gccccctctgc ctggctgccc agtctggaaa gtgaggagcg tctccgcccg gccgccatcc    8460
catctaggaa gtgaggagcg cctcttccca gccgccatca catctaggaa gtgaggagtg    8520
tctctgcccg gccgcccatc gtctgagatg tggggagcgc ctctgacccg ccgccccatc    8580
tgggatgtga ggagcgcctc tgcccggccg agacccgtc tggaggtga ggagcgtctc    8640 tgcccggccg ccctgtctga gaagtgagga gaccctctgc ctggcaacca ccccgtctga    8700
gaagtgagga gcctctccgc ccggcagcca ccccatctgg gaagtgagga gcgtctccac    8760
ccggcagcca ccccgtccgg gagggaggtg gggggggtca gccccccgcc cggccagtcg    8820
ccccatccgg gagggaggtg gggggggtca gccccctgcc cggccagtcg ccccatccgg    8880
gagggaggtg gggggggtcag ccccagccc ggccagccgc ccgtctggg aggtgagggg    8940 cgcctctgcc cggccgtccc tactgggaag tgaggagccc ctctgcctgg ccagccgccc    9000
cgtccgggag ggaggtcagg gggtcagccc ccgcccggc cagccgcccc gtccgggagg    9060
tgaggggcgc ctctgcccgg ccgccctac tgggaagtga ggagccctc tgccctctgg    9120 gcccgtctgg gaggtgtgcc caacagctca ttgagaacgg gccaggatga caatggcggc    9180
```

-continued

```
tttgtggaat agaaaggtgg gaaaggtggg gaaaagattg agaaatcgga tggttgccgt    9240
gtctgtgtag aaagaagtag acatgggaga ctttcattt tgttctgcac taagaaaaat    9300
tcttctgcct tgggatcctg ttgatctgtg ccttacccc  aaacctgtgc tctctgaaac   9360
atgtgctgtg tccactcagg gttaaatgga ttaaggtgg  tgcaagatgt gctttgttaa   9420
acagatgctt gaaggcagca tgctcgttaa gagtcatcac caatccctaa tctcaagtaa   9480
tcagggacac aaacactgcg gaaggccgga aggccgcagg gtcctctgcc taggaaaacc   9540
agagaccttt gttcacttgt ttatctgctg accttccctc cactattgtc ccatgaccct   9600
gccaaatccc cctctgtgag aaacacccaa gaattatcaa taaaaaata  aattaaaaaa   9660
aaaaaaaaag ttactcagga gacccttta  gaaatactta gggaaagata agctgtctcc   9720
ttgggatgac tgggctggtg tctgtgcata tgccttctct ggatccaagt gactttacca   9780
caccaagcct taagactgcc agactgttct ctccattgaa agccattctg caccactggc   9840
catacagaag gaatctcata ttccaggaga ctggcccaaa caggactgtt gagtggcctc   9900
taaggctttt agacgtcaaa agggtttata agaataatca tcataatata gttatgaatc   9960
agaaacatgc atacatttc  ttaaatgacc ctgtggggac tggagttaaa aagggaggag  10020
tacccagatg caggcgtcta gcagaatgga cttgcttgag aatatcaagc aagacagcca  10080
aagaggactc ctaggattgt ctcaccagga cttctgaggc gactctaatg aaatgactta  10140
aaagtgtggt ggagtggctt ctgtggctcc cacaccggcc taatcctggt tgatattgca  10200
caaccagggt gcactgacaa tctctgggaa aaaagcaagg tctaatattc aaagcttggc  10260
aaacatgacc aagactttt  ctctttcctt tgaattattt tagttccta  atttttgtc   10320
ccatatgcca cttaattctt tttattttgt attaaaagtt gtgctcttgt ctcaaccttc  10380
tttctagatt ggatcctgca tgtttttttt atcattatac ttttggcagc cctaccacta  10440
ggcttcctga aatatagcac ctttgtttt  gtttgtttgt ttgtttgttt tgagaccgag  10500
tttcgctctg tcacccaggc tggagtgcaa tggcacaatc tcagctcact gcaacctctg  10560
cctcctgggt tcaagcgatt ctcctacctc agcttcctga gtagctggga ttacaggtgc  10620
gtgccaccac ccccggctaa tttttgtgtt tttattgaga tggggtttca ccatgttggc  10680
cagactggtc tcaaactcct gatcccatga tctgcctgcc taggccttcc aaagtgctgg  10740
gattataggt gtgagccacc gcgccctgcc tgcacctttg ttatatagaa aattcttatc  10800
aacattattg tctacttta  gactttattt tgttctattg aactattctg gttctagtac  10860
catacattaa aattatagct ttataatact ttttaacatc tgacaggatg tgctccctt   10920
atcatccttc tttttcaata ttttatcatt ctcacagttt ttctcagatc aacttcacat  10980
gtaatttaca aagaaatta  aaattacatt ggtatttagg tggaaattat gttaaattta  11040
tgtactaatc tggagaagtc ttgttttgta ataataattc ttaccatgaa ggaaaatagc  11100
ttctctctcc gctgattcat gttttttctc atgtctctca gtagagttta tagctttttt  11160
tgtataagtt ctcataattg cttgaatata ttcctaatta tttaaaaaa  aaaaaagaa   11220
aataaaaggt ttccactttc aaagttcccc ttcttgttaa agaatgaatc ataagtgtta  11280
gaaataacag tttctttttt tttttttttg gaagcatttc ccattttat  tcataaaatt  11340
attacttaaa attgcaaaag tagatttaca gagccacagg taacaaaaca ggaaatgaaa  11400
tgttccagac attccgaaaa gttcgaaaga aacacaccct agcctcaaaa tctccggtta  11460
aaccgtggtt gcaacacagg ttctatttat tcctgcattt tctcaataag ttcttcttta  11520
tatttgcctt tctctttcc  aacttgttga gacttggctt tgcgttcaag aattttttc   11580
```

```
cgatccttgt ccagttttag cctggtgata accaccttgc ttgggtgaat gcccacgtgg    11640
acagtcgtgc cgttggcctt ctcacgctgc acccgctcga tgtagatgac atatttcttt    11700
ctgtacacct ggattacctt gccaatttgc tgacctttgt agtgtcctcg aactacctgg    11760
acctcgtcgt ccttgcggat gggcatgagg cggacattgt acttctgccg cagctccttg    11820
gagagcgggg atgacatgat cttcctgcgc acgtgtgagg gggcattgaa gtaacgtttg    11880 cggttttttac tgcggtccga ggtaacgaag ggattgaact tcatggtgac cctccggcta    11940
ctagctgcct cagaccctca acagtttctt ttaaagacta actttcttca agcctccttg    12000
ctttgtgcta ataactcttt gttaagctct atcctatgta actgttggac atcctcacca    12060
acatattcca gctcacagcc tatgccccttt ccttatttgg tgatgttatt gcctcctgag    12120
acttttcata agcaacttat ttgttcttcc ctgcacttac ctatttagga agttttcagg    12180
ttattagcaa atcgggtatc actttaagat tgtgaggtcc cactccagcc aatggatgca    12240
ggacatagca gtaaggacaa cccaaatgcg taagggataa atacatctgc ttttcctttg    12300
ttcaggtgtg ctctcaccat tgttccatct gcgactgagc accatttctg caaaaagtaa    12360
agatggcctt gctgagagat cttttgtctc tgtgctgact tttcttcacg gcactgatta    12420 tcttttttcta acaattttgg tggcaattgt atggggatat actttcctcc agggggcgtct    12480 ctagtcctct ctcacgaggg ggcactctgc tgcctcttgc agtggcctca ggggtaaggg    12540
accgagaccc atccggtgtg accaataaac ccggactctc agcaatgtgg aaagaaactg    12600
gccaacaacc tggggtaaag gatcctcaca taccgaggtg acgactctgt gcacagacca    12660
acgaaggaga agccacggga gccggtaaag tacttcttgg tggtcagatt ctgggggggct    12720 gaatgtgtgt gtgcacgtga atgatcacag acaaccctgc ttgcggtgtt gtgtggatgg    12780
tgacaaatcc tactgctgga cggagtgttt gggtcctctc tgtgcttcca gagcaacctc    12840
agatggctta gggcagatcc tgccatggga tttatactgg cacgccaact ctaagagggg    12900
cctagctctc ccttggggga gtggccagag aggacaacac aagtgggaag tgtgcaaggg    12960
accttcagag gaggaaaggg aggaaacagg tcaacctctc acggcaggca aggcaagaca    13020 cccccctggtt tgaggggggtc ttctgcaaat ttcagggagt tgaacctcat acaaacctcc    13080
ggtagtaaga aaaatattca gagttctcct ttcccttctt ctcgggggaa gaaagaggct    13140
aagctccact ccgcttgtcc cttccctagg gaaggggaa ggagaaggga gaatagcagc    13200
ataagcgact ggcagaggca gggaaagacc ggcagaaagg aaagagaaac tgggagagga    13260
agtcagagag agagagagac aaagagggag tcaaagagag agaaagagag agacagagag    13320
tcagagagag agaaagagag acagagagac aaagagggag ttagagagag aaaagagag    13380 acagagagta agagagagag agtcagagag agagaaagag aagtagtaaa gagaaaacag    13440
tgtaccctat tccttttaaaa gccagggtaa atttaaaacc tataattgat cattgaagat    13500
cttctctgtg accctagaac actccaatac tgcctgtaaa gaagcaagac gagtcacacc    13560
agtgactgca agaccctaga gctattaacc agttagtcca aactacccac cctgttgtta    13620
cagtaataga tgtaaaagat gccttctggg cttgtccatt tgcagaggac agccaggacc    13680
tatatgcctt tgagtgagaa gaccctcact ccggtggaaa atggtaatac caatagacgg    13740
tcttacccca agggtttacg gagtctccaa atttatttgg tcaaatattc aaataagtca    13800
tttaattagc aaaggtaaac agaaaattga gcttgaatgg attgaaggca tcacattctt    13860
gcctctgctg gagactaaat aagagcttag aaaattttgg gattagttgt atggataccg    13920
tcgtctatgg gtagactcat gccctaaaaa caaaactctt acacaaaaag ctcacacgag    13980
```

```
acagaccaaa ccccctcatg tggcaattac cagaaatcca acaggtggga aggttaaaac   14040
atctattagt aactgcccct gtcctagctt tactctcctt aagcagccat tccaccttgt   14100
tggtggtgta aacaacggcg tagcccaaaa acactgaggc cactgacaac ccatagcctt   14160
cctaatcaaa aatccttaac ccagtaaccc gcggatggtc caaatgcatt caatctgtag   14220
cagcaacttc tttgctgaca gaagaaagta gaaaataaac tttgagaaga aacctcattg   14280
tgagcacacc tcaccaggtc agaactatcc taagtcaaaa aaaaaaaaaa aaaaagaaaa   14340
gcaaaaaggt agcttactaa ctcaaaaaat ttaaatatg aagcgattct gtcagaaaaa    14400
gatgatttaa cattaaccac tgatcattcc cttaacccag caggtttgct aacaggggat   14460
ctaactctta atgaattacc atacaaaggt ccaaccagac ctagaaggaa ctcccttcaa   14520
gacaggacaa tagatggttc ctcccaggtg aatgagggaa aaagccacaa tgggtattca   14580
ttaagtaatg gggaaatagg agtagagtta ggaaaattgc ctaggagttg gggagttgtt   14640
tgcactgagc caagccttaa gatactgaca gaatcaggaa ggagtcattg tgaaaagtga   14700
agtagagttt acctcctcaa aagactttcc tcccccatct aatcaggaat aaatagtaac   14760
ttctcttagt agcaaaatgt attcaaagac cagcgctaac attcttaaat atctgctaga   14820
cgtaataaag aaatcaatgt actttatgtc cttagctccc acaatttagt ctaaatgttt   14880
gctctggcat gcttatactg gtccaggcaa gcattaggtc ctatcctgtt cctcttcctt   14940
gtttgtgtct cacatgtccg tgtgaaaaga ccaccaaaca ggctttgtgt gagcaacaag   15000
gctgtgtatt tcacctgggt gcaggcgggc tgagtccgaa aagagagtca gcaagggtg    15060
gtggattatc attagttcct acaggttttg gggtaggcgg ttgggttagg agcaatgttt   15120
tgccagcagg gggtggatct cgcagagtac attctcaagg gtggggagaa ttacaacgaa   15180
ccttcttaag ggttggggag attacagagt acattgatca gttagggtgg ggcagaaaca   15240
gatcacaatg gtggaatgtc atcagttaag gctattttca cttcttttgt ggatctttgg   15300
ttgcttcggg ccatctggat gtatacgtgc aggtcacagg ggatatgatg gtttagcttg   15360
ggcccagagg cctgacagtt tgaaggtgtt tttacctttc tcagcattcc acgagttact   15420
tcttcctttg ttctcctctg cctttgcctc ttttaaaaag ttctaagttg ctagccagtc   15480
gggacaaatg cagaatgtca ggcctctgag cccaagctaa gccatcgcat cccctgtgac   15540
ttgcacgtat atacgcccag atggcctgaa gtaactgaag aatcacaaaa gaagtgaata   15600
tgccctgccc caccttacct gatgacattc caccacaaaa gaagtgtaaa tggccggtcc   15660
ttgccttaag tgatgacatt accttgtgaa atcccttctc ctggctcatc ctggctcaaa   15720
aatctccccc actgagcacc ttgcgacccc ccactctgct cgccagagaa caactccact   15780
ttgactgtaa ttttccttta tctacccaaa tcctataaaa cggccccacc cttatctccc   15840
ttcgctgact gtcttttcgg actcagcccg cctgcaccca ggtgaaataa acagccgcgt   15900
tgctcacaca aagcctgttt ggtggtctct tcacacggac gcgcgtgaaa cagaatgtga   15960
ggtcccgttc cagccaatgg aaaccagaca cagcagtagg gtggacgcgt caggttataa   16020
atgaccctgt ctcctttgct cagtgtactc tcgtggcaaa actgctgccg agtgtaccct   16080
ttctacagaa agtataaaaa tgaccttgcg taggaaatta aatttatgtt caagtgccat   16140
ttctttatgg caccggggag caagcatttc aaacatcatt tgtaccaatt ctaagttaaa   16200
tttggactaa acaaggtctt attaatagca aaggataatt gaaatcccaa acttacaagg   16260
ttttcaacaa aagtaaagtt tgctaaaagt taacagtata acatgtatta tcctaacttc   16320
taatgttgtg accttaggct gtctagtcca cagacataaa ggaagttcgc tttggaaaag   16380
```

```
aatggttatc atctttgaga gaaaaaaaat tgtttcgaag gtttaagcaa gttttgaaat    16440
attcattgta aaggaaacat attggctaaa gttaaagggg tatcttccag tttttctgtg    16500
aactggacat taaaataaaa gcccagtggg ttttttcttaa agcgctaacc tgctctttaa    16560
caaaaattac gaaaggttaa aaattataaa agttaaaaaa aagagtctgg aaatctcacc    16620
ttgtggtcag accttaaaat tggatacata tgtctacaag gttttattaa aatgaagttt    16680
aacacgaata acacactaat gtaaaggtga aatttagctg atctggtata aaatcacaca    16740
ggaagcactg tcaaatataa aatggtgttt ggctttcttt ggtctaaaaa ctaataaaaa    16800
taggtactaa aggaaatttc tcagcaagaa ggcactaagg actataaaat ccactgctga    16860
tgtccccacc tttaaaacaa aagatcaatt tttagaaatg atatacttgg tttatcctcc    16920
acccttaaaa caaaggtct tctagcacag gccctgccct gagagtttcc agtacatcag    16980
caccagcctg gggatcccgt tctcatcaaa gggtggaaag aagggaaact ggagccagcc    17040
tgggaaggac cctgccttgt gctgctgact accgagattg ctattcgtac aacggaaagg    17100
gggtggacac gtcccaccag agtcaagcaa gcaccattat caacagaatc atgggccatt    17160
gtttctggat caagccctac caaattaaag ctaaggaaag ctgagtctat ctctttcctt    17220
tccttttccta acccagtgcc tatatccatg actattccta ccactagcaa ctctaacccc    17280
actttagaga gttctgtgg tttgggagca gaggtcactg gaagggatcc tataggcttc    17340
aaggtgcgct ttgttctccc tcctccacct cctacgactg cccctttccc aaacctacaa    17400
catcaaacta tgcctcgcct catgccaaat gacacaagca agttcttaga agtagaaata    17460
ggagacccaa ggcaaaccct agccattgaa agagggtata aagacataaa tgccggttaa    17520
aacggattaa atatcccgtt cgcacttaa gcaaaagtga ccattaagct tgtgggcgcg    17580
gtaggccaga ggctcaggat gcctcctttc cactgggacg gtcctcaaat caagcggaca    17640
tggagtgcgt ggtagctctt ttcgaagatt ccaccacctg gaataacgaa ttgtgccaag    17700
ctctttctct gctatttcct gaagttcagt gccctgtggg tcagcccccg agggccatcc    17760
agccttcatc ttccaaaacc aattttacct cgtgtctcca acaacgaggg gaaaaaactt    17820
ggcattcctt ggagacttaa aaggttgcag taaagtcagg cacctccaaa agctgaccca    17880
tcggtctgcc cttattcatc cctgagcgga tgtatggtgg tattatggag gacctttact    17940
ggacactctg ccaaataatg agagcagtac tgatgctgta gttcagttgg ctatccctt    18000
tactctggca tttcatcaac cagaaaaaga aaaaaaaatg tagcctcaat tcttacctct    18060
ttaacaacgc taataagtat actctttctt cgtaggtgtt atgtcgtacc atacatccag    18120
gagttcatca aaacaactaa gccaagacat gctaagaaag tttgaagagg aaaactatac    18180
agtaaaagag gagggaattg taggaagtaa aaagtttctg cttcaaagtt ccccttcttg    18240
ttaaagaata aatcataagt cttagaaata atagattctt ttaaagacta attttcttca    18300
agcctccttg ctttgtgcta atagctcttt gttaagccct atcctatgta actgttggac    18360
atgctcacag acacattcca gctcacagcc tatgcccctt ccttaattgg aaatgttatt    18420
gcttcctgaa acctttttgta agcaacttct ttgttcttcc ttgcacttac ctatttagga    18480
aagtttcaaa tcgggtatca gtttaagata gtgaggtccc actccagcca atggatgcag    18540
gacacagcag taaggacaac ccaaatgcgt aagggataaa tacatctgct tttcctttgt    18600
tcaggtgtgc tctcaccatt gttccatctg cagttgagca ccctttctgc agaaagtaaa    18660
gatggccttg ctgagagatc ttttgtctct gtgctgactc ttcttcgcag caccgattat    18720
ctatttctaa caatttttggt atttctaaca ggcccacaca cactgtgtgg gccaagctgc    18780
```

```
ttcactcagt ccactgatca aatgctcatc tcatcctcac agacacaccc aggatactgc    18840
ttgaccaaat atctggacaa cccatggccc agtcaagtcg acagaccaaa tgaactgtca    18900
cagacagctt ctgtccttgg aacggggtgg gattccacgg actctctccc ttcacagtgg    18960
agatgctcag tcagcaagct gccagaagtt cagagctggg gaagatataa agaggactgg    19020
gcatggaagc tgcaggaact agtcaggaac tgggagtacc taggagtcag ctcctgagtg    19080
tgcaggatca tggtgaaata gaaagttaga gaaggaagag tgtgtcaata tcagagcatt    19140
gtcttatagc acaggactta accctctcct aaggttccag ggagacagtg ccaaatcatc    19200
acttgagtgg tgcttagaag cttcagggca aaagagccaa ccctaagtac atttgtctac    19260
tggggctgcc atcacaaagc accgcagaca gggtggctta tacaacagac tcattgtctc    19320
acaatcctgg cggctggagt ccaagatcaa ggttttgcaa ggctagctcc tcctgaggcc    19380
tctcttggct tgtagatgac cggggccttc tctctgtgtc ctcacagggt cttccctcag    19440
tgcgtgtccg tgtcctcacc tcctcttgta agactccagt cctatgagat taggacccac    19500
tgtcatgaac tcattactg ttgattacct ttgttttatg tttttttgttt ttttgagaca    19560 gggtcagtct ctgtcaccca ggctggagtg cagtggtgca atcatggctc actgcagcct    19620
caaactcctg ggctcaagga atcctcccac ctcaatctcc caagtagctg ggactacaga    19680
tgcataccac tgtgcctggg tgtattagtc tgttattgca cagctataaa gaaatacctg    19740
agagtgggta acttataaag aaaggaggtt taattggctc acggttcata gctgcttctg    19800
gggaggcctc aggaaagttt cagtcatggt ggaaggtgaa ggggaagcag acacgtctta    19860
cacggccaga cagttcctcc tacactggct gacactctct cctgccacct tgtgaagaag    19920
gtgcctgctt ccttttctgc catgactgta agtttcctga ggcctcccca gccatgtggg    19980
actgtgagtc aattaaacct cctttgttta taaattgccc agtctccggt agtatcttta    20040
taacagtgtg aggatgagct aatacacaca ggaagcagca atgccatcaa agagccaggg    20100
gccttgactg gcagaactag tgagaccatc accaaaacat ggcattcctt gggcaaggca    20160
ggtgcgcagc cagcaaggta ttgcttaatc tacatgatca aaagacatca ggatggttgt    20220
tcaggaggct gagaacagcc atcctattat ggctgagttg tgtcccctca aaatttatat    20280
actgaagtct taaccccca ggacctcagt gtgtaagtat ttggagaaag ggccttaaa     20340 gatgtagtta aattaaaatg aagacattag ggtgggccct aatccaatct gactggtgtc    20400
cttgtaagaa gaggagatga ggacacatgc agaggcatga ccacatgagg acacagggag    20460
aaggtggcca tctgcaaatc aaggagtgag gcctcgggag gaaccagcac taccaacacc    20520
ttgatctcgg acttccagtc tccagaacca tgagatgatg aaagtctgtg tttaagctgc    20580
ccagtctgtg atattgtttt gcaaccctaa tagatgaata catacccaa tgaaaaagca    20640 tgatctcttg cccagtttct gcacctgaga cagttttcaa acccaaaccc cactgattga    20700
aggagggatt aggtcccagg aggacggacc ctgcagtacc atagcaggct ccccagtcc     20760 ttccccaccc caccactaaa ggtgtatttc agtaactgtg cactaggaaa agggcaatgc    20820
ccagggctgg gggactccgg gaccaagttg acactgagag ctggagtcaa ggtaccatca    20880
tgggcccact agagtagggc gtatggaggc cagcaaagtg caatcctggt ccacctctag    20940
ctcacactga gtcatccctt tgcattccca gaatgctgca tattccccca daccctaaaa    21000
gtacactcag acaatcttgg tagttggcag aatcctcacg taggctcatt gtcctgtagg    21060
gtaaaaacta tcatagtgtt accaagtaga aacttctgaa actgcccacc accttagcca    21120
aggcaataca ccaaaaagaa aatctcattg gtggggaatg gcagagatgt gggccccttt    21180
```

```
ggaagacttg aaggttgcag gtgaggcgat tcccatcatc tcccccattt tccagagaat   21240
gctaacagac tactgtcaac ttgtgatggg aaatttatg cgtccacttc actgggccat    21300
ggtgcccaga tgtttggtta aacattattc tgggtgtgtc tgcaaggtgt ttctggatat   21360
gcttagcatt tgaatctgtg gactgagaaa agcaggtcac tctctctggt aaaggtgggc   21420
ctcatccaat cagttgaagg tctgactaaa acaaaaagat taagcaagag aaaattcgct   21480
ctccctgcct gtcttagtct gtttatgttg ctataaagga atattggagc tgggtaatt    21540 gataaagaaa agaggtttat ttggctcatg gttctgcagg ctgtacaaga aacatgacat   21600
ctgcatctgc tgctggtgag ggcctcaggc                                     21630
```

<210> SEQ ID NO 11
<211> LENGTH: 37113
<212> TYPE: DNA
<213> ORGANISM: Homo sapiens

<400> SEQUENCE: 11

```
tgtgggctcc cctctgctga tgggttcccc tctccagctg tggcttccct ctgctgatgg     60
ggtcccctct ccagctgggg ctccctccac tgatgggggtt ccctctacag ctgtggctct   120
ctccactgat ggggtcccct tccagctgg ggctccctcc actgatgtgg tccctcttc     180 agcttgggct ccctccactg atggggtccc ctcttcagct ggggctcctc tccactgaca   240
gggtctcctt tccatctggg gctcccttgg ctgatgaagt cccttctcca ggtgaggctg   300
ctctctgctg acagggtccc ctctccagct aggtctcctc tctgttgata gggtcccctc   360
tccgggtggg ctcccctctg ctgacggggt cctctgatgg ggtccctact ccaggggggc   420
tcccctccat agatgagctc cccttcctgg gttgggtgac cctccgccc tatctgtgtc    480 tgcaggttgg ggctaggcag tgctggccag catctgacaa cctcccctttt ctgttcttgg   540 gcactgctca cttattcagg tctcagccag gcagccccctc caatggtaat cttcagagtc   600
cccttcagca acacagcttc ccctctgtgg cccagctcat gctgaagtaa acaaggcaat   660
gtcattaacg gctggtatca gcttgtacgg ggaaccagtg gccccagaag cctctgggga   720 gcccaggct gtgaggatca ggggtccgga agagcctcta gagcgggaga aagaggcctc    780
aggggtccct cctcacaggg gatggtgaca acacggtagg gaatggaggg gtcagggctg   840
ggtccaggac acggtgaccc tggcagaaa aggccgggcc tggctggcac ccgcacgaag    900
ggaacggagc cagtgtggaa aagcaggccc gcgtcctctt ctgcactccc agccccttta   960
aactacacac agcttgtagg aaggggatca gaggcccctg ggcgtccat ggctatgctg    1020 cacctgggga catgaagcct agggtagctc agccagctct ggtcacggct gacagacagc   1080
ctcaccccaa cagcctcacc catccctcct cagggaacag gtcctaaca agctgctttc    1140 cccatcccag tgttgaacaa aaactcatgg gtttagacaa gagtgaaggt gactcctcca   1200
ccacccatcc cacctccagc aggcagccac cccaaaaatt attgatttat taataaatca   1260
atgacaggtg ccagccagcc ccacctgtcc ccaacctgca aatgcagaca ggggtcactt    1320
ggtccaggga gaggagaccc tcagtggagg ggagacaccc tggagagggg acccccatcag  1380 caaaggggag ccccagctgg agacagtaaa taggcagact attcactgtc ttccccctca   1440
agccaggccc acagagtcac agagtatagc caccagcctc ctgggcccac ccggggaggcc  1500 ccaaccacac tccccctgct cagctcagcc cggatttctg gattctgctg cctgccaggg   1560
atcctgagga ggagatggta tcagagcctc accagcccctt ctcataccca ggagtcctca   1620
tgatgataac agtgtgtgcg ccaggctgtg caggtgctgg ccgggatcct ctgaggggac   1680
```

-continued

```
gagatctcca tgggagggca ccactctgat gtccatcctg ggcttccgtg ccctgcctg    1740 gccactgccc gctgctcttg gtcaagatca tggaccctca gaggccaacc aggcctcagc   1800
ctgtgcctac agcatcctct ctactgccgg gcttctgaat tgctccttcc tcctgtctcc   1860
cacccagagc aagaacgaag gggaggcccc cagagcctg cagcgccggg agagactccc    1920
atccccaccc cgcatgccat caacacaaac tgccggagag tttaggggat cccacgactt   1980
ggggtctcca aagagacccc cgggacatct catcgagacc ccctgggca ctgcatgctc    2040 aggcttccca ccccctggccc accccatggg gtgtgcccag tcccgcatct caccccatat  2100
ccatgcatgc atgcatgaac ctgaaagcac cccacaccct ctggtgctca gtcctcccct   2160
cctccctggg gtcccctccc ctccctgccc cccaagcctt gcatccccct gcaaacctca   2220 caaggggggaa ctatttctgt cctgaaagca gagagggccc ttttcttggg acctctccgc  2280
catctctgcc tccactccca gctgctgtca gctctggcct ggcccctgca ggaagcaatc   2340
actggtctcc ctgtttccca tctggcccca aggtctgttc ttgcccttcg accagagagg   2400
tttgaaagca caactcgggc cctgcgtgcc ctgctcccca gggctccaca cctctgagca   2460
cccgcgcagt aacggaggct cccagccccg cctcgcccca gggtcccctc caacactctc   2520
tggccttggg cctttgctat acccggggcc tggaagggcc ccctcatccc caagtgtca    2580 ggcaaaggtc tcagagcact gtccctgccc ggcgtgcttg gtcctgactg ctaggcccca   2640
aatcattcct tttcccatta cctcttggtt tctctgtagc tggggtcact accccaaatt   2700
cttgaattga ctgacgtgtc caactatttc atgttttccc cctctacact gggagcccta   2760
caagggcagg gccccctggg caagaatagt gccagccagg agccctgga gaagatagct    2820 acacatgtgc cccaggcccc agatggcact cagccctgcc tgtcaatgct ggacataggg   2880 cagttttttat cctggctttc tacacaagga ggaaagacta accatgccag cgggcagcgg  2940
ccggatcacg tatgtcagta gaactctgac ccctgagaag cctggaagcc aaaccacacc   3000
tctgtagcaa tcacgccaca gactcaggcc acggctaacg gctgccagtt cacctatttt   3060
tgcccccaac tcaagaccaa ctggaggaag gcaaatatgt ccctgacgaa gggtggccgc   3120
ctccagcctc cccagcccag agcctcagcc tccccagccc actgcctcca gcaacacaca   3180
tctgaagcct tctctgttgg ttggtttttat tggtattttg gaagattgtt tgttttttgt   3240
tatgagatgg agcctcgctc tgtccccag gctggagtgc agtggcgcga tctcggctca    3300
ctgcaagctc cgcctcctgg gttcaagcca ttctcctgtc tcagcctccc gagtagctgg   3360
gactacaggc acccgccacc gtgccaggct gattttttg tattttagt agagacgggg     3420 tttcaccatg ttagccatga tggtcttgat ctcctgacct catgatctgg ccatctcggc   3480
ctcccaaagt gctgggatta caggcgtgag ccactgcacc tggcctttgg aaggtctttt   3540
atacctttat tgagataaaa ttcttatgac ataaaactta gcataaactg tagacttagt   3600
tggtgtgact ttagagtagt ctcagaattg tgcaaccatc accactgcct acttttagaa   3660
cattttcaac atcccaaaga cagaaccccg taggcacctg ttagcagcca ctccccaccc   3720
agtccacgaa gccccaggca gccactcacc aatctacttt ccattaattt gcccattcta   3780
aacacttgaa aaaaatggta tcacaatggt cttttgggtt tggcttcttt ccctcagcat   3840 catacccctca aagttcatcc atgttgtagc tcgtatcggt acttcattca tttttatggc  3900
tgaataatat tccactgtat ggatagaccg atattttgtt tatttattta ttcattgatg   3960
aacatttgaa ttgttcccac ttttttagcta ttaaaactag tgctggctgc gtgcagttgc   4020
tcatgcctgt aatcctagca ctttgggagg atgaggcagg cggatcactt gaggccaaga   4080
```

```
gtttgagacc agcctggcca acatggtgaa accccatct ctaataaaaa tacaacaatt    4140
agccagacac ggtcatgcgt gcctgtaatc tcagctactc aggaggctga ggcagggaa    4200
tctcttgaat ccgggggca gaggttgcag tgagccaaga tcgcgccact gcactccagc    4260
ctgggcaaca gaccaagact ctgtctcaaa aacaaaaca aaacaaaaca aaacaaacca    4320
gtactgctat gaacatgcat gtgcatattg ttatacagac atatgctttc atttctcttg    4380
gatacacaca cacacacaca cacacacaca cacacacacg tatatctagg              4440
actggaattg ctgattttta tggaaactct atatttagca ttttgagaaa cggccagtct    4500
gttttccgaa gtggctgcac tattttgcat tcccaccagc aatgaaggag ggttccaatt    4560
tctccatacc tctgccaaca cttgttattg tctgtctctt ttatttatag ccatcttgat    4620
gggtgcatcg tggtatctcg ctgtgttttg atttgcattt ccctgatgac taatgatggg    4680
gacatctttt catgagctta tcggtcatat gtacatcttc tttggagcaa gctctattct    4740
aatcctttgc ccatcattaa aggtaggtgg tttgtcttct tgttgataag ttagagttct    4800
ttacatgttt agatactagt cccttatcaa atagatgatt cacaaatgtt tgctgtcatt    4860
tcttgggttg tcttttccact tccttgatgg tgtcttttca cgcacaaatg tttttagctt    4920
tggccaagtc caatttatct attttttctt ttgttgcctg tgcttttggt agtgtatatt    4980
aaaaaccatt gtttaacaca aggtcaccaa gatttattcc tatgttcttt cctaaggatt    5040
ttattttttc ttttctttt tttctttt tttgagacaa agtctctctc tgtcgccaaa       5100
gctggagtgc aacggcacaa tctcagctca ctgcaacccc tgcctcctgg gttcaagcga    5160
ttcttctgcc tcagcctccc gagtagctgg gattacaggc gcccaccacc atgcccagct    5220
aatttttgtg ttttttagcag agacggggtt tcaccatgtt ggccaggctg gactcaaact    5280
cctgatctca ggtgatccac tcgcctcggc ctcccaaact gctgggatta caggtgtgag    5340
ccactgcgcc tggccttcct aaggatatca taatttagt gcttacattt aggtctacga    5400
tccatttga gttaatttt gtgcacagca tgaggtaggg gtccaacttc attcttttgc      5460
acatggatat ctagttgtcc cagcaccatt ttctgaaaag actattcctt ccccattga    5520
attgtcttgg taccttgtc aaaaatcaac tgatggccgg tctgaaggta gtgagttatc    5580
tcaattgatt gttcacagtc agttacagat ggaacacctc gttctactct ttcccgcctt    5640
ctcactgctg cacttgaaca gtctttaaaa aaatcaattg accataaatg caaggatttg    5700
ttcttggagt ctcaacttta ctgcattgat ctgtaggtct atccttatgc cagtaccaca    5760
ttgtcttgat tactgtagct ttgcagtaag tttgaatcag gaaatgtgag ccctccggtt    5820
ttgctcttct cttttctagat tgttttggct attctgaaac ccttgtattt ccttatgaat    5880
ttgaggatca gcttgtaaaa agacagatgg gattttgata gagattgtga agctatagat    5940
gaattcggga gtttggccat cttaacatta tgtctcctga tccatgactg caggatatct    6000
ttccatttaa ttcgatactc tttgattcct ttcaaaaata ttttgtattt ttcagtacac    6060
aagtttatg catcttttgt tgcatttatt tctaggtatg ttcttttgc caatattata      6120
aatgagattg tcttcttcac ttcatttttg gatggttcat tgctagtgta tagaaataaa    6180
atcgatgttt gtatattgat cttgtatcct gccacattgc tatgcatgtt tattagtttt    6240
aagggtttta gtggattttc tatatataat gtcatataat cagcaaatag aaagtttaat    6300
gtcttagtcc ttttgagctg ccacaacaga ctaccataaa ctgagtggct tataaacaac    6360
acaaatgtat ttcccacagt tctggagact gggatgtcca agatcaagac acccgtaggt    6420
ttggtgtctg gtcggggcct acttctgggt tcatagatga ctgtcttctc gctgtgtccc    6480
```

```
ccccatagtg aaaggaaggg gcccagggtc tttctaaggc ttcttttata aggacactaa    6540
tccaatatag gaaggctctg ccctcataac ctaatctccc aaaggcctca cttccaaatt    6600
ccatcacctg gggagtaaga atttcaacac tgggggggaca cagatattca gacatagcat   6660
ttttcttctt cctttctaat atgggtgccc ttgacatctt tttcttacct aattgccctg    6720
ccagagcctt ccagacagtg ttgaatggaa gtggggagca ttcaccccac cttactcctg    6780
atcatagggg aagaactatc cggctttcac cactgagcac cacgttagct ggggtatttt    6840
tgtcagcgct ctttatcagg tggaggcagg tcccttctat ttctagtgag ttcagtgctt    6900
tttttttttt ttaatcaggg aagagtgtga gcttgtgttt gggtgccttc cctgcgtctg    6960
ttgagatgat cttacggttt ctgtctctta ttctattgat atggcgtatt tattaccttg    7020
gttgcttttt ggatgttgat aacatccaaa ctcttctgcc accccttta  atagaaagct    7080 gtacaactcc ccaacctgcc tgggcgtgtc tgcccaagat gagtgctagt ggccgactcc    7140
ctgctagagt gagcactgca taaacagcct ctgcttgtcc tcatttgagt gatcttcatg    7200
tattccacga gaaatcaagg cacaggggtc tcatggtctc atgaatggct ccaccaactg    7260
aaggtgtgct ccatcgggc  tgtgagtcac ctcacgccag gcagaaaggt ctctctgtca    7320
aacatggctt caaggaacca gggacctggt tcctcccaca ggccaggccc tgcccctaag    7380
tgcaatggga atatatgcac atgtcacctg tcccaaaatg ctgggagatg gcacttctgc    7440
agatggggaa actgagggac cagcccgaag tcacggggag gggaagactc ctacacacag    7500
ggaggagaag aacccagccg ggctgcaaac gcctgcccct cctcaacgtg cctccggctg    7560
tgcccacatc gctccagcag ctctgccttc ctcaggcata agccttctca gggcagggga    7620
ggcccaggga gcggcgctcc catcccaggc cgggctgctg agcaagcccc tccccttctt   7680
cccctcatcc tctgacagag tccacctgaa tatttgtcct ggagccagga tggaagctcc    7740
accaggccca gctaacaaca ggaaccctt  cagacgcact tctgggtgcg tactgtgcca    7800
gtatcacaca gacacaagcc atgtccttgt cagccatggg atccccaagg tccccatgag    7860
gtcacaccag tgggccactg ggaagggcac ttcagatgtg gagctcccat gggccaggcc    7920
ctgcgaagtg gtcctcctac ccctcatag  ccagtcttcc ctgtgagcct gcaagtgact    7980
gtgaatgtga gttccactct ggagctaaga cgggctgctg ccccgcaat  cagatgtcag    8040 gcccatgaag ccctccatca tcccactgca gtcagaataa aatgcagcct ccctctggcc    8100
tccaggtccc aaggccagcc ccctgcctc  ccaggctcac acctgcccct aacctgtgtc    8160 cagcccttt  ccctggctc  tgtctcctgc ttccttgtg  ttcctccaac ctcacctgtc    8220
tgtctggagt gctcctcccc ggctctgcct agctggctcc ttctcaggca tcagggcctg    8280
gatccactgt ggctcttcca agcctctgca cttggagtgc ctcagcccg  tggttgagga    8340 gtgccccaac cctgtgaccc tctagcaagc atcctaggaa ttccgtccct ccccagcact    8400
gatatgacca tcgtgctgtg acacgtgtca tctccgccag agttgcagat cctccagggg    8460
aggggtctgc tgcctggctc ccacagccag ggcctggaac agtgcctgac acacagcagg    8520
cacccactaa atatttgatg catggctgaa gaggacaggc aggctggctg ctggctgggc    8580
atggcctgct tctgaggctg gtggtcaagg acacagtgtg catggatctg cccctcctc    8640 ccacttcctg agagtggagc cagtgtctcc ctccacctac cacccctgc  tgaggacaca    8700 gctcacacct ttaacgggaa atgtcccat  cactggggac agcagggagc tgatggggaga   8760 gcaggtgtcc aggacatcca gagaaatgtt tcctcacact ggaacccttt tctattccct    8820
tctaaacaaa aagaatcctc gaagactctc aagtgaccat atagtgtctt ttcttataat    8880
```

```
gtcacttcga caggcacaaa atgtaaaacc aggcataaac tactagtgct tgcagttctt    8940
acgcaggcat gaagccaaaa ccagtttaca aattaaccac caagaaaacc ggtagagcac    9000
agatgatgac gatagagctg ttttgtccaa tgtgagcgct actggccacc cagggccatg    9060
tgaatttaaa ttacgatgaa acacaatgaa aaatttggtt ccttgtggcc acatttccag    9120
tacccagtag tcatctgtgc caggggggtta tccaggtaca gaacattccc atcgttgcag    9180
aaggttctat cagctagcac tgggttggac gacacttgcc aagacgagct ggctagagga    9240
tggttctccg gacctggtcc cacgtggttc ccaggtaagc ccccgcccag gatgcagccc    9300
cgttgtccat cagttttctt ggagagggca tgggaaacct tcgtcagtgt gtcatctcct    9360
gcaaaggcct tcgctccttc ctctggggag aaagcaccct tcactctctg aatcattagc    9420
ccaaagcagt aagtgcagca ggcctggccc cacaccttcc ggaagagcca cggtgtgagg    9480
ctggcatccc tggggcacga cacaaccagg atgtagacga aatagatgca atatctggag    9540
gttctcctat aggtgtctct ggcctcctgg acacttcaca ctgttctggg agctgccctc    9600
tcaggcccca gtgaccttt cagatgcaga ctcccacagc atgggtcagc aattctcccc    9660
ttccgtgaga cagggattgg ttacctgtac taggaccttg aggccaacac tgactagggg    9720
gcctcatgcc tgcccaggtt ccagccccgg agagcaatgt gagcaaagct tgctgtcttt    9780
gcaaagccaa ccactgtggc atcaactcct tcaggaagcc ctcccggatt gtccaaggtg    9840
ctcacctcct ttggggagcc ctcccagatt gtccaaggtg cttgagggag ggaggaatgg    9900
gttgttctcc cggcaccggg gctgcactcc tgggcagacg ctgcatgcct gtcctcaggc    9960
gcggccctgc tgccaccccc ttgggggctc ggagcgcgac agcagcttgg ggacgcctcc   10020
cgcgcccagc acggtgcacc tgggccctga ggtcctggcc gaaacgcgcc aagttggggg   10080
taggtgcagc gaccccatac ccctcggctg cgcgccctgg cggcaggagg cggggccggg   10140
ggcgggggcgt gagctggccg ggggcgggggc ctatggaggg gcgggaccgc ggcgccctat   10200
aagtactgcg gagcgcaggc gcgcgcccgg ccagagagcg agcgcgcaac ggcggcgacg   10260
gcggcgaccc caccgcacat cctgccaggc ctccggcgcc cagggcgcac ggcgcgcccc   10320
cgtgccggcg gcccctgcgc ccatttcttg gcgccccgc ccggtcggcc cgccaggccc   10380
ctttgccggc caccagccag gccccgcgcc ggcccgcccg ccgcccagga ccggcccgcg   10440
ccccgcaggc cgcccgccgc ccgcgccgcc atgggagtgg agggctgcac caagtgcatc   10500
aagtacctgc tcttcgtctt caatttcgtc ttctgggtaa gggctgcgcc gggggccggg   10560
gcgggagggg gcaggcacac actccacgtt gggcaggtcc cgcggcagcg tgctaggccc   10620
cgcgggcgca gcgcgggccg cgaagttgtg gggccacctg tgggctccag gagcggggtg   10680
gggggtcgcc cggggccacc gcgccccccg acattgggggc tgagggctgc gagccgagtt   10740
tcggggcctc tgtgctcggg ggcccacctc tgcggccggg ccggggcttc tggggggccgc   10800
cgggcagttc ccgctgtggt ggtgatgggt gcggtggtcg cgggtcggga cccgagtacc   10860
cggccgcccc tcagctaagg aggggcctgc gcgggtccct ggccgcggat tccggactgc   10920
tgcttcgcgg ggacgagggg ggggctcgcg gcgggactc ctggcgcccc gccccatga    10980
gctcatcaag agccgccgcc cctggatggt gggggcgggggg cgcacacttt gccggaggtt   11040
gggggcgatc cgcctcactc ttttccccagc ccagctcact ctccaatctg cggtcaccac   11100
ccgagacctt cctggggggtc gcgcctaaaa ggagcgcaga ctcccgccgg gatggcccag   11160
aagctgggggt gcgcgcaccc tggccgtccc tgcctgggag ccgatctccc tctcctcacc   11220
cagacacgtt ccagcggagg cctcctccca gaagggctct ggaggcctcg caggagtggg   11280
```

-continued

```
gatcccgcgg ttctgagttg gcacaaggaa gagagtggca ccaggggcct ggagtggatg    11340
gcagggtccg ggagtggggc cgctgctttg caagaggggc ccccacgctg gcatctttg     11400 ggtgccagcg tgggtggagg agggtctttt gctgagaatg gctttctcct gaccgcagtc    11460
tttgctgctg ggaagtgact gatgggcttt cgccttttgt ttccatttcc tgtcggtgtt    11520
agaattgggg aggggtgga aatcccttct tggcctggaa ggactggagt gggtgtccat     11580
ggccgcggcc tccccgtggc cacgcccctg gcatagact gcaagcccct ccccgtgccc     11640
cccaggctgt cacccccttc tcgtggaaga ctcggctgat gtcccagtgg accgagtgtt    11700
tctcaagttg aggcagggag ggcaaacttt ttaaatggcc cctggagcca gtgtgtggga    11760
ccagagacat ctgtttccca tctggacggc tgaggatccc agtgcggatg attatttgga    11820
gggggaagga cggaggctga actgaactct cagctgggag atgagtgggg cagtcacatc    11880
ccaccttccc caagccgggc tgttctgcac agcctgcttg ggacgctggt gggagtcact    11940
gtggctttcg gcactgccct ggcagtgggg gcagctaggc catttgggag gggctcgctt    12000
tccccaggcc gggccctggg acctcagccg ttgcttagtg gtggcctgct tcagcccagg    12060
catgtgggag aggcaccaga cacaggatgt ccctctgcca gccctgaag ccccgtcccc      12120 tgacgaggcg agtgtggacc tgggggtggg ggctgaggga gactgtggac ctggggtgg     12180 gggctgaagg aagtgtgga cctgggggca ggggccgagg gaaggtgtag gcctgggggt     12240
agtaggggct gagggagagt gtggacctgg gagtaggggc tgaggaggg tgtaggcctg      12300 ggggtggggg ctgagggaga gtgtggacct gggggtaggg gctgaggga agtgtggacc     12360 tgggggtggg ggttgaggga gggtgtggac ctgggggcag gggctgaggg agagtgtgga    12420
cctaggggca gaggctgaag gggagtcacg ggagggact tctccggagg tggattttg      12480 ctctctggac ggtgtgtcag cactgggtga gcccctcctg cctgcccagg ctgagaggtc    12540
tccctggcag ccccctggga gtgtcgccag ggcgggcctg gaagtttccc aggcagctgg    12600
ggtggagacc tgacacatcc caagggtgct tgttattaag gctcaaggaa atgtctctga    12660
ggcctcaccg ctcctctccc cagggcctgc tccctgcaaa gcattgagaa ctgagtccgt    12720
ccacagtcac tgtggaccca cccatccact ggggctcagt ggtagccagc aatgccaggc    12780
tgggtgaggt ggggttggtg ggcaccaccc tggtggaccc ccctccaccc tggtgtcgca    12840
gggtgtgtgg ctgagagcac agtgccatgg gcttgggcct ccttggtgga gtccccaaca    12900
cactgctctg gtcctgggcc tcggccttcc ccgtctgcag tgggggccca cagtgagcct    12960
acctcctggt ggtgttggtg gatttgctga catgcctgag tgttgacagg gggcttggtg    13020
caggaagggc tcagggcgtg ggtgttggcc aggggtccaa agggacctct gcctcagaga    13080
gcccagccca gacaggcagg atgtgcagtg gggaagggc tgcgggaacc ctgcagggtc     13140
cagaaggaca cagtgcagtc ctgtgggctc tggggaggct ggtggggagg aggttgacaa    13200
tggatatctg ggtggggcac ttgttagaag ttccatttta gagaggaaag aggccttgcc    13260
tgtgggagaa ggcagctggg gtagcctgac ctctttccca ggaaggagcc cacacacaca    13320
cgcacaggca ctcacacaca cgaatgtgca cacacacaca ctcccacctt cacacacact    13380
cacactcttg ctgtctccct tcccaagcca aggtgcgagg gggaaggtct gggcagcatg    13440
cacctgcgcc ctgaccgctt tggggggccag tgagaactgg gctccctggg tgcgcggcgg   13500
gcccaagcag ggaggacatt gcagatgccc tggccaagca gcgtggaaat cctgtccctt    13560
gggtgggtct cggagcctcc atcagaggcg gctggcacct gagacccacc tgctgccagg    13620
agcagggcag gagagtttgt gtcccgggac agggaactgg cctgtgggag ccttgccttc    13680
```

```
ctcatctgtg taatggatat aagagtcttc tcctcggggg ctggccaggg agtccagaag    13740
aggtgtcacc agtccccgca gggagaagag cggtgtcccc cgcctgggac tggctgctcc    13800
cccaagctaa tgcagctggt agccacctcc cagtggcagg gcagccaaac ccggccggga    13860
aagagactga ttagaagcct cgctcacggg tatttctcgc ttccagacag cacatgactg    13920
tcatttggca cgtctttcgc cgtccttccg ggagaggggc tgcaaccctg gcaggcgctg    13980
tgggggaggg ggctaggaca tcctgtgcct ggtttcacca agtgggtgtg tggacttttc    14040
ctggctcccc caggctgtct ggctgcacag ctttgggaa cggccactg gtcaagcgg     14100 gccgagaaga ggaagtctgt ggtttgtctc tgctacagac tggccccagt gaggctgtcc    14160
agcagtgcag ggcacagagc aaaagcaggg aggtatgggc ctacttcccc ggtcgcccct    14220
gtggctggct gtggctctgc cgggtgctga caagtcactc gccctccctg cggtcaccag    14280
ggtgcatgcc cgaaagccct ccattctttc ctgggtttga gggtccttct cctgcaccca    14340
ccccagcgcc cagttcagct caactttcag aaatctggtt cacccccaat ccctttctca    14400
taactgcttc caagcccaga caaggagaca gaccccaaaa gatccctacc cctatttccg    14460
cacctgaaat cgcaccacgg gaagagcttt gctcatagag tcaataaggc ttagagtcca    14520
ggcgcctgtg cgagggagca ggtcatcacc cttgtaccca ccgtggtttt agacaggacc    14580
ctgaggttgg ggtggggctg gggctggaga ggagccaggt gccctgcccc ttgcttgggc    14640
cccgtgtccc tgtgatccag gctgggcgtg ctatgggtgc tgggtgatat tccagccctg    14700
caggtgtccg ccttgttccc agcacccctc tgggcaagaa gaaccaggct ctcccagaaa    14760
tgggcttcag tgatctccac ttccaagtcg tccccacctg ccttgtagga cacagtggta    14820
cctggtatgc tgggcagcct tccaggaacc tctggactta tcagtgtcc cccagccta    14880 cacaccattc tttgtgtttc tgggcccaaa ctaagccccc caacctgggc tgcagagcaa    14940
gtgctgaatc atgagagacc cttgagggtc tccaggtag gccccagtg ctggaggagt     15000 cccctcaggc agggggccac gcccaagggt gtggaaggtc agctggcagc cggatctcac    15060 tttttggggct gtaggcttcc tgcactggcc gccaatgcca tggccgtggg atggccagga    15120
taaggcatct gccccccacc cccacccccc gcacaaggtc tttgagggct gcgggctcaa    15180
ggagttggcg gtagggctgg gggaccaggg gcacagagct tgtaagcgcc tctctccagg    15240
atgtgggtgg cccagcaggg gagctttgag agtccaggtg tgagattcca aatgctaggg    15300
gcctgagagg agggagccac cagcttggcc agagcctggt ggatcacgcc cccaccacgc    15360
cttgcccttc tctctggtca tgtgctctcc caccacgttt ggaaagttac tgcttccctc    15420
ttcctcagcc cctcgggctc ccagttatgg aagtggcgtg attcagagaa ggtaaaggat    15480
gggagggaga gggctgggtg atgggggacc ccgcagggcg ccctgtgctg ttacatggag    15540
ctccaggatc agggcaggtg ggcagcctgg ggtcctcact tctctcccca gccaggccag    15600
gtccctcaca gccctgccag gagcatgata tccgctgcgg tgcagaacta atctcaaagc    15660
tcaaacccag gtaacagtgt aggtaaaaca gatgacaggg catgagactc accccaggac    15720
aggcgaagga cccaggccga tgggggccca gaacagtcct gatcctggag ctccttcccg    15780
agtgggaccc caggggtttc cgaggggctt agagtagggc ttagaggctt agagtagggc    15840
tagggacttc ctggcttccc tgcctcggga acagctggtc ctggaagggg cttggtcctc    15900
ggggcactgg tgcccaccac ccctgatgcc tgggagacac cagcatcctc tgagcatgtg    15960
tgcgtcctcc tggtcccgag ggaagtgact cctcacatcc cccagctggc ggggccagag    16020
ggccagcatc ctcgcctgac acctattttt agatgctgag acaggcggct tcctcggggc    16080
```

```
caggggccct gtgagtggag cttccgcttc ctggcctagg agagaattcc tgctcctctt   16140
ccctccatgc tgccttttcg ccectggagg ccacaacggg gtcagagggg cagctgctca   16200
ccacctagga gggcctgaga gggccctacg tcacccaggg aggagtctgg ccccgtcccc   16260
aacctccaca cccaggcctg gcactgcccc ttcttggtgg gcagagagtg aggggttggc   16320
ctgcagggac ccaggctgga ggggccgttc acctccggcc cccagcgtcc cttcctggaa   16380
gcaccttggt gagcccctcc cctccttcac ccagtatctc caggggtact tcctcctttc   16440
cttcctgcct cagggcctca ctgtcctcct ggggagggtg tctcaggccc cagcacctcc   16500
cagtggctga gccgaatggg cacttccgg tgtgtttccc atatgtgcag tcctaggtg    16560 tcggtgagca ggcacagagc ccgcagcgtg gccctgcctg gtggaccccc tccccaagag   16620
catcaaggga gggcctggac tagagacaca cagatgccca gcctgtacgt aaaggcgggt   16680
gagctgatgt accatcgtcc tcgtccccca ctggggtgcc tgggcaggac ttggggtgac   16740
cacttggccc gtctgggtgg gggtaaggta tgggtggggc gaccagatcc ctgcccttc   16800 ctgcagctgt gggggtgtgt gtgctggcct ggagagctcc cacccgaagt tctggctcct   16860
ggctgtccgg ggcctgcggg gcagcgagc agctggcatg ggtaggggag ctgacctagg    16920
cctgcccggg cagcgcctgc tgccttttgc tcccttcag ctgcttcttg gaaacagcgg    16980
acaggctggg caggaaccca gtgtgcttgg cagcccccct tttaaagtcg attctgttat   17040
ttattaattc ccaggaagga gaaagaaaga aacaatcctt catagagtac aaacactgct   17100
tttagtagcc ttgcaaggag ccctccagga accccacagg ttacctggc tccatcctga    17160 gagccaccct ccatccccaa tccccagcag agcatcttgt ggggtggggc ggcttgtggg   17220
gcggggcgcc ttgggaggcg gggtgtctcg ggaagcgggg cgtctcggga ggtggggtgg   17280
cttgtggggt gggcatttc ctggggtggg gcgtctcgtg gggtgggaca gcttgggggg    17340 tgggcatct cgggaggcgg ggcgtcttgt ggggtagggc ggcttgtggg gtggggcatc    17400
ttgtggggta gggcggcttg tggggtgggg catcttgtgg ggtgggacgg cttgtggggt   17460
ggggcatctc gggaggtggg gcatctctgg ggcccggcca cttgggaggc ggggcatcct   17520
gggggcgggg catctcagag ggcgcctccg gaggctggaa tatcttggga ggtgggagca   17580
ggtggcagag aggcttccca caggtgagct ttgagcaggg aggtgcctgt atggatggct   17640
ctgtggggag aggggtgaca ggagttccag attccggcac ttatgaaacc tcacagtgat   17700
ggagagccga gtgctgctgt gcaggctaag ttgtgtgcat gtcagcttct gcacttttat   17760
ttccttgttt gtagacaagg cagagagaag ctgagatggg cctgaggtcg ccttggtgaa   17820
aggcactcag cagccagggc cttgggctgc cctccctcat caccgtgaaa gcgggactct   17880
cttttaactg acatcgggct ccatagttac tccagtccta actttgatgg atcctaaaag   17940
tgcacttcta aggacgcggc ttcggtgttt cccatgccgc tgcttgcccc tgggaagcgt   18000
tggctctgcc tcggaagaag ttagcgccaa gatggcagcc tggggtcttt ggggcccaga   18060
agaaacactg gccccgggga gttcagtcat cagggactta ggatgtgggg gcttttcaaa   18120
cagctttatt tagacgtgat tgacacacag taaatacaga tgtttaaggg tacaacttgg   18180
taagttttga caaatttata ccccgtgaa accatcacca actccccagg tgcccctggg   18240
gcccttggga tctctgcttc ctgccctcc tccccgtccc agggcaacca cgggccgtcg    18300
ctgtgggtgc acacagcatg catttcttca acaagcggac tcagaaggca cttgcacatc   18360
gttgctgttc tgcctctttg cttcagcatg attacccaga ggcgcacccg tgccgtggcc   18420
tgcccgtcgt ctatgcaccc gtgctgtggc gtgcccgtcg tctgtgtggc atgcctgtct   18480
```

```
gtgcacccgt gctgtggcgt gcccgtcgtc tgtgtggcat gcctgtctgt gcacccgtgc   18540
tgtggcgtgc ccgtcgtctg tgcacccgtg ctgtggtgtg cccgtcgtct gtgcacccgt   18600
gccgtggcgt gcccgtcgtc tgtgcacccg tgctgtggtg tgcccttcgt ctgttccttt   18660
tattgccggg cagggttgca cccacatgtg caagccagcg acggacccca ggttcacccg   18720
ttcaccggtc agtgggcata tgggttgttt cagtttgggg catttacaag aaacgtgcta   18780
gaacatttgt gtacaagtct tgtgtgaacc taagttcatt tctcttgggt aaatacctgt   18840
gcgtggagca gctgggtcat gtggtgaatg tgggtttcac tgcttaagca gcagttttac   18900
ataactgcca aactgttatt caaggtggct ggaccgtttt acagcccccg ttgtatgcgt   18960
cccagttgcc tcccccagca gcatgtggtg tggttggtct ttttcgtggc agccagtcca   19020
ctgggtgcgc tcggcatgtg gctgcagctt gacctgggtt tcctggtccc tgcaaggtg    19080 gagcatctct tcatgtgctt ttttgctgtg tgtggatctt gcggggaagg gtctgttcct   19140
gttttttgcc catctttcaa agattgggtt gccagttttc ttgctgttga gtttggaaag   19200
ctctgcatac gttcagggca caggtccttt accaggctct gccccaggtc tttcggagag   19260
caggtgtctt tcgcattcct gactctgggg aacctctagc cctgccacat ggggtttgtt   19320
atggggcagg ggcacctgtg cctttcccac cacggggctt gggatttgg tgctgccatt    19380 gccctccctc gtaggtggcc ctagggggg t ccctccgcct ccgtttcctc atccagaaac   19440
cggcagtgac catcaccacc attgttgtca cctagctcca gctcaaggtc cctgctgaag   19500
gtcggagagc ttggcatggc cccgtttgtc catgctaggg ctgggaagac caaggctcag   19560
gtgaggcctc tgcccagtgc ctggcactcc ttcttgcccc atttttccac ccagggtggc   19620
tcccgactac ttctggtagc ctcggggaca gttgaggtgg acaggctggc gtcacccca    19680 tttccggctg tccctcccac cccctcctgg cccagctgtt ctgccctatt aaaagtcaca   19740
tgggccctcg ggtccttcct ggtgttggcc caggctcttt caggccctgc aggccaggac   19800
cagccttccc tgcaaccctc ggcagaggcc tggggccggg gcttgtctag gggcagcctc   19860
cccatacggc cctggagtct gaacagaagc cccttcccag agcacagcaa gaagctgcaa   19920
cgtggcctga agtcccacca ttagcaggtt tggggtttag gctgagcttt gccatcacta   19980
cctttctgtt aggacggtat gcccattaga tgggatcatc ccctcagcgc ccaggctaga   20040
ggaggggtgg tccctgccca gccagggagg gctgggggtg gatgggcctc tacagagcag   20100
cttccgagcc aggcacggtt ccatgatcag ctctgtttta tagagggggga cactgaggaa   20160 ccgggagcct ggggaccttc cagtggcccc acagctcctg tggctgagtc agggtttgtc   20220
accaggcctc tgtggggatg aggctccccc atccacctgc ccactctgt cctggaacag    20280 ctctcaaaac ggtctctgga ccacagtttc aaaagaaaat aagcaatgtt ttcaaaggcc   20340
ctggaggaag ccagagttac cacggcaact ctcggcctcg ccacctcctc ccgccaggct   20400
gcatctggag ccagctcagg agggcagcag ggtgaggaca gccaggctct ctggggccac   20460
cccccagccc ccacccttcc tgcctctcct gcactgtcca cggccctccc tgtgctccca   20520
cgggtataat gggcacagaa gaaccaggag ctgtctgccc ctgcaggatt ctggaagcca   20580
ggggcccctg gcctccctgg ggccttgtca tgtgaggggc acacgtgggg tcccagctgc   20640
cacatggctt ccgcgctgc ccgcaggtgt atgttgggcc cttggtgact ctaatgcacc     20700
ttccactcgg cacagaagag cttcagtctg gggcctgggc gggggaagta ggctgccatc   20760
ctcgctaaac caaagtgtga aaattgagtt gaaactccca taggagggca ggaggcacag   20820
ctcctcagaa gaaggtctga gaaaccacag cccaggttgt tgtttcgggt gtgtggagaa   20880
```

```
ggtgctctgg cagtcctgct acaggggac  catcaacagc ccctttgggg tgagagcccc   20940
gtggctgctg gcaccagcag ccctatgag  gcttatttta ttttgagac  agggtcttgc   21000
tctgtcaccg aggctggagt gcagtggcac aatcataact cactgtagcc tcaacctcct   21060
gagctcaagc gatcctcctg cctcagcctc caaaggtgct gggattacag gcgcttgcta   21120
ccacgcccag cccctctgg  ccttattgtt tgccaggccc agctcaggtc cggaggagg    21180
ggagacagga gtgtgaggga aggggaag   aggtatagag cccccagctc ctccacccac   21240
ccgaaccctc accgaggccc tagaccctag accggctga  ccgggggtc  ctcaggccgg   21300
ggacttgggt gcaggccatg gtgctgggc  ctgaagctca cgctctgctg agcacagccc   21360
cctgcccaac cccaccctgg ggccctgctt ccctggccag ggccattgga acaggagtgg   21420
ggctgtccag gtggtgttct tgggtccagc cctcagtttc tcttctgcag ttgaccggca   21480
gccctgcatc tgtggtgggg tcggcgcctg gtgctggtga ggcaaggcct cagctgctgg   21540
gacaggacct gcctggcacc cagctggtgg cagagccaag cattccgact cagctctggg   21600
agcagctgcc ttctgggctg gcattctccg ccagggggt  tgtgccctcg tggcccccc    21660
cgggtgcctc ctcacctggc tgatttcatc tcctgtcccc ctgcctcctc ctccaggaag   21720
cccccagggc ctggccctcc ttgagagtgg catggaggag gaagaagact cgcccaggcc   21780
catgggagtc ggatggtggc cgcacttgtg gggccctgac cccataggct tcttcagcac   21840
gccctggcct gggtgatccc tgcctgaggg ctgtgcacgg ctcatctgcc agaccagatt   21900
ttaggggatt cttgtactgt cctcctggag cagcaggggg taaagcctga cccacccaga   21960
ctgtccagca acaagggcct cctgctgtgg gccagggacc ctggaactga ccaattgtgt   22020
cctaggacg  cagagtcccc aggctgctag agggctgtgg ggccctgttt catgcctgaa   22080
gcaggaagaa accccaggag aggtctgaag gggacccagc ccccaccctg tctagcaggg   22140
aggagcctct gcaagaggcc gagggtgct  gaagtggagg aggatagagg cagcaggact   22200
cagggtcact ggtcatttat ggggatcaca cggctgcagt gtgccctgca tggtgctagg   22260
caccagggac agcagaggac aagcctgtgt cctctcccac caccagaggg ctgggcactg   22320
cccctaggga gagaggggc  cttggtgtgt gcagaggggg gctggggca  cgtgcctggc   22380
ctggtcagat gatcagagtg ggctgggctg ggcctggtct ggggcccagt ctcaagggca   22440
gaccccacct ggctagagtt gattgtgtgc acaccggatg accggcgtt  gaaggcctct   22500
cctctctgtg agcctcatcc ccacctgcca gactcccagc acagcctgct tcctgcccca   22560
gctgctgagc gacagcgctg ggccggcttc tgcgcgcccc ttcccccagc ccatcttgga   22620
aaccacagca gcgtccttcc tcccaagtcc cttcccaggg ctgacatccc acagcaggga   22680
tgtatcccac aaacccgca  ggccctggtg cctacagctt ggcctggtaa catcaaatcc   22740
taccctctcc tcctggcagc aaagatgggg tgccccacc  ccagagttct cagcaccccc   22800
agacagaagc agtcccccag cgacctcaga actcttgggg cgctgccaca cccttgcagg   22860
aggggcagt  gttcctggga tgctcaggtc ctggtatcac ctctggccag atacggaagg   22920
tgaaactaca gggcatccaa ttcaccttga acttcagata aacaccagat tatttttttg   22980
tatgtcccgt gcaatatttg ggacacactt accctaaaga agtattctgt tttcatctga   23040
gaggcagatt taaccggcgt cccgtgtctt cctggcagtc ctgccctgga gtcacactcc   23100
acaggtgcag ggcagggcca ggctccaagt agatggcggc caaagcaccc gccccatgct   23160
cctgactccc ggggctcttc agggcattgc gaaaaccagc agcagagctg acacctggtc   23220
cctgctcggg agccagcaag gcaggaggct gcttaggcct tgcgtgtggg gtgggcgcac   23280
```

```
tccctgctgc agtgctcttc gtacatgtga cactgttccc gctctttccc agctggctgg   23340
aggcgtgatc ctgggtgtgg ccctgtggct ccgccatgac ccgcagacca ccaacctcct   23400
gtatctggag ctgggagaca agcccgcgcc caacaccttc tatgtaggtg agtgcacatg   23460
tggccgcaga cgcattcagg gagggcttct aggaggaggc aggtcctagc cttttggatg   23520
gggacatgga gggtgaaaga cagtcgggca tggcgtgtcc gggcagggag gcggccctgg   23580
aaagggctct gggcacaagg gttgagatgg aggtgggcct gtggcctgct ggcccttctg   23640
gtctgagcca gggcaggggg tggcagctag gcctgggcag ggactgtgtg gagaccttgc   23700
ttattttaag tgtggggtta tttcggggga ggctccctga aagggtggg gctggatgcc    23760 tgggccacac agagcagccg aggcagctgg cgctgtggag cccgggaggg agggagggat   23820
ggagctcaag ggatggaacc cagtgagggg tggagacggg gcaggggagg ggtggagagg   23880
ggtggagacg ccccagaggc ggtgtgactc agctgcccct gcaggcagct gcaccttgct   23940
gccttattag gctgcgtgtg ggggactggg ctgccctccc tgcccccagg agcaggagca   24000
ggagtgatgg aggaggagga ggggagggc aaggccagga ggaggaggag ggccatctca    24060
ctgtgcagag agcagcaccc ttcctcctgg tgccctggc agggctggtg ctggtggggc     24120
tctgggagca tttgttgaga tgcttctggc cttgaaagga ggccctggg atggctctgt     24180 tgccctcaca ggctgagggg tgggtgaggt gggcagcctg tgtgtcccca gtcctcaggg   24240
cttccctcag ccggcaggtg cccccaggcc tggagctgca gggccaggcc ccctgccagt   24300
tacggaggct gcttggcttg gttgctgaac cagggcccca ggaggccgaa atagccccac   24360
acctgcgccg tcccacctct ttgtccagtc accccagggc caggtgaggg ccctggccac   24420
acagcgtgcc cgttccttct tccccatgcc ccgctcatgg gtcagagggc cggtgctggg   24480
gtccagatgg tgtcaacagg gatggtccct gtcctcccca gagacagaag cctgtggccc   24540 acggaggtt tctgggccca gccgatccta gggagggtcc catggccctg cccataggtt     24600
cctggcctct ctcggggccg tggtgccctc acaggtggtg tcaggaagga cgggaaaggc   24660
tgcttgtccc aggggctcat gtggagacca cccctgcac gcagctgggg cgctcctgcc     24720
tgtgtcctca gaagcactcg gcttagcttt gcccatgtgc ctgggctgtg ggtggcagag   24780
cccggccagc atcctccgat ctccaagggt gcatctctac tggaggcccc tcctgggcct   24840
cttgctcccc gcttcccaga tcattaggat atttggggtc cagaagggcc tcccagccat    24900
cctgggcctt gtcctccggg gccaccagtc cagccagtga caaccacagc atccccggcc   24960
tggaacgagg ctgccccag cacgttcctc gtactcctgt ccagggacag gaggggctgc    25020
ccctgccacc gagtccccctt ctccaggacc tggggcctgt gggtgtgagg caggtgttct   25080 tggaagggt cactctccag gcacccgcg gccaaggctt gtggctggag cagctcccgc     25140
tgtggggtcg gcgtcgggcc ccgtgtggcc ggagaggagc tgaagggtca cttagcttcg    25200
ggctggggcg aggacagggg acaccccaga gaggtatgcc aggcctcctt cctgcgcccc    25260
actctcggca gaagcagagg tcacaggctg tgctgaggcc ccatggtgct gccccatga    25320 tgccagggtg aggctggcgt tggaagcagg tgtctgacct gcatggtgtc accgtggcca   25380
catcagagct ccagcccag agccgcccac cctcggtcct tggctgtggt ttccctgggc   25440 tggaggagc tgccgttgtg ttggccacac gaccacagga cctgccaccc ccgacgtggg   25500
ctctgcctgg gcccccactg gacagggacc ccttggagct cctctggcca ccaagtcctc   25560
gcccattcca gaatcggcct tctgagcct cttgctgtcc ctgatgcggg ctgggccttg    25620
ccaagggctt ttttttcctgc gccgggaaca gggtggattt gctgggctca ctcccctcag   25680
```

```
agacgctgcg ggtgcggtgg gttaggccca agggcgttaa gagaggaggc tggggtgggg    25740
ctggggcctg gcaggggtc tggcagccct gggcctccca cctcctgtca ggaccaaaaa     25800
aggcaacgcg cctctcctga cctgtacccc ggagtgaacc caaccttgca acccaggagt    25860
gtcagggcct gaggggaggg agacctggct cctgggtgcc gtgcccgtaa ggaggtggcc    25920
acctgcaggg cattcctggc agaggcttca tctggccagg taggaggctg ggtggccgag    25980
ccccaaatct gggtgtgttc tctgcctggc ggtgggtcct gccccaggca ccttctcctc    26040
tgggctggct gggcagggac aatgggcctg gctgcgagga gggggcctgg gctgccttct    26100
gcattgcctc ggtgacggga gatggcccct gcctgctgag ggataggga gtgggcaggc     26160 agtgagagac actgacagct gtcccgcggg tacagggccc tgtctgggtg gccaggccca    26220
tgtctcgggc ccacagtgcg ccccccaccc ttggacggcg ccttctccct ccccaggtgc    26280
atgctgccca gccagggagc gtgggggagt tcgggagggc tggcctacac gccctggtcc    26340
agctgtccca ggtggggtgc tgggcttcag ccctcagccc agggcctagg aatccaactt    26400
gatcctcccc acacagcagc caggttcaaa tgcaggtccc gtaacggaag tgctgctgtg    26460
cagcccagat tggggggcag gagccagcag ggcccccca ccctcttctc gcaccacact     26520
ggggaggcag cattggttcc agttccggtt cctgggctgc cctctcaacc ccggcctaca    26580
gtggggccca ccctgtgcct tctgatgcca ctcccacccc acgccaagtc ccagaggctt    26640
tgggagcggg tgaaggcggt gggtggcggg tggcaggtgc aggcggtggg tggtgggtgt    26700
ggcaggtggc gggcccccacc gcaggtgtca tccctgcgaa gcacctgtcg ccagcactca    26760
gagcgctcat gaggtgccca gtccccatgt ggcctcctta gtctccgtcc tgtgtcatgg    26820
aagaggtaac tgaggcacag aaaactcacc aggccaggct gggatgtgag gtcccttgct    26880
gctcatccct ggcagtcagc aaccctacat cttcccagct gggcggcccg tggtgggttc    26940
ggcacccagg accctccggg gtcttgggct gtggcgagtg tgtaggcacc cacctggtgt    27000
ctctctcccc gcaaggcatc tacatcctca tcgctgtggg cgctgtcatg atgttcgttg    27060
gcttcctggg ctgctacggg gccatccagg aatcccagtg cctgctgggg acggtaaggc    27120
agggaggcgg gcctgtgcct gggccgggga ggggctgggg gctgcgtctg gcctgagga     27180 gggggcagag ctggtgctca gggcggagcc tagaattctg ggggaggtgg ctcctgtgcc    27240
ctgcttttcc cgtttggttt ttaaattaaa tcccaccgtg cttggtctcc atcgtggcca    27300
gttcctacgt gaccgctttt ctttgtcaaa aaatagccac aaatataaca gggagcaagc    27360
ctcagctctg aggccagcct cggcgtcccg ggcacaccgc ccctgtggg aagcccaggc     27420 ctggctgtgc catccagggc ctggccagtc caggaagagg gagcctatgc ccgtgtctcc    27480
agtgggggaa actgaggcag atcccatggc tcccccttcc gtggggagca ggaacaaggg    27540
ggtggggaag atcagtcagg ggtcatgctg ctgcacacgc ctccctgggg gctgcagaca    27600
tcctggactc accagcctgt gaccccaaac cacacgcccc gccccatcca ccccgtcctg    27660
tggagcctgg tgccgcgtgg ggacatcctg ggctttgacg gctcctccct gcgctgagtt    27720
ttagcctctg tgcccagggc ctccacacaa gccgctcact cctggtcagg tcgtgggctg    27780
gtggctccca ctagcccctc acagacacgc ctgctgggca cctgggtgtg tgtccttggg    27840
ccccgcctac agcctgccct cttttcctcc tctggccact gcccggctcc agttcttcac    27900
ctgcctggtc atcctgtttg cctgtgaggt ggccgccggc atctggggct ttgtcaacaa    27960
ggaccaggtg agcctgggtg tgcagggaca gggtggggtg ggtgacgggg gcaccctcct    28020
ctcctgtcgc gggtgggggt tgggctgact catggcttgt gggagctctt tgggctcttc    28080
```

```
ctgggtccca cttgccagga ggatctccag gggctttatg gaggaggcag cattggggct    28140
gagcaccagg ccagcctccc gtgtcccagc actcccgggg cagctgagag tgcagagtcc    28200
ttgtcctctg gggtctagcc tcgaagccac cctgcccagg gagagcctgg gaaaagtgcg    28260
tccgcctggg gcggggcggg gtgggggcaa ggaggggaga gttcccctg tgcatgtgac     28320 cgcacccctc ccccagatcg ccaaggatgt gaagcagttc tatgaccagg ccctacagca    28380
ggccgtggtg gatgatgacg ccaacaacgc caaggctgtg gtgaagacct tccacgagac    28440
ggtgcggccc cggggggcga gggcgggag cagggccccg ggaacccggc ggggtgtgtc     28500
tcgtcctgga tgaatcctgc ctacgcccag acctcaggag caggaggtgc ccttgggacc    28560
tccaggaccc ctggtctcaa ctggtcctcg ggtgggaacc tagtgggcca gggtggccca    28620
gggtgcggaa agctctgagc agcgcagctg aggaggaaga aggctggccc ctggatgcat    28680
tctgcagtgg ggagcgctgc gtaccctgg ccacctcccc atgggttccc tagagccacc     28740
gtccccctgg gcacatccag ggctgacctt gcaccctgc tctctgcagc ttgactgctg      28800
tggctccagc acactgactg cttgaccac ctcagtgctc aagaacaatt tgtgtccctc      28860
gggcagcaac atcatcagca acctcttcaa ggtgcgcgag gccggtgggg ccgcgcctga    28920
ccccccgcat gtcccgcccc tgggtggggt cctaggggtg ggcaggtcac acggcagccc    28980
cacagggagc gaccacactg ggtggcatgg cccctgtcag ggctgctctg ctgggagggt    29040
tggggtggga ccgcatctgg cccacgagga aggcaggcgc cctgtgctgc gcattccggg    29100
tgaagaaggt ggaggctctg gggggtggga actcacctgc accccagct ccacgtgtgc     29160 actcgtgggt gtggacgccc ctgacagcct gtagctggca gggcctgcag gccatatagt    29220
gccctgtgga agtttcctgc tgaggcctca gtggaagtcg tcatcagtga tgctttaggg    29280
gtctagtgac accaatgacc gtgatctcag tggaaaaggg cacagtgtgt cccaggcatt    29340
tcgcgtttat gttaaaacgg gtggaagata gcaagccggc agaggccggg ccgctgcacc    29400
cgcctgttcc gaggtgggta gggggtgggg ggctgttccc aggattcccc tctacgctt     29460 ctgtggtgac cacggattac tgcgtgacaa cgggaagccg ggagccgagg cccggtccct    29520
gaccacgcgt gcctggccac ccctgcagga ggactgccac cagaagatcg atgacctctt    29580
ctccgggaag ctgtacctca tcggcattgc tgccatcgtg gtcgctgtga tcatggtgag    29640
cgggcggggg cggagggcct gctctctggg ctgccccttc cgcgggggcct tgtgctgact   29700 gcgccccca ccaccctcct gcagatcttc gagatgatcc tgagcatggt gctgtgctgt    29760
ggcatccgga acagctccgt gtactgaggc cccgcagctc tggccacagg gacctctgca   29820
gtgcccccta agtgacccgg acacttccga gggggccatc accgcctgtg tatataacgt   29880
ttccggtatt actctgctac acgtagcctt tttactttg gggttttgtt tttgttctga    29940
actttcctgt taccttttca gggctgacgt cacatgtagg tggcgtgtat gagtggagac    30000
gggcctgggt cttggggact ggagggcagg ggtccttctg ccctggggtc ccagggtgct    30060
ctgcctgctc agccaggcct ctcctgggag ccactcgccc agagactcag cttggccaac    30120 ttgggggct gtgtccaccc agcccgcccg tcctgtgggc tgcacagctc accttgttcc     30180
ctcctgcccc ggttcgagag ccgagtctgt gggcactctc tgccttcatg cacctgtcct    30240
ttctaacacg tcgccttcaa ctgtaatcac aacatcctga ctccgtcatt taataaagaa    30300
ggaacatcag gcatgctacc aggcctgtgc agtccctcag tgccagtggt gtctgagacc    30360
taggggttgg ccggagggca ggggaatctg acatcggtgg ggcttggctc tgtgactct    30420 gtggggtcca gggtgagggt gggtgggtcg ggatccctgg tgttcaccaa aggagtcact    30480
```

```
ctgtaaaatt tggggagtta tttattctga gccaaatatg agcaccggtg gcctgtgaca    30540
cagccccagg tcctgagaac ttgtgcccaa ggcggtctgg ctacttaatt gtatacattt    30600
tagggacata ggacattgat cattacatct aagatgtacg ttggtttagt cggaaaggtg    30660
ggacgatttg aaggggaggg actttcaggt cataggcgga ttaaaagatg ttctgattaa    30720
taattggttg attttatcta aagacctgaa atcaatagaa tggactatct gggttaagag    30780
gagttgtgga gaccaagatt attatgcaga tgaagccgcc agattgtaaa tgtttcttat    30840
cagacttaaa aaggtaccag aatcttagtt aattctctcc tggatcagga aatagacctg    30900
gaaagggagg gggattctct atagaatgta gattttccca agagacagct ttgcagggcc    30960
atttcaaaat acatcagaga aatatatttt ggggtaaaat acttcggttt ctttcagggc    31020
ctgctgtcac gttggtatct tattactaca gagtctgttt tgtgagtctt aaggtctttt    31080 tattttaga cagagttttg ctcttgtcac ccaggttgga gtgcaatggc gtgatctcag    31140
ctcactgcag cctcccctcc acctcccagg ttcaagcgat tctcctgcct cagcctcctg    31200
agtagctggg acaacaggca tgcaccaccc cacccagcta attttgtatt tttagtagag    31260
acggtgtttc gccacggtgg ccaggctagt ctcgaactcc tgacctcacg tgacacacca    31320
ggttttggga ttacaggtgt gagccaccac accggactaa ggtctctgtt ttaatgtgaa    31380
tgctggtcag ctgtgcctat gaggcatgtt cggccaccca cagtcatcat ggcctcaacg    31440
agcttttcag gtttacttta gaatgcattt ggccaagagg tgcccattca gttggtttggg    31500 gttgcttaga atttactttt gggtttaaac cagggagcaa ctccaggtag caagggccct    31560
ttttgggagc gttctctcta ttctcttttg ggagaggccc tgtgttgcct gcagccactt    31620
ccaccctgcc ccttgggcac acaaggggca cacagtgtaa gcaggtgggc aggaggggtc    31680
gggcagccag ggaatgcagt gagatgggct tggggtaggg gctgggtgcg ctgcaggact    31740
cctcttcctc ctgagggatg gtaaaggatg gacacactgc cccctcccga gcatttgagg    31800
gtctctgccc tgcccatctg ttacctgtaa atgttccttt gaggagctga tggctcaggc    31860
ctgagccaca tctcagaggg tctggagggg aagaaagacc tcatcctact agggagcccc    31920
cccagcccac cagcgagcgg tggttggggg cagacaggct gtggggctaa ggagcccctg    31980
cactcccccg tccttttccc tttgtctgag cacctccagc cagtgggctt ggtctagact    32040
ctcctatctt tccccacatc gtggggtggg gcttgctctg ggttaggcta cttttcccta    32100
gttgtgggga gggggtgct ggcacatttc actgttccct ggaggaaatg agtgcctggg    32160
aattcatatc tagggctccc agcagcctct ttgcaggcca atttggaaac tgtccccagc    32220
cctgcatttt aggggttac agagtctctc agcaggccct cctcccctgc tgctcccaac    32280
ttgcaagcct gcactggttg ggagaacata atggtccaag gagccccctc tctactttcc    32340
gctgtgttcc ctgtggggag ggaagagcag tttaagaaat aaggaatccc aaaggcgcac    32400
agcagaccgg gggccgagga gtgggtcctg cttcccctcc ttttttctag gctgagccac    32460
agcaggtcct tgaatcctat ttcccagcgg atgccaggac agcaggccct gggggagttc    32520
tctctcgagc ctttcagagg gaccagaggt ctagcagcca aggagaactc agaatccttg    32580
agtgtgtggg gcaggaactc tcccagctga aaggggcac aaggtgccaa ccatctaggg    32640
cccagtggcc aaggaagacg cggcttgtcg caggagaat ctgggccctg gtcctccctt    32700
tcagggcggg cagctgacct gccccctgct gcggacaggc gaggccaggc tgctggctcg    32760
caagcatggc ggagcccaaa ccttccctgc tgccgcccgc ccagccacgg ctgacttgga    32820
agcttgagga gcgttcagca gcctccatcc tgcccgggag gaccggggac ctggaagggc    32880
```

```
ctggccctcg cttccctgca gcgccctagg gggacgtctc agtgcctccc ggagcccgga  32940
ccaatgcacc agagctgagg gcccaagggt gtgagggtgg ccgggcagtg gccccgagga  33000
cggcgcccca caagtttgcg gccagggccc agcaaacccc taggggtggg aaagcgtcgg  33060
cccagctagc gggtccagca gggctgcccc cttcaccgtg gcccagcggt cacgacccca  33120
cgtcctcatc gcgggctggg actgcctctg cgtctggcct gagcgggacc gtgggatcct  33180
ggggagcccc gcctcggtgc actgacagag cccagaagga gtgacggtta ccgcttccgg  33240
tcaggaccgg aagtgccggg aacggcattc gtcctccgtg cgagatgacg cacttcctgc  33300
ctgaggcggc cgctgttctc gcggcttccg gcaggtggcg ctgagaccac gggaagccag  33360
cctggctgtc ggttagccct cgagcattct gggaattgca ggcctggccc ctcctcttcc  33420
tgttcttggt caattccggt cttgtttccc caacaaatgc cgtcgtttcc ggggctgctt  33480
ccgagccgga cccaagggcc ggggcgtgga ggagtagagg ggcgagcgca tgcgcacagg  33540
actacacgtc ccgacaggcg tcgggagcgg cggcccagtt ccttgtggga gctgtagttc  33600
tgcaggcgcg gaagccgtgg tgctcggccg gcagagcact cggtttccca gagggctgag  33660
cgcgccgcac ggaggtgcgg cgccgaccaa gatggagact gccgagcagc cttgagccgg  33720
taggtttgtg gtgagggagg acgggccgcg cgggccggcc gagcctccgg gaggtcaccg  33780
agcgcagctt taatacctga gctcgaaggc cccgctgtgc tcgccgaccc ccgtacctcg  33840
cggccgggcc cttgggaccc acagcatcct tgtgaggccc ggaggcctgt ccagcccgac  33900
tggacagtgc cgaggggcac cgagagccag cttggcaccg agagttcgtt tgttctctgg  33960
cggggaggtc ttgctggcac atatagtgga gaaaggccgg gctctgcgtt catgtggaga  34020
aagagacggc ttccttcagc ctacggacat gaaggagtca actctacctt ccactcgttg  34080
ccggctttcg ccgagaaccc cgagaaacgg actaccggag tccctatctt gcagcccgat  34140
ccccgctacc cgtcggagtg ccccgctgac caggctgctt ctggccgcgg cggcgttccg  34200
ctgcagagga cgggagtgcg aatctgggaa gcagggttct ggttgaactc cagcttcgtc  34260
tgcaacatac tgtgtgactt gggcaaatta tttcccccgc cccgttcctg ccagcttaa  34320 aacggtcatc agtgggggt gctgcgtatc ccctttcact ggggtggctt cttcactgag  34380
gagagtcgcg cctcagagga actgaggtcc tgcctgtgtt cgacctggtg gggggcacta  34440
agagcccctg atagtacccc tgaccccatc cttattgggt gcacaagaca caggtcactc  34500
tgggcgggca aggagttttg gtagcaggag aggagtcggt ggatggatgg ctgaggacag  34560
tgcagaaggg tgtggctggg ccgtcttttt ttgcctggaa attcaagttc tgaggcaccc  34620
agtcactcca gcactaaatg ggtgcaggag gcagcacttg tctgcccagc tggaaaggca  34680
gggtatgtgc tgagtgttac aggtggaagg ccactggagg tcgctccagg agccgcgggg  34740
atttacctct gcctaacagg gctgctcaag gtgatggtcg acaccccact ttcctgagag  34800 cttgacccctc agatgccagg gccttggctg cagattcctt gggagctccc gggatcttc  34860 cagcaaatag gagcaaatct tttccccgtg gatcaggaag gtgcacgctc tttgtggaat  34920
acgactgctc accccgcaca gcaagcagct tataagtggc cctcctgcct gatttcagcc  34980
ctgggttcaa gccctgggtg gctgcttact accaaaatcg ctcagtagct ccaagcctgc  35040
ctgcagaggg ttggcaccat taatgaggt aacgagtcaa aagtccctac cctgggtcct  35100
agcctgtcag gggctccgaa aacccaggct caggtcggtc ctgcccggca cctgtttcac  35160
acatgtacac tccggtctga ggttggtcct ctcccccacc ccaccacct gcagttgagc  35220 agctgaacag aggccatgcc ggggcactcc gaggcctgag acgaccacgc ctgtgccgct  35280
```

| | |
|---|---|
| gaggaccttc atcagggctc cgtccacttg gcccgcttgg ctgtccaatc acactccagt | 35340 |
| gtcaaccact ggcacccagc agccaagaga ggtgagagga gggcttggag ggggaggcgg | 35400 |
| gactccaccc tgtgtgggac agttctgtca gttgaccctc cacttgtcca ggggcagtgg | 35460 |
| atctgcaggg ggaactcatt ctcaatactg ttcctcctga gaaacaaatt ttctgggctg | 35520 |
| ttttggttta ggtgtggcgt ggccctgggg acgcatggct gaggcaggaa caggtgagcc | 35580 |
| gtcccccagc gtggagggcg aacacgggac ggagtatgac acgctgcctt ccgacacagt | 35640 |
| ctccctcagt gactcggact ctgacctcag cttgcccggt ggtgctgaag tggaagcact | 35700 |
| gtccccgatg gggctgcctg gggaggagga ttcaggtcct gatgagccgc cctcaccccc | 35760 |
| gtcaggcctc ctcccagcca cggtgcagcc attccatctg agaggcatga gctccacctt | 35820 |
| ctcccagcgc agccgtgaca tctttgactg cctggagggg gcggccagac gggctccatc | 35880 |
| ctctgtggcc cacaccagca tgagtgacaa cggaggcttc aagcggcccc tagcgccctc | 35940 |
| aggccggtct ccagtggaag gcctgggcag ggccatcgg agccctgcct caccaagggg | 36000 |
| gcctccggtc cccgactacg tggcacaccc cgagcgctgg accaagtaca gcctggaaga | 36060 |
| tgtgaccgag gtcagcgagc agagcaatca ggccaccgcc ctggccttcc tgggctccca | 36120 |
| gagcctggct gcccccactg actgcgtgtc ctccttcaac caggatccct ccagctgtgg | 36180 |
| ggaggggagg gtcatcttca ccaaaccagt ccgaggggtc gaagccagac acgagaggaa | 36240 |
| gagggtcctg gggaaggtgg gagagccagg caggggcggc cttgggaatc ctgccacaga | 36300 |
| caggggcgag ggccctgtgg agctggccca tctggccggg cccggagcc cagaggctga | 36360 |
| ggagtggggc agccaccatg gaggcctgca ggaggtggag gcactgtcag ggtctgtcca | 36420 |
| cagtgggtct gtgccaggtc tcccgccggt ggaaactgtt ggcttccatg gcagcaggaa | 36480 |
| gcggagtcga gaccacttcc ggaacaagag cagcagcccc gaggacccag gtgctgaggt | 36540 |
| ctgagaggga gatggcccag cctgacccca ctggccactg ccatcctgct gccttcccag | 36600 |
| tggggctggt caggggcag cctggccact gcctagctgg aatgggagga agcctgcagg | 36660 |
| tggcaccggt ggccctggct gcagttctgg gcagcatcct cccaagcaga gccttgctg | 36720 |
| aagctcctgg ggtgtgggt gtgggctgga agcactggct ccctggtagg gacaataaag | 36780 |
| gttttgggtc tttctgagac tttgtgtcta tctgggccct gcttacccaa agggctcagt | 36840 |
| tggcagcaag agctccccac acctgaccct cggtgccgga ccactcgagg gtggctgaca | 36900 |
| cctgcatccc tcaccagcac atcacccagg tgacagtgag aattggaaac cccaggcctc | 36960 |
| ctctagggct tgtggctcag tggcaggtgt ccagtgagtg ccctcaatgg gcctgagtgg | 37020 |
| gtacagaatc tgccctcccc caaccaaagc ccacatgatg ccatcagccc caggcctagt | 37080 |
| gcagaccaca gcttgggaag cgaaagggag atg | 37113 |

<210> SEQ ID NO 12
<211> LENGTH: 15540
<212> TYPE: DNA
<213> ORGANISM: Homo sapiens

<400> SEQUENCE: 12

| | |
|---|---|
| agccaagcat tccgactcag ctctgggagc agctgccttc tgggctggca ttctccgcca | 60 |
| gggggggttgt gccctcgtgg ccccccccgg gtgcctcctc acctggctga tttcatctcc | 120 |
| tgtcccctg cctcctcctc caggaagccc ccagggcctg gccctccttg agagtggcat | 180 |
| ggaggaggaa gaagactcgc ccaggccat gggagtcgga tggtggccgc acttgtgggg | 240 |
| ccctgacccc ataggcttct tcagcacgcc ctggcctggg tgatccctgc ctgagggctg | 300 |

```
tgcacggctc atctgccaga ccagatttta ggggattctt gtactgtcct cctggagcag    360 caggggtaa agcctgaccc acccagactg tccagcaaca agggcctcct gctgtgggcc     420
agggaccctg gaactgacca attgtgtcct agggacgcag agtccccagg ctgctagagg    480
gctgtggggc cctgtttcat gcctgaagca ggaagaaacc ccaggagagg tctgaagggg    540
acccagcccc caccctgtct agcagggagg agcctctgca agaggccgag gggtgctgaa    600
gtggaggagg atagaggcag caggactcag ggtcactggt catttatggg gatcacacgg    660
ctgcagtgtg ccctgcatgg tgctaggcac cagggacagc agaggacaag cctgtgtcct    720
ctcccaccac cagagggctg gcactgccc  ctagggagag aggggggcctt ggtgtgtgca   780 gagggggcc tggggcacgt gcctggcctg gtcagatgat cagagtgggc tgggctgggc    840
ctggtctggg gcccagtctc aagggcagac cccacctggc tagagttgat tgtgtgcaca    900
ccggatgacc cggcgttgaa ggcctctcct ctctgtgagc ctcatcccca cctgccagac    960
tcccagcaca gcctgcttcc tgccccagct gctgagcgac agcgctgggc cggcttctgc   1020
gcgccccttc ccccagccca tcttggaaac cacagcagcg tccttcctcc caagtccctt   1080
cccagggctg acatcccaca gcagggatgt atcccacaaa ccccgcaggc cctggtgcct   1140
acagcttggc ctggtaacat caaatcctac cctctcctcc tggcagcaaa gatggggtgc   1200
ccccacccca gagttctcag cacccccaga cagaagcagt ccccagcga  cctcagaact   1260 cttgggcgc  tgccacaccc ttgcaggagg gggcagtgtt cctgggatgc tcaggtcctg   1320
gtatcacctc tggccagata cggaaggtga aactacaggg catccaattc accttgaact   1380
tcagataaac accagattat tttttgtat  gtcccgtgca atatttggga cacacttacc   1440
ctaaagaagt attctgtttt catctgagag gcagatttaa ccggcgtccc gtgtcttcct    1500
ggcagtcctg ccctggagtc acactccaca ggtgcagggc agggccaggc tccaagtaga   1560
tggcggccaa agcacccgcc ccatgctcct gactcccggg gctcttcagg gcattgcgaa   1620
aaccagcagc agagctgaca cctggtccct gctcgggagc cagcaaggca ggaggctgct   1680
taggccttgc gtgtgggtg  ggcgcactcc ctgctgcagt gctcttcgta catgtgacac   1740
tgttcccgct cttccccagc tggctggagg cgtgatcctg ggtgtggccc tgtggctccg   1800
ccatgacccg cagaccacca acctcctgta tctggagctg ggagacaagc ccgcgcccaa   1860
caccttctat gtaggtgagt gcacatgtgg ccgcagacgc attcagggag gcttctagg    1920 aggaggcagg tcctagcctt ttggatgggg acatggaggg tgaaagacag tcgggcatgg   1980
cgtgtccggg cagggaggcg gccctggaaa gggctctggg cacaagggtt gagatggagg   2040
tgggcctgtg gcctgctggc ccttctggtc tgagccaggg caggggtgg  cagctaggcc   2100 tgggcaggga ctgtgtggag accttgctta ttttaagtgt ggggttattt cggggaggc    2160 tccctgagaa gggtggggct ggatgcctgg gccacacaga gcagccgagg cagctggcgc   2220
tgtggagccc gggagggagg gagggatgga gctcaaggga tggaacccag tgaggggtgg   2280
agacggggca gggagggt  ggagaggggt ggagacgccc cagaggcggt gtgactcagc    2340
tgcccctgca gcagctgca  ccttgctgcc ttattaggct gcgtgtgggg gactgggctg   2400
ccctccctgc ccccaggagc aggagcagga gtgatggagg aggaggaggg gaggggcaag   2460
gccaggagga ggaggagggc catctcactg tgcagagagc agcacccttc ctcctggtgc   2520
ccctggcagg gctggtgctg gtggggctct gggagcattt gttgagatgc ttctggcctt   2580
gaaaggaggc ccctgggatg gctctgttgc cctcacaggc tgaggggtgg gtgaggtggg   2640
cagcctgtgt gtcccagtc  ctcagggctt ccctcagccg gcaggtgccc ccaggcctgg   2700
```

```
agctgcaggg ccaggccccc tgccagttac ggaggctgct tggcttggtt gctgaaccag    2760
ggccccagga ggccgaaata gccccacacc tgcgccgtcc cacctctttg tccagtcacc    2820
ccagggccag gtgagggccc tggccacaca gcgtgcccgt tccttcttcc ccatgccccg    2880
ctcatgggtc agagggccgg tgctggggtc cagatggtgt caacagggat ggtccctgtc    2940
ctccccagag acagaagcct gtggcccacg gagggtttct gggcccagcc gatcctaggg    3000
agggtcccat ggccctgccc ataggttcct ggcctctctc ggggccgtgg tgccctcaca    3060
ggtggtgtca ggaaggacgg gaaaggctgc ttgtcccagg ggctcatgtg gagaccaccc    3120
cctgcacgca gctggggcgc tcctgcctgt gtcctcagaa gcactcggct tagctttgcc    3180
catgtgcctg ggctgtgggt ggcagagccc ggccagcatc ctccgatctc caagggtgca    3240
tctctactgg aggcccctcc tgggcctctt gctccccgct tcccagatca ttaggatatt    3300
tggggtccag aagggcctcc cagccatcct gggccttgtc ctccggggcc accagtccag    3360
ccagtgacaa ccacagcatc cccggcctgg aacgaggctg cccccagcac gttcctcgta    3420
ctcctgtcca gggacaggag gggctgcccc tgccaccgag tccccttctc caggacctgg    3480
ggcctgtggg tgtgaggcag gtgttcttgg aaggggtcac tctccaggca cccggcggcc    3540
aaggcttgtg gctggagcag ctcccgctgt ggggtcggcg tcgggccccg tgtggccgga    3600
gaggagctga agggtcactt agcttcgggc tggggcgagg acaggggaca ccccagagag    3660
gtatgccagg cctccttcct gcgccccact ctcggcagaa gcagaggtca caggctgtgc    3720
tgaggcccca tggtgctgcc cccatgatgc cagggtgagg ctggcgttgg aagcaggtgt    3780
ctgacctgca tggtgtcacc gtggccacat cagagctcca gccccagagc cgcccaccct    3840
cggtccttgg ctgtggtttc cctgggctgg aggagcctgc cgttgtgttg ccacacgac    3900
cacaggacct gccacccccg acgtgggctc tgcctgggcc cccactggac agggacccct    3960
tggagctcct ctggccacca agtcctcgcc cattccagaa tcggccttct ggagcctctt    4020
gctgtccctg atgcgggctg ggccttgcca agggcttttt ttcctgcgcc gggaacaggg    4080
tggatttgct gggctcactc ccctcagaga cgctgcgggt gcggtgggtt aggcccaagg    4140
gcgttaagag aggaggctgg ggtgggggctg gggcctggca ggggtctgg cagccctggg    4200
cctcccacct cctgtcagga ccaaaaaagg caacgcgcct ctcctgacct gtaccccgga    4260
gtgaacccaa ccttgcaacc caggagtgtc agggcctgag gggagggaga cctggctcct    4320
gggtgccgtg cccgtaagga ggtggccacc tgcagggcat tcctggcaga ggcttcatct    4380
ggccaggtag gaggctgggt ggccgagccc caaatctggg tgtgttctct gcctggcggt    4440
gggtcctgcc ccaggcacct tctcctctgg gctggctggg cagggacaat gggcctggct    4500
gcgaggaggg ggcctgggct gccttctgca ttgcctcggt gacggagat ggcccctgcc    4560
tgctgaggga tagggagtg gcaggcagt gagagacact gacagctgtc ccgcgggtac    4620
agggccctgt ctgggtggcc aggcccatgt ctcgggccca cagtgcgccc ccacccttg    4680
gacggcgcct tctccctccc caggtgcatg ctgcccagcc agggagcgtg ggggagttcg    4740
ggagggctgg cctacacgcc ctggtccagc tgtcccaggt ggggtgctgg gcttcagccc    4800
tcagcccagg gcctaggaat ccaacttgat cctccccaca cagcagccag gttcaaatgc    4860
aggtcccgta acggaagtgc tgctgtgcag cccagattgg ggggcaggag ccagcagggc    4920
ccccccaccc tcttctcgca ccacactggg gaggcagcat tggttccagt tccggttcct    4980
gggctgccct ctcaacccog gcctacagtg gggcccaccc tgtgccttct gatgccactc    5040
ccaccccacg ccaagtccca gaggctttgg gagcgggtga aggcggtggg tggcgggtgg    5100
```

```
caggtgcagg cggtgggtgg tgggtgtggc aggtggcggg ccccaccgca ggtgtcatcc   5160
ctgcgaagca cctgtcgcca gcactcagag cgctcatgag gtgcccagtc ccatgtggc    5220
ctccttagtc tccgtcctgt gtcatggaag aggtaactga ggcacagaaa actcaccagg   5280
ccaggctggg atgtgaggtc ccttgctgct catccctggc agtcagcaac cctacatctt   5340
cccagctggg cggcccgtgg tgggttcggc acccaggacc ctccggggtc ttgggctgtg   5400
gcgagtgtgt aggcacccac ctggtgtctc tctccccgca aggcatctac atcctcatcg   5460
ctgtgggcgc tgtcatgatg ttcgttggct tcctgggctg ctacggggcc atccaggaat   5520
cccagtgcct gctggggacg gtaaggcagg gaggcgggcc tgtgcctggg ccggggaggg   5580
gctgggggct gcgtctggcc ctgaggaggg ggcagagctg gtgctcaggg cggagcctag   5640
aattctgggg gaggtggctc ctgtgccctg ctttttcccgt ttggttttta aattaaatcc   5700
caccgtgctt ggtctccatc gtggccagtt cctacgtgac cgcttttctt tgtcaaaaaa   5760
tagccacaaa tataacaggg agcaagcctc agctctgagg ccagcctcgg cgtcccgggc   5820
acaccgcccc ctgtgggaag cccaggcctg gctgtgccat ccagggcctg gccagtccag   5880
gaagagggag cctatgcccg tgtctccagt gggggaaact gaggcagatc ccatggctcc   5940
cccttccgtg gggagcagga acaagggggt ggggaagatc agtcaggggt catgctgctg   6000
cacacgcctc cctgggggct gcagacatcc tggactcacc agcctgtgac cccaaaccac   6060
acgccccgcc ccatccaccc cgtcctgtgg agcctggtgc cgcgtgggga catcctgggc   6120
tttgacggct cctccctgcg ctgagtttta gcctctgtgc cccagggctc cacacaagcc   6180
gctcactcct ggtcaggtcg tgggctggtg gctcccacta gcccctcaca gacacgcctg   6240
ctgggcacct gggtgtgtgt ccttgggccc cgcctacagc ctgccctctt tcctccctct   6300
ggccactgcc cggctccagt tcttcacctg cctggtcatc ctgtttgcct gtgaggtggc   6360
cgccggcatc tggggctttg tcaacaagga ccaggtgagc ctgggtgtgc agggacaggg   6420
tggggtgggt gacgggggca ccctcctctc ctgtcgcggg tggggttgg gctgactcat    6480
ggcttgtggg agctctttgg gctcttcctg gtcccacttt gccaggagga tctccagggg   6540
cttttatggag gaggcagcat tggggctgag caccaggcca gcctcccgtg tcccagcact   6600
cccggggcag ctgagagtgc agagtccttg tcctctgggg tctagcctcg aagccaccct   6660
gcccaggag agcctgggaa aagtgcgtcc gcctggggcg gggcggggtg ggggcaagga    6720
ggggggaggtt ccccctgtgc atgtgaccgc acccctcccc cagatcgcca aggatgtgaa   6780
gcagttctat gaccagggcc tacagcaggc cgtggtggat gatgacgcca acaacgccaa   6840
ggctgtggtg aagaccttcc acgagacggt gcggccccgg ggggcgaggg cggggagcag   6900
ggccccggga acccggcggg gtgtgtctcg tcctggatga atcctgccta cgcccagacc   6960
tcaggagcag gaggtgccct tgggacctcc aggacccctg gtctcaactg gtcctcgggt   7020
gggaacctag tgggccaggg tggcccaggg tgcggaaagc tctgagcagc gcagctgagg   7080
aggaagaagg ctggccctg gatgcattct gcagtgggga gcgctgcgta cccctggcca   7140
cctccccatg ggttccctag agccaccgtc ccctgggca catccagggc tgaccttgca    7200
cccctgctct ctgcagcttg actgctgtgg ctccagcaca ctgactgctt tgaccacctc   7260
agtgctcaag aacaatttgt gtccctcggg cagcaacatc atcagcaacc tcttcaaggt   7320
gcgcgaggcc ggtgggggccg cgcctgaccc cccgcatgtc ccgcccctgg gtgggtcct   7380
aggggtgggc aggtcacacg gcagcccccac agggagcgac cacactgggt ggcatggccc    7440
ctgtcagggc tgctctgctg ggagggttgg ggtgggaccg catctggccc acgaggaagg   7500
```

```
caggcgccct gtgctgcgca ttccgggtga agaaggtgga ggctctgggg ggtgggaact    7560
cacctgcacc cccagctcca cgtgtgcact cgtgggtgtg gacgccctg acagcctgta     7620 gctggcaggg cctgcaggcc atatagtgcc ctgtggaagt ttcctgctga ggcctcagtg    7680
gaagtcgtca tcagtgatgc tttaggggtc tagtgacacc aatgaccgtg atctcagtgg    7740
aaaagggcac agtgtgtccc aggcatttcg cgtttatgtt aaaacgggtg aagatagca    7800 agccggcaga ggccgggccg ctgcacccgc ctgttccgag gtgggtaggg ggtgggggc     7860 tgttcccagg attcccctct acgctttctg tggtgaccac ggattactgc gtgacaacgg    7920
gaagccggga gccgaggccc ggtccctgac cacgcgtgcc tggccacccc tgcaggagga    7980
ctgccaccag aagatcgatg acctcttctc cgggaagctg tacctcatcg gcattgctgc    8040
catcgtggtc gctgtgatca tggtgagcgg gcggggggcgg agggcctgct ctctgggctg   8100 cccccttccgc ggggccttgt gctgactgcg cccccacca ccctcctgca gatcttcgag    8160
atgatcctga gcatggtgct gtgctgtggc atccggaaca gctccgtgta ctgaggcccc    8220
gcagctctgg ccacagggac ctctgcagtg ccccctaagt gacccggaca cttccgaggg    8280
ggccatcacc gcctgtgtat ataacgtttc cggtattact ctgctacacg tagccttttt    8340
acttttgggg ttttgttttt gttctgaact ttcctgttac cttttcaggg ctgacgtcac    8400
atgtaggtgg cgtgtatgag tggagacggg cctgggtctt ggggactgga gggcaggggt    8460
ccttctgccc tggggtccca gggtgctctg cctgctcagc caggcctctc ctgggagcca    8520
ctcgcccaga gactcagctt ggccaacttg ggggctgtg tccacccagc ccgcccgtcc     8580
tgtgggctgc acagctcacc ttgttccctc ctgccccggt tcgagagccg agtctgtggg    8640
cactctctgc cttcatgcac ctgtcctttc taacacgtcg ccttcaactg taatcacaac    8700
atcctgactc cgtcatttaa taagaagga acatcaggca tgctaccagg cctgtgcagt     8760
ccctcagtgc cagtggtgtc tgagacctag gggttggccg gagggcaggg gaatctgaca    8820
tcggtggggc ttggctctgt ggactctgtg gggtccaggg tgagggtggg tgggtcggga    8880
tccctggtgt tcaccaaagg agtcactctg taaaatttgg ggagttattt attctgagcc    8940
aaatatgagc accggtggcc tgtgcacacag ccccaggtcc tgagaacttg tgcccaaggc    9000
ggtctggcta cttaattgta tacattttag ggacatagga cattgatcat tacatctaag    9060
atgtacgttg gtttagtcgg aaaggtggga cgatttgaag gggagggact ttcaggtcat    9120
aggcggatta aaagatgttc tgattaataa ttggttgatt ttatctaaag acctgaaatc    9180
aatagaatgg actatctggg ttaagaggag ttgtggagac caagattatt atgcagatga    9240
agccgccaga ttgtaaatgt ttcttatcag acttaaaaag gtaccagaat cttagttaat    9300
tctctcctgg atcaggaaat agacctggaa agggaggggg attctctata gaatgtagat    9360
tttcccaaga gacagctttg cagggccatt tcaaaataca tcagagaaat atattttggg    9420
gtaaaatact tcggtttctt tcagggcctg ctgtcacgtt ggtatcttat tactacagag    9480
tctgttttgt gagtcttaag gtcttttat ttttagacag agttttgctc ttgtcaccca     9540
ggttggagtg caatggcgtg atctcagctc actgcagcct cccctccacc tcccaggttc    9600
aagcgattct cctgcctcag cctcctgagt agctgggaca acaggcatgc accacccac     9660 ccagctaatt ttgtattttt agtagagacg gtgtttcgcc acggtggcca ggctagtctc    9720
gaactcctga cctcacgtga cacaccaggt tttgggatta caggtgtgag ccaccacacc    9780
ggactaaggt ctctgttttta atgtgaatgc tggtcagctg tgcctatgag gcatgttcgg    9840
ccacccacag tcatcatggc ctcaacgagc ttttcaggtt tactttagaa tgcatttggc    9900
```

```
caagaggtgc ccattcagtt ggttggggtt gcttagaatt ttactttggg tttaaaccag    9960
ggagcaactc caggtagcaa gggccctttt tgggagcgtt ctctctattc tcttttggga   10020
gaggccctgt gttgcctgca gccacttcca ccctgcccct tgggcacaca aggggcacac   10080
agtgtaagca ggtgggcagg aggggtcggg cagccaggga atgcagtgag atgggcttgg   10140
ggtaggggct gggtgcgctg caggactcct cttcctcctg agggatggta aaggatggac   10200
acactgcccc ctcccgagca tttgagggtc tctgccctgc ccatctgtta cctgtaaatg   10260
ttccctttgag gagctgatgg ctcaggcctg agccacatct cagagggtct ggaggggaag   10320
aaagacctca tcctactagg gagcccccc  agcccaccag cgagcggtgg ttgggggcag   10380
acaggctgtg gggctaagga gcccctgcac tccccgtcc  ttttcccttt gtctgagcac   10440
ctccagccag tgggcttggt ctagactctc ctatctttcc ccacatcgtg gggtggggct   10500
tgctctgggt taggctactt ttccctagtt gtggggaggg gggtgctggc acatttcact   10560
gttccctgga ggaaatgagt gcctgggaat tcatatctag ggctcccagc agcctctttg   10620
caggccaatt tggaaactgt ccccagccct gcattttagg gggttacaga gtctctcagc   10680
aggccctcct cccctgctgc tcccaacttg caagcctgca ctggttggga gaacataatg   10740
gtccaaggag cccctctct  actttccgct gtgttccctg tggggaggga agagcagttt   10800
aagaaataag gaatcccaaa ggcgcacagc agaccggggg ccgaggagtg ggtcctgctt   10860
cccctccttt tttctaggct gagccacagc aggtccttga atcctatttc ccagcggatg   10920
ccaggacagc aggccctggg ggagttctct ctcgagcctt tcagagggac cagaggtcta   10980
gcagccaagg agaactcaga atccttgagt gtgtgggca  ggaactctcc cagctgagaa   11040
ggggcacaag gtgccaacca tctagggccc agtggccaag gaagacgcgg cttgtcgcag   11100
ggagaatctg ggccctggtc ctccctttca gggcgggcag ctgacctgcc ccctgctgcg   11160
gacaggcgag gccaggctgc tggctcgcaa gcatggcgga gcccaaacct tccctgctgc   11220
cgcccgccca gccacggctg acttggaagc ttgaggagcg ttcagcagcc tccatcctgc   11280
ccggaggac  cggggacctg gaagggcctg gccctcgctt ccctgcagcg ccctagggg   11340
acgtctcagt gcctcccgga gcccggacca atgcaccaga gctgagggcc caagggtgtg   11400
agggtggccg ggcagtggcc ccgaggacgg cgccccacaa gtttgcggcc agggcccagc   11460
aaacccctag gggtgggaaa gcgtcggccc agctagcggg tccagcaggg ctgccccctt   11520
caccgtggcc cagcggtcac gaccccacgt cctcatcgcg ggctgggact gcctctgcgt   11580
ctggcctgag cgggaccgtg ggatcctggg gagccccgcc tcggtgcact gacagagccc   11640
agaaggagtg acggttaccg cttccggtca ggaccggaag tgccgggaac ggcattcgtc   11700
ctccgtgcga gatgacgcac ttcctgcctg aggcggccgc tgttctcgcg gcttccggca   11760
ggtggcgctg agaccacggg aagccagcct ggctgtcggt tagccctcga gcattctggg   11820
aattgcaggc ctggccctc  ctcttcctgt tcttggtcaa ttccggtctt gtttccccaa   11880
caaatgccgt cgtttccggg gctgcttccg agccggaccc aagggccggg gcgtggagga   11940
gtagaggggc gagcgcatgc gcacaggact acacgtcccg acaggcgtcg ggagcggcgg   12000
cccagttcct tgtgggagct gtagttctgc aggcgcggaa gccgtggtgc tcggccggca   12060
gagcactcgg tttcccagag ggctgagcgc gccgcacgga ggtgcggcgc cgaccaagat   12120
ggagactgcc gagcagcctt gagccggtag gtttgtggtg agggaggacg ggccgcgcgg   12180
gccggccgag cctccgggag gtcaccgagc gcagctttaa tacctgagct cgaaggcccc   12240
gctgtgctcg ccgacccccg tacctcgcgg ccgggccctt gggacccaca gcatccttgt   12300
```

```
gaggcccgga ggcctgtcca gcccgactgg acagtgccga ggggcaccga gagccagctt    12360
ggcaccgaga gttcgtttgt tctctggcgg ggaggtcttg ctggcacata tagtggagaa    12420
aggccgggct ctgcgttcat gtggagaaag agacggcttc cttcagccta cggacatgaa    12480
ggagtcaact ctaccttcca ctcgttgccg gctttcgccg agaacccga gaaacggact     12540 accggagtcc ctatcttgca gcccgatccc cgctaccgt cggagtgccc cgctgaccag     12600
gctgcttctg gccgcggcgg cgttccgctg cagaggacgg gagtgcgaat ctgggaagca    12660
gggttctggt tgaactccag cttcgtctgc aacatactgt gtgacttggg caaattattt    12720 ccccccgcccc gttcctgcca gctttaaaac ggtcatcagt ggggggtgct gcgtatcccc   12780
tttcactggg gtggcttctt cactgaggag agtcgcgcct cagaggaact gaggtcctgc    12840
ctgtgttcga cctggtgggg ggcactaaga gcccctgata gtaccctga ccccatcctt     12900 attgggtgca caagacacag gtcactctgg gcgggcaagg agttttggta gcaggagagg    12960
agtcggtgga tggatggctg aggacagtgc agaagggtgt ggctgggccg tcttttttg     13020 cctggaaatt caagttctga ggcacccagt cactccagca ctaaatgggt gcaggaggca    13080
gcacttgtct gcccagctgg aaaggcaggg tatgtgctga gtgttacagg tggaaggcca    13140
ctggaggtcg ctccaggagc cgcggggatt tacctctgcc taacagggct gctcaaggtg    13200
atggtcgaca ccccactttc ctgagagctt gaccctcaga tgccagggcc ttggctgcag    13260
attccttggg agctcccggg gatcttccag caaataggag caaatctttt ccccgtggat    13320
caggaaggtg cacgctcttt gtggaatacg actgctcacc ccgcacagca agcagcttat    13380
aagtggccct cctgcctgat ttcagccctg ggttcaagcc ctgggtggct gcttactacc    13440
aaaatcgctc agtagctcca agcctgcctg cagagggttg gcaccattaa atgaggtaac    13500
gagtcaaaag tccctaccct gggtcctagc ctgtcagggg ctccgaaaac ccaggctcag    13560
gtcggtcctg cccggcacct gtttcacaca tgtacactcc ggtctgaggt tggtcctctc    13620
ccccacccca cccacctgca gttgagcagc tgaacagagg ccatgccggg gcactccgag    13680
gcctgagacg accacgcctg tgccgctgag gaccttcatc agggctccgt ccacttggcc    13740
cgcttggctg tccaatcaca ctccagtgtc aaccactggc acccagcagc caagagaggt    13800
gagaggaggg cttggagggg gaggcgggac tccaccctgt gtgggacagt tctgtcagtt    13860 gacccctccac ttgtccaggg gcagtggatc tgcaggggga actcattctc aatactgttc   13920
ctcctgagaa acaaattttc tgggctgttt tggtttaggt gtggcgtggc cctggggacg    13980
catggctgag gcaggaacag gtgagccgtc cccagcgtg gagggcgaac acgggacgga     14040
gtatgacacg ctgccttccg acacagtctc cctcagtgac tcggactctg acctcagctt    14100
gcccggtggt gctgaagtgg aagcactgtc cccgatgggg ctgcctgggg aggaggattc    14160
aggtcctgat gagccgccct caccccgtc aggcctcctc ccagccacgg tgcagccatt     14220
ccatctgaga ggcatgagct ccaccttctc ccagcgcagc cgtgacatct ttgactgcct    14280 ggaggggggcg gccagacggg ctccatcctc tgtggcccac accagcatga gtgacaacgg   14340
aggcttcaag cggcccctag cgccctcagg ccggtctcca gtggaaggcc tgggcagggc    14400
ccatcggagc cctgcctcac caagggtgcc tccggtcccc gactacgtgg cacaccccga    14460
gcgctggacc aagtacagcc tggaagatgt gaccgaggtc agcagcagca gcaatcaggc    14520
caccgccctg gccttcctgg gctcccagag cctggctgcc cccactgact gcgtgtcctc    14580
cttcaaccag gatccctcca gctgtgggga gggagggtc atcttcacca aaccagtccg     14640
aggggtcgaa gccagacacg agaggaagag ggtcctgggg aaggtgggag agccaggcag    14700
```

```
gggcggcctt gggaatcctg ccacagacag gggcgagggc cctgtggagc tggcccatct   14760
ggccgggccc gggagcccag aggctgagga gtggggcagc caccatggag gcctgcagga   14820
ggtggaggca ctgtcagggt ctgtccacag tgggtctgtg ccaggtctcc cgccggtgga   14880
aactgttggc ttccatggca gcaggaagcg gagtcgagac cacttccgga acaagagcag   14940
cagccccgag gacccaggtg ctgaggtctg agagggagat ggcccagcct gaccccactg   15000
gccactgcca tcctgctgcc ttcccagtgg ggctggtcag ggggcagcct ggccactgcc   15060
tagctggaat gggaggaagc ctgcaggtgg caccggtggc cctggctgca gttctgggca   15120
gcatcctccc aagcagagac cttgctgaag ctcctggggt gtggggtgtg ggctggaagc   15180
actggctccc tggtagggac aataaaggtt ttgggtcttt ctgagacttt gtgtctatct   15240
gggccctgct tacccaaagg gctcagttgg cagcaagagc tccccacacc tgaccctcgg   15300
tgccggacca ctcgagggtg gctgacacct gcatccctca ccagcacatc acccaggtga   15360
cagtgagaat tggaaacccc aggcctcctc tagggcttgt ggctcagtgg caggtgtcca   15420
gtgagtgccc tcaatgggcc tgagtgggta cagaatctgc cctcccccaa ccaaagccca   15480
catgatgcca tcagcccccag gcctagtgca gaccacagct tgggaagcga agggagatg   15540

<210> SEQ ID NO 13
<211> LENGTH: 25760
<212> TYPE: DNA
<213> ORGANISM: Homo sapiens

<400> SEQUENCE: 13
gatcacgata gccaagaaat agactcacac atgaggacag ctagtttgac aaaggtgcaa     60
agtcagttta atagagaaat tgtatctttt caaccaatga tgctggaaca attggatatc    120
cacctgcaaa aagacaaaat aactttgacc aattcctcaa gctgtattca aattcattaa    180
tgtaaaatga attagtaacc taatataaat gtaaaactgt gaaactgtta gatgaaaaca    240
tggtggaaaa tctttgtgac cttagattag tcacagaaag gatatgacgg caaaggcaca    300
attcataaaa gaaggtggc taatggaat gtcatcaaaa tttaaaaatt ccactctttt    360
gaaaggcagt cataagagaa taagaaagc aagccatcag ctgataggaa atattcacaa    420
atcatattac gatgaaggac ttatatccag aatattcatt gcatattctc tgtgtatttt    480
caaaaatgaa tagtaagaaa acaaccctat aaaaatgagc aaaaaagata tacagatatc    540
tcctacacac ttgaccaaag aagatatatg gataataaat aaggtcatga aaacatgctc    600
aacatcatta atcattagga aatgaaaat taaaatcgt aatgagatat cgctacacac    660
ctattagaat ggttaaattt tcttgctta aaactgatca taccaacttt tggcaaaggt    720
aggagaaact gtaattctca tgcactgtga gtgggaagat taatggtaca accccttta    780 aaaatgattt ggtagattct taaaaggtga acacacacc ggccggccat atgatccatc    840
cattccactc ctaggtattt attcaagaaa atgaaagca tttgtctcca caaagacttg    900
ttcatgaatg tttatagcat tggatcatag atagcccaaa ccagaaacaa tccaagtgac    960
gcctaacaag tgaaggtata agcaaatata cccattcatg ttatttatca ataaaaataa   1020
atgaacgatt gatacctgca acaatatcaa tgaatctcaa aataagtata tggcatgaga   1080
taagccagac aaaagaatac atcctgtatg tgtccattga cataacaccg tagaatgcaa   1140
agaatacctg atagaaggcg gatcagtggt tacctaaggc tggggaggag gggtgggagg   1200 aaggattac acagttgtaa tttaattacg aatttaaaac ttacaagaaa ttgttgacgg   1260
tgatgatggt ctcactgttg tacacatatg tcaaaattca taaaactctg catttggcc   1320
```

```
cagtgtggta gctcacgcct gtaatcccag cactttggga ggctgaggca ggtggatcac   1380
ctgaggtcag gggttccaga cctgcctggc aacgtggtg aaacctcatc tctattaaaa    1440
atacaaaaaa cttagccggg cgtggtggca cgcacctata gtcccagcta ctcaggaggc   1500
tgaggcagga taattgcttg aaccctagat gcagaggttg cattgagccg agattgcacc   1560
actgcactct agcctgggca acagagagag acctatctaa aaaaaaaaa aaaaaaaaa    1620 aaaaaaaaa acaaaaaaaa acctctatat tttaaatatg tgtagtttat tgtatgtcag    1680
ttagccccca ataaacctat aacttcccag gggaaatggc tgagattgat gccaccttca   1740
aagagttaaa gaaggcctag gtagtaaccc ccaccatctc tctcgtgatt tcccctctct   1800
ggcctctctg cagactggct gaatcagaat agatgattgc agacctcaaa ctcaaccaag   1860
tagcaacacc aaatgggctg ccaggccaga tgtggtatct tcgtttaatc ttagattaaa   1920
ttagattcat ttaatctaag attaaattaa cactgcccct ggtacccggt atcagtagct   1980
acggattctg tgaatgaatt ctcttccatc tcatcaggag agagtgtgag aagcaatttg   2040
cattcgcaca ggagggacaa cagtacacag tcacagtttt gccccaggga tatgttaatt   2100
cttctgctct ttgtcacagt atagtccaaa gggaaaaggc cctctggaca ttccacagat   2160
tatcacgtta gttcactata ctgatggcag tctgttaact ggatctgacg agcaagcagg   2220
ggaaagtact ctggacgccc caagtaaggc acacgagcca ggctgggaga taaattccac   2280
gaagctttag aggcctgcta catcatgatc ttattaccat gaagttattg ccataaaatc   2340
tggcaaatcc catggtacaa gaggtatttg caatggagaa agacaccaca cacacagagc   2400
ccctggagaa cttcaaagaa gagtcatggc ccagactcct tgggctctgg aagaaggccg   2460
tgcagagaac gataccattc agaaagaggt tcctgctctc ctgtgggaac ctctagagaa   2520
agagtttctg gtcatggacg ttaagtgacc atgtggtcag agatgcccat cttgagctag   2580
gatctgttaa acccaccaaa tcagaaggtc aggcaagccc agcagcatcc agtatacatg   2640
ggaaaagaca cctcctggga ctgcgaacaa gcagagggca aaagaaagcg acataatccg   2700
gggatcggaa cccccacgtc atctaccagt gttgcactga cacctcttct tcagtccaca   2760
cctgtggcct cctgcagagg tccctctgac cagccgatgg agaaggaagg ggcctgagct   2820
tcactcattg gcaggttagc tagaaacgtt agtgagcccc caaaggactg ctcctgcact   2880
gcagcccact caggtggtgg tgatggtggc gatgggtaa ccctcccagg gggccgagct    2940
ttgagtgcag gacctggtcg tgcacttgta gggagagaag cgaaccaaat cagtggttct   3000
atttctagca gttttaggct ctacaggcc attcccagag cggacgctt ccaccggaag     3060 acgctattaa gacagcttcc acctggtcac ttcgggctcc tggtatcaac aatctggcag   3120
agagaatgaa gttcccatac tggcagggt aactggctgg gagcatcatg agaaggtatg    3180
aatacagtca tcaatggggg cgggcaggtg acccaccagg ggcatctctt ggtgctgcca   3240
tgcacagatc ttcccgcaag tagcaagcgc cacagtgtga gcatgataag gccatggtga   3300
ccacaggctg ctcaaggtcc cggctatctg acacggatgg aggaggaagg ggcggtggct   3360
atcagtcagg gccccaggca atgaaaatgg caatggcaat ggcaggagta ggcactggcg   3420
ttcatcccac tcagcctgtt agtgtcaatt tcccctggtg ttgggaccaa tttgatcctg   3480
gagaagctct cctcagggga gcaaacctcc tacacaggtg ggctgtgcgg ggggtggggg   3540
tggagtaagg cgtgttgggt catgggtgct actggtgtcc tccccaactc cttttatctg   3600
gaccgtgtgc ctatccccca gctgttaagt gttgacaact aatggctcaa tgaagagctg   3660
tttagctaaa gggaagcccc acatccggga cgtgtgtgcc ctgggggaca cacagcaaat   3720
```

-continued

```
gactgacaag gaggaacaga aggcagcctc ttgcttccag tcctgggaga ccatgctgaa    3780
gccctgcctc ctggcttatc tgtatctcct gcacaagaat tccagcccag gctctgtttc    3840
tagggagtgt gccctgagat gccagcgctt gagcttcgag agcacgaggg ggtaggttct    3900
ggtggacagg gaccccggtg tgacgacaac tgcaaggttc accttggacc ctggcactat    3960
cctcccacca ggctggaaaa ggagaccagg acatggcccc agcacagccc ccaggtgggc    4020
aaaccggcag gctgggctgg ctaagctctt ggtgttcttt gtgtggggt aggtggggct     4080
ggtgagggcg ggactggctg caggtccttc agcgggtccc tgctggacct ccgtggcggg    4140
gacagggatg aaattaaaac agacccgact ccattcaatc tcagcgatcc atgactcagt    4200
gatgcccgga gctgcctccc tttctcctcc ctgggctccc accccgccgc gccccacccc    4260
attatgatcc cccccaaaat gcagagagcc cactagaggg aggaggctga gggctccagg    4320
ctgccctggt cagacaacac atcatgttcc ttcacctgca gatagaccct gagcccatca    4380
gtgaaacaag gggcccccag gagaatcaga atcctgaccc catcccaccc tccacaccag    4440
ctcaacggac tcccaggctg ccagaaaggc ctcatacgtc aaagtcagcc tcccagtcgg    4500
cctccgtttc caggtgtggg cctggagtgc cgtggcccag gtggtatcag aagctcgcag    4560
ggataggcct aagaggtgac cccaggggag ggccaggcca aggagctgca gagagggctg    4620
gggaagctcc agatccccca cctccttcaa aacacacctg aaacaccagc cagcaccagc    4680
accaccaaga tgagaaaggg ccctggaccg tctccaccag tgtcatgcag cagctgggct    4740
ggtcccctcc cttgggtccc catctgcccc acttgtacag gagctaacga cgcctgctgc    4800
ccacccagga ggacctagca ggagcccagt gtgaaggtgt ttgcaaaact ctggggaaag    4860
tgaaggtcag aggtgactcc cagcttccac ttaggacata gagagctgga aagagcccgg    4920
ctcccatcct taaactgcag cagcaacaaa aggcaccaag caacctgaaa agtcaggact    4980
tttctcaaaa ctctctgaga gctgaggtca cagggcaacc aactaaccca aaacaaaggg    5040
aaggcaggcg cctgcaggag gagacgggat gcaggctgtc accgagacag acgaggccag    5100
acaccaggaa gaagaacaca gccaaaatgt ttaatgagtt ggcaagggtc ggtgtggggt    5160
aatgggagag cacagaagcc ccaggggctg cggagtgaag ggaaatccac atccactgga    5220
aggtccccgt ggatttcacg ggatgctctc tttgtggtgt aggcccagca gaggggaaca    5280
gcagccactg tccaaaggt acaaaaccta cataggttat tctcctcaat ggaacaaaac     5340
ccttagattg ctggaggaaa ggcaaaaaag gcaaaaaaca ctgtcacact tagggcacga    5400
gtagaaacca tcgaaactgg gggaatccta aaagccctgt gccctgggga gggataagct    5460
acatggtggg cccagagcta cagctgagcg tagggcagga gtcccaagaa tgcttcaccc    5520
acaagaccca aaggacatag ggttaatcag aaaaaaccga acagcccccc acctccagca    5580
cctgctgaca agcaccatgt aacaagtgac cctggagtgg gagaggccgc agagtgtggc    5640
ctgggagagt ctgcggagtg tggaaaccct ctccaaggta agcttatagc cgaaggctgg    5700
ttggacactg ggaaaagcct ctctatggta aacacaaagt agtgctggag ggatttgatg    5760
actgtggtgc tccagagata accatgacaa caccaaactg aaaccagct caactctgga     5820
cgagattagc cccaagcccc gcagtaaagg aacagcaaaa agaagggtat gcccatttcc    5880
aaaagcacaa aacgaatttc ttcagtctct actgtcctct gcacgatgtc tggatttcaa    5940
aaaattgatg aggcctatta aaaaaataaa taaataggcc agggtctgtg gctcacgcct    6000
gtaatcccag cactttggga ggccgaggca ggtggatcac gagttcaaga gatcgagacc    6060
atcctggcca atatggtgaa accccatctc tactaaaaat acaaaaatta gccgggtgtg    6120
```

```
gtggcacacg cctgtagtcc cagctacttg ggaggctgag gcaggagaat cgcttgaacc   6180
cgggagacag aggttgcagt gagccgagat cgcgccactg cgctccagcc tgggcaacaa   6240
gtgagactcc gtctcgaaaa ataaataaat aaataaataa taaataatag atgaatagat   6300
aacgtgctat caagacaaag caagcaaaat aatcagactg aaaggctggt ctcagtggct   6360
cacacctgga atcccagcac tttgggagac tgaggtggga ggatcgcttg agcccaagag   6420
tttgagacca gcctgggcaa cacagagaga cctacctcta caaaaaataa aaataaaaaa   6480
atcaactgtg catggtggtg cccacctgtg gttccagcta ctcgggaggc tgaagcagga   6540
gaatcacttg agcccaggag gtcaagcctg cagtgagtta agattgtact tctctactcc   6600
ggcccggggc agcagagtga ggccttgtct caaaataata atgataaaaa aagaaacaga   6660
ctcagatatg acacagccgt cggaactgtc agacaggaca ttttaaatac aataaatatg   6720
ctaaagactc taaggaccct aatggagaag ggggaaaata tgcaagctca gataggtcac   6780
ttcagcaaag agatggaaac tagaagaaga aatcaaatgg aaaagctaaa ataaaaaaca   6840
gtaacagcca tgaagaagaag cctctggtgg gctcatgaat gtactagaca cagcaggaca   6900
gggtccgtga acttgaacac agttcagtaa aaaataccta aaatgcagag gaaaaaatat   6960
tgaaaggggg gaaaagatg cccaaatctt tccaagaagt gtgggacata ttaagtgatc   7020
taacatatgt gtgaatggaa atctcagaaa gaaaagatag aaaacacagt gaaaagaca   7080 gagttgaaga aataatgggt aagaatttta taaaatcatt gacaaacaat aagccacatg   7140
gccaagttca gagaatacca agcaagataa gtaccacatt tttttttttt ttttgagaca   7200
tagtttcgct cttgtcgccc aggctggagt gcaatggtgt gatctcggct cactgcaacc   7260
tctgcctcct gggtccaagt gattctcctg cctcagcctc ccaagtagct gggattacag   7320
gtgcctgcta ccaggcccgg agtagagaca gagtttcacc atgttggcca ggctggtctg   7380 gaaccctga cctcaggtga tccacccacc tcagcctccc aaaggctggg attacaggtg   7440
tgagccactg tgcccggccg gtaagtacca tttttaaaa actgaaggca tatcacattt   7500
aaactgctga aacccaaga caaaagcgaa atcttgaaaa gcaaccagag aatacaggta   7560
cattccatag agacacaaga aaaacagaaa tatggtagca gacttctaaa cttctcgtca   7620
gaaacaaagt cagccaggga tgaagaaaa acaacaacaa aaaaactgtt gattcagaat   7680
tctatatccg gtacaaatat cttcagaaa aaaaggagaa ataaagtctt tctcagacaa   7740
acaaaaactg tagaatttgt tactgaaaga ccttcactat aagaaatgtt aaaggaagtt   7800
cttcaggcaa aaacatgata ccagacagag acttggatct acacaaagaa gcaaagtgca   7860
ctagaaatgg aataaatgaa agtacaaata gaatttcttt cttctcatt tttaattgct   7920 ctaaagata actgactaaa gaaaaaattg tggtcacgta ttatatgtct atagtataat   7980
gtaaaataga atgtatgaca ataatagcac aaacagtggg aggaaggaat tgagaatatg   8040
cagttgtaaa tttattatat aacacacaga gcaaggtaat atcatttggt agacaatgat   8100
tatttaaaga tgtatattat aaaacctaag acaactatta atttaaaaaa taagatataa   8160
atgataagcc aatagtggaa actaaatgga atcataaaaa gtactcagtt aatccaaaag   8220
aaggcagaaa agggagtggg gggacaacag acggaataaa tagaaaagag ttagcaagat   8280
ggtaaattaa atccaagcat atggccagaa gcagtggctc gggcatgtaa tcccaacatt   8340
ttaggaggct aaggtgggag gattccttaa gcccaggagt tcagaggcta taatgagcta   8400
tgatcatacc accgcactcc agcctgggca acagaatgag atcccatctc taaaaaaaga   8460
aaaacactcc aaatacataa ataaataatt atattaatct caacacacca atgaaaagag   8520
```

```
atgatcaatt tgaataaaca aaagacccaa ctatatgcta tctatatgaa acccacttta   8580
aatataaaga cataaataag gttaaagtaa aaggatggaa aatatgtgac acagaagcat   8640
gcgtcaaaat aaagatgcag cagctacatt catctcagac aaagtaggct tcagaacaag   8700
gactattaca agggataagt gagacctcac ataacaataa aggagttgca ttttctgaga   8760
aaacaatcct cagtgtgtag gcacctacca acaaggctg aaaacacaga agcaaaaaa    8820
tgataaaata aaatgtaaca ctcattcatg attttaaaa aactgtcaac aaacaaggaa    8880
tgtaagagaa ctgaacctaa taaaaggcga agctgaaata caaaaaaaaa aaaaaaaaa    8940
gctaacatac taaatggtga aaggctgagt acccctaaga ttgtaaagaa ggtatgatat   9000
cccctctcac acttctttt ttttttttt gagagtctcg ctctgtcgcc caggctggag    9060
tgcagtggcg cgatctcggc tcactgcaag ctccgcctcc tgggttcacg ccattctcct   9120
gcctcagcct cccaagtagc tgggactaca ggcgcccacc accacgcctg gctaattttt   9180
tttgtatttt tttagtagag acggggtttc accatgttag ccaggatggt cttgatctcc   9240
tgacctcatg atctgcccgc ctcggccttc caaagtgccg ggattacagg cgtgagccac   9300
tgcacccggg cccctctcac acttctattc catattttac aggaaggcct agccaagata   9360
ttaaggcaag aaaagaaag aaatggtata caaatttgaa aggcagaaat aaaactaagt    9420
caattcacaa tgacatgaat gttgcataga aaattcccca aacaactaga gaaaactcct   9480
caaatgaaca ggagagttga gcaagatctc agtataaagt caatatacaa aagtgagttg   9540
tattaatatt tctgtttgct agcaacaaac aattagaatt ttacattttc aaaatagatc   9600
cacttataat aatgctcccc atatgaaaaa cttgggcaca gatgtaacaa aaaaagtatt   9660
ctgatctaaa cgaacagaaa aatatactat gttcatggat tagatgagtc aatattatta   9720
agatgtcagt tctccccacg ttgatctaga tattcataca tcccaataat tttcccagca   9780
gaatgttttg tagatgttga caagttgatt caaaaattca tatggaaatt aaaatgctct   9840
aggatagtca aaataattta ggaaaattat tttctggtca ctatctgatt tcactgatat   9900
gttactatat atttactatt tactacctga tttgactata aagctatagc aatcaagaca   9960
ctgaggtatt ggtgaaggcg tagactcagc tcagtgggat tgaatagaga gcccagaagt  10020
ggatccatat aaatatagtc aagtcaattt tggcaaagat gcaaagggaa atcagtagag  10080
aaagggcagc ttatcaaca aacggaactg gatctattgg atgtccatat gcaaaaaatg   10140
aacctggaca cacatatatc acaccttaca caaaaattaa ctctaaatga atcatagacc  10200
ttaacgtaaa atatacaact ataaaacttc tagaagaaaa cagagaaaat ctttgtgcct  10260
ataggaaagc cagggtcttc agcctcggta ctgttgccat ttggggatgt agctcctgtg  10320
tgggggctgg tctgtgcacc agggaggttt agcagcggtg tgctccagtt gtgacaacta  10380
acaatgtccc cagacactgc ccaatgtcct ctggggcaa acaggcctg aattgagaag     10440
agaaagttct cagctgtgac gtggaagcat aacccataac aggaaaaaaa aaagttaata  10500
cacgggactt tgttaaatgt aaaacttttc ttctgtaaat ggccatgtta agatattgaa  10560
aagacaaacc acaggctggg aaaaaatatt tgcaattaca ttatcagatg cagaatttgt  10620
attcagaata cacaaagaac tcgaaactca acaatcagaa aacaaacagc ccaattaaaa  10680
aaatcggcaa agggcttgac agacatgtca ccaaagaagg gaggcagatg gcaaagaagc  10740
cccaaaagat gtgccacagg gttcgtttca gggaaatgca aaccgcaaga gacctgtgtg  10800
ctcctgcgtg ctcccgtgtg ctcctgctta ctcctgtgtg ctcccgtgtg ctcctgtgta  10860
ctcctgctgc gaagggtaaa atgaagcaaa acagcgaaaa ctcacagcac acaacctagt  10920
```

```
gccagcgagg atgggagca agtgggcctc acgccctgct gcagagtgca ctatggcaca   10980
gcccctgtgt gtgcctgggg ggcctgtggg tgacaggggg acaaagaaga ggttggcaga   11040
gatggcagag cagcctcctg gtgctggact tcctcaccca gccaggatgg cctgggcctg   11100
caccagtgct gcctgagaca gcgagtctca acctgctcca ggggcgtgtg cgtttctgcg   11160
tgtgtgtgtg tgtgtgtgtc catgcatgtg tctctatgaa tatatgtgct gtatttgcat   11220
gtgtgtgtgt gtctatgtgt gcatatgtct gtgtctgtgt gtctttctgt gtgtgcggtc   11280
tgtgtctgtg ggtctacacg tgtatatgtg catgtgtctg tgtgtcgc agtgtgttac   11340 tgtgtctgcg cgtgtgtgca tgcatatgtg caggagggag ggagggctca ggccttagca   11400
gagtccctgg ggctctggga gtggagggca gtgaggctga ggctggtgca aggtggttt   11460 caggcgctca ggtgaagtgg agcagaaaca gaagttggaa tccagcccca gcgggcgggc   11520
ggcagcagca gtgccggccc tgcccagaac aggttcgacc tgagccggca ctgcccggct   11580
gccctggggc tagggaggct gagacagaga agggaagcca gagggtgggg gtgggggccc   11640
ggcactggca gagctgcctg ccctcaacga ccgcccctgc cggagacccc cgccccaccc   11700
gctgtggttc tgctggccca ggtttcgctg ggcccactcc cagggtttgg catcactgga   11760
gcccagggtc ccccccgcac cctccccaca gccttggccc tgctgctgcc tgcctcctcc   11820 agggtaccc gaggcccacg tcaggagacc cgcctcaggc agcagtgcc cggtggctgc   11880 ttctgcctag cccgcagcac gtgccaccct gggcgcactg ccttcccgaa ggctctcctc   11940 cctcccggg gcgctccctc ccactctgga atgcctccct gcctgcacag caggagtgtt   12000
tggctgaggt ctgcagcccc gacacaggtc acctcccacg cctatgggg cttcagaaag   12060 tcccggaatc ggccgggcgc cctggctcat gcctgtaatc ccagcacttt gggaggccga   12120
ggcgggcgga tgatgaggtg aggagatcga ccatcctg gctaacacag tgaaaccccg   12180
tctctactaa aaatacaaaa aattagccgg gcgcggtggc gggcgcctgt agtcccagct   12240
actcgggagg ctgaggcagg agaatggcgt gaacccggga ggcggagctt gcagtgagcc   12300
gagatcgcgc cactgcactc cagcctggga gacagagtga gactccgtct caaaaaaaaa   12360
aaaaaaaaaa aaagaaagt cccagaatcc cagacatcta acaggatggg gtcccagaga   12420
ccctccaccc acccatctcc ctgacttcca cacaggcagg gatgaaggac tgagggagag   12480
tgggagaggg taactgtggc ggtcacgaag ggtcctcagg tccccgtcct tatcccaagc   12540
cccatccagg ccagaaccgc ggagtgggtg tgcagagcac tcaggcagcc tgtgaatccc   12600
cacagccact tccctaccct gagacctcag agaatgacct ggcctctgtc tttctgtttc   12660
attttattta tttttatctc cagcttgttt gtgaagttca ggggtaccag tgcaggatgt   12720
gcaggatcct tgtcacaagc atccttctca cgaccctgcc tcactccaaa agggggtatca   12780 ggtaggtgag cagaaacgcc ccttcctgaa tgcctgtcct tgtcccacca caaggatgag   12840
gatgcctgct cagagggcac agggagaagc caatggcata gggtgcacag cagcgaggc   12900 caagggacaa ggagtgggg gccccacct gcccagcgtg acctgctgac cacagctcct   12960
cagcggcgga acaaagcctg cccatggggc cctcagtggc caccctggat gcaaacacgg   13020
ttaatggtca ggcccagcct gtcccctcct gcgcacaaac tcagggcaga gcagagagct   13080
tacatccacc aagacccaga caaaagaaag cccttaaag gcagccaaac   13140 cctggagctg cctcgggccc atcgatggga gcacaagagg tgaatcctgc tacgggcacc   13200
gtggccgtct acgcgaccgc agcaaagagg aacatggacg actcacagac gcagagacgg   13260
ggggtccatg ctgtgtggtg atgttcacct gcagctcagg gacaaaccct acctacggtg   13320
```

-continued

```
acagatgtca ggaggggtga agggtgaggg agggagggcc tgttagctgg agcgggtctc    13380
agggatgcct gctgctgctg ctggaaacat tctgcacagg ggttcgggtg gaggttctgg    13440
gagtgtcacc cgtgcacact tgtcagcatg ctctccaggt cctgcatttg aggtgcctgt    13500
accccagtgg aaagatgacg gacagagctg ctcaaccact gccctggacc gcattctgca    13560
gggtgcctta gaaggcccag gaggaaaggg gactccaggc tgggcaccgg tggtccacag    13620
gcttccagag cagcccagct tggccgttgt gtcccagtca ctgggagcta acgaggacgc    13680
accctcatgg gggtatgtgc ccacccagtc ccctccgtag agagcctggg agcctctgtg    13740
atagggcgtc ctggcccagg gctcccaagg ccaagtatga agtctcattc ccccagacaa    13800
ccttcacctc caggctgcat aacctctact gaccccctctc aatcccacct cttcttttg    13860 tccatgaagg cagtcgggaa atgcagcctg tgcttcggag aggcgggcag ggctggggtc    13920
acccccgccc caggcagtgg gataggagat gcgccagggt caggtcccctt gctgcaagcc    13980 tgcaacccgt gcctgtatgt gccagccggg cctgccaatc catccttcac cctgcaggac    14040
cctcccgtct acaggtccca gctctgtgtg ggcctggcca gccctggggc catggctgag    14100
acctgagtcc tcaaaggact gccccttctg agagcagaat cctgctgccc ccagaagacc    14160
aggtgttcaa cctgagccct gatcctaaaa cccatggtcc tctctctcct ccagaatccc    14220
tctgccagcc tccaagagcc gcctgctgct ctcctggtgc ttctcacacc cctgggggat    14280 ggcaggggggg cggggagccc agcagaaatt ggagcagaga ggacatggag ggctgagggg    14340 tgaggggggca gaccgaatgt atcctctctg cccatgcgtc ttccccccagg atgctacctg    14400 aggtctcggg agaggggcat ctgggaaggc ttcctggagg aagatgagtg cctctctctc    14460
atgagggagg ggctccaggg aggtcagtgt gaacttgtgt tggcacaaag gcagccctgg    14520
ccgagggggc gaaggcagtg tgaagtggga ctcacttccc ccaaagatgc agagggatgt    14580
cgggagacct ggcaggcggc cctgggcagt tcagttgacc ccaccttacc ctaccaggct    14640
gcaggaagcc cctgccccca cctggagccg ctacgggttt tcctagctca gccctaaagg    14700
ctcagcccga ctagatacag gccaactaga gaggtcatgt cagggctgag ggggtggctg    14760
ccaggggtgg ctgctgtggg gaagagcatc ccagcccgca ggccctgcta ccccaggcag    14820
agctgcccgt tgtgtcccgc acgaagagct ttccctgcct gggaatcccg ctctgccccc    14880
caccagccag tggctttgga agttcgtcca gcaaccctgg agtctcagtt tccatgcctg    14940
taatatgggc acagcactca ctccaggatg aacagaagcc gggccaggaa agcagtccct    15000
ggcctggcac cacagcaggg gctgtgaggg ggatggttcc acagttgctg gaggtcgaca    15060
gggaccgaag cacacatgag tgccagatgg gccccacgat gggattccgg cgagggtggt    15120
gcagggagcc acctatacag aggacaattg actgcagaag tgccaggctc atgccctcca    15180
cggatggaga ggccgtcacc tccgggggat gccccagggc cgcatacccg tgcagtggcg    15240
ctggagtggc agtgggcgcc tgccccacac taatgcacac acacatcagt gcacacccac    15300
agccacgcca gagaaagcca caggccctga ggggctgccc catgccagcc tgccagctgc    15360
cacacccctc ccacaaagcc tggctctggc ccgggacaca gggagcccag acccatccag    15420
ctttcccctc aatgccccgg gtcctcccac aaattcatcc tgcctcaagc ctcagtctcc    15480
acttccgaca aatgggtctc aagctctctg ctctgtccac cctgcatggc ggtgtgggca    15540
gcacagagcc agcctggtgg gggctgggga ctctggaagg ggtgctcagg gaggggccgg    15600 gctctgggggc ccagaaggcc ttggaaggta gtccaggcgg gtcccggaac aagtgttgca    15660
tgagcaccaa atggctcaga gctcccgaaa cctggcgtgc ctgtgagagc cgttgagacc    15720
```

```
ccttttcaag gccctgcctg acagcccaca aaagacattc aaatgagaga caaatatttg    15780 gggcccaag  gttgagccca gcccagcctc tcaggcccag cccaagctgc tcccaggctc    15840
tcatttgggt attaattgca tttcgtttag agatttgcat gcttatcacg cgggtggtgg    15900
ccagccgtgg gggcctggcc agcctggaca gaatcccaag gctcgtaggc aaatgccagg    15960 aggaggggt  gggcagagga cccaggagcc tcccgaatgg tatcaggaga gcaagcctgg    16020
gctaggctgc gggccatcag cgtgggccct gggccacgac ctggcatcca tgtgacctg    16080 agcacgacaa caggacaagc agagaaaaaa gtggatccca aaaacagggc tcccaggcca    16140
acttctccct aacaccagct cccagcaccc caccggggac tgcagcccct ccatggtcaa    16200
tcagggtagc cctggggtcc ctgtcacatg acgtatgccc accctccgac agccctgcag    16260
cctgtgggac ggcccgtgtg ctcgccgagg cgcttggaac cttggagggc aggctctcag    16320
aagattggct cagggaccct ctggtccacc ctctcggcat cccagggtgt cctggtccca    16380
ggagatgcct catcccaggc cacacggggc cctaggcctt tccgtcctca gcccgtgtcta   16440 ctctaccctc tacaagagag gtccagaagg ggcagtgctt gacccaagaa gaagaggctg    16500
taactatgga gaggttggga gggggaagtg gccctaaggg ctggagtttt agaaagccct    16560
cttgttcctg cccattatgg gttggatttt atgccctcca gactcacatg tggctgtttt    16620
tggagccagg gcctttaaag aggtaattaa gttaaagtga ggtcattggg gggaccctaa    16680
tcccatgtga ccgatatcct tagtaagagg aggtgaagac acagacacgc acagagggat    16740
ggccacgtga agacacaggg agaaggcagc gtctacaagc caaggagaga ggccttcgga    16800 ggtgggggc  ctgcggaatg tgagagact  aatttctgct gtgtaggccc cctagtgtgc    16860
ggggcttttt cacgcagcac aggccaaccc attgcagcct ctcctgctgt taggaccca    16920 agtccatcct cagggacatt aattaacata ggaactttt  atcctgatgg tgtcacctcc    16980
taggcagaac agggacccgg aggcaggcct agctgcgaac ccccagccct ccctgtcctt    17040
ctcgcaggac agcgggtctg gggctgaagg ctgtgacgct gccctgcct  ggatcacaac    17100 aggcaggacg gctgagcagg cacacatctg tctctccctc tgctgatctg tggccttgga    17160
caggggctac tctgggggag ctgacaggtg accccccag  gaggccctc  cctgcctctg    17220 ggctgggaat ccacctctgt ggagcccctg ggaatggcct gtttcaaata cgtaagtggg    17280
agcaaggtct catcctcagc ggggacatc  gctgggggca aggccagtgg gtgggtggga    17340
aggtttctgt ggcactgggg cctcctgttg attgattcac ccaattaatc acagccagca    17400
gctggggagg gggtaggaag gcggtgaagg gaaaaggagc ccacagccgg gaggccctgg    17460
gaggttggca gaggcctgca cctgcctgca gccagccctc cggcccagcc ctcttccctc    17520 cttcggagg  ggcagagca  tggggtgcta agggctcagt cttaacccc  tcccagctc    17580 tcagggagcc cctcccatgc tccccaggcc tctgcccac  ttgcacctcc ccgggcccca    17640
gggcacagga cgcttttcccc acccttgggg aggctgaggg tgtcaggagg cctgggctga   17700
gtgctggctt ccgtctcact ggcttgcaga caagaccctc catttcggtg gaaaaacagc    17760
aagaacagca ccccctcca  ggcagaccca agggaggcat cggtgtgagg gcttcaagct    17820
ctgtactgtg ggtttaagcc ttgcacctct ggatacctgt gggcctcggg cagatcactg    17880
agcctccctg catctggaag tcggggtgag acccctcaga gggggctggg aggaggaagg    17940
gcccctcttg atgggcagcc cccaccctcc acctactgcc ctgccctccc agccttcagg    18000
gtcctcccca gcttctgtgg gctcccaggt ggacctgggc caccctgag  accccgaaga    18060 gctcaaggcc agctaatagc ccacaggctc aggacagcac tggacaggcc tctgggccca    18120
```

```
cctggccccca ctcccgattt ttatgggaac aaagactgaa ggtgtggccc caaaggaacc   18180 accccctcccc cagtgccccg ctgctgggaa aagggtcagc agagtttggg tctccccca    18240 caagccctct gggctgtgcg tgctacagct gaggacatgg cgttgagggg caggccgcct   18300
ccaaccccgt ccaccttgcc ctgtctagct ctgtccaagg ctctctccgg ctggctaatc   18360
acctctgggc acagctgtgc tgctgaggtc tctgggatga ctgaaggtct ttgaaggcca   18420 cttttgggaga agcgaaggtg catggacacc agggaccctg ctcacagcga gtgtccctgc   18480 cccatcccctt tctgcattga gtgggacaag cttgcttcca tttgggggat cgccatctga   18540
ctattccact tgtcttaggg tggggcagag attaggtgat gtggaggggc ttctctacat   18600
ggcccccctg ccccagctct gaggggtagc accagagtgg gtttcaccag cgtagggcac   18660
gtaggccccg ccatgaacag ggccccaacc ttggtttaat gctttgctac tgccatctta   18720
aagttctttt tttattttt attttgcttt atttttatt agagatgggg tctcccagtg    18780
ttgcccaggc tggtcttgaa ctcctggctc aagcaatcct ccggcctcag cctcccaaag   18840
cactgggatg acacgtgtga gccaccttgc ctggcctttg gaatctgact acttttatct   18900
tctaacttgt tttgcaggtg caggccaacg gcatacagca gcactcacat aagcaaagga   18960
gagcgtgcac aaggcgccaa atgtatatcc accctcactc gtcccccccac ttgagtagcg   19020 catccacgat gcccacagac accaggccac acagaaaagg tgccagggac ccacagcagt   19080
gcaaggcagc gtgtcacacc tacgcatgag caagccgggc gctgatggcc accgagcagc   19140
cacgttttcc attcaaatcc gcacttgcta aggatgcagc aggaagccag tggtgttcta   19200
acaaacgtgc aggacccggg aacctgtcat gtcctttctt acttgtgcga cttctctgtg   19260
ttagccgagg tctcttgctg atggatctac ccacagtgcc ttttgtcttt gaacttgtcc   19320
cttccctcct tcctcgccca tcagcgagca ggaggtggag ggtgctggtg aacaagcct    19380 gcgtcaagga gtgaaatcag ctgatttcat ttttgtgcag tttccactgt tctagtagca   19440
aatgaaatag agacgcctgt gccaggacaa aacacacact gtgtcattcc agtgattccg   19500
catagaagtt aaatgctctt atgcttgcat tttaaactgg catcacataa tataaagatg   19560
gataactaca ttcacgctag tcacttaaat tcctaatctt tcttactcag aatggcatta   19620
aatagtgagt ataaaataag aagtataaaa tagtaagtca agaggttgac tatagaagaa   19680
agaaaaatgc tttatatttt agcaccttga acatgacatc acgatcacct tctccctgga   19740
atcagtttct aacttccagg tggggactag gcctggacca tgagctccta gcagagccct   19800
gctgccccca cagcagagcc caggacaggc tggcacctgg gccaggtgag gctctgtcca   19860
ggctcactga tctcaaatgc tgaactgcta aggatgtcat gtccccaaag gagccgccag   19920
gctcagcctc acttcctgga aggcgtgaac attgcaagaa tgtggaagtg aaagagtcca   19980
gggcttaaat ctcaattctc atcattttca agctgagtcc aagggagaga agacagtcat   20040
ggattcttag tttctgtttc tggttgagcc agcagggtcc cttcctcatc cctcttttct   20100
gcttatcact agagacagaa actaaaacca tgactttagg ctgctgagag cctaaaacaa   20160
aacgacagca agagaaggtg ggttggacca gcttgcctgt gacttcaggc acttcatctt   20220
tactgggcac tgggtgaatg acagtgtggg gaggggtctt cataacacgg caatcagcag   20280
cccactgtgc ccaggagact cgcctgtggt cctggttatc aaccacagcc ctttccagtc   20340
tcaaaaatgt ccccgctggg acagcaagtt acatcgtcgc tacaagtcct gtctcctggg   20400
agatgcagtc cagcagcact acatcctctg agcagcaggt gccaagtggg atgaactgga   20460
taaggactgc attcggggaa acgcccgtgt gaaaggaaat acacaggaag gaggtggcaa   20520
```

```
cgggtgggaa gccactagac cacgacgcga ttctgcccca gtgaaggcga ggggatagcc    20580
tgggcctaga tcgctgtgag gtctatggaa gtttccacaa gcttgctggg tagttctcga    20640
ggcaaactcg gaaagggagt cccttgtctc cctggaacgg atctttcttg gcatctctgt    20700
cacactcatt aggtgggcct ggtgtcaacc ccatttgcag gccacccaa acttgatcaa     20760 aggtccgctt ctggcacccc ataccctgtc ctacaggaaa tacagggaca ggctcccaat    20820
aacaacaccc agcacggtgc catcaacacc accacgcaca cggggggctca acggaacaga   20880 catctccgct tcttcaatga agacactgga gggaaattgc ttacaaggcg cttaagagac    20940
ctattaagca aacttgatgt gtggacctgc ggcggatccc gattctataa ggccaactgc    21000
acaaaaccac gagacccct gaggactgcg ccattggctg gtccccgat gatatgaaag      21060 aacggtggtt catttgagcg ggtgatgttt ttgcggtttc ctttagaggc acacgtgaaa    21120
catgacgggt gaaaggattc aaagtctggg atttgcttca aagcaacgca gggatggcgt    21180
gggggatgga tggggcagga agggccttga aactggtgct ggaggcttcc cagggctgcc    21240
ctggagccca gtgcgtcctc caccggccag actgtacaac ggttggatcc tgtgtccact    21300
gctaggaccc aggctccacg agcacgggct tgtgtggcac acggatgcac cctaagtcct    21360
ggcacagaga ctgctcaaca aaggcctcgg tgcttttgtg tatgtttgaa attttccata    21420
ataaaatgaa aaatgggaaa atgggaaaac aaaaatggca gcactactta ccctctgcag    21480
agttttgtcc gcttcacgcc agtgggtggc agtcgtttcc tctgccctgg ccttccatcg    21540 tttccccct accctcttca cccacccaac agcccctgt ggtcctggca gctgtgggcc      21600
tttccttgag gtcaaggtgt ggagtcctgg ggagggctca gggaggccac cgacccgggt    21660
gtggattctg ggagaagcct gtgggatgtc cctccctggg tgaccacggc aatgtgcccc    21720
ctcctgtccc ttggccaagg ccagttccct gagccctgca gccccaagcc acagctggtc    21780
cactgacccc agttgagcct ggtcctcatc agaccagctg accccttga ccccgctac      21840 agactcggct ttgaccttgg ctgctgagga gccccacct ggactgaggc tgcagctggc     21900
gagagaggag ccctgagctc ctctgataag aagggacctg gccagcctga cgtttgagac    21960
ccaggcatcc cggtagcctg ggtgtcctgt tgccgtggtt attcaggagc cacccactct    22020
gggacaacac cagctgctcc cacctcgcag ggctcccacg gctctgtccc aaccactcct    22080
ttctgaagga aggggtgcct ctgcgcccta agaaaccgg gggagcccca caaccccctcc   22140 cccaccagga cactaaaagg cagctttcgg tacagtgaga catcaaagcc tcctaggccc    22200
tgagtcaaag gtatagccgt gtaatatccc agtgccagct ctccggctgc ggggagcctg    22260
gcgcaaagct tccaagcctt ccttgttcct ttcaagagcc gctcttagaa ttcaggtgag    22320
cggagacctg cagggcctcc ccagtgcggg caaaacccaa agctagcgag agggcagcct    22380
ccaggcacct ctcactaact cctcccagag gccgttgagg tgggtctggt caaacccatt    22440
tgcaagttaa cccacttgcc ctgggctgcc cagctgccac gttagtggag atctgagcgt    22500
ggtggcctgc gcaggagccc atgccctcag ccccacagcc ggtgctctct ggtcagacca    22560
cctcagccta gccccacacc cagcacttac cccagccctc gggatgggtc agcagcctcc    22620
agcctgcagc ttccaagcca gcgagtagcc ctgtctggac aacccaccag cccaccacct    22680
cctggaggat gccccagcc tcacaaggtg tcccaatggc tccgctatca acggcctggc    22740
tgcactccag atctcaccca gacccaccct acggaggagg cagcagggtt tgaggagtag    22800
tgaccacgga agtctggccg tcacctggga agtgtaggtg ataggagcca ctggtaaaca    22860
gaactgattt attttataaag ttcacgctcc cttgaagagg tgtgccccac acaggcttct    22920
```

```
ccctagcaga gcagcagtgc ccacaaaccc accccagggt gggctgtcac gggggcctca    22980
cgccagggac cccgcccctc agggactgct cgtgtccaga tcttggccag catggaaaac    23040
tccagatagt gggggcaggg gtccaggtca tctttattac gccccaggtc aagggttctt    23100
tgtacaaaaa taggtctccg tttgccagca gtgtccctcc agcagctcaa gttaatgtgt    23160
agaaaatgga ttctctgtgc ccttagaaaa tcctctcccc tccggaaaaa tctccaagtg    23220
ttggtgcccc ccgccccact gcagtcgaga agctgtgggg aggggcggcg tcggaggaag    23280
ccgccagccc ttatggggcc agctccaagc ccgtttccac cgcggcattg gtcaggctgg    23340
gccggacgaa cgaggcggcg tcggcggtgc ggggggtggt gggtgggtcc ccggctcgct    23400
gggggcggag cgcgggccgg tccacctggc gggctccccg gcgatgagcg cgccggccgc    23460
tcgctcggct tccggggctg aggctgcggg gggaaggtgg ggaaccaaac gcgcgtcaac    23520
gcgggcgcgg gcccggggca gaccccgccc gggccggccc tgcccgcacc tcccccaagc    23580
gaactcggca gtttcgtttg ctcggttggt tttggagtct tgagtccgtg ggtgccgcga    23640
ctcggtctga gacacggcgg gggcggggcg ggcgctcgga gccgcggtga gtcagggctc    23700
cgcgcccgcc gactcatttc tgccgccccg gcccgggagc gcgatttgca atgcaaagtc    23760
accccgcctc cagcacccca atctgcccca ggatccgcca gcactagaga cctcaacggc    23820
ccgacggccg ctcccctccc ctcgtctacc cctccctcgt cggcggctga gccgcgaggg    23880
gaagttttgc aatcccggac aaacaaacgc cggtcttgca cgggcttgaa aaactttggg    23940
ggaaatgaag agtgagcgaa atcgaagcca tcgctcgggc ctggcgctcg gctccgcggg    24000
ctcctggggg cgcgacccgc cgggcctgcc caccccgtcc ctccaccccg gccccgggcc    24060
ctccctcctc cctgcctccc ggctgttacc tcataggtcg agggcgctca gtagcccccct   24120 aaccagctgg agaagtcgag tagctcgcgc tccgcaggac tcagcgcgcc ttcgcagccg    24180
ctgtcgtccg acgagtaggc ggaacgcggg gagccgggct ccgagctgcc cccgcggccc    24240
ggggacgaag aagcgcggga gggcgaggcg gcgaccgggg tggtccctgg cggcccgcgg    24300
ggcgcagacg gccgcacggc ctgcggcctc agccctcccg ccagcgcgtt gcgcacggcg    24360
tcgtgctcgg ccagcaggcg ctgcagcgcg cggatgtact ccacggctga gcgcagcgtc    24420
tccaccttgc tcagcttctt gctggcgccg ccgtgcggca cgtgctgccg cagcgcctgg    24480
aagcccaagt tcaccagctt cacgcggttg cgctcgcgct cattgcgccg cgctacggcc    24540
gctgcgccgc ctccggtctc tgcggtggcc ggtcgccgcc gcggctgca gcgcaacagt    24600 tccggggacg cgggtctccg ccgggcagcg cagccgacag ggacgggggg cgcagggggc    24660
gcggacctgg gcagtgtgcc gccgtccatc gcgcctgcat ccacccgccc gctccaggtc    24720
ccggcgcgcc gcaggaaggt gcaggcagag gaaccgagg cgacggggaa aactgtggcg    24780
ccccaagggg gcttctggca cggcgccgcc aggcaactcc ccagggcacg cgtcctaggt    24840
cgtctggagc ccggggatag gaggcctagt ggtggcaggc cgtacgcgcc agggagcgtg    24900
ggacgctcgt gtcccgcgcg tgcggccgga ctctcccagg tctccgcagg cgcggcgcag    24960
gcggctggtt tttaaatgta tagataaccc tcctccgcgc cgccgccgtc gccttttctca   25020 cgccctcctt ccttcgcctc gccctcccgc cacgcttcgc cctcccccctc gcgcgatcac   25080 attctgtaag gcccaaagcg tgcgcatgtc ccctagccc atcccccgga cgcagtccac    25140
agatccccag tgcgcccaac tggcgaaatc tgcgagttcc cggtgcgccc cctgctcccg    25200
gcaggtgctt agtgcgcccc caaagcaagg tacgcaggtc ctgggttgag ccttcccgta    25260
cccccaccct aaccccgcgc gcagcccgc cagtcccaag agccgccaga ccttcgcacg    25320
```

```
cgcagcgcgc gctgtgggag ggaaggcgcg gccctggcga caacacggct gttcgggagg     25380
cgcgcaagat cccccggggc agcacgcgcc gcgcagccca cacccacgcc ccaccctcct     25440
ggggccgagg aggcggggc  cagggtctca gccaatcgtg ggccacccgt ttggccaatc     25500
gcgcagggcg cggctccacg cccggcccca ttgaggaagc gcgtacgcgt ggcgcgtggc     25560
tcacggggag catcgctaac aaagctgggt tcctgctggg ccccgccctg ctcctcgccc     25620
ccgcgactgg gctgggcgcg ctgtcccta  gcgcagctat gtcccgagcg cgcccccacc     25680
tgtgcgttaa tctactggga atgggggtgg actgcgcctt acctggggcg gggtgggct     25740 taaggagtgg tcgagactga                                                 25760

<210> SEQ ID NO 14
<211> LENGTH: 38360
<212> TYPE: DNA
<213> ORGANISM: Homo sapiens

<400> SEQUENCE: 14
tgtgcaaggg accttcagag gaggaaaggg aggaaacagg tcaacctctc acggcaggca       60
aggcaagaca cccccctggtt tgaggggtc  ttctgcaaat tcagggagt  tgaacctcat      120 acaaacctcc ggtagtaaga aaaatattca gagttctcct ttcccttctt ctcgggggaa      180
gaaagaggct aagctccact ccgcttgtcc cttccctagg ggaagggga  ggagaaggga      240 gaatagcagc ataagcgact ggcagaggca gggaaagacc ggcagaaagg aaagagaaac      300
tgggagagga agtcagagag agagagagac aaagagggag tcaaagagag agaaagagag      360
agacagagag tcagagagag agaaagagag agacagagac aaagagggag ttagagagag      420 aaaagagag  acagagagta agagagagag agtcagagag agaaagagag aagtagtaaa      480
gagaaaacag tgtaccctat tcctttaaaa gccagggtaa atttaaaacc tataattgat      540
cattgaagat cttctctgtg acctagaac  actccaatac tgcctgtaaa gaagcaagac      600
gagtcacacc agtgactgca agaccctaga gctattaacc agttagtcca aactacccac      660
cctgttgtta cagtaataga tgtaaaagat gccttctggg cttgtccatt tgcagaggac      720
agccaggacc tatatgcctt tgagtgagaa gaccctcact ccggtggaaa atggtaatac      780
caatagacgg tcttacccca agggtttacg gagtctccaa atttatttgg tcaaatattc      840
aaataagtca tttaattagc aaaggtaaac agaaaattga gcttgaatgg attgaaggca      900
tcacattctt gcctctgctg gagactaaat aagagcttag aaaattttgg gattagttgt      960
atggataccg tcgtctatgg gtagactcat gccctaaaaa caaaactctt acacaaaaag     1020
ctcacacgag acagaccaaa ccccctcatg tggcaattac cagaaatcca acaggtggga     1080
aggttaaaac atctattagt aactgcccct gtcctagctt tactctcctt aagcagccat     1140
tccaccttgt tggtggtgta acaacggcg  tagcccaaaa acactgaggc cactgacaac     1200
ccatagcctt cctaatcaaa aatccttaac ccagtaaccc gcggatggtc caaatgcatt     1260
caatctgtag cagcaacttc tttgctgaca gaagaaagta gaaaaataac tttgagaaga     1320
aacctcattg tgagcacacc tcaccaggtc agaactatcc taagtcaaaa aaaaaaaaa      1380 aaaagaaaa  gcaaaaaggt agcttactaa ctcaaaaaat ttaaaatatg aagcgattct     1440
gtcagaaaaa gatgatttaa cattaaccac tgatcattcc cttaacccag caggtttgct     1500
aacaggggat ctaactctta atgaattacc atacaaaggt ccaaccagac ctagaaggaa     1560
ctcccttcaa gacaggacaa tagatggttc ctcccaggtg aatgagggaa aaagccacaa     1620
tgggtattca ttaagtaatg gggaaatagg agtagagtta ggaaaattgc ctaggagttg     1680
```

```
gggagttgtt tgcactgagc caagccttaa gatactgaca gaatcaggaa ggagtcattg    1740
tgaaaagtga agtagagttt acctcctcaa aagactttcc tcccccatct aatcaggaat    1800
aaatagtaac ttctcttagt agcaaaatgt attcaaagac cagcgctaac attcttaaat    1860
atctgctaga cgtaataaag aaatcaatgt actttatgtc cttagctccc acaatttagt    1920
ctaaatgttt gctctggcat gcttatactg gtccaggcaa gcattaggtc ctatcctgtt    1980
cctcttcctt gtttgtgtct cacatgtccg tgtgaaaaga ccaccaaaca ggctttgtgt    2040
gagcaacaag gctgtgtatt tcacctgggt gcaggcgggc tgagtccgaa aagagagtca    2100
gcaaagggtg gtggattatc attagttcct acaggttttg gggtaggcgg ttgggttagg    2160
agcaatgttt tgccagcagg gggtggatct cgcagagtac attctcaagg gtggggagaa    2220
ttacaacgaa ccttcttaag ggttggggag attacagagt acattgatca gttagggtgg    2280
ggcagaaaca gatcacaatg gtggaatgtc atcagttaag gctattttca cttcttttgt    2340
ggatctttgg ttgcttcggg ccatctggat gtatacgtgc aggtcacagg ggatatgatg    2400
gtttagcttg ggcccagagg cctgacagtt tgaaggtgtt tttacctttc tcagcattcc    2460
acgagttact tcttcctttg ttctcctctg cctttgcctc ttttaaaaag ttctaagttg    2520
ctagccagtc gggacaaatg cagaatgtca ggcctctgag cccaagctaa gccatcgcat    2580
cccctgtgac ttgcacgtat atacgcccag atggcctgaa gtaactgaag aatcacaaaa    2640
gaagtgaata tgccctgccc caccttacct gatgacattc caccacaaaa gaagtgtaaa    2700
tggccggtcc ttgccttaag tgatgacatt accttgtgaa atcccttctc ctggctcatc    2760
ctggctcaaa aatctccccc actgagcacc ttgcgacccc ccactctgct cgccagagaa    2820
caactccact ttgactgtaa ttttccttta tctacccaaa tcctataaaa cggccccacc    2880
cttatctccc ttcgctgact gtcttttcgg actcagcccg cctgcaccca ggtgaaataa    2940
acagccgcgt tgctcacaca aagcctgttt ggtggtctct tcacacggac gcgcgtgaaa    3000
cagaatgtga ggtcccgttc cagccaatgg aaaccagaca cagcagtagg gtggacgcgt    3060
caggttataa atgaccctgt ctcctttgct cagtgtactc tcgtggcaaa actgctgccg    3120
agtgtaccct ttctacagaa agtataaaaa tgaccttgcg taggaaatta aatttatgtt    3180
caagtgccat ttcttatgg caccggggag caagcatttc aaacatcatt tgtaccaatt    3240
ctaagttaaa tttggactaa acaaggtctt attaatagca aaggataatt gaatcccaa    3300 acttacaagg ttttcaacaa aagtaaagtt tgctaaaagt taacagtata acatgtatta    3360
tcctaacttc taatgttgtg accttaggct gtctagtcca cagacataaa ggaagttcgc    3420
tttggaaaag aatggttatc atctttgaga gaaaaaaaat tgtttcgaag gtttaagcaa    3480
gttttgaaat attcattgta aaggaaacat attggctaaa gttaaagggg tatcttccag    3540
tttttctgtg aactggacat taaaataaaa gcccagtggg ttttcttaa agcgctaacc    3600 tgctctttaa caaaaattac gaaaggttaa aaattataaa agtttaaaaa aagagtctgg    3660
aaatctcacc ttgtggtcag accttaaaat tggatacata tgtctacaag gttttattaa    3720
aatgaagttt aacacgaata acacactaat gtaaaggtga aatttagctg atctggtata    3780
aaatcacaca ggaagcactg tcaaatataa aatggtgttt ggctttcttt ggtctaaaaa    3840
ctaataaaaa taggtactaa aggaaatttc tcagcaagaa ggcactaagg actataaaat    3900
ccactgctga tgtccccacc tttaaaacaa aagatcaatt tttagaaatg atatacttgg    3960
tttatcctcc accccttaaaa caaaaggtct tctagcacag gccctgccct gagagtttcc    4020
agtacatcag caccagcctg gggatcccgt tctcatcaaa gggtggaaag aagggaaact    4080
```

```
ggagccagcc tgggaaggac cctgccttgt gctgctgact accgagattg ctattcgtac    4140 aacgaaagg  gggtggacac gtcccaccag agtcaagcaa gcaccattat caacagaatc    4200
atgggccatt gtttctggat caagccctac caaattaaag ctaaggaaag ctgagtctat    4260
ctctttcctt tcctttccta acccagtgcc tatatccatg actattccta ccactagcaa    4320
ctctaacccc actttagaga gtttctgtgg tttgggagca gaggtcactg gaagggatcc    4380
tataggcttc aaggtgcgct ttgttctccc tcctccacct cctacgactg cccctttccc    4440
aaacctacaa catcaaacta tgcctcgcct catgccaaat gacacaagca agttcttaga    4500
agtagaaata ggagacccaa ggcaaaccct agccattgaa agagggtata agacataaa     4560 tgccggttaa aacggattaa atatcccgtt cgcacttaa  gcaaaagtga ccattaagct    4620
tgtgggcgcg gtaggccaga ggctcaggat gcctcctttc cactgggacg gtcctcaaat    4680
caagcggaca tggagtgcgt ggtagctctt ttcgaagatt ccaccacctg gaataacgaa    4740
ttgtgccaag ctcttctctg ctatttcct  gaagttcagt gccctgtggg tcagcccccg    4800
agggccatcc agccttcatc ttccaaaacc aattttacct cgtgtctcca acaacgaggg    4860
gaaaaaactt ggcattcctt ggagacttaa aaggttgcag taaagtcagg cacctccaaa    4920
agctgaccca tcggtctgcc cttattcatc cctgagcgga tgtatggtgg tattatggag    4980
gacctttact ggacactctg ccaaataatg agagcagtac tgatgctgta gttcagttgg    5040
ctatcccttt tactctggca tttcatcaac cagaaaaaga aaaaaaatg  tagcctcaat    5100 tcttacctct ttaacaacgc taataagtat actctttctt cgtaggtgtt atgtcgtacc    5160
atacatccag gagttcatca aaacaactaa gccaagacat gctaagaaag tttgaagagg    5220
aaaactatac agtaaaagag gagggaattg taggaagtaa aaagtttctg cttcaaagtt    5280
ccccttcttg ttaaagaata aatcataagt cttagaaata atagattctt ttaaagacta    5340
attttcttca agcctccttg ctttgtgcta atagctcttt gttaagccct atcctatgta    5400
actgttggac atgctcacag acacattcca gctcacagcc tatgcccctt ccttaattgg    5460
aaatgttatt gcttcctgaa accttttgta agcaacttct tgttcttcc  ttgcacttac    5520 ctatttagga aagtttcaaa tcgggtatca gtttaagata gtgaggtccc actccagcca    5580
atggatgcag gacacagcag taaggacaac ccaaatgcgt aagggataaa tacatctgct    5640
tttcctttgt tcaggtgtgc tctcaccatt gttccatctg cagttgagca ccctttctgc    5700
agaaagtaaa gatggccttg ctgagagatc ttttgtctct gtgctgactc ttcttcgcag    5760
caccgattat ctatttctaa caattttggt atttctaaca ggcccacaca cactgtgtgg    5820
gccaagctgc ttcactcagt ccactgatca aatgctcatc tcatcctcac agacacaccc    5880
aggatactgc ttgaccaaat atctggacaa cccatggccc agtcaagtcg acagaccaaa    5940
tgaactgtca cagacagctt ctgtccttgg aacggggtgg gattccacgg actctctccc    6000
ttcacagtgg agatgctcag tcagcaagct gccagaagtt cagagctggg gaagatataa    6060
agaggactgg gcatggaagc tgcaggaact agtcaggaac tgggagtacc taggagtcag    6120
ctcctgagtg tgcaggatca tggtgaaata gaaagttaga gaaggaagag tgtgtcaata    6180
tcagagcatt gtcttatagc acaggactta accctctcct aaggttccag ggagacagtg    6240
ccaaatcatc acttgagtgg tgcttagaag cttcagggca aaagagccaa ccctaagtac    6300
atttgtctac tggggctgcc atcacaaagc accgcagaca gggtggctta tacaacagac    6360
tcattgtctc acaatcctgg cggctggagt ccaagatcaa ggttttgcaa ggctagctcc    6420
tcctgaggcc tctcttggct tgtagatgac cggggccttc tctctgtgtc ctcacagggt    6480
```

```
cttccctcag tgcgtgtccg tgtcctcacc tcctcttgta agactccagt cctatgagat    6540
taggacccac tgtcatgaac tcatttactg ttgattacct ttgttttatg ttttttgttt    6600
ttttgagaca gggtcagtct ctgtcaccca ggctggagtg cagtggtgca atcatggctc    6660
actgcagcct caaactcctg ggctcaagga atcctcccac ctcaatctcc caagtagctg    6720
ggactacaga tgcataccac tgtgcctggg tgtattagtc tgttattgca cagctataaa    6780
gaaatacctg agagtgggta acttataaag aaaggaggtt taattggctc acggttcata    6840
gctgcttctg gggaggcctc aggaaagttt cagtcatggt ggaaggtgaa ggggaagcag    6900
acacgtctta cacggccaga cagttcctcc tacactggct gacactctct cctgccacct    6960
tgtgaagaag gtgcctgctt ccttttctgc catgactgta agtttcctga ggcctcccca    7020
gccatgtggg actgtgagtc aattaaacct cctttgttta taaattgccc agtctccggt    7080
agtatcttta taacagtgtg aggatgagct aatacacaca ggaagcagca atgccatcaa    7140
agagccaggg gccttgactg gcagaactag tgagaccatc accaaaacat ggcattcctt    7200
gggcaaggca ggtgcgcagc cagcaaggta ttgcttaatc tacatgatca aaagacatca    7260
ggatggttgt tcaggaggct gagaacagcc atcctattat ggctgagttg tgtcccctca    7320
aaatttatat actgaagtct taacccccca ggacctcagt gtgtaagtat ttggagaaag    7380
ggcctttaaa gatgtagtta aattaaaatg aagacattag ggtgggccct aatccaatct    7440
gactggtgtc cttgtaagaa gaggagatga ggacacatgc agaggcatga ccacatgagg    7500
acacagggag aaggtggcca tctgcaaatc aaggagtgag gcctcgggag gaaccagcac    7560
taccaacacc ttgatctcgg acttccagtc tccagaacca tgagatgatg aaagtctgtg    7620
tttaagctgc ccagtctgtg atattgtttt gcaaccctaa tagatgaata catacccccaa   7680 tgaaaaagca tgatctcttg cccagtttct gcacctgaga cagttttcaa acccaaaccc    7740
cactgattga aggagggatt aggtcccagg aggacggacc ctgcagtacc atagcaggct    7800
cccccagtcc ttccccaccc caccactaaa ggtgtatttc agtaactgtg cactaggaaa    7860
agggcaatgc ccagggctgg gggactccgg gaccaagttg acactgagag ctggagtcaa    7920
ggtaccatca tgggcccact agagtagggc gtatggaggc cagcaaagtg caatcctggt    7980
ccacctctag ctcacactga gtcatccctt tgcattccca gaatgctgca tattccccca    8040
gaccctaaaa gtacactcag acaatcttgg tagttggcag aatcctcacg taggctcatt    8100
gtcctgtagg gtaaaaacta tcatagtgtt accaagtaga aacttctgaa actgcccacc    8160
accttagcca aggcaataca ccaaaaagaa aatctcattg gtggggaatg gcagagatgt    8220
gggccccttt ggaagacttg aaggttgcag gtgaggcgat tcccatcatc tcccccattt    8280
tccagagaat gctaacagac tactgtcaac ttgtgatggg aaattttatg cgtccacttc    8340
actgggccat ggtgcccaga tgtttggtta acattattc tgggtgtgtc tgcaaggtgt    8400
ttctggatat gcttagcatt tgaatctgtg gactgagaaa gcaggtcac tctctctggt    8460 aaaggtgggc ctcatccaat cagttgaagg tctgactaaa acaaaaagat taagcaagag    8520
aaaattcgct ctccctgcct gtcttagtct gtttatgttg ctataaagga atattggagc    8580
ctgggtaatt gataaagaaa agaggtttat ttggctcatg gttctgcagg ctgtacaaga    8640
aacatgacat ctgcatctgc tgctggtgag ggcctcaggc tgcttccact cctgacagaa    8700
gatgaagggg agccagtgtg tgcagaggtc acatggtgag agaaacaagt gaacatggga    8760
ctgccaggtt gttttcaaca accagctgtc aggggaactc agagtgagaa ctcactcact    8820
accatgagga tggcaccaag ccatccatga gggatctgcc ctcacaaccc aaacaccccc    8880
```

```
attagacacc acctccagca ctgaggacca aatttcaaca tgattgatag cccagctcaa    8940
agagccgctt gtctttgagc tgggatatca gtgttctgcc ttcacactca gattggaact    9000
tacaccatca gctctcctgg gtctccagct tgcagatggc agatggggat actttccaac    9060
ctccataatc acaggagcca attcccccta aaaagcccct gtgtatatgt acagctaatc    9120
ccaagctcca ctgagcagta gcccagtgga ttgttgctgt gccagctgtg ctatatttgc    9180
tggagcagag ggctgtggaa tggggtacat gttaagcacc cattagtggg tggatttgtt    9240
ctatgccatc cctatttaaa aagagccctg acacctttt gggggacatc atcattctgc    9300
ccaccacccc gggacaggag gcacatgaat gaactcacag gtgtggccat gagaggtgaa    9360
gagcttggta tcacgtgttc attcccaaca gagagcatcc accagggagc cactaagcaa    9420
ccagttagac agaatggccg cagtccttga cttcagccag cctctgtccc cgaccacctg    9480
agtgctggcc ccctgggtgc atgcatggag cagctttggt ggtagaaagg gatgctgacc    9540
atgaaatcaa cagcacagct ccacccacca aggctggtct agccactgct gccacaaatg    9600
cccaacctgt ctgcaacatg ggctgctgag aagcccccac taggcactat ccatagagaa    9660
agttgacaag gcaacagaag catccatccc attgggggca gcaattcaac tccactagaa    9720
ttgacacata acccaggctg atccccaggc cttattaagt gttgatccac caaacagggc    9780
atgcgtagca gtgccttgga ccaagggacc cactttacaa cacagggagg aggtgcagcc    9840
atggcacatg gcacatggca catggccatg gcatctgctg gtcctatcac agcccacacc    9900
actcagacgc agccagcacc acagagcagg ggagcagcct tttcagagct ccatgaaggc    9960
cccagcgtgg gggtgatact gttcaaggat ggggtgtcac attgtggaac tcagtagtca    10020
ctccaactca acagccacca tggggtgcta tgtccccaac aggcctcgga accaaggggc    10080
agaagcagca gcggcccctg taccaccact gccagtgacc tgctgtgggt tttgtgcatg    10140
ctgttccctc cactctaggc tgccagtccg gggtcgtggt ttccacaggg acaacgcca    10200
ccagtggaca gataggagac ccactgaaat ttaggctaca gccgatgcct tgtcactttg    10260
gattatttgt ccctggagac caacagtcat gacaacgagc ccccaaactg ggagggaggt    10320
gggccgtggc catcaggagg cagtagaact gctactccat gaggggacag gaaagaatac    10380
atttggtgcc tggtgatcca agtggtggga cttgggggac ttggtgttcc ctcaactgct    10440
ttattcatga gtgacaagt acaacagcca tggcctgagc agggatggtg accagggccc    10500
cagacccctc actgaggagg gtcccagttg gcccactggg taggccacag agactagaag    10560
aggtgcccac tgacagggaa ggaaccaaac atgagtcagg gaagaacaag ggtcatgaca    10620
gccatggcca agacgctatg gggcacaggc tgtagttggc tgtttctcta aacttgtaaa    10680
cccaggtatt agtcagcgtt ctccagagaa tcagaacccc aggatatata catcagaca    10740
tatgagagga tttatgaggg gaatcggctc acatgattat gcaggctgag aagtctcatg    10800
acaggctgtc tgcaagctgg aaacctagag aagctggtgc ggggctcatt ccaagtccaa    10860
aggcctcaga accaggggag cggattgtgt aactctgagt ccgaggccaa aggcctgaaa    10920
actggtggtg gtgagtggc tactggtgtg agtcccagag cacaatggct ggagaacccg    10980
gagttccgat gtccacagtc aggagaagat gggttgccta gccctggaga aaggagaat    11040
tcgtcattcc ctgcctttt tctctctcta ggccctcaac ctattggatg gtgccaacca    11100
catcaagtga gggtagatct tccttattca gtccatggat tcaaataaca atctctttca    11160
aatctaccct cacagatacc cagaaataat gctttgcaag atgtgatggt taatttggg    11220
tgtcaacttt actagattaa gtgatacccca ggtatctgga aaagcattat ttctgggtgt    11280
```

```
gtctgtaata taggttggat gtcaccctct acccccctacc caaatctcat gttgaattgt    11340
aatccttcat gctggaggtg gggcctggtg ggaggtgatt ggatcacgag gtggatcctt    11400
catagcttga tgatgtcctc atggcagtca taagatcagg ctgtttgaaa gtgtgtggca    11460
cctcccccac ctctctcttg ctcctgcttt tgccatgtga tgtgcctatt ccccctttgc    11520
cttccaccat gattggaagt ttcctgaggc gtccccagaa gcagatgctt ctatgcttcc    11580
tgtacagcct gcagaactgt gagccaatta aacctctttt cttataaatt atccagtctc    11640
ttttatctca ggtctttctt ttcttttctt ttcttttctt ttctttctttt tctttctctt    11700 ctctttctct ttctttctttt ttcttttctttt ctgtctttct ttctttcaga cagatttccc    11760
tcagtctcct acagtgcagt ggcgcaatct cagctcactg caacctccac atcccaggtt    11820
caagccattt tgtgcctca gcctctcgag tagctgggat tacagtcatg caccactgtg    11880
cccagctaat tttgtgtttt tggtagacac agggtttctc catgctggcc aggcttgtct    11940
caaactcctg acctcaggtg atccacctgc cttggcccct caaagtgctg ggattatagc    12000
caccatgcct ggccccaggt atttttttac aggagtgcaa gaatggccta atacagaaac    12060
ttggtaccag ggagaaagat atttctataa agatatctga aaatgtggaa gcaactttgc    12120
aactgggtta caggcagaag ttggaagatc ttgaaaggct cacaagaaga gaggaagatg    12180
aaggaaagtt tggaacctct tagagactgg ttaaatggct gtgaccaaaa tgctaatagt    12240
gatatggaca gtgaaggaca ggctgatgaa gtctcagatg gaaatgagaa acttatttgg    12300
aactacagca aaagtcacat gtgttatgcc ttagcaaaca cttgactgca tcctgttcat    12360
gccttaggga tctgtggaag tttgagcttg agagtgatga ctcaaggtat ctggcagaag    12420
atatttctag gcagcaaagc attcaagatg tggcctggct gcttctaaca acctacacac    12480
agatgcggga gcaaagaaat gacctaaagt tggaatttac atttaaaagg aaagcagagt    12540
gtaaacattt aaaaaaattt gcagcctggt caagtggtag agaaagaaac agcttttca    12600 ggaaataaat tcaagcacac tctggagcta ccgcttacta gagaaatttg cacaactgaa    12660
acagagccaa gtgctaatat ccaaagacaa tggggaaaag gcctcaaagg catttcagaa    12720
acttccaaag aagcccctcc catcacaagc tcagaggcct aggaggaaag aatggtttca    12780
tggaccaaac ccagggccca gtgccctgca cagccttggg acactgttcc ccacatctcg    12840
gccactctgg gttcagcctc agctaaaacg ggtccaggta caacttgggc tgccattaca    12900
gctccagaga gtgcaagcca taagccttgg cagcttccgt gtagtgttaa acctgcagcc    12960
acacagaatg taaaagtgaa ggaggcttag gagcctccac ctagatttca gaggatgtat    13020
ggaaaagcct gggtgcccag gaggaagcct gccacagggg cagttacctc acagagaacc    13080
tctactaagg cagtgcaggg ggggaatgtg gggctgagg ccccacacag agtctccagt    13140
ggggcacttc ctagtggacc catgggaagg aaggggggcca ctgtcctcca ggccccagga    13200
tggtagatcc actggaagct tgcactctgc acatagaaaa gcagcaggca ctcaacaacc    13260
tgtgacagca gccacaagag ctgcaccctg cagagataca ggggcagagt ggcccaaggc    13320
ctggggtggc acacccctcg caccagcatg ccctggaaat gggacatgga gtcaaaggag    13380
actaccctag agctttaaga tttaatgact gccctgctgg gttttggact tgtatgcagc    13440
ctgtagtccc tttctttttgg ccaatttctc ccttttggaa catgaatgtt tacccaatgc    13500
ccatatcccc aatgtatctc agaagtaaat aacttttta attttacagg cttgtagatg    13560
gaagggactt gccttgactc agttgagaca ttgaactttt gagttaatgc tgaaatgagt    13620
gaagactttg gaggactatt aggaaggtat gattgtattc ggcaacagga gaaggatatg    13680
```

```
agatttggag gcccaggggc taaatgatat agtttggatg tccttttccaa acttcatgtt   13740
gaacagtaat ctccaatgtt ggaagtggag ccttggtggg aggtgattgg atcacagggg   13800
cagatcccac atggcttggt gatgtccttg atctggacac aagatctggc tgtttaaaag   13860
tgtgtggcac ctcccccccac ctctctcttg ctcatgcttt tgccatgtga catgcctgct   13920
ccccctttgc cttttgccat gattggaagc ttcctgaggc ctccccagaa gcagatgctg   13980
ctgtgcttcc tatacagcct gcagaaacat gagccaatta catctgtttt cttataaatt   14040
acccagttgc aggtctttcc taatagcagt gcaatgacag cctaatacag tctgtgaagg   14100
tgttctcaga agacatcggc acttgaatca gtggactgag tgtcttagtc catttgtgct   14160
gctataagaa aatgcctgaa actgggtact ttatagagaa gataaactta ttttctcaca   14220
gttctggagg ccgggaagtt caagatcaag gtgccagcaa gtatattgtc tggtgaggga   14280
ccctatctct gcgtccaaga tggtgtgttg tggcagcctt ctccagaggg aacgaatgct   14340
ggggtcctcg catggaggat agtggaagag caatacaggg tgaactgtcc ttgaagcctt   14400
tttgacaggg tagtaattca gttatgagga cagagcctgc ataacttaat cacttcccaa   14460
aagccctact tcttaatacc accacaatgg gattacattt caacatgaat ttctaggggg   14520
tatgttcaaa tcatagcatt ctactcctag tcccccaaaa tgtatgacct tatcacatta   14580
aaaatacata cattccatcc cagtaactcc aaaagtctta actcattcca gcatcaactt   14640
taaaatcaaa gtccaaagtc ttatttaaac atcgtctaca tcagatatga ttgacactct   14700
aggtaacatt catcttgagg caaattgctc tccagctgta aacctatgaa atcaaacaag   14760
ttacatgctt ccaaaatatc atggtaggac agacagggga tagatatttc cattgcaaaa   14820
gggaacacta ggaaagaaaa aagcgataat agatcccaag taaatccaaa atccaacaag   14880
gcaagcaaaa tcagatcttg aaacttgaca atgatctcct ttgactccct gtcatgcctt   14940
ccagataccc tagggtggga gttgggcccc caagtctcca ggtggtcctg cccccatggc   15000
tttgccggct gtggctccca agcatgacag tcccctgctt ttggctgtcc caggctggag   15060
ttgcacagca gtgttttctac tggcttgtgg ttgaggggc cctgaccccca tggctctatt   15120
aggccatgcc tccatagcac gtgctctgtg tgtgcctgca aagatgctg ccaaggcgta   15180
ttgcctgtgc ctctggaggg gcagcctgag ccacacctgg gcccatgtga gccatagctg   15240
aggcagctga ggagtgctac actggaatgc agggagcaga gacttgaggc agtactgggc   15300
atgaaggccc aaggtcccat aggtactcag ggaccctcca gagccctggg ttcctcccctt   15360
gactccattc tgccctcaaa gcaaatgcag ggagcagaga cttgaggcag tactgggcat   15420
gaaggcctaa ggtcctgtag gtacccaggg accgtccaga gccctgggtt cctcccttga   15480
ctcccttctg ccctcaaagc cctagaactc taagcctgtg atggccatgg cagcctggaa   15540
gagctttgag atgccgtcag ggcctttctt ccattgtctt aacggacagc acctgacttc   15600
cctctatcgc caggaatctt atcaaatggt ccctgggcca cacccctttgt tttctctcct   15660
acacgcgtgg ccaagctgag actcttccaa acctttaagt tctgcttctc ttttgattat   15720
agattctgtc tttaactcat ttctctcttt cttgcatttt accatacaca gttgagaaa   15780
gccatgcagc tcccttagcg ttttgcttag agatttcttc ctctgaatat tctagttcat   15840
cactgttaaa ttctgcctcc cacaaagccc tcaggcacag acacaattca gcctagttcc   15900
ttaccacttt gtaacaggaa cggtctttcc tccagattcc aataagatat tccttgctgt   15960
gatctaacac ttcatcttta ctattcatat ttctaccagc attgggatca tgattactta   16020
aacatttctc tttttttttt agatggagcc ttgctctgtc gcccaggctg gagtgcagtg   16080
```

```
gtgggatctc ggctcactgc aagctccacc tcccgggttc acgccattct cctgcctcag  16140
cctcccgagt agctgggact accggcgccc gccaccacgc ccagctaatt ttttgtattt  16200
ttagtagaga cggggtttca ccgtgttagc caggataatc tctatctcct gaccttgtga  16260
tccgcccacg tcggcctccc aaagtgctgg gattacaggc gtgagccacc gcgcccggcc  16320
cacttaaaca ttcctaagaa gactgaggct ctgtctacag atctcctctt cttctaaacc  16380
tgcaccagaa ttgcctttaa tactctgttc atagccattt aggcttttc tgccatgcac  16440
tctgaaacac ttccagactc taccagcagt ttgaaatctg cttccacatt ttcaggtatt  16500
tataacatca acaccccact tatgtttagc aaattatgtc tccgtccctt tgtgcggcca  16560
taataaaata cctgtaactt ggtcatttct acaacagatt tattatgtca cagtacggga  16620
ggctggaaaa agtgcaagat caggacactg gctgttttgg tgtctggtga gggtcccagt  16680
ctcttcttca agatgaagac ttgttgctgc ctctcctgaa ggggacaaat gctgtgtcac  16740
cacactgtgg atagtggaag agcaatacaa ggtgaactgt ctctgaagcc ttttttataa  16800
gagcgttggt ccattcatga ggactgagcc ctcatgactt aatcacttct caaaaaacgc  16860
taccgcttaa taccaccaca gcggggatta agtttaaata taatgtttgg aggccaggtg  16920
cagtggctca tgcctgtaat cccagcactt tgggagggtg aggcgggcag atcgcttgag  16980
gtcatcagtt caagaccagc ctggccaaca tggagaaact ctatctctac aaaatacaaa  17040
aattaactgg gcgtggtggt gcgtgcacac ctatggtccc agctactcgg gaggttgagg  17100
catggcttaa agccaggagg ttgcagtgag ctgagatcgc gccactgcac tccagcctgg  17160
gcaacagact gagactctgt ctcaaaaaaa aaaaaaaaa acttggagaa ggcaaattca  17220
aagcacgaca gtagagaagg tccatcctcg cccaacgtga gtgggcactg tccaatcagc  17280
agtgggccca gataaggaaa aaaggtagaa gaaaggcgaa ctctccctct ctgcctctcc  17340
ccactctccc ttctgcagct gggacaccca tcttctcttg cctttggata tcagaactcc  17400
agattcttca gccttcgcac tctgagactt gtaccagtgg cctccgggtc tcaggccttc  17460
agctgcagac tgagagttac ccaactggct ttcctgattg acgcttagac tgtaccacat  17520
aaatggcttc cctggtcccc agcttgcaga tggcctattg tgggaatttt cagcctctgt  17580
aatcattgta atcatatgag cccattccca taataaatcc cttctcatgt atctatgtat  17640
ctatacctgt atcaatccta tttcttctt tttttttttt ttgagacaga gtcttgctct  17700
gtcacccagg ctggagtgca gtggcgtgtt ctcagctcaa tgcaacctcc gcctcccagg  17760
ttcaggcgat tctcctgcct cagcctcccg agtagctggg actacaggca cccgccacca  17820
cgcccagcta attttttgtat ttttagtaga cggggtttt catcatgttg gccaggatag  17880
tctccatctc ttggcctcgt gattcacccg cctcggcctc ccagagtgct gggattacag  17940
gcgtaagcca gcacacctgg cctcgatgct atttctatcc tatcggttct gtttacctga  18000
agaaccctaa cataggtttt ggtatcagga tgattctaga gaaacagaat cataagaatg  18060
agttttctga atgtgtattg tgttttcgg aattggtttt ctaatatgac ttgacttaaa  18120
agtgagaaga actctacttc caacagtaca caggacactg atggtccatg gtgtgaatag  18180
tttatgaaaa tatgcaaatt tctgcattgt atactcctag taaaccactt acaagaggca  18240
aggagcttag tgactctgta tatgatattt tcgaacattt gtggaaaacc agggaatata  18300
gtgacgtggg ctggttacca gttggttgct ggacaaagtg atgaaatcac aggatgtgct  18360
cagtgattca aattcccagt tccagctctg tataaataac ctgtgagtgg ctgagtgaac  18420
cctgaaggag aacctccttt cctgtagccc tggggccaag actgctgaaa agcaaccaca  18480
```

-continued

```
agtcctcgtc ctgaaactgg atgaattaca acgcaagttg aactctcagc cttgcgggt  18540
gtccactgtt ccagtgaggg cattggctgg gaaacagagg atcctgtaag ttgggatgaa  18600
gacatatgga aggaccctga tgaagctggg gacggtcagc ctctaagtta ggatgagtca  18660
ttttgtcagc agaagcagcc tccctgcacc cagtggcagt gctacaccca cccccagtgc  18720
tacaccccte ccccagtggt actggccttt ccaccttctc tgaggcatta atctgtgttg  18780
cctgaggaaa gggtaaggac ttcccctaag gcagttgctg attctcctcg ggtccctccc  18840
ccaacccttc cctttgcttt aagacctata acaagactca cagcccagca ggccctgaa   18900
ggtgaggccc acagtgtgac acaggaggag gcgagccaca ccccagaaga gccactcgac  18960
ctctctgatt tatacagaca gacacctggg agcatgagtg ggaacggacg ttgggtgtag  19020
ggcactgggg gaggaacatg gaggtggagg gaccaggtgt gcaggcatgt ccaccaagta  19080
gagcctgaat tccaggctgc aactcaggga cttggaaaag ctctaactgg ctggtcggtt  19140
gaaacatgga tcaaaggatg cctgcagtga gcgagctgga gatgcctaaa ctcccttggc  19200
ttaacataga ggaaggggtt caaaggctca ttcccaaagg agatcagaat gtgacaatga  19260
aaacctcctc acctaccctg ggagggccca aaacgcagac cttttcacaac agggatcccc  19320
aaccccccgg gccatggact ggtactggtc catggcctgt taggaactgg gccacacagc  19380
aggaggtgag cggtgggtga gtgagtgaaa tccgtattta tagccactcc ccatcacttg  19440
catgaccacc tgagcttggc ctcctgtcag atcagcagca gcatcagatt ctcataggag  19500
tgcaaaccct actgtgaact gcacatacga aggatctagg ctgcaacgct ccttatgaga  19560
atctaatgcc tgatgatgtg tggctgtctc ccatcctccc cagatgggac tgtctagttg  19620
caggaaatcg agcgcaggcc tcccactgat tctacatgat ggcgagttgt ataattattt  19680
ccttacatat tacaatgtaa taataataca gataaagtga acaataaatg taatgtgttt  19740
gaatcatccc aaaaccatcc tccaactccg ggtctgtgga aaaatattct gccatgaaac  19800
tagtccctca tgccaaaaag gttgaggact gctgtctcac aacactgaaa tatagacttg  19860
tgagggagcc cagtctcctt gaagagctct gagattgttc ttctctgtag gccagactca  19920
ctgtgggaac tgcagtcaat caactgagaa acttacatgt gatgggaata attggatcct  19980
ggggtagcag tggccaagtg ggggcattca agcaccaaag gcaaagttgg catggttacc  20040
atgatagaca gcagaggcaa agtagcagtc agacctgagt tacaggtcca acccatgtag  20100
acctatggca ctggctggtt accatgttt tcctagcagt gaaacagatg ggaagcctgc   20160
tcaattccta ctggatacaa gcagaaaact tacagatcaa gtggacaaaa ctctaagtcc  20220
aatcataaaa acagagaatc atggcctcag tctttcacag acttgagcca gtctatgaac  20280
ccagaaaagt gaaagaaag gctgggtacc cttgaggaag gacccaggga tggccaaaaa  20340
tgtatatata ctgttaattc tttccctggt cttctccaaa ggggtctatg gccttctatc  20400
tgtgtaactg tgtattggaa aaagaaaat aatgtggcat ttcaggacga ttggacactg   20460
gctctgtcct gacattgatt ttaggagatg ctggaacgac actgtggccc tccagttagg  20520
gaggggctta gggagccagg tgatcaatgg agttttagct caggtctgac tctgtgggtc  20580
cagcgggtac ccagcccatc ctgtggtcat cttcccagct ccagatgtgt aagtggaaca  20640
gacacactca gcgccagca gagtcccac atgcgtcccg tgacctggtg tgtgaaggct    20700
actgtggtgg gaaaggccaa gtggaagcca ttagagaggt ctctacctag aaccgtcagt  20760
caaaagccat cccacatccc tggagggact gcagacatca gtgccaccac caaggacttg  20820
agaggtgcag gggcggcgat ccccaccaca gcccattctc cccacctatt cggcccacag  20880
```

```
gggagacagg tgggtcctgg agaatgacag gggactgtcc taagtttgac tccagctgca   20940
gctgctgggc cagacgaggt tccatcgctt gagcaaatta gcacatctcc tgctccctgg   21000
tgcgaagctc ttgatccagc aaatgcgttc tcctccaccc ccgtccacag ggcccagcag   21060
aagccaggcc agcgatgcac cctcgccgcc ccacctgagg ggcctctcgc ctctccagcc   21120
cgtgtcagag gtaattctca ggagtctcga tcacctctcc cttccccagg atgtcacact   21180
ggcccattac actggtgaca tcatgttgat gggacgtaag gcacaagaag tagcctccat   21240
cctagacttg ttggtgtcgg agggtgggga ataaacccaa ctggaattca gagcctttcta  21300
cctcagggaa atttccagtg gtgtgaggcc tgttctaagg tgaaggacag gttgttgcag   21360
ctgaaccctc ctacaaccaa agagaagaa cggcactaag tgggcctgtc tgatgtgggg    21420
ttgacacgtt ctttctcttt gaggtgtcca actctgtcca tttactgagt gatttgaaaa   21480
gctgctagtt agttttaagc atggcccaga gcaagagaag tctctgcagt aggtccaggc   21540
tctgtgcatg ccgctctgcc acgtgggcca catgacccgg cagatccact ggtgcctggg   21600
gtgtcagtgg cagacagaga ccctgtgtgg agtctttgcc aggcccctgt aggtgaatca   21660
cggctcaggc ctttaggatt ttggaggaag gtcctgtcat cattcacaga taacccactc   21720
tccttcagag aaacagctct tgccctgctt ctgggccttt gtagaaatta aacacttggc   21780
agtgtgaatc tataatccca gcactttggg aggctgaggt gggcaggtca cctgaggtca   21840
ggagttcaag accagcctgg ccaacatggc gaaaccctgt ctctactaaa aatacaaaat   21900
tagccaggtg tggtggcgag tgcctgtaat accagctact gggaggtgg aggcacgaga    21960
atcagttgaa cccgggaggc ggaggttgca gtgagccaaa atggtgccgc tgcactccag   22020
cctgggtgac agagggagac tctgtctcat aaaaaaagaa aagaaaagaa agaaaaaaag   22080
aaaaggaaac taaactagac aagggccacc aagttaccac gtgacttgaa tggctcatca   22140
tgatctgggg actttctgac ccacgtagcc ataaagtcgt gtgcacagca gtgctgcatc   22200
agccagtgga agcaggggat aggtgatcag gcccaagcag gtcctgaagg cacaaggaag   22260
ttacgtgaag tagtggccca aagcctgtgg ccccactgct gctcccctgc cttctccctc   22320
cctgtctgca cctgtggctg catggggagt tcctctgatt agttgacgga ggaagagaag   22380
actcaggccg gacttacaaa tggttctgct cagtatgcag acactaccgg aaagtggaca   22440
gctgcagccc tgtagcccct gggggatatc cctcagacag tggtgaagag gaatcttccc   22500
cgtgggtaga acttccggca tgcacctgtg tgtgctccgc ttagaaggag cagatgtgtg   22560
atgatatttc attcatggct gttgccagta atttaagtgg atggaggtgc ttgaaaggaa   22620
catgattgga aaattggtga tgaagaaatg tgtggaagag atgtatagat agcccttcct   22680
gaacatgcta atgacatcca gatatttgtg tcccatgtga atgctcacca aagggtgacc   22740
tcagcagagg acttcagtaa tcaggtggac agcatgagct actctatgga caccagtgag   22800
cctttttccca gccaccctc tcatcaccca gtgagctcct gagcgaagtg gctgtggtgg    22860
cagggatgga ggttgtgcgt gggctcagca acatggactt ccactgacca aggccaagct   22920
gagtaccacc agcactgtat gcccagtgtg ccagcagcag agaccaacac tcagcctgat   22980
aagctccatt cctgagtgat cagcccagtg cctgggggca ggtgggtgac actggacagc   23040
tcccatcatg aaggggcgc tgaggctcca ttccccagcg tgttgagccc ggtgcctggg    23100
ggcgggtggg tgacactgga cggttcccat catgggaggg gcgctggttt gttctcactg   23160
ggataggcgc ctgccatgga tatgattttg tcttccctgc acacagtgct tctgtcgtca   23220
ctaccatctg tgggctcaga actcctcatc taatgccgtg ctgtccacac agcattgctt   23280
```

```
tgacgaagga actcactttg cagccaaaga agcgtggcag tgggctcatg ctcgtggtat    23340
tcacgggtct taccgtgttc tccatcatcc tgaagcagct ggcgtgatag aacggtggaa    23400
tgggcttttg cagacacagc tccagcacaa gctgggtggc agtcccttgc agggctgggg    23460
caaggtgctc ctccaggagg ctgtccgtgc tctgaatcag tgtccaatat gtggagctgt    23520
ctctcccaca gtcaggattc acccgtccgg gaaccaaggg gcagaagtgg gagtggcacc    23580
acccaccatc agcccagtg acccactagc agtgttttg tttcctgttc ccatgactt    23640 acgctctgct ggcctagggg ccttggttcc aaggtgagga atgctgccac caggagacac    23700
aacaatgact ccattgaact ggaagttaag gtggcacctg ggcagttggg gctcctcaag    23760
cctcagaatc aacaggccga taagagagtt tggatgctgg ctggggattg atccagagga    23820 cccagggggac atcgaactgc actccacacc agaggtgcgg aagagcacgg ggaatgcagg    23880
aggcccctta gggcttcttt aagtgtaacc acaccctgtg gttaagatcc ctggggccag    23940
gctcggtggc tcacgcctgt aatcccagca ctttgggagg ccgaggcggg cggatcacga    24000
ggtcaggaga ttcagaccat cctggctaac acggtgaaac cccatctcta ctaaaaatac    24060
caaaaaatta gccgggcatg gtggcaggca cctgtagtcc cagctacttg tgaggctgaa    24120
gcaggagaat ggcgtgaacc cgggaggcgg agcttgcagt gagccgagat cgcgccactg    24180
caccccagcc tggcgacag agcaagactc cgtctcaaaa ataaaaaata ataataaaaa    24240
aataatccct gggaaagcac agcaatgcaa gtttccttag gaaactacag caaggccgag    24300
acccttaagc actgaggcct tgggtcacct ggccaggtac agaaccacta ccggctgagg    24360
tgcttgctga gggcaaaggg actacagaat gggcagtggt tataaacacc aggtactcct    24420
gtagcttggc cagtagcaga aatgaggatt gcaactttca cgagtgttc ctctccattt    24480 tgttaagaaa gcatttgtgc atatgtgtac ataagttaag caaatatctg ttttctttcc    24540
tctcttactc ctttatcatg taacataaga tctattgatt ttgtctcagt atcaaggtat    24600
cgtgaatttt acatgacagt attgaggtcg tgcgatatcg ggagagtcga catcactcga    24660
ggacttcacc tcctcttcca gggaaggagt cagtgcgtgt ctggttgtat gcgggacagt    24720
catcacatgt tagttggaac catgaccttg ctgctgtcta tttggagatg aagtacggtt    24780
taaggaggtg tgtatgggtt ccaagctgac aaggagtgaa cttgtgacgg ttcgtttcag    24840
ctgtcaactt gactggatga agggatatcc agagagcatg aaagcattat ctctgggtgt    24900
gcctgtgagg gcatttccgg agagactggc gattgaatcc gtgggctgaa taaggaagat    24960
ctgtcttcac ccaaagtggg agggcaccat ccaatccact gagggcccag gcagaacggg    25020
aagatgaatt cgtgctctct tgctctctct tcccccacca gagctgggac acccacctcc    25080
tactgccctt agacatcaga actcctggtt ctctgggctt tggaccctgg aacttatacc    25140
agtggcccct ctgactgcga gttacactgt cggcctccct ggttctcaga tcttcaggct    25200
tgaactgagc cacactacca gcctcctgg gtctccagct tgcacagaca gggcaaatca    25260
tgggacttct cagtctccat actcatgtga gccgattccc atcataaacc ccctttcttc    25320
catccatcca tccatccatc catccatcca tccagctta tctatctagc    25380 taccgagcta gctacctgta tctttactta tctctatcta tgtctaccta tatctatatc    25440
tctgtctaca tctctatatc tatctgatct atctctatct ctatggtaat ctcaatctgt    25500
ctgtctgtct gtccgtctct ctgtctatct gtctccctcc ctgtctgtct atctgcctgt    25560
ctgcctgcct gtctatctgt ctgtctgcct gtctgcctgt ctgtctgcct gtctgcctgt    25620
ctatctgact gtctgcctgc ctatctgtct gtctgtctgt ctttatctct atggatctgt    25680
```

```
acttatttat ctatctcatt ccgtgtatct gtctctatat ctatacatct acatcatgga    25740
ggactatggt agatgctcac tgctgtgcac tgcaccgtcc ctcccagcgg gaccacagca    25800
ctggtccagc cagctgccca cagctctcag cttgctcctc ccgaggaaat gccctcagcc    25860
aaaggcagct gcctcaccca tggcttctcc ctgcccctgga agccacctct acccaatgaa    25920
tggtcgatgg aggaagcaac aggtcaggtc cttcacctga attcatggcc tctctaaagg    25980
gccccttcag ctccaaaagc acccgaggca tcatcagaaa ccttctttgc gagtggagca    26040
cagctcagct gcccccacct gctccttccc tctctcacag cctttgtccc caagagcact    26100
tgccacttta cccttgacct acatgtctct atctggcagt gtctcttggg gaaccgaacc    26160
tcagacagtt tgcaagcaac aaattccaaa ggtcgtgcct gggcctggag ctctgctgac    26220
atggaagcca tgcccacctg ggacctgagg gtgtttcttg tctcacaggc ctgatattga    26280
gtggtgtgca tctgcatacc caggtggttg ttaaaacaca gaacggcttc catgctggtt    26340
gaacgacccc taccttgagc ctccaggtgt ccccagagg ccaccccggt tccttccccc    26400
agggtccaag cagggcacga cagacagctt ctggaacatc actcaatgcc gtggccagcc    26460
ccattctgat gggtctgcac caatcggggc tgcttgttaa gcatgactaa agtcctctgc    26520
agtcgtctgc taggactgcc acagcaaagc gccacagtct ggcagccttc acagagacat    26580
ttatctcccc agccctgggg gcctcaagtc caagctcaag ttgttgttgg ggctggttcc    26640
ttcgggggct acgaggtggc ctctgcccag tccctccagc ctctgcccag tccctccagc    26700
ctctggggct cccaggcagc ctcgtgtttc ttggctcgtg gagcatcact ctaatctctg    26760
ccttcacctt cacatggcgt ccttcctgtg tgtgcgtctg catccaactt ccctgttcc     26820 taaggtcacc ggtcagatct gagcaggata ctaatggcca tatcttagtt acatctgcag    26880
tgaccctatt tccaaataag gtcacatatg aggcactgaa ggtcgggact gcaacatgct    26940
tgttctccta tcatggaatc agaccagcag gtgggtcaca ttccgccaga gggagagtgg    27000
gcagacgccc aaagggctgg atgtatacag ctccaggaag aaccgcagtt gcagctgctt    27060
ggacaggtgt gggcactcac agcctcccat gacagccctg gctgggggct ccatccacag    27120
cccctggtgg ggtggggcaa ggcccttcct tctgacccac aggaccttgg accccctgggg   27180 cactgcagag ggactcaggg tcagaccagc agcctttgac atggccaaga gtgaaagtga    27240
tggggaccca cgagccatca gagctctgtc tccagagcct gcacagggag tgttgggaca    27300
aggagcaaag gaatcgggag cacatcaagg caggcaccag atttggaaga acgccccggg    27360
ggaggtgctc ccaggcgagt ggggcagagg gcagtctcct cctgggcttc cctgggtccc    27420
agcccggccc ggctgggcgt cccactgtct ttggtgtggt gtgctccctg cctgtggccc    27480
tgtgatggga gtcctgcttc tctaaacagt gagaccctca cagaacccgt cagcatgtcc    27540
aaagcacctg gaggagaaaa gatttgtctc ctcattcgtc actaggttca tggttgaggc    27600
tctcacagca aaagacagat taacaagaga aaagcagaca catttattca atataagttt    27660
catctcgtat aggagccttc ggaaatgagg acccagcact tcgggaggcc gaggtggaca    27720
gaccatttga agtcaggagt tccgagacca gcctggccaa catggtgaaa ccccatctct    27780
actaaaaata caaaattagc cgggcatggt ggcatgtgcc tgcagtccca gctaccgggg    27840
tggctgaggc aggagacttg cttgaacccg ggaggtggag gttgcagtga gccgagatca    27900
cgccattaca cttcagccag ggtgacagag tgaaactccg tctcaaaaaa aaaaaaaaaa    27960
agaaaaagaa aaggaaaaag aaatgaggac ccaaggggaag agggaaaccc gtgtattttt    28020
atgtggagtt tgatggagag tcatgcagag tgtgattgga ttagacaaag tgggtgtact    28080
```

-continued

```
cgtccgttct tgcactgtat aaagaatact tgagactgcg taattcataa agaaaggagg    28140
tttacttggc ttacagttcc ccaggctgta cagaaagcat ggtgctggca tccacatggc    28200
ttctgggggc gggctcagga aacttacaat catggcggaa ggcaaaggag gagctggcac    28260
ttcacgtggc cggagcagga ggaagcccag agggagagag gggaggtgcc atatgccttt    28320
aaacaagcag gtctcatgag aactcactat cacgagaaca gcactggggg gaaatccacc    28380
cccatgagcc aatcacctcc agcaggcccc acctccagca ttggggatta caattcaaca    28440
tgagatttag gcaggtacac agatccaaac cgtatcaggg tgtggcctaa tggtgataca    28500
ctggggagac ttggcctgtg gtcttagtcc atcgtgtgct gttagaacag aaaaccacag    28560
actggctaac ttattggccc ctggtcctag aggctgggag gtccgagatc gacaggccac    28620
ctctggcaag ggtctttgtg ctgccttatc ccatgacaga agggcaaaga gagggagaga    28680
gagacagcca gagagaaggg gaccaaactc atccttctgt cagagcccgc tcccacgaca    28740
atgatgttag tccatcatga ttacagagat ggggacaca ttcagaccac agcagccccc     28800
tcaacccgca cacactgcac attgagggga gggccgggag actggaagga aacatcagag    28860
tctggagaag accaccagga tcaccagggc tatgctctca cccggcaccc agcaccgagg    28920
ggctcatggg aaacaagacg ggtctctcgg tgcacgagtg ctgggcacac atagtccacc    28980
gtgcatcctg ggctgatgat ctggaccctg gtcctgtgca gccctggggt ggggctccag    29040
gctgagatca gccacgtctg ggggaggaga cagtgttccc agtctcacct tgccccacgg    29100
actctgacag gggttgaaga agcaaggagg ctccaaggac tggggagggg gagtctggcc    29160
gacgatctag gagcatcaag gcgcctgctc cctctcggcg tggcccggtc ctgtaggtgg    29220
tcagttatgc aatgccactg ccttcctacc tcacaaggag ggtgggtgga ctcagaagcc    29280
aggcccaggc ttccttcttg gctcaggcaa ggaacatagg gggctttgag ctttgcttat    29340
tcatttaaca actgaacccc tagtctgtgc caggccccca tttaaatggt ccctgggata    29400
cagcagggtc cagaatgggc ccagaccctg ccccatagc tgaccttctg gagagcctga     29460
ggagtgaggg gtgccctcca ggcacggcag acggggcagg ctctgcattc gggggctcca    29520
gctgcttttcc caccacccac ccactccacc cgagcccttc tgggtcagct gggctcctgg    29580
ctctgcccgc ctggggtgca agacgccaag ttccttcctg gacagtgaga gaaccatgcc    29640
aaaaagaaat gaaaggaagg cagacggcga gatgagggag agggtgggca cccagccagg    29700
gaccgcagag acgaggagga ggcacagaga cccactgtcc ccagccactg ccagtgaggc    29760
tggcccaggg ccaggggctg ggcgtccctg gcatgcatgt ggctcccagt gccccacgt     29820
ccaacaggag tggggcggcc ccctcttctg ccacatcccc atcccacctc ccattccatt    29880
cactggtctc attttttaagt ttttctctcc cagttattca ggattgattt ggagagcaga    29940
gcgatggctg caggtggctc ttcatttttcc ttcacctaag aagcaaacca tcatccaccc    30000
caagcttgtc tctccagcct gcccctaca tgaggacaac ctcccctcctc ttccacggtg     30060
gcgctgttcc cactggaggc ccaggcttgg ccatccgttc attcttggag tcctcaagag    30120
attgtcagct ctgcagtggg gagcagccgc tgtcaaagac cctggaactt cctcccctgct    30180
gcgtccacca accccccactg cccgctgggc actcccaacc tgaaacaagc ttgctcgctg    30240
caaaagcctc acctctgacc caacttccca ctcccaggat acccaacctg gccttccctc    30300
tggatacccc tgtgggctcc cctctgctga tgggttcccc tctccagctg tggcttccct    30360
ctgctgatgg ggtcccctct ccagctgggg ctccctccac tgatgggtt ccctctacag     30420
ctgtggctct ctccactgat ggggtcccct ctccagctgg ggctccctcc actgatgtgg    30480
```

```
tcccctcttc agcttgggct ccctccactg atggggtccc ctcttcagct ggggctcctc   30540
tccactgaca gggtctcctt tccatctggg gctcccttgg ctgatgaagt cccttctcca   30600
ggtgaggctg ctctctgctg acagggtccc ctctccagct aggtctcctc tctgttgata   30660
gggtcccctc tccgggtggg ctcccctctg ctgacgggt cctctgatgg ggtccctact    30720
ccagggggc tcccctccat agatgagctc cccttcctgg gttgggtgac ccctccgccc    30780
tatctgtgtc tgcaggttgg ggctaggcag tgctggccag catctgacaa cctcccctt    30840
ctgttcttgg gcactgctca cttattcagg tctcagccag gcagcccctc caatggtaat   30900
cttcagagtc cccttcagca acacagcttc ccctctgtgg cccagctcat gctgaagtaa   30960
acaaggcaat gtcattaacg gctggtatca gcttgtacgg ggaaccagtg ccccagaag    31020
cctctgggga ggcccaggct gtgaggatca ggggtccgga agagcctcta gagcgggaga   31080
aagaggcctc aggggtccct cctcacaggg gatggtgaca cacggtagg gaatggaggg    31140
gtcagggctg gtccaggac acggtgaccc tggccagaaa aggccgggcc tggctggcac    31200
ccgcacgaag ggaacggagc cagtgtggaa aagcaggccc gcgtcctctt ctgcactccc   31260
agcccctttta aactacacac agcttgtagg aaggggatca gaggccctg ggcgtcccat    31320
ggctatgctg cacctgggga catgaagcct agggtagctc agccagctct ggtcacggct   31380
gacagacagc ctcaccccaa cagcctcacc catccctcct cagggaacag ggtcctaaca   31440
agctgctttc cccatcccag tgttgaacaa aaactcatgg gtttagacaa gagtgaaggt   31500
gactcctcca ccacccatcc cacctccagc aggcagccac ccccaaaatt attgatttat   31560
taataaatca atgacaggtg ccagccagcc ccacctgtcc ccaacctgca aatgcagaca   31620
ggggtcactt ggtccaggga gaggagaccc tcagtggagg ggagacaccc tggagagggg   31680
accccatcag caaaggggag ccccagctgg agacagtaaa taggcagact attcactgtc   31740
ttccccctca agccaggccc acagagtcac agagtatagc caccagcctc ctgggcccac   31800
ccgggaggcc ccaaccacac tccccctgct cagctcagcc cggatttctg gattctgctg   31860
cctgccaggg atcctgagga ggagatggta tcagagcctc accagcccct ctcatacccca  31920
ggagtcctca tgatgataac agtgtgtgcg ccaggctgtg caggtgctgg ccgggatcct   31980
ctgaggggac gagatctcca tgggagggca ccactctgat gtccatcctg ggcttccgtg   32040
gccctgcctg gccactgccc gctgctcttg gtcaagatca tggaccctca gaggccaacc   32100
aggcctcagc ctgtgcctac agcatcctct ctactgccgg gcttctgaat tgctccttcc   32160
tcctgtctcc cacccagagc aagaacgaag gggaggcccc cagagcctg cagcgccggg    32220
agagactccc atccccaccc cgcatgccat caacacaaac tgccggagag tttagggat    32280
cccacgactt ggggtctcca aagagacccc cgggacatct catcgagacc ccctgggca    32340
ctgcatgctc aggcttccca ccctggccc accccatggg gtgtgcccag tcccgcatct    32400
caccccatat ccatgcatgc atgcatgaac ctgaaagcac cccacaccct ctggtgctca   32460
gtcctcccct cctccctggg gtcccctccc ctccctgccc ccaagccttt gcatcccct    32520
gcaaacctca aaggggggaa ctatttctgt cctgaaagca gagagggccc ttttcttggg   32580
acctctccgc catctctgcc tccactccca gctgctgtca gctctggcct ggcccctgca   32640
ggaagcaatc actggtctcc ctgtttccca tctggcccca aggtctgttc ttgcccttcg   32700
accagagagg tttgaaagca caactcgggc cctgcgtgcc ctgctcccca gggctccaca   32760
cctctgagca cccgcgcagt aacgaggct cccagcccg cctcgcccca gggtcccctc     32820
caacactctc tggccttggg cctttgctat acccgggggcc tggaagggcc ccctcatccc   32880
```

```
ccaagtgtca ggcaaaggtc tcagagcact gtccctgccc ggcgtgcttg gtcctgactg    32940
ctaggcccca aatcattcct tttcccatta cctcttggtt tctctgtagc tggggtcact    33000
accccaaatt cttgaattga ctgacgtgtc caactatttc atgttttccc cctctacact    33060
gggagcccta caagggcagg gcccctgggc aagaatagt gccagccagg agcccctgga     33120
gaagatagct acacatgtgc cccaggcccc agatggcact cagccctgcc tgtcaatgct    33180
ggacataggg cagtttttat cctggctttc tacacaagga ggaaagacta accatgccag    33240
cgggcagcgg ccggatcacg tatgtcagta gaactctgac ccctgagaag cctggaagcc    33300
aaaccacacc tctgtagcaa tcacgccaca gactcaggcc acggctaacg gctgccagtt    33360
cacctatttt tgcccccaac tcaagaccaa ctggaggaag gcaaatatgt ccctgacgaa    33420
gggtggccgc ctccagcctc cccagcccag agcctcagcc tccccagccc actgcctcca    33480
gcaacacaca tctgaagcct tctctgttgg ttggttttat tggtattttg gaagattgtt    33540
tgttttttgt tatgagatgg agcctcgctc tgtcccccag gctggagtgc agtgcgcgca    33600
tctcggctca ctgcaagctc cgcctcctgg gttcaagcca ttctcctgtc tcagcctccc    33660
gagtagctgg gactacaggc acccgccacc gtgccaggct gattttttg tattttagt     33720 agagacgggg tttcaccatg ttagccatga tggtcttgat ctcctgacct catgatctgg    33780
ccatctcggc ctcccaaagt gctgggatta caggcgtgag ccactgcacc tggcctttgg    33840
aaggtctttt ataccttat tgagataaaa ttcttatgac ataaaactta gcataaactg     33900
tagacttagt tggtgtgact ttagagtagt ctcagaattg tgcaaccatc accactgcct    33960
acttttagaa cattttcaac atcccaaaga cagaaccccg taggcacctg ttagcagcca    34020
ctccccaccc agtccacgaa gccccaggca gccactcacc aatctacttt ccattaattt    34080
gcccattcta aacacttgaa aaaaatggta tcacaatggt cttttgggtt tggcttcttt    34140
ccctcagcat cataccctca aagttcatcc atgttgtagc tcgtatcggt acttcattca    34200
tttttatggc tgaataatat tccactgtat ggatagaccg atattttgtt tatttattta    34260
ttcattgatg aacatttgaa ttgttccac ttttttagcta ttaaaactag tgctggctgc    34320
gtgcagttgc tcatgcctgt aatcctagca ctttgggagg atgaggcagg cggatcactt    34380
gaggccaaga gtttgagacc agcctggcca acatggtgaa accccatct ctaataaaaa     34440 tacaacaatt agccagacac ggtcatgcgt gcctgtaatc tcagctactc aggaggctga    34500
ggcaggggaa tctcttgaat ccgggggca gaggttgcag tgagccaaga tcgcgccact     34560
gcactccagc ctgggcaaca gaccaagact ctgtctcaaa aaacaaaaca aaacaaaaca    34620
aaacaaacca gtactgctat gaacatgcat gtgcatattg ttatacagac atatgctttc    34680
atttctcttg gatacacaca cacacacaca cacacacaca cacacacaca cacacacacg    34740
tatatctagg actggaattg ctgattttta tggaaactct atatttagca ttttgagaaa    34800
cggccagtct gttttccgaa gtggctgcac tattttgcat tcccaccagc aatgaaggag    34860
ggttccaatt tctccatacc tctgccaaca cttgttattg tctgtctctt ttatttatag    34920
ccatcttgat gggtgcatcg tggtatctcg ctgtgttttg atttgcattt ccctgatgac    34980
taatgatggg gacatctttt catgagctta tcggtcatat gtacatcttc tttggagcaa    35040
gctctattct aatcctttgc ccatcattaa aggtaggtgg tttgtcttct tgttgataag    35100
ttagagttct ttacatgttt agatactagt cccttatcaa atagatgatt cacaaatgtt    35160
tgctgtcatt tcttgggttg tcttttccact tccttgatgg tgtcttttca cgcacaaatg    35220
tttttagctt tggccaagtc caatttatct atttttttctt ttgttgcctg tgcttttggt   35280
```

```
agtgtatatt aaaaaccatt gtttaacaca aggtcaccaa gatttattcc tatgttcttt    35340
cctaaggatt ttattttttc ttttcttttt ttttcttttt tttgagacaa agtctctctc    35400
tgtcgccaaa gctggagtgc aacggcacaa tctcagctca ctgcaacccc tgcctcctgg    35460
gttcaagcga ttcttctgcc tcagcctccc gagtagctgg gattacaggc gccaccacc     35520 atgcccagct aattttgtg tttttagcag agacggggtt tcaccatgtt ggccaggctg     35580
gactcaaact cctgatctca ggtgatccac tcgcctcggc ctcccaaact gctgggatta    35640
caggtgtgag ccactgcgcc tggccttcct aaggatatca taattttagt gcttacattt    35700
aggtctacga tccattttga gttaattttt gtgcacagca tgaggtaggg gtccaacttc    35760
attcttttgc acatggatat ctagttgtcc cagcaccatt ttctgaaaag actattcctt    35820
cccccattga attgtcttgg tacccttgtc aaaaatcaac tgatggccgg tctgaaggta    35880
gtgagttatc tcaattgatt gttcacagtc agttacagat ggaacacctc gttctactct    35940
ttcccgcctt ctcactgctg cacttgaaca gtctttaaaa aaatcaattg accataaatg    36000
caaggatttg ttcttggagt ctcaacttta ctgcattgat ctgtaggtct atccttatgc    36060
cagtaccaca ttgtcttgat tactgtagct ttgcagtaag tttgaatcag gaaatgtgag    36120
ccctccggtt ttgctcttct ctttctagat tgttttggct attctgaaac ccttgtattt    36180
ccttatgaat ttgaggatca gcttgtaaaa agacagatgg gattttgata gagattgtga    36240
agctatagat gaattcggga gtttggccat cttaacatta tgtctcctga tccatgactg    36300
caggatatct ttccatttaa ttcgatactc tttgattcct ttcaaaaata ttttgtattt    36360
ttcagtacac aagttttatg catctttgt tgcatttatt tctaggtatg ttcttttgc      36420 caatattata aatgagattg tcttcttcac ttcattttg gatggttcat tgctagtgta     36480
tagaaataaa atcgatgttt gtatattgat cttgtatcct gccacattgc tatgcatgtt    36540
tattagtttt aagggtttta gtggatttc tatatataat gtcatataat cagcaaatag     36600
aaagtttaat gtcttagtcc ttttgagctg ccacaacaga ctaccataaa ctgagtggct    36660
tataaacaac acaaatgtat ttcccacagt tctggagact gggatgtcca agatcaagac    36720
acccgtaggt ttggtgtctg gtcggggcct acttctgggt tcatagatga ctgtcttctc    36780
gctgtgtccc ccccatagtg aaaggaaggg gcccagggtc tttctaaggc ttctttata    36840 aggacactaa tccaatatag gaaggctctg ccctcataac ctaatctccc aaaggcctca    36900
cttccaaatt ccatcacctg gggagtaaga atttcaacac tgggggggaca cagatattca    36960 gacatagcat ttttcttctt cctttctaat atgggtgccc ttgacatctt tttcttacct    37020
aattgccctg ccagagcctt ccagacagtg ttgaatggaa gtggggagca ttcacccccac   37080 cttactcctg atcatagggg aagaactatc cggctttcac cactgagcac cacgttagct    37140
ggggtatttt tgtcagcgct ctttatcagg tggaggcagg tcccttctat ttctagtgag    37200
ttcagtgctt ttttttttt ttaatcaggg aagagtgtga gcttgtgttt gggtgccttc     37260
cctgcgtctg ttgagatgat cttacggttt ctgtctctta ttctattgat atggcgtatt    37320
tattaccttg gttgcttttt ggatgttgat aacatccaaa ctcttctgcc accccttta    37380 atagaaagct gtacaactcc ccaacctgcc tgggcgtgtc tgcccaagat gagtgctagt    37440
ggccgactcc ctgctagagt gagcactgca taaacagcct ctgcttgtcc tcatttgagt    37500
gatcttcatg tattccacga gaaatcaagg cacagggggtc tcatggtctc atgaatggct    37560
ccaccaactg aaggtgtgct ccatcggggc tgtgagtcac ctcacgccag gcagaaaggt    37620
ctctctgtca aacatggctt caaggaacca gggacctggt tcctcccaca ggccaggccc    37680
```

```
tgccoctaag tgcaatggga atatatgcac atgtcacctg tcccaaaatg ctgggagatg   37740
gcacttctgc agatggggaa actgagggac cagcccgaag tcacggggag gggaagactc   37800
ctacacacag ggaggagaag aacccagccg ggctgcaaac gcctgccctt cctcaacgtg   37860
cctccggctg tgcccacatc gctccagcag ctctgccttc ctcaggcata agccttctca   37920
gggcagggga ggcccaggga gcggcgctcc catcccaggc cgggctgctg agcaagcccc   37980
tcccctttct cccctcatcc tctgacagag tccacctgaa tatttgtcct ggagccagga   38040
tggaagctcc accaggccca gctaacaaca ggaacccttt cagacgcact tctgggtgcg   38100
tactgtgcca gtatcacaca gacacaagcc atgtccttgt cagccatggg atccccaagg   38160
tccccatgag gtcacaccag tgggccactg ggaagggcac ttcagatgtg gagctcccat   38220
gggccaggcc ctgcgaagtg gtcctcctac cccctcatag ccagtcttcc ctgtgagcct   38280
gcaagtgact gtgaatgtga gttccactct ggagctaaga cgggctgctg cccccgcaat   38340
cagatgtcag gcccatgaag                                              38360
```

US 8,399,639 B2

ISOLATED GENOMIC POLYNUCLEOTIDE FRAGMENTS FROM THE P15 REGION OF CHROMOSOME 11 ENCODING HUMAN ACHAETE-SCUTE HOMOLOG 2 (HASH2)

PRIORITY CLAIM

This application is a divisional of application Ser. No. 09/999,121 filed Oct. 31, 2001, the contents of which are incorporated herein by reference. This application also claims priority under 35 U.S.C. 119(e) from provisional application Ser. No. 60/244,705, filed Oct. 31, 2000, the contents of which are incorporated herein by reference.

FIELD OF THE INVENTION

The invention is directed to isolated genomic polynucleotide fragments located in the p15 region of chromosome 11.

BACKGROUND OF THE INVENTION

Chromosome 11 contains genes encoding, for example, KCNQ1, a voltage-gated potassium channel; IPL, a homolog of a mouse apoptosis-inducing entity; human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4). Human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4) are discussed in further detail below. Genes for the latter six proteins are located in the p15 region of chromosome 11, a region known to be associated with the Beckwith-Wiedemann Syndrome (Itoh et al. Am. J. Genet. 92, 111-6, 2000) and some childhood tumors.

Beckwith-Wiedemann Syndrome is characterized by pre and postnatal overgrowth up to 160% of normal birthweight, macroglossia, hypoglycemia, hemi-hypertrophy and childhood tumors, such as Wilm's tumor (Reik et al., 1998, Trends Genet. 13:330-334). This syndrome appears to be associated with deregulation of imprinting. Imprinted genes are genes that are predominantly expressed from one of the parental chromosomes. There appears to be two imprinted subdomains, since the imprinted gene domain of 11p15 contains at least two imprinted subdomains (Lee et al., 1999, Hum. Mol. Genet. 8:683-690). Mosaicism may also play some role in the Beckwith-Wiedemann Syndrome phenotype and may explain the variable phenotypes in Beckwith-Wiedemann Syndrome patients (Itoh et al., 2000, Am. J. Med. Genet. 92:111-116).

Human Achaete-Scute Homolog 2 (HASH2)

HASH2 is a basic helix-loop-helix protein that serves as a critical transcription factor for the development of the trophectoderm. Mice deficient in the HASH2 homolog, MASH2, die 10 days postcoitum due to placental failure (Guillemot et al., Nature 371, 333-6, 1994).

Human Tumor Suppressing Subtransferable Candidates 4 and 6 (TSSC4 and TSSC6)

Both TSSC 4 and TSSC6 are believed to function as tumor-suppressing proteins in that the genes are among the genes of a subchromosomal fragment that suppresses in vitro growth of the rhabdomyosarcoma cell line RD (Koi et al., Science 260, 361-4, 1993).

Human Ribosomal Protein L26 (RIBO26)

RIBO26 is one of the approximately 80 proteins that compose the human ribosome (Kenmochi, N. et al., Genome Res. 8, 509-23, 1998). It has been found in mice to be induced by LPS and IFN gamma but is down regulated by TNF-alpha (Segade et al., 1996, Life Sci. 58:277-285).

Human Cluster of Differentiation Antigen 81 (CD81)

CD81 (also called TAPA1) binds the E2 envelope protein of the human hepatitis C virus and is believed to play a role in hepatitis C infection (Pileri et al., Science 282, 938-41, 1998). CD81 also appears to play a role in T cell activation (Witherden et al., 2000, J. Immunol. 165:1902-1909).

OBJECTS OF THE INVENTION

Although cDNAs encoding the above-disclosed proteins have been isolated, their precise locations and exon/intron/regulatory element organizations on chromosome 11 have not been determined. Furthermore, genomic DNA encoding these polypeptides have not been isolated. Noncoding sequences play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

There is also a need to develop means for identifying mutations, duplications, translocations, polysomies and mosaicism associated with Beckwith-Wiedemann syndrome.

SUMMARY OF THE INVENTION

The invention is directed to an isolated genomic polynucleotide, said polynucleotide obtainable from human chromosome 11 having a nucleotide sequence at least 95% identical to a sequence selected from the group consisting of:

(a) a polynucleotide encoding a polypeptide selected from the group consisting of human achaete-scute homolog 2 (HASH2) depicted in SEQ ID NO:1, human SMS3 depicted in SEQ ID NO:2, human tumor suppressing subtransferable candidate 6 (TSSC6) depicted in SEQ ID NO:3, ribosomal protein L26 (RIBO26) depicted in SEQ ID NO:4, cluster of differentiation antigen 81 (CD81) depicted in SEQ ID NO:5, and tumor suppressing subtransferable candidate 4 (TSSC4) depicted in SEQ ID NO:6;

(b) a polynucleotide selected from the group consisting of SEQ ID NO:7 which encodes human HASH2 depicted in SEQ ID NO:1, SEQ ID NO:8 which encodes human SMS3 depicted in SEQ ID NO:2, SEQ ID NO:9 which encodes human TSSC6 1 depicted in SEQ ID NO:3, SEQ ID NO:10 which encodes ribosomal protein L26 (RIBO26) depicted in SEQ ID NO:4, SEQ ID NO:11 which encodes human CD81 depicted in SEQ ID NO:5 and SEQ ID NO:12 which encodes human TSSC4 depicted in SEQ ID NO:6;

(c) a polynucleotide which is a variant of SEQ ID NOS:7, 8, 9, 10, 11 or 12, (d) a polynucleotide which is an allelic variant of SEQ ID NOS:7, 8, 9, 10, 11 or 12:

(e) a polynucleotide which encodes a variant of SEQ ID NOS:1, 2, 3, 4, 5, or 6;

(f) a polynucleotide which hybridizes to any one of the polynucleotides specified in (a)-(e);

(g) a polynucleotide that is a reverse complement to the polynucleotides specified in (a) to (f) and (h) containing at least 10 transcription factor binding sites selected from the group consisting of AP1FJ_Q2, AP1_C, AP1_Q2, AP1_Q4, AP4_Q5, AP4_Q6, ARNT_01, BRN_01, CDPCR3HD_01, CEBPB_01, CETS1P54_01, CMYB_01, CP2_01, CREB_02, CREB_Q4, CREL_01, DELTAEF1_01, E47_01, FREAC7_01, GATA1_02, GATA1_03, GATA1_04, GATA1_06, GATA2_02, GATA2_03, GATA3_02, GATA3_03, GATA_C, GC_01, GFI1_01, HFH2_01, HFH3_01, HFH8_01, IK1_01, IK2_01, LMO2COM_01, LMO2COM_02, LYF1_01, MAX_01, MYCMAX_02, MYOD_01, MYOD_Q6, MZF1_01, NF1_Q6, NFAT_Q6, NKX25_01, NKX25_02, NMYC_01, OCT1_02, PADS_C, RORA1_01, S8_01, SOX5_01, SP1_Q6, STSSC6_01, SRV_02, STAT_01, TATA_01, TCF11_01, USF_01, USF_C, USF_Q6 and VMYB_02, as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The invention is further directed to polynucleotides that hybridize to noncoding regions of said polynucleotide sequences as well as antisense oligonucleotides to these polynucleotides as well as antisense mimetics. The antisense oligonucleotides or mimetics may be used for the manufacture of a medicament for prevention, treatment or amelioration of a medical condition. The invention is further directed to kits comprising these polynucleotides and kits comprising these antisense oligonucleotides or mimetics.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

The invention is also directed to an isolated polynucleotide from the p15 region of human chromosome 11 selected from the group consisting of SEQ ID NOS: 13 and 14. SEQ ID NO:13 consists of nucleotide sequence immediately preceding the HASH2 gene; SEQ ID NO:14 consists of the gap between the RIBO26 and CD81 gene. Both of these polynucleotides are located in the imprinted subdomains of 11p15. Oligonucleotides derived from these sequences may be used to identify mutations, duplications, translocations, polysomies and mosaicism associated with Beckwith-Wiedemann syndrome. Furthermore, oligonucleotides derived from SEQ ID NO:13 may also be used as a marker for the HASH2 gene and SEQ ID NO:14 may be used as a marker for the RIBO26 and/or CD81 gene.

DETAILED DESCRIPTION OF THE INVENTION

The invention is directed to isolated genomic polynucleotide fragments that encode HASH2, human SMS3, human TSSC6, human RIBO26, human CD81 and human TSSC4, which in a specific embodiment are the HASH2, SMS3, TSSC6, RIBO26, CD81 and TSSC4 genes, as well as vectors and hosts containing these fragments and polynucleotide fragments hybridizing to noncoding regions, as well as antisense oligonucleotides to these fragments. As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The HASH2 gene is 17290 base pairs in length and contains a single exon (see Table 1 below). The HASH2 gene is situated in genomic clone AC002536 at nucleotides 17081-34370. The SMS3 gene is 25970 base pairs in length and contains 3 exons (Table 2). The SMS3 gene is situated in genomic clone AC002536 at nucleotides 34371-60340. The TSSC6 gene is 30196 base pairs in length and contains 9 exons (Table 3). The TSSC6 gene is situated in genomic clone AC002536 at nucleotides 51731-81926. The RIBO26 gene is 21630 base pairs in length and contains a single exon (see Table 4 below for location of the exon). As will be discussed in further detail below, the RIBO26 gene is situated in genomic clone AC002536 at nucleotides 77701-99330. The CD81 gene is 21573 base pairs in length and contains 8 exons (Table 5). The CD81 gene begins at nucleotide 120961 in genomic clone AC002536 and extends to nucleotide 3640 in the downstream genomic clone AC003693. Clones AC002536 (140977 base pairs) and AC003693 (155074 base pairs) have a 2084 base pair overlap. The TSSC4 gene is 15540 base pairs in length and contains a single exon (Table 6). The TSSC4 gene is situated in genomic clone AC003693 at nucleotides 3641-19,180.

The polynucleotides of the invention have at least a 95% identity and may have a 96%, 97%, 98% or 99% identity to the polynucleotides depicted in SEQ ID NOS:7, 8, 9, 10, 11 or 12, as well as the polynucleotides in reverse sense orientation, or the polynucleotide sequences encoding the HASH2, SMS3, TSSC6, RIBO26, CD81 or TSSC4 polypeptides depicted in SEQ ID NOS:1, 2, 3, 4, 5 or 6 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time, the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include, on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted (indels), deleted, or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 7, 8, 9, 10, 11 or 12. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3, 4, 5 or 6 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the HASH2, SMS3, TSSC6, RIBO26, CD81 and TSSC4 genes. These include but are not limited to an intron, a 5'-non-coding region, a 3'-non-coding region and splice junctions (see Tables 1-6), as well as transcription factor binding sites (see Table 7). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of the human achaete-scute homolog 2 (HASH2) gene, 17290 bp, reference cDNA accession number U77629; reverse strand coding.

| Exon | Location (nucleotide no./amino acid no.) |
|---|---|
| 1 | 7031-7609 |
|   | 193-1 |
|   | stop codon 7028-7030 |

TABLE 2

Exon/Intron Regions of the human SMS3 gene, 25970 bp, reference cDNA accession number AB029488; reverse strand coding.

| Exon | Location (nucleotide no./amino acid no.) |
|---|---|
| 3 | 18962-19210 |
|   | 132-50 |
| 2 | 20023-20118 |
|   | 49-18 |
| 1 | 21261-21311 |
|   | 1-17 |
|   | stop codon 18959-18961 |

TABLE 3

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|---|---|
| 1 | 5011-5100 |
|   | 1-30 |
| 2 | 6249-6347 |
|   | 31-63 |
| 3 | 10879-10953 |
|   | 64-88 |
| 4 | 15797-15898 |
|   | 89-122 |
| 5 | 16628-16714 |
|   | 123-151 |
| 6 | 18372-18455 |
|   | 152-179 |
| 7 | 18719-18811 |
|   | 180-210 |

TABLE 3-continued

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|---|---|
| 8 | 19488-19664 |
|   | 211-270 |
| 9 | 20005-20064 |
|   | 271-290 |
|   | stop codon 20065-20067 |

TABLE 4

Exon/Intron Regions of the human ribosomal protein L26 gene, 21630 bp, reference cDNA accession number AF083248; reverse strand coding.

| Exon | Location (nucleotide no./amino acid no.) |
|---|---|
| 1 | 11490-11924 |
|   | 145-1 |
|   | stop codon 11487-11489 |

TABLE 5

Exon/Intron Region of the human CD81 gene, 37113 bp, reference accession number NM_004356; plus strand coding.

| Exon | Location (nucleotide no./amino acid no.) |
|---|---|
| 1 | 10471-10536 |
|   | 1-22 |
| 2 | 23333-23446 |
|   | 23-60 |
| 3 | 27015-27113 |
|   | 61-93 |
| 4 | 27893-27964 |
|   | 94-117 |
| 5 | 28334-28441 |
|   | 118-153 |
| 6 | 28790-28891 |
|   | 154-187 |
| 7 | 29549-29635 |
|   | 188-216 |
| 8 | 29725-29784 |
|   | 217-236 |
|   | stop codon 29785-29787 |

TABLE 6

Exon/Intro Region of the human tumor suppressing subtransferable candidate 4 (TSSC4) gene, 15540 bp, reference cDNA accession number NM_005706; plus strand coding.

| Exon | Location (nucleotide no./amino acid no.) |
|---|---|
| 1 | 13982-14968 |
|   | 1-329 |
|   | stop codon 14969-14971 |

TABLE 7

TRANSCRIPTION FACTOR BINDING SITES

| BINDING SITES | HASH2 | SMS3 | TSSC6 | RIBO26 | CD81 | TSSC4 |
|---|---|---|---|---|---|---|
| AP1FJ_Q2 |  | 14 | 8 | 10 | 16 |  |
| AP1_C | 4 | 6 | 8 | 10 | 8 |  |
| AP1_Q2 | 4 | 7 | 5 | 10 | 6 |  |
| AP1_Q4 |  |  | 4 | 5 | 5 |  |
| AP4_Q5 | 30 | 44 | 55 | 12 | 71 |  |
| AP4_Q6 | 14 | 22 | 26 | 4 | 34 |  |
| ARNT_01 | 7 | 4 |  |  | 6 |  |
| BRN2_01 | 5 |  |  | 4 |  |  |
| CDPCR3HD_01 |  |  |  | 5 | 8 |  |
| CEBPB_01 |  | 9 | 5 | 13 | 4 |  |
| CETS1P54_01 |  |  |  |  |  | 5 |
| CMYB_01 | 4 |  |  |  |  |  |
| CP2_01 |  | 4 | 5 |  |  |  |
| CREB_02 |  |  |  |  | 4 |  |
| CREB_Q4 |  |  |  |  | 4 |  |
| CREL_01 | 5 | 11 | 11 |  | 7 |  |
| DELTAEF1_01 | 42 | 49 | 67 | 57 | 84 |  |
| E47_01 |  |  | 6 |  | 17 |  |
| FREAC7_01 |  | 4 | 6 |  |  |  |
| GATA1_02 | 6 | 7 | 6 | 9 | 11 |  |
| GATA1_03 | 8 | 7 | 4 | 15 | 5 |  |
| GATA1_04 | 9 | 16 | 10 | 11 | 10 |  |
| GATA1_05 |  | 5 | 7 | 5 |  |  |
| GATA1_06 | 4 | 7 |  |  |  |  |
| GATA2_02 | 7 | 12 | 6 | 8 | 4 |  |
| GATA2_03 |  | 6 |  |  |  |  |
| GATA3_02 | 4 | 6 |  |  |  |  |
| GATA3_03 |  | 4 |  |  |  |  |
| GATA_C | 6 | 13 | 5 | 7 | 7 |  |
| GC_01 |  |  |  |  |  | 7 |
| GFI1_01 |  | 6 |  |  |  |  |
| HFH2_01 |  |  | 4 | 4 |  |  |
| HFH3_01 | 5 |  | 9 | 7 | 4 |  |
| HFH8_01 |  |  | 4 | 5 |  |  |
| IK1_01 |  |  | 4 |  |  |  |
| IK2_01 | 22 | 24 | 34 | 33 |  | 56 |
| LMO2COM_01 | 21 | 33 | 41 | 18 | 57 | 7 |
| LMO2COM_02 | 13 | 15 | 10 | 11 | 14 |  |
| LYF1_01 | 5 | 7 |  | 4 | 6 |  |
| MAX_01 | 4 |  |  |  |  |  |
| MYCMAX_02 | 4 |  |  |  |  |  |
| MYOD_01 |  |  |  |  | 4 |  |
| MYOD_Q6 | 13 | 13 | 22 | 5 | 34 | 11 |
| MZF1_01 | 73 | 106 | 136 | 63 | 211 | 21 |
| NF1_Q6 |  | 5 | 6 |  | 6 |  |
| NFAT_Q6 | 23 | 33 | 20 | 39 | 16 |  |
| NKX25_01 | 6 | 4 | 4 | 7 | 4 |  |
| NKX25_02 |  |  |  | 4 |  |  |
| NMYC_01 | 14 | 15 | 4 | 10 |  |  |
| OCT1_02 |  |  |  | 6 |  |  |
| PADS_C |  |  | 6 |  | 4 |  |
| RORA1_01 |  | 4 |  |  |  |  |
| S8_01 | 5 | 25 | 15 | 23 | 7 |  |
| SOX5_01 | 5 | 9 | 5 | 8 | 11 |  |
| SP1_Q6 | 6 |  |  |  | 11 |  |
| SRY_02 |  | 4 |  | 6 | 9 |  |
| STAT_01 | 5 |  |  |  | 5 |  |
| TATA_01 |  |  | 6 |  |  |  |
| TCF11_01 | 24 | 27 | 27 | 43 | 43 | 9 |
| USF_01 | 14 | 16 | 4 | 10 | 12 | 4 |
| USF_C | 14 | 16 | 4 | 10 | 12 | 6 |
| USF_Q6 |  | 10 |  |  | 6 |  |
| VMYB_02 | 9 | 5 |  | 4 | 11 |  |

Abbreviations:
HASH2, human achaete-scute homolog 2;
TSSC6, tumor suppressing subtransferable candidate 6;
RIBO26, ribosomal protein L26;
CD81, cluster of differentiation antigen 81; and
TSSC4, tumor suppressing subtransferable candidate 4.

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides
Isolated Polynucleotide Sequences

The human chromosome 11 genomic clone of accession number AC002536 has been discovered to contain the HASH2 gene, the SMS3 gene, the TSSC6 gene, the RIBO26, part of the CD81 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC002536 was compared to the HASH2 cDNA sequence, accession number U77629, the human SMS3 cDNA sequence accession number AB029488, TSSC6 cDNA sequence accession number NM_005705, and the RIBO26 cDNA sequence, accession number AF083248. The remainder of the CD81 gene and the TSSC4 gene were found by similar means in the downstream clone AC003693. The accession numbers for the CD81 and TSSC4 cDNAs are, respectively, NM_004356 and NM_005706.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of each gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684). Once the DNA fragments are generated, identification of the specific DNA fragment containing the desired HASH2 gene, the SMS3 gene, the TSSC6 gene, the RIBO26 gene, the CD81 gene, the TSSC4 gene, SEQ ID NO:13 or SEQ ID NO:14 may be accomplished in a number of ways. For example, if an amount of a portion of the HASH2 gene, the SMS3 gene, the TSSC6 gene, the RIBO26 gene, the CD81 gene or the TSSC4 gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NOS:7, 8, 9, 10, 11, 12, 13 or 14. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous HASH2, SMS3, TSSC6, or RIBO26 polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:7, 8, 9, 10, 11 or 12 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the HASH2, SMS3, the TSSC6, RIBO26, CD81 or TSSC4 polypeptide.

A gene encoding HASH2, SMS3, TSSC6, RIBO26, CD81 or TSSC4 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the HASH2 gene (nucleotides 7028-7609 of SEQ ID NO:7), SMS3 gene (nucleotides 18959-21311 of SEQ ID NO:8), TSSC6 gene (nucleotides 5011-20067 of SEQ ID NO:9), RIBO26 gene (nucleotides 11487-11924 of SEQ ID NO:10), CD81 gene (nucleotides 10471-29787 of SEQ ID NO:11) or TSSC4 gene (nucleotides 13982-14971 of SEQ ID NO:12) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 7, 8, 9, 10, 11 or 12 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the prokaryotic beta-lactamase gene (Villa-Komaroff et al., 1978, *Proc. Natl. Acad. Sci. USA* 75: 3727-3731), as well as the tac promoter (DeBoer et al., 1983, *Proc. Natl. Acad. of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423-488.

Eukaryotic promoters may be obtained from the genomes of viruses such as polyoma virus, fowlpox virus, adenovirus, bovine papilloma virus, avian sarcoma virus, cytomegalovirus, a retrovirus, hepatitis-B virus and SV40. Alternatively, heterologous mammalian promoters, such as the actin promoter or immunoglobulin promoter may be used.

The constructs of the invention may also include enhancers. Enhancers are cis-acting elements of DNA, usually from about 10 to about 300 bp that act on a promoter to increase its transcription. Enhancers from globin, elastase, albumin, alpha-fetoprotein, and insulin enhancers may be used. However, an enhancer from a virus may be used; examples include SV40 on the late side of the replication origin, the cytomegalovirus early promoter enhancer, the polyoma enhancer on the late side of the replication origin and adenovirus enhancers.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or pro-polypeptide (or a zymogen in some cases). A pro-polypeptide is generally inactive and can be converted to a mature active polypeptide by catalytic or autocatalytic cleavage of the propeptide from the pro-polypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated.

Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. An example of suitable selectable markers for mammalian cells are those that enable the identification of cells competent to take of the nucleic acids of the present invention, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980).

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, or a *Streptomyces* cell, e.g., *Streptomyces lividans* or *Streptomyces murinus*, or gram negative bacteria such as *E. coli* and *Pseudomonas* sp.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, embryonic kidney cells (293), lung cells, H9 and Jurkat cells, mouse NIH3T3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences by lipid-mediated, calcium phosphate mediated or DEAE-dextran mediated transfection (reviewed in Sambrook and Russell, Molecular Cloning, A Laboratory Manual, Cold Spring Harbor Laboratory Press, Cold Spring Harbor, N.Y., 2001). Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells. The polynucleotide may be directly introduced into the eukaryotic cell via electroporation, bolistics, or polybrene (reviewed in Sambrook and Russell, supra).

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proc. Natl. Acad. Sci. USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates. The polypeptides may be detected using methods known in the art that are specific for the polypeptides. These detection methods may include use of specific antibodies, formation of an enzyme product, or disappearance of an enzyme substrate. For example, the presence of the HASH2 and RIBO26 protein may be detected using standard transcription assays. The presence of TSSC4 and TSSC6 may be detected by assaying for tumor suppressor activity in rhabdomyosarcoma cells (Koi et al., 1993, Science 260:361-364).

The presence of CD81 may be detected by assaying for binding to E2 hepatitis C protein (Allander et al., 2000, J. Gen. Virol. 81:2451-2459).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the HASH2, SMS3, TSSC6, RIBO26, CD81 or TSSC4 polypeptides produced according to the method of the present invention may be used as an immunogen to generate any of these antibodies. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the HASH2, SMS3, TSSC6, RIBO26, CD81 or TSSC4 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the HASH2, SMS3, TSSC6, RIBO26, CD81 or TSSC4 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the HASH2, SMS3, TSSC6, RIBO26, CD81 or TSSC4 polypeptides.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al.,"Monoclonal Antibodies And T-cell Hybridomas" (1981); Kennett et al.,"Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides

Diagnostics

Polynucleotides containing noncoding regions of SEQ ID NOS:7, 8, 9, 10, 11, 12, 13 or 14 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis. Alternatively, these polynucleotides may be used as PCR primers and be used to amplify the genomic DNA isolated from the patients. Additionally, primers may be obtained by routine or long range PCR that yield products containing contiguous intron/exon sequence and products containing more than one exon with intervening intron. The sequence of the amplified genomic DNA from the patient may be determined using methods known in the art. Such probes may be between 10-100 nucleotides in length and may preferably be between 20-50 nucleotides in length. Specifically, probes derived from SEQ ID NOS: 13 or 14 may be used to identify mutations duplications, translocations, polysomies and mosaicism associated with Beckwith-Wiedemann syndrome.

Thus the invention is thus directed to kits comprising these polynucleotide probes. In a specific embodiment, these probes are labeled with a detectable substance.

Antisense Oligonucleotides and Mimetics

The antisense oligonucleotides or mimetics of the present invention may be used to decrease levels of a polypeptide. For example, HASH2 is required for development of the trophoblast. Therefore, the HASH2 antisense oligonucleotides of the present invention could be used as an antifertility agent. RIBO26 is expressed in abundance in small cell tumors of the lung. RIBO26 antisense sequences could be used to inhibit small cell tumor growth. CD81 plays a role in T cell activation, and its antisense sequences may help control autoimmune disorders in which T cell activation is uncontrolled. CD81 also binds the human hepatitis C virus; thus CD81 antisense sequences may, by reducing CD81 expression, reduce the infectivity of the human hepatitis C virus. The TSSC4 and 6 proteins act as tumor suppressors. Therefore, antisense sequences may act as antiapoptosis agents.

The HASH2, SMS3, TSSC6, RIBO26, CD81 and TSSC4 genes are all situated in a region of chromosome 11 known to be associated with the Beckwith-Wiedemann Syndrome. Thus, antisense sequences of any of these six genes may provide means of managing patients with the Beckwith-Wiedemann Syndrome. Furthermore, antisense oligonucleotides of SEQ ID NOS:13 or 14 may be used for the same purpose.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, HASH2 is necessary for development of the trophoblast, RIBO26 is a component of the ribosome, TSSC6 and TSSC4 are involved in repressing tumor growth, and CD81 is involved in T cell activation. Therefore, the HASH2 gene may be used to treat some forms of infertility. The CD81 gene may be used in patients whose ability to activate T cells is impaired. CD81 also binds the human hepatitis C virus, thus gene therapy designed to yield a secretable form of CD81 may, by binding the virus in an excretable form, reduce the spread of hepatitis C. Given the tumor suppressing actions of TSSC6 and TSSC4, their genes may be used to prevent tumor growth. RIBO26 may be used to treat disorders in which ribosome assembly is defective. The SMS3 gene is situated within the Beckwith-Wiedemann Syndrome locus and may thus be useful for treatment of patients in which the SMS3 gene is nonfunctional.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," Science, 247, 1465-1468, 1990; and Wolff, Jon A, "Human dystrophin expression in mdx mice after intramuscular injection of DNA constructs," Nature, 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous polyA addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN and LIPOFECTACE, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is $N^4$-spermine cholesteryl carbamate (GL-67) disclosed in U.S. Pat. No. 5,767,099. Additional preferred lipids include $N^4$-spermidine cholestryl carbamate (GL-53) and 1-($N^4$-spermidine)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class 1 molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated polynucleotide selected from the group consisting of: (a) an isolated polynucleotide consisting of a nucleic acid which is at least 99% identical to the polynucleotide of SEQ ID NO: 7; (b) a polynucleotide fragment of (a) comprising at least nucleotides 7028-7609 of SEQ ID NO:7, wherein (a)-(b) encode a polypeptide which is at least 99% identical to SEQ ID NO:1 and has human achaete-scute homolog 2 (HASH2) activity or (c): a reverse strand of the polynucleotides of (a) or (b).

2. A nucleic acid construct comprising the polynucleotide of claim 1.

3. An expression vector comprising the polynucleotide of claim 1.

4. A recombinant host cell comprising the polynucleotide of claim 1.

5. A method for obtaining human achaete-scute homolog 2 (HASH2) comprising:
   (a) culturing the recombinant host cell of claim 4 under conditions that provide for obtaining human achaete-scute homolog 2 (HASH2) and
   (b) recovering said human achaete-scute homolog 2 (HASH2).

6. An isolated polynucleotide at least 50 nucleotides in length identical to a region of SEQ ID NO: 7, said region selected from the group consisting of a 5'-noncoding region, a 3'-non-coding region and a contiguous coding and non-coding nucleic acid sequence of SEQ ID NO:7 or reverse strand of said polynucleotide.

7. The isolated polynucleotide of claim 6, wherein said 5'-noncoding region consists of nucleotides 7610-17290 of SEQ ID NO:7 and said 3'-non-coding region consists of nucleotides 1-7027 of SEQ ID NO:7.

8. A composition comprising the polynucleotide of claim 1 and a carrier or diluent.

9. A composition comprising the polynucleotide of claim 6 and a carrier or diluent.

10. A kit comprising the polynucleotide of claim 1.

11. A kit comprising the polynucleotide of claim 6.

12. A method for detecting the presence or absence of a nucleic acid sequence of SEQ ID NO: 7 or its complementary sequence in a sample, said method comprising contacting the sample with the polynucleotide of claim 6.

13. A method of detecting the presence or absence of a variant of human achaete-scute homolog 2 (HASH2) in a sample using the polynucleotide of claim 1.

14. A method for isolating the polynucleotide of claim 1 comprising
   (a) isolating genomic polynucleotide from a subject;
   (b) providing primers, probes and optionally polymerase, wherein said primers or probes are at least 50 nucleotides in length identical to a region of SEQ NO: 7, said region selected from the group consisting or a 5'-non-coding region, a 3'-non-coding region and a contiguous coding and non-coding nucleic acid sequence of SEQ ID NO:7 or reverse strand of said regions and
   (c) incubating (a) and (b) under conditions promoting the isolation of said polynucleotide.

15. A method for isolating the polynucleotide of claim 6 comprising
   (a) isolating genomic polynucleotide from a subject;
   (b) providing primers, probes and optionally polymerase, wherein said primers or probes are at least 50 nucleotides in length identical to a region of SEQ ID NO: 7, said region selected from the group consisting of a 5'-non-coding region, a 3'-non-coding region and a contiguous coding and non-coding nucleic acid sequence of SEQ ID NO:7 or reverse strand of said regions and
   (c) incubating (a) and (b) under conditions promoting the isolation of said polynucleotide.

16. The polynucleotide according to claim 1, wherein said polynucleotide is DNA or RNA.

17. An isolated polynucleotide consisting of a 5'-noncoding region, a 3'- non-coding region or a contiguous coding and non-coding nucleic acid sequence of SEQ ID NO:7 or reverse strand of said polynucleotide, wherein said 5'-noncoding region consists of nucleotides 7610-17290 of SEQ ID NO:7 and said 3'-non-coding region consists of nucleotides 1-7027 of SEQ ID NO:7.

18. An isolated polynucleotide fragment of claim 17, wherein said isolated polynucleotide fragment is at least 500 nucleotides in length.

19. The method according to claim 14, wherein said polynucleotide is DNA or RNA.

20. The method according to claim 15, wherein said polynucleotide is DNA or RNA.

21. The isolated polynucleotide according to claim 17, wherein said polynucleotide is DNA or RNA.

22. A kit comprising the polynucleotide of claim 17.

* * * * *